US009452980B2

(12) United States Patent
Groebke Zbinden et al.

(10) Patent No.: US 9,452,980 B2
(45) Date of Patent: *Sep. 27, 2016

(54) SUBSTITUTED BENZAMIDES

(75) Inventors: Katrin Groebke Zbinden, Liestal (CH); Roger Norcross, Olsberg (CH); Philippe Pflieger, Schwoben (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 97 days.

This patent is subject to a terminal disclaimer.

(21) Appl. No.: 12/969,613

(22) Filed: Dec. 16, 2010

(65) Prior Publication Data

US 2011/0152245 A1 Jun. 23, 2011

(30) Foreign Application Priority Data

Dec. 22, 2009 (EP) .................................... 09180504

(51) Int. Cl.
| | | |
|---|---|---|
| C07D 207/09 | (2006.01) |
| C07D 207/10 | (2006.01) |
| C07D 207/12 | (2006.01) |
| C07D 211/26 | (2006.01) |
| C07D 241/04 | (2006.01) |
| C07D 265/30 | (2006.01) |
| C07D 267/08 | (2006.01) |
| C07D 295/135 | (2006.01) |
| C07D 401/04 | (2006.01) |
| C07D 401/12 | (2006.01) |
| C07D 413/12 | (2006.01) |
| C07D 413/14 | (2006.01) |
| C07D 417/12 | (2006.01) |
| C07D 417/14 | (2006.01) |
| A61K 31/40 | (2006.01) |
| A61K 31/495 | (2006.01) |
| A61K 31/496 | (2006.01) |
| A61K 31/454 | (2006.01) |
| A61K 31/553 | (2006.01) |
| A61P 25/00 | (2006.01) |
| A61P 25/24 | (2006.01) |
| A61P 25/18 | (2006.01) |
| A61P 25/16 | (2006.01) |
| A61P 25/22 | (2006.01) |
| A61K 9/20 | (2006.01) |

(52) U.S. Cl.
CPC ........... *C07D 207/09* (2013.01); *A61K 9/2018* (2013.01); *C07D 207/10* (2013.01); *C07D 207/12* (2013.01); *C07D 211/26* (2013.01); *C07D 241/04* (2013.01); *C07D 265/30* (2013.01); *C07D 267/08* (2013.01); *C07D 295/135* (2013.01); *C07D 401/04* (2013.01); *C07D 401/12* (2013.01); *C07D 413/12* (2013.01); *C07D 413/14* (2013.01); *C07D 417/12* (2013.01); *C07D 417/14* (2013.01)

(58) Field of Classification Search
CPC C07D 207/09; C07D 207/10; C07D 207/12; C07D 211/26; C07D 241/04; C07D 265/30; C07D 267/08; C07D 295/135; C07D 401/04; C07D 401/12; C07D 413/12; C07D 413/14; C07D 417/12; C07D 417/14; A61K 31/40; A61K 31/495; A61K 31/496; A61K 31/454; A61K 31/451; A61K 31/553; A61P 25/00; A61P 25/24; A61P 25/18; A61P 25/16; A61P 25/22
See application file for complete search history.

(56) References Cited

U.S. PATENT DOCUMENTS

| | | |
|---|---|---|
| 2,161,938 A | 6/1939 | Sonn |
| 2,457,047 A | 12/1948 | Kyrides |
| 2,731,471 A | 1/1956 | Synerholm et al. |
| 2,744,909 A | 5/1956 | Speeter |

(Continued)

FOREIGN PATENT DOCUMENTS

| | | |
|---|---|---|
| CA | 2246027 | 2/2000 |
| CH | 609558 | 3/1979 |

(Continued)

OTHER PUBLICATIONS

Tomita et al., caplus an 1995:305181.*

(Continued)

*Primary Examiner* — Sun Jae Yoo

(57) ABSTRACT

The invention relates to compounds of formula

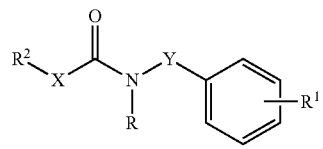

I wherein R, $R^1$, $R^2$, X, and Y are as defined herein and to a pharmaceutically suitable acid addition salt thereof.

Compounds of formula I have a good affinity to the trace amine associated receptors (TAARs), especially for TAAR1. The compounds can be used for the treatment of depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

14 Claims, No Drawings

(56) References Cited

U.S. PATENT DOCUMENTS

| | | | |
|---|---|---|---|
| 2,744,910 A | 5/1956 | Speeter | |
| 2,778,836 A | 1/1957 | Morren | |
| 2,919,274 A | 12/1959 | Faust et al. | |
| 3,161,653 A | 12/1964 | Fruhstorfer et al. | |
| 3,354,175 A | 11/1967 | Fruhstorfer et al. | |
| 3,377,247 A | 4/1968 | Eble | |
| 3,480,630 A | 11/1969 | Stahle et al. | |
| 3,577,415 A | 5/1971 | Robins | |
| 3,577,428 A | 5/1971 | Suh et al. | |
| 3,586,695 A | 6/1971 | Wysong et al. | |
| 3,622,579 A | 11/1971 | Stahle et al. | |
| 3,660,423 A | 5/1972 | Wysong et al. | |
| 3,758,476 A | 9/1973 | Rippel et al. | |
| 3,818,035 A | 6/1974 | Binon et al. | |
| 3,818,094 A | 6/1974 | Stahle et al. | |
| 3,981,814 A | 9/1976 | Nikawitz | |
| 3,992,403 A | 11/1976 | Roebke | |
| 4,125,620 A | 11/1978 | Stahle et al. | |
| 4,146,647 A | 3/1979 | Lafon | |
| 4,311,840 A | 1/1982 | Condon | |
| 4,323,570 A | 4/1982 | Stenzel et al. | |
| 4,636,504 A | 1/1987 | Rossy et al. | |
| 4,665,095 A | 5/1987 | Winn et al. | |
| 4,735,959 A | 4/1988 | Grell et al. | |
| 5,135,949 A | 8/1992 | Von der Saal et al. | |
| 5,610,174 A | 3/1997 | Craig et al. | |
| 5,658,938 A | 8/1997 | Geerts et al. | |
| 6,184,242 B1 | 2/2001 | Bley et al. | |
| 6,268,389 B1 | 7/2001 | Esser et al. | |
| 6,355,660 B1* | 3/2002 | Ricks et al. | 514/357 |
| 6,444,686 B1 | 9/2002 | Ko et al. | |
| 6,777,428 B1 | 8/2004 | Krushinski, Jr. et al. | |
| 2002/0019390 A1 | 2/2002 | Wong et al. | |
| 2003/0105135 A1 | 6/2003 | Bovy et al. | |
| 2003/0181354 A1 | 9/2003 | Abdulrazik | |
| 2003/0236274 A1 | 12/2003 | Tasaka et al. | |
| 2004/0157849 A1 | 8/2004 | Lee et al. | |
| 2004/0235888 A1 | 11/2004 | Yamamori et al. | |
| 2006/0111392 A1 | 5/2006 | Wood et al. | |
| 2007/0099919 A1 | 5/2007 | Rana | |
| 2007/0249620 A1 | 10/2007 | Kurata et al. | |
| 2007/0254894 A1 | 11/2007 | Kane et al. | |
| 2008/0076760 A1 | 3/2008 | Ohtake | |
| 2008/0119535 A1 | 5/2008 | Galley et al. | |
| 2009/0036420 A1 | 2/2009 | Galley et al. | |
| 2009/0036452 A1 | 2/2009 | Galley et al. | |
| 2009/0163545 A1 | 6/2009 | Goldfarb | |
| 2009/0306077 A1 | 12/2009 | Mogi et al. | |

FOREIGN PATENT DOCUMENTS

| | | |
|---|---|---|
| CN | 101434570 | 5/2009 |
| DE | 842065 | 6/1952 |
| DE | 1083803 | 6/1960 |
| DE | 1695005 | 2/1971 |
| DE | 1795517 | 2/1972 |
| DE | 2203373 | 8/1972 |
| DE | 2123246 | 11/1972 |
| DE | 2253555 | 11/1972 |
| DE | 2446758 | 4/1976 |
| DE | 2849537 | 5/1980 |
| DE | 3133887 | 3/1983 |
| DE | 3830054 | 9/1988 |
| DE | 0857483 | 8/1998 |
| EP | 0024829 | 3/1981 |
| EP | 0086043 | 8/1983 |
| EP | 0125410 | 11/1984 |
| EP | 0166937 | 1/1986 |
| EP | 0167459 | 1/1986 |
| EP | 0331374 | 9/1989 |
| EP | 0392929 | 10/1990 |
| EP | 0424059 | 4/1991 |
| EP | 440195 | 8/1991 |
| EP | 661266 | 12/1994 |
| EP | 0717037 | 6/1996 |
| EP | 0748800 | 12/1996 |
| EP | 0924209 | 6/1999 |
| EP | 1103243 | 5/2001 |
| EP | 1413576 | 4/2004 |
| EP | 2009005 | 12/2008 |
| EP | 2 351 744 | 8/2011 |
| EP | 2401275 | 1/2012 |
| ES | 323985 | 12/1966 |
| FR | 1355049 | 3/1964 |
| FR | 6551 | 12/1968 |
| GB | 877306 | 9/1961 |
| GB | 1016514 | 1/1996 |
| JP | 61-233678 | 10/1986 |
| JP | 2001151742 | 6/2001 |
| JP | 2007051121 | 3/2007 |
| JP | 2007-191471 | 8/2007 |
| JP | 2010241764 | 10/2010 |
| WO | 96/22768 | 8/1996 |
| WO | 97/12874 | 4/1997 |
| WO | 98/12183 | 3/1998 |
| WO | 98/24764 | 6/1998 |
| WO | WO9909024 | 2/1999 |
| WO | 99/65499 | 12/1999 |
| WO | 01/30762 | 5/2001 |
| WO | 01/81334 | 11/2001 |
| WO | 02/20501 | 3/2002 |
| WO | 02/22801 | 3/2002 |
| WO | 02/40453 | 5/2002 |
| WO | 02/053544 | 7/2002 |
| WO | 02/059080 | 8/2002 |
| WO | 02/76950 | 10/2002 |
| WO | 03/092374 | 11/2003 |
| WO | 03101444 | 12/2003 |
| WO | 2004/014898 | 2/2004 |
| WO | 2004/039764 | 5/2004 |
| WO | 2004073634 | 9/2004 |
| WO | 2004/094380 | 11/2004 |
| WO | 2004094380 | 11/2004 |
| WO | 2005014554 | 2/2005 |
| WO | 2005/040166 | 5/2005 |
| WO | 2005/087217 | 9/2005 |
| WO | 2006009741 | 1/2006 |
| WO | 2006018662 | 2/2006 |
| WO | 2006/077425 | 7/2006 |
| WO | 2006070878 | 7/2006 |
| WO | 2006/107923 | 10/2006 |
| WO | 2007/003967 | 1/2007 |
| WO | 2007/017728 | 2/2007 |
| WO | 2007/024944 | 3/2007 |
| WO | 2007031791 | 3/2007 |
| WO | 2007/064818 | 6/2007 |
| WO | 2007/085556 | 8/2007 |
| WO | 2007144400 | 12/2007 |
| WO | 2008000729 | 1/2008 |
| WO | 2008/058033 | 5/2008 |
| WO | 2008054702 | 5/2008 |
| WO | 2008/092785 | 8/2008 |
| WO | 2008/098857 | 8/2008 |
| WO | 2008/141976 | 11/2008 |
| WO | 2008148849 | 11/2008 |
| WO | 2008/148868 | 12/2008 |
| WO | 2008153959 | 12/2008 |
| WO | 2009055519 | 4/2009 |
| WO | 2010/010014 | 1/2010 |
| WO | 2006/119411 | 3/2010 |
| WO | 2010111711 | 9/2010 |
| WO | 2010118347 | 10/2010 |

OTHER PUBLICATIONS

Parkinsons—treatment, 2012, http://health.nytimes.com/health/guides/disease/parkinsons-disease/overview.html#Treatment.*
Parkinsons—prevention, 2012, http://www.webmd.com/parkinsons-disease/guide/parkinsons-disease-prevention.*
Goldfarb, 2009, caplus an 2009:846114.*
ClinicalTrial, 2011, http://www.nature.com/news/2011/110928/full/477526a.html.*
Botros et al., caplus an 1990:235261.*
Patani et al., Chem. Rev., 1996, 96, 3147-3176.*

(56) References Cited

OTHER PUBLICATIONS

Li et al., caplus an 2006:49622 (2006).*
Bolin et al., 2010, caplus an 2010:757048.*
Blanco-Pillado et al., caplus an 2004:927173, 2004.*
(Written Opinion for Corres. PCT/EP2010/070045 Dec. 21, 2011).
DeLucca, G. et al., Journal of Medicinal Chemistry 45:3794-3804 (2002).
U.S. Appl. No. 12/639,076, filed Dec. 16, 2009, Decoret et al.
U.S. Appl. No. 12/028,028, filed Feb. 8, 2008, Decoret et al.
U.S. Appl. No. 12/558,772, filed Sep. 14, 2009, Decoret et al.
Deutch et al., (1999) Neurotransmitters. In Fundamental Neuroscience (2nd ed.) pp. 193-234, Academic Press.
Wong, et al., (2001) Nat. Rev. Neurosci. 2, pp. 343-351.
Carlsson et al (2001) Annu. Rev. Pharmacol. Toxicol. 41, pp. 237-250.
Tuite et al. (2003) Expert Opin. Investig. Drugs 12, pp. 1335-1352.
Castellanos et al., (2002) Nat. Rev. Neurosol. 3, pp. 617-628
Usdin, E. and Sandler. M.; Editors. Psychopharmacology Series, vol. 1: Trace Amines and the Brain. [Proceedings of a Study Group at the 14th Annual Meeting of the American College of Neuropsychoparmacology, San Juan, Puerto Rico] (1976) pp. 1-281.
Lindemann et al., (2005) Trends in Pharmacol. Sci. 26, pp. 274-281.
Branchek et al., (2003) Curr. Opin. Pharmacol. 3, pp. 90-97.
Premont et al. (2001) Proc. Natl. Acad. Sci. U. S. A. 98, pp. 9474-9475.
Mosseau et al, (1995) Prog. Blain Res. 106, pp. 285-291.
McCormack et al. (1986) J. Neurosci. 6, pp. 94-101.
Dyck, L.E. (1989) Life Sci. 44, pp. 1149-1156.
Parker et al., (1988) J. Pharmacol. Exp. Ther. 245, pp. 199-210.
Lindemann et al. (2005) Genomics 85, pp. 372-385.
Habib et al., Synthesis, 1984, pp. 825-827.
Trani et al., J. Heterocycl. Chem. 11, pp. 257-262 (1974).
Abstract corresponding to Foreign Document 1 (DE 842 065).
Bunzow, J.R , et al., Molecular Pharmacology, vol. 60(6), pp. 1181-1188 (2001), XP008008060.
Holt, Andrew, J. of Psychiatry & Neuroscience, vol. 28(6), pp. 409-414 (2003), XP002438693.
Timmermans, P B M W M, et al., Life Sciences, vol. 28, No. 6, pp. 653-660 (1981), XP002442517.
Prisinzano, Thomas, et al., Bioorganic & Medicinal Chemistry Letters, vol. 14, No. 18, pp. 4697-4699 (2004), XP002442518.
Olmos, G., et al., European Journal of Pharmacology, vol. 262, No. ½, pp. 41-48 (1094), XP000567119.
McLennan, P. L., European Journal of Pharmacology, vol. 69, No. 4, pp. 477-482 (1981), XP002442519.
Nathanson, J.A., Molecular Pharmacology, vol. 28., No. 3, pp. 254-268 (1985), XP009085722.
Hirashima, et al., Bioorganic and Medicinal Chemistry, vol. 10, No, 1, pp. 117-123 (2002), XP002442520.
Flippin et al., Tetrahedron Letters, vol. 34, pp. 3255-3258 (1993).
Liebigs, Ann. Chem. pp. 2061-2071 (1980).
Huh et al., Tetrahedron, vol. 58, pp. 9925-9932 (2002).
Huh et al., Tetrahedron, vol. 60, pp. 9857-9862 (2004)
Law et al., J. Med. Chem. vol. 41, pp. 2243-2251 (1998).
Debernardis et al., J. Med. Chem. vol. 29, pp. 1413-1417 (1986).
Mohammadpoor-Baltork, Bull. Korean Chem. Soc. vol. 24, p. 1354-1356 (2003).
Melloni et al., Eur. J. Med. Chem. vol. 26, pp. 207-213 (1991).
Abdollahi-Alibeik et al., Bioorg. Med. Chem. Lett. vol. 14, pp. 6079-6082 (2004).
Amemiya, Synth. Commun. vol. 20, pp. 2483-2489 (1990).
Ohta, Chem. Pharm. Bull. vol. 35, pp. 1058-1069 (1987).
Olah, Synlett pp. 647-650 (1992).
Katz et al., Tetrahedron, vol. 45, pp. 1801-1814 (1989).
Wentland et al., J. Med. Chem. vol. 30, pp. 1482-1489 (1987).
Campos et al., Heterocycles, vol. 40, p. 841-849 (1995).
Ohta, Synthesis, pp. 78-81 (1990).
Mancuso et al., J. Org. Chem. vol. 43, pp. 2480-2482 (1978).
Mohammadpoor-Baltork, Synlett, pp. 2803-2805 (2004).
Cahiez et al., Synthesis, pp. 2138-2144 (1999).
Evans et al., Tetrahedron Lett. vol. 39, pp. 2937-2940 (1998).
Nakamura et al., J. Chem. Soc. Perkin Trans. 1, pp. 1061-1066 (2002).
Yoshiya, et al., J. of Medicinal Chemistry, vol. 35(4), pp. 750-755 (1992), XP002151512.
Faust, J.A., et al., J. of Organic Chemistry, vol. 26, pp. 4044-4047 (1961), XP002442336.
Savola, J.M., et al., Drug Research, vol. 38(1), pp. 29-35 (1988), XP002033085.
International Search Report issued Mar. 1, 2011 in corresponding PCT application PCT/EP2010/070045.
Matsunaga, et al., Bioorganic & Medicinal Chemistry, p. 4314-4336 (2004), XP002444990.
Matsunaga, et al., Tetrahedron: Asymmetry, Elsevier Science Publishers, vol. 15, No. 13, pp. 2021-2028 (2004), XP004520137.
Ojida, A., et al., Tetrahedron: Asymmetry, Elsevier Science Publishers, vol. 15, No. 10, pp. 1555-1559 (2004), XP004508431.
Zhang, et al., Journal of Medicinal Chemistry, vol. 40, pp. 3014-3024 (1997), XP002108693.
Ojida et al., Org. Lett. 2002, 4, pp. 3051-3054 (Supporting document attached).
Khimiya Geterotsiklicheskikh Soedinenii, 1988, pp. 77-79 (English language abstract attached).
Reimann et al., Arch. Pharm. 1989, vol. 322, pp. 363-367.
Klapars, et al., J. Am. Chem. Soc. 2001, vol. 123, pp. 7727-7729.
Anderson, et al., Tetrahedron, 2002, vol. 58, pp. 8475-8481.
Touzeau et al., J. Med. Chem. 2003, vol. 46, pp. 1962-1979.
Debernardis et al., Conformationally Defined Adregernic Agents. 5. Resolution, Absolute Configuration, and Pharmacological Characterization of the Enantiomers of 2-(5,6-Dihydroxy-1,2,3,4-tetrahydro-1-naphthyl)imidazoline: A Potent Agonist at α-Adrenoceptors, J. Med. Chem. (1987), 30:1011-1017.
Altenbach et al., Synthesis and Structure-Activity Studies on N-[5-(1H-Imidazol-4-yl)-5,6,7,8-tetrahydro-1-naphthalenyl]methanesulfonamide, an Imidasole-Containing α1A-Adrenoceptor Agonist, J. Med. Chem. (2004), 47: 3220-3235.
Carroll et al., In Vitro and In Vivo Characterization of Alpha-1A Selective Agonists and Their Utility for Stress Incontinence, Med. Chem. Res. (2004), 13:134-148.
Jetter et al., Synthesis of 4-Substituted Imidazoles via Palladium-Catalyzed Cross-Coupling Reactions, Synthesis (1998), 829-831.
Bagley et al., Synthesis and α2-Adrenergic Activities of Imidazole and Imidazolidine Analogues: In Vitro and In Vivo Selectivity, Medicinal Chemistry Research (1994), 4:346-364.
Lee et al., 4-[(N-Imidazol-2-ylmethyl)aniline]pyranopyridine Analogs as Novel Anti-Angiogenic Agents, Bull. Korean Chem. Soc. (2005), 25 619-628.
Agami et al., Tetrahedron 2001, vol. 57(1) pp. 195-200.
Ueda et al., Bioorganic 8, Medicinal Chem. Letters 2004, vol. 14(2) pp. 313-316.
Abstract corresponding to Foreign Document 34 (EP0167459).
Abstract corresponding to Foreign Document 15 (FR 6 551).
Cordi et al,, Journal of Med. Chem. vol. 44(5) pp. 787-805 (2001) XP002475805.
Vassiliou et al., Synlett, 2003 pp. 2398-2400.
Schollkopf, U. Topics Curr. Chem. 1983 vol. 109 p. 65.
Hosseinzadeh et al., Tetrahedron Letters (2008) vol. 49 pp. 840-843.
Chen et al., Org. Letters (2008) vol. 10 pp. 4565-4568.
Strieter et al., J. Am. Chem. Sco. (2009) vol. 131 pp. 78-88.
Perner et al., Journal of Medicinal Chemistry vol. 50, No. 15 (2007) pp. 3651-3660.
Moormann, et al., (1090) J. Med. Chem. pp. 614-626.
Hlasta et al., (1987) vol. 30, J. Med. Chem. pp. 1555-1562.
Dash et al., (2006) J. Heterocyclic Chem. pp. 401-404.
Gentili et al., (2004) J. Med. Chem. vol. 47 pp. 6160-6173.
Dias et al. (2005) J. Med. Chem. vol. 40 pp. 1206-1213.
Pigini et al., (1987) Eur. J. Med. Chem. vol. 22 pp. 273-276.
Wu et al., Synthesis (2003) pp. 1657-1660.
Fujioka et al., (2005) Tetrahedron Lett. vol. 46, pp. 2197-2199.
Ishihara et al., Synlett (2006) pp. 227-230.
Pinza et al. (1976) Heterocycles, vol. 4 pp. 1699-1706.
Kornicka et al. (2006) Heterocycles vol. 68 pp. 687-699.

(56) References Cited

OTHER PUBLICATIONS

Kosasayama et al., (1979) Chem. Pharm. Bull. vol. 27 pp. 831-840.
Lloyd et al., (1980) Tetrahedron vol. 36, pp. 2675-2679.
Freiter, E.R , et al., J. Heterocyclic Chem., vol. 10, No. 3, pp. 391-394 (1973), XP008087527.
Tarnchompoo, B., et al., vol. 31, No. 40, pp. 5779-5780 (1990), XP002118267.
Wilkinson, C.F., et al., Biochem. Pharmacol., vol. 21, pp. 3187-3192 (1972), XP :008087536.
Raddatz, Rita , et al., J. Pharmacol. Exp. Therap., vol. 292, No. 3, pp. 1135-1145 (2000), XP008087488.
Shafiee, A., et al., Journal of Heterocyclic Chemistry, pp. 607-610 (1998), XP001069546.
Robertson, David W., J. Med. Chem., vol. 29, pp. 1577-1586 (1986), XP008087539.
Database CA, Chemical Abstracts, Yamaguchi, Hideaki, XP002465006 & JP 06 268356 (1994).
Saunders et al., Journal of the American Chemical Society vol. 80 pp. 3328-3332 (1958).
U.S. Appl. No. 12/789,484, filed May 28, 2010.
Lewis D.A. & Lieberman J.A., Neuron. vol. 28, pp. 325-334 (2000).
Vandenberg R. J. & Aubrey K. R., Exp. Opin. Ther. Targets vol. 5(4) pp. 507-518 (2001).
Nakazato A. & Okuyama S., Exp. Opin Ther. Patents vol. 10(1) pp. 75-98 (2000).
Sharma T., Br. J. Psychiatry, vol. 174 (Suppl. 38) pp. 44-51 (1999).
Javitt D. C. et al., Biol. Psychiatry, vol. 45 pp. 668-679 (1999).
Mohn A. R. et al., Cell, vol. 98 pp. 427-436 (1999).
Bliss, T. V. & Collingridge G. L., Nature, vol. 361 pp. 31-39 (1993).
Tang J. P. et al., Nature, vol. 401, pp. 63-69 (1999).
Gainetdinov R. R. et al., Trends in Pharm. Sci. vol. 23(8) pp. 367-373 (2002).
Lopez-Corcuera B, et al., Mol. Mem. Biol. vol. 18 pp. 13-20 (2001).
Bergeron R. et al., Proc. Natl. Acad. Sci. USA vol. 95, pp. 15730-15734 (1998).
Chen et al., J. Neurophysiol. vol. 89(2) pp. 691-703 (2003).
Armer R. E. & Miller D. J., Exp. Opin. Ther. Patents vol. 11(4) pp. 563-572 (2001).
Pralong E. et al., Prog. in Neurobiol. vol. 67, pp. 173-202 (2002) .
Carlsson M. L., J. Neural Trans. vol. 105, pp. 525-535 (1998).
Liebigs, Ann. Chem. 80: pp. 80-82 (1963) (English language translation attached).
Chem. Ber. vol. 97: 2276 (1964).
Chemical Abstract XP002435251.
Chemical Abstract XP002435252.
Chemical Abstract XP002436293.
Clitherow et al., J. Med. Chem. vol. 37(15) pp. 2253-2257 (1994).
Lee et al., Macromolecular Rapid Communications vol. 23(12) pp. 665-671 (2002).
Mitsutake et al., Journal of Agricultural and Food Chemistry vol. 34 pp. 725-732 (1986).
Kim et al., Journal of Combinatorial Chemistry vol. 4(6) pp. 549-551 (2002).
Waisser et al., Pharmazie vol. 53(3) pp. 193-195(1998).
Perry et al., Journal of Organic Chemistry vol. 61(21) pp. 7482-7485 (1996).
Partridge et al., Journal of the Chemical Society pp. 3043-3046 (1949).
Shi et al., Journal of Medicinal Chemistry vol. 39(17) pp. 3375-3384 (1996).
Abramovitch et al., Journal of Organic Chemistry vol. 48(23) pp. 4391-4303 (1983).
Jackson et al., Perkin 1 vol. 2 pp. 205-210 (2000).
Srivastava et al., Agricultural and Biological Chemistry vol. 40(1) pp. 213-214 (1976).
Clark et al., Journal of Medicinal Chemistry vol. 29(8) pp. 1534-1537 (1986).
Beaver, et al., Journal of the American Chemical Society vol. 79 pp. 1236-1245 (1957).
Kobs et al., Chemische Berichte vol. 123(11) pp. 2191-2194 (1990).
Katritzky et al., Journal of Organic Chemistry vol. 71(9) pp. 3375-3380 (2006).
Waisser et al., Magnetic Resonance in Chemistry vol. 35(8) pp. 543-548(1997).
Kumar et al , Journal of Medicinal Chemistry vol. 27(8) pp. 1083-1089 (1984).
Gilbert et al., Journal of the Chemical Society pp. 2323-2331 (1931).
Klemm et al., Journal of Organic Chemistry vol. 23 pp. 349-353 (1958).
White, G. A., Pesticide Biochemistry and Physiology vol. 34(3) pp. 255-276 (1989).
Griffith et al., Journal of the Chemical Society, Transactions vol. 127 pp. 990-995 (1925).
Hong et al., Taehan Hwahakhoe Chi vol. 17(3) pp. 193-197 (1972).
Ito et al., Nippon Noyakuj Gakkaishi vol. 10(4) pp. 697-702 (1985).
Mehrotra et al., Tetrahedron Letters vol. 4 pp. 321-322 (1971).
De Ruiter et al., Journal of Medicinal Chemistry vol. 32(5) pp. 1033-1038 (1989).
Lee et al., Journal of Physical Organic Chemistry vol. 7(6) pp. 273-279 (1994).
Chase et al., Journal of Pharmacy and Pharmacology vol. 16(3) pp. 163-173 (1964).
Yoshimo et al., Journal of Medicinal Chemistry vol. 29(5) pp. 820-825 (1986).
Heinicke et al., Australian Journal of Chemistry vol. 37(4) pp. 831-844 (1984).
Burn, D., Bulletin de la Societe Chimique de France vol. 3 pp. 848-858 (1965).
The English translation of the Japanese Office Action, issued on Mar. 4, 2014, in the corresponding Japanese Application No. 2012-545252.
Registry No. 1017367-32-6, Apr. 25, 2008.
Journal of Pharmaceutical and Biomedical Analysis, 1989, vol. 7, No. 3, pp. 355-359.
Bioorganic & Medicinal Chemistry Letters, 2009, vol. 19, No. 2, pp. 550-553.
Registry No. 794559-77-6, Dec. 8, 2004.
The Australian Examination Report, issued on Jan. 22, 2016, in the corresponding Australian application No. 2010335277.
The European Communication, issued on Oct. 22, 2015, in the corresponding European application No. 10793256.8.
Verma et al., "Indolyl Compounds as Antiinflammatory Agents," Arch. Pharm. vol. 315, pp. 358-363, 1982.
F. Manetti et al., "Building a pharmacophore model for a novel class of antitubercular compounds," II Farmaco, vol. 55, Issues 6-7, Jul. 2000, pp. 484-491.
The European Communication, issued on Mar. 31, 2015, in the corresponding European application No. 10793256.8.
The English translation of the Japanese Office Action, issued on Jan. 20, 2015, in the corresponding Japanese Application No. 2012-545252.
Li et al., "Design and Synthesis of 5-Aryl-pyridone-carboxamides as Inhibitors of Anaplastic Lymphoma Kinase," J. Med. Chem. 2006, 49, 1006-1015.

* cited by examiner

SUBSTITUTED BENZAMIDES

PRIORITY TO RELATED APPLICATION(S)

This application claims the benefit of European Patent Application No. 09180504.4, filed Dec. 22, 2009, which is hereby incorporated by reference in its entirety.

BACKGROUND OF THE INVENTION

Some of the physiological effects (i.e. cardiovascular effects, hypotension, induction of sedation) which have been reported for compounds which may bind to adrenergic receptors (WO02/076950, WO97/12874 or EP 0717 037) may be considered to be undesirable side effects in the case of medicaments aimed at treating diseases of the central nervous system as described above. Therefore it is desirable to obtain medicaments having selectivity for the TAAR1 receptor vs adrenergic receptors. Objects of the present invention show selectivity for TAAR1 receptor over adrenergic receptors, in particular good selectivity vs the human and rat alpha1 and alpha2 adrenergic receptors.

The classical biogenic amines (serotonin, norepinephrine, epinephrine, dopamine, histamine) play important roles as neurotransmitters in the central and peripheral nervous system [1]. Their synthesis and storage, as well as their degradation and reuptake after release are tightly regulated. An imbalance in the levels of biogenic amines is known to be responsible for the altered brain function under many pathological conditions [2-5]. A second class of endogenous amine compounds, the so-called trace amines (TAs) significantly overlaps with the classical biogenic amines regarding structure, metabolism and subcellular localization. The TAs include p-tyramine, β-phenylethylamine, tryptamine and octopamine, and they are present in the mammalian nervous system at generally lower levels than classical biogenic amines [6].

Their dysregulation has been linked to various psychiatric diseases like schizophrenia and depression [7] and for other conditions like attention deficit hyperactivity disorder, migraine headache, Parkinson's disease, substance abuse and eating disorders [8,9].

For a long time, TA-specific receptors had only been hypothesized based on anatomically discrete high-affinity TA binding sites in the CNS of humans and other mammals [10,11]. Accordingly, the pharmacological effects of TAs were believed to be mediated through the well known machinery of classical biogenic amines, by either triggering their release, inhibiting their reuptake or by "crossreacting" with their receptor systems [9, 12, 13]. This view changed significantly with the recent identification of several members of a novel family of GPCRs, the trace amine associated receptors (TAARs) [7,14]. There are 9 TAAR genes in human (including 3 pseudogenes) and 16 genes in mouse (including 1 pseudogene). The TAAR genes do not contain introns (with one exception, TAAR2 contains 1 intron) and are located next to each other on the same chromosomal segment. The phylogenetic relationship of the receptor genes, in agreement with an in-depth GPCR pharmacophore similarity comparison and pharmacological data suggest that these receptors form three distinct subfamilies [7,14]. TAAR1 is in the first subclass of four genes (TAAR1-4) highly conserved between human and rodents. TAs activate TAAR1 via Gαs. Dysregulation of TAs was shown to contribute to the aetiology of various diseases like depression, psychosis, attention deficit hyperactivity disorder, substance abuse, Parkinson's disease, migraine headache, eating disorders, metabolic disorders and therefore TAAR1 ligands have a high potential for the treatment of these diseases.

Therefore, there is a broad interest to increase the knowledge about trace amine associated receptors.

REFERENCES USED

1. Deutch, A. Y. and Roth, R. H. (1999) Neurotransmitters. In *Fundamental Neuroscience* (2$^{nd}$ edn) (Zigmond, M. J., Bloom, F. E., Landis, S. C., Roberts, J. L, and Squire, L. R., eds.), pp. 193-234, Academic Press;
2. Wong, M. L. and Licinio, J. (2001) Research and treatment approaches to depression. *Nat. Rev. Neurosci.* 2, 343-351;
3. Carlsson, A. et al. (2001) Interactions between monoamines, glutamate, and GABA in schizophrenia: new evidence. *Annu. Rev. Pharmacol. Toxicol.* 41, 237-260;
4. Tuite, P. and Riss, J. (2003) Recent developments in the pharmacological treatment of Parkinson's disease. *Expert Opin. Investig. Drugs* 12, 1335-1352,
5. Castellanos, F. X. and Tannock, R. (2002) Neuroscience of attention-deficit/hyperactivity disorder: the search for endophenotypes. *Nat. Rev. Neurosci.* 3, 617-628;
6. Usdin, Earl; Sandler, Merton; Editors. *Psychopharmacology Series, Vol.* 1: *Trace Amines and the Brain. [Proceedings of a Study Group at the* 14*th Annual Meeting of the American College of Neuropsychoparmacology*, San Juan, Puerto Rico] (1976);
7. Lindemann, L. and Hoener, M. (2005) A renaissance in trace amines inspired by a novel GPCR family. *Trends in Pharmacol. Sci.* 26, 274-281;
8. Branchek, T. A. and Blackburn, T. P. (2003) Trace amine receptors as targets for novel therapeutics: legend, myth and fact. *Curr. Opin. Pharmacol.* 3, 90-97;
9. Premont, R. T. et al. (2001) Following the trace of elusive amines. *Proc. Natl. Acad. Sci. U.S.A.* 98, 9474-9475;
10. Mousseau, D. D. and Butterworth, R. F. (1995) A high-affinity [3H] tryptamine binding site in human brain. *Prog. Brain Res.* 106, 285-291;
11. McCormack, J. K. et al. (1986) Autoradiographic localization of tryptamine binding sites in the rat and dog central nervous system. *J. Neurosci.* 6, 94-101;
12. Dyck, L. E. (1989) Release of some endogenous trace amines from rat striatal slices in the presence and absence of a monoamine oxidase inhibitor. *Life Sci.* 44, 1149-1156;
13. Parker, E. M. and Cubeddu, L. X. (1988) Comparative effects of amphetamine, phenylethylamine and related drugs on dopamine efflux, dopamine uptake and mazindol binding. *J. Pharmacol. Exp. Ther.* 245, 199-210;
14. Lindemann, L. et al. (2005) Trace amine associated receptors form structurally and functionally distinct subfamilies of novel G protein-coupled receptors. *Genomics* 85, 372-385.

SUMMARY OF THE INVENTION

The invention provides compounds of formula I

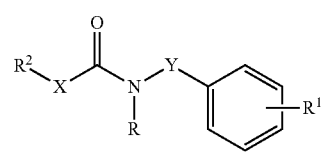

wherein
R is hydrogen or lower alkyl;
$R^1$ is —$(CH_2)_n$—$(O)_o$— heterocycloalkyl or —C(O)-heterocycloalkyl, wherein the heterocycloalkyl group is optionally substituted by lower alkyl, hydroxy, halogen or by —$(CH_2)_p$-aryl;
n is 0, 1 or 2;
o is 0 or 1;
p is 0, 1 or 2;
$R^2$ is $CF_3$, cycloalkyl, optionally substituted by lower alkoxy or halogen, or is indany-2-yl,
  or is heterocycloalkyl, optionally substituted by heteroaryl,
  or is aryl or heteroaryl, wherein the aromatic rings in aryl and heteroaryl are optionally substituted by one or two substituents, selected from lower alkyl, halogen, heteroaryl, hydroxy, $CF_3$, $OCF_3$, $OCH_2CF_3$, $OCH_2$-cycloalkyl, $OCH_2C(CH_2OH)(CH_2Cl)(CH_3)$, S-lower alkyl, lower alkoxy, $CH_2$-lower alkoxy, lower alkynyl or cyano, or by —C(O)-phenyl, —O-phenyl, —O—$CH_2$-phenyl, phenyl or —$CH_2$-phenyl, and wherein the phenyl rings are optionally substituted by halogen, —C(O)-lower alkyl, —C(O)OH or —C(O)O-lower alkyl,
  or the aromatic rings are optionally substituted by heterocycloalkyl, $OCH_2$-oxetan-3-yl or O-tetrahydropyran-4-yl, optionally substituted by lower alkyl;
X is a bond, —NR'—, —$CH_2NH$—, —CHR"—, —$(CHR")_q$—O—, —O—$(CHR")_q$ or —$(CH_2)_2$—;
Y is a bond or —$CH_2$—
—R' is hydrogen or lower alkyl,
R" is hydrogen, lower alkyl, $CF_3$, lower alkoxy,
q is 0, 1, 2 or 3;
or a pharmaceutically suitable acid addition salt thereof.

The invention includes all racemic mixtures, all their corresponding enantiomers and/or optical isomers. In addition, all tautomeric forms of compounds of formula I are also encompassed by the present invention.

The preferred position of $R^1$ on the phenyl ring is the para position.

The inventions provides not only compounds of formula I and their pharmaceutically acceptable salts, but also pharmaceutical compositions containing such compounds. The invention further provides methods for the preparation of the compounds and compositions of the invention.

Compounds of formula I have a good affinity to the trace amine associated receptors (TAARs), especially for TAAR1.

The compounds are useful for the treatment of depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

The preferred indications using the compounds of the present invention are depression, psychosis, Parkinson's disease, diabetes, anxiety and attention deficit hyperactivity disorder (ADHD).

DETAILED DESCRIPTION OF THE INVENTION

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes a lower alkyl group as defined above that is attached via an oxygen atom.

As used herein, the term "lower alkyl substituted by halogen" denotes a lower alkyl group as defined above, wherein at least one hydrogen atom is replaced by halogen, for example $CF_3$, $CHF_2$, $CH_2F$, $CH_2CF_3$, $CH_2CH_2CF_3$, $CH_2CF_2CF_3$ and the like.

As used herein, the term "lower alkoxy substituted by halogen" denotes a lower alkoxy group as defined above wherein at least on hydrogen atom is replaced by halogen.

The term "lower alkynyl" stands for a straight-chain or branched hydrocarbon residue comprising a triple bond and up to 7, preferably up to 4, carbon atoms, such as e.g. ethynyl or 2-propynyl.

The term "halogen" denotes chlorine, iodine, fluorine and bromine.

The term "cycloalkyl" is an alkylene ring, containing from 3 to 6 carbon ring atoms.

The term "aryl", relates to an aromatic carbon ring such as to the phenyl or naphthyl ring, preferably the phenyl ring.

The term "heteroaryl" refers to an aromatic 5 to 6 membered monocyclic ring or 9 to 10 membered bicyclic ring which comprises 1, 2 or 3 heteroatoms selected from nitrogen, oxygen and/or sulphur, such as furyl, pyridinyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, thiadiazolyl, benzoimidazolyl, indolyl, indanyl, indazolyl, benzothiazolyl, benzoisothiazolyl, benzoxazolyl, benzoisoxazolyl, quinolinyl and isoquinolinyl. Preferred heteroaryl groups are pyridinyl, pyrazolyl, pyrimidinyl, benzoimidazolyl, quinolinyl and isoquinolinyl.

The term "heterocycloalkyl" refers to a non-aromatic 5 to 7 membered monocyclic ring which comprises 1, 2 or 3 heteroatoms selected from nitrogen, oxygen and/or sulphur, such as piperazinyl, piperidinyl, morpholinyl, pyrrolidinyl, [1.4]oxazepanyl, or thiomorpholinyl.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

One embodiment of the invention provides compounds of formula I, wherein X is NR' and R' is hydrogen, for example the following compounds:
(RS)-1-(4-Butyl-2-methyl-phenyl)-3-(4-pyrrolidin-3-yl-phenyl)-urea;
1-(3,4-Dichloro-phenyl)-3-[4-(4-methyl-piperazin-1-yl)-phenyl]-urea;
(RS)-1-(3,4-Dichloro-phenyl)-3-(4-pyrrolidin-3-yl-phenyl)-urea;
(RS)-1-(4-Chloro-phenyl)-3-(4-pyrrolidin-3-yl-phenyl)-urea;
(RS)-1-Phenyl-3-(4-pyrrolidin-3-yl-phenyl)-urea;

(RS)-1-(2,4-Dichloro-phenyl)-3-(4-pyrrolidin-3-yl-phenyl)-urea;
(RS)-1-(3-Chloro-phenyl)-3-(4-pyrrolidin-3-yl-phenyl)-urea;
(RS)-1-(4-Pyrrolidin-3-yl-phenyl)-3-(4-trifluoromethyl-phenyl)-urea;
(RS)-1-(5-Chloro-pyridin-2-yl)-3-(4-pyrrolidin-3-yl-phenyl)-urea;
(RS)-1-(6-Chloro-pyridin-3-yl)-3-(4-piperidin-3-yl-phenyl)-urea;
(RS)-1-(5-Chloro-pyridin-2-yl)-3-(4-piperidin-3-yl-phenyl)-urea;
(RS)-1-(5-Chloro-pyridin-2-yl)-3-[4-(2-pyrrolidin-3-yl-ethyl)-phenyl]-urea;
(RS)-1-(4-Chloro-phenyl)-3-[4-(2-pyrrolidin-3-yl-ethyl)-phenyl]-urea;
(RS)-1-(4-Chloro-phenyl)-3-[4-(2-piperidin-3-yl-ethyl)-phenyl]-urea;
(RS)-1-(4-(Morpholin-2-yl)phenyl)-3-(4-(trifluoromethyl)phenyl)urea;
(RS)-1-(4-Chlorophenyl)-3-(4-(morpholin-2-yl)phenyl)urea;
(RS)-1-(4-(Morpholin-2-yl)phenyl)-3-p-tolylurea;
(RS)-1-(6-Chloropyridin-3-yl)-3-(4-(morpholin-2-yl)phenyl)urea;
(RS)-1-(3-Chlorophenyl)-3-(4-(morpholin-2-yl)phenyl)urea;
(RS)-1-(4-(Morpholin-2-yl)phenyl)-3-m-tolylurea;
(RS)-1-(2-Chlorophenyl)-3-(4-(morpholin-2-yl)phenyl)urea;
(RS)-1-(4-Methylbenzyl)-3-(4-(morpholin-2-yl)phenyl)urea;
(R)-1-(4-(Morpholin-2-yl)phenyl)-3-(4-(trifluoromethyl)phenyl)urea; and
(S)-1-(4-(Morpholin-2-yl)phenyl)-3-(4-(trifluoromethyl)phenyl)urea.

A further embodiment of the invention provides compounds, wherein X is a bond, for example
(RS)—N-(4-Pyrrolidin-3-yl-phenyl)-benzamide;
(RS)-4-Chloro-N-(4-pyrrolidin-3-yl-phenyl)-benzamide;
(RS)—N-(4-Pyrrolidin-3-yl-phenyl)-4-trifluoromethyl-benzamide;
(RS)-2,4-Dichloro-N-(4-pyrrolidin-3-yl-phenyl)-benzamide;
(RS)-3-Chloro-N-(4-pyrrolidin-3-yl-phenyl)-benzamide;
(RS)-4-Chloro-N-[4-(1-methyl-pyrrolidin-3-yl)-phenyl]-benzamide;
(RS)-4-Chloro-N-[4-(1-ethyl-pyrrolidin-3-yl)-phenyl]-benzamide;
(RS)-4-Chloro-N-[4-(pyrrolidin-3-yloxy)-phenyl]-benzamide;
(RS)-5-Chloro-pyridine-2-carboxylic acid (4-pyrrolidin-3-yl-phenyl)-amide;
(RS)-6-Chloro-pyridine-3-carboxylic acid (4-pyrrolidin-3-yl-phenyl)-amide;
(RS)-4-Ethoxy-N-(4-pyrrolidin-3-yl-phenyl)-benzamide;
(RS)-4-Propyl-N-(4-pyrrolidin-3-yl-phenyl)-benzamide;
(RS)-4-Ethynyl-N-(4-pyrrolidin-3-yl-phenyl)-benzamide;
(RS)-4-Cyano-N-(4-pyrrolidin-3-yl-phenyl)-benzamide;
(RS)-3,4-Dichloro-N-(4-pyrrolidin-3-yl-phenyl)-benzamide;
4-Chloro-N-(4-piperidin-4-yl-phenyl)-benzamide;
(RS)-4-Chloro-N-(4-piperidin-3-yl-phenyl)-benzamide;
4-Chloro-N-(4-piperazin-1-yl-phenyl)-benzamide;
4-Chloro-N-[4-((3RS,4RS)-4-fluoro-pyrrolidin-3-yl)-phenyl]-benzamide;
(RS)-4-Chloro-N-[3-(pyrrolidin-3-yloxy)-phenyl]-benzamide;
(RS)-6-Pyrazol-1-yl-N-(4-pyrrolidin-3-yl-phenyl)-nicotinamide;
(RS)-6-Chloro-N-(4-piperidin-3-yl-phenyl)-nicotinamide;
(RS)-4-Chloro-2-fluoro-N-(4-pyrrolidin-3-yl-phenyl)-benzamide;
(RS)-5-Chloro-pyridine-2-carboxylic acid (4-piperidin-3-yl-phenyl)-amide;
(RS)-4-Chloro-N-[4-(4-methyl-morpholin-2-yl)-phenyl]-benzamide;
(RS)-Quinoline-2-carboxylic acid (4-pyrrolidin-3-yl-phenyl)-amide;
(RS)-Isoquinoline-1-carboxylic acid (4-pyrrolidin-3-yl-phenyl)-amide;
(RS)-4-Chloro-pyridine-2-carboxylic acid (4-pyrrolidin-3-yl-phenyl)-amide;
(RS)-5-Bromo-pyridine-2-carboxylic acid (4-pyrrolidin-3-yl-phenyl)-amide;
(RS)-2-Fluoro-4-methoxy-N-(4-pyrrolidin-3-yl-phenyl)-benzamide;
(RS)—N-(4-Pyrrolidin-3-yl-phenyl)-6-(2,2,2-trifluoro-ethoxy)-nicotinamide;
(RS)-6-Methoxy-quinoline-2-carboxylic acid (4-pyrrolidin-3-yl-phenyl)-amide;
(RS)-3-Chloro-N-(4-piperidin-3-yl-phenyl)-benzamide;
(RS)-3,4-Dichloro-N-(4-piperidin-3-yl-phenyl)-benzamide;
(RS)-4-Ethoxy-N-(4-piperidin-3-yl-phenyl)-benzamide;
(RS)—N-(4-Piperidin-3-yl-phenyl)-4-trifluoromethyl-benzamide;
(RS)-4-Chloro-2-fluoro-N-(4-piperidin-3-yl-phenyl)-benzamide;
(RS)-4-Chloro-N-(4-pyrrolidin-2-ylmethyl-phenyl)-benzamide;
(RS)-1-Chloro-isoquinoline-3-carboxylic acid (4-pyrrolidin-3-yl-phenyl)-amide;
(RS)-4-Chloro-N-[4-(2-pyrrolidin-3-yl-ethyl)-phenyl]-benzamide;
(RS)-4-Chloro-N-[4-(2-piperidin-3-yl-ethyl)-phenyl]-benzamide;
4-Chloro-N—((R)-4-piperidin-3-yl-phenyl)-benzamide;
(RS)-5-Chloro-pyridine-2-carboxylic acid [4-(2-pyrrolidin-3-yl-ethyl)-phenyl]-amide;
(RS)—N-(4-Piperidin-3-yl-phenyl)-4-propyl-benzamide;
(RS)-5-Trifluoromethyl-pyridine-2-carboxylic acid (4-piperidin-3-yl-phenyl)-amide;
(RS)-5-Trifluoromethyl-pyridine-2-carboxylic acid (4-pyrrolidin-3-yl-phenyl)-amide;
(RS)-5-Trifluoromethyl-pyridine-2-carboxylic acid (4-morpholin-2-yl-phenyl)-amide;
(RS)-4-Chloro-N-[4-(2-pyrrolidin-2-yl-ethyl)-phenyl]-benzamide;
4-Chloro-N—((R)-4-morpholin-2-yl-phenyl)-benzamide;
4-Chloro-N—((S)-4-morpholin-2-yl-phenyl)-benzamide;
(RS)-4-Chloro-N-[4-(pyrrolidin-3-yloxymethyl)-phenyl]-benzamide;
(RS)-4-Chloro-2-fluoro-N-(4-morpholin-2-yl-phenyl)-benzamide;
(RS)-3,4-Dichloro-N-(4-morpholin-2-yl-phenyl)-benzamide;
(RS)-5-Chloro-pyridine-2-carboxylic acid (4-morpholin-2-yl-phenyl)-amide;
(RS)-4-Chloro-N-(4-pyrrolidin-3-ylmethyl-phenyl)-benzamide;
3,4-Dichloro-N—((R)-4-piperidin-3-yl-phenyl)-benzamide;
(R)-3-Chloro-N-(4-(piperidin-3-yl)phenyl)benzamide;
3,4-Dichloro-N—((S)-4-piperidin-3-yl-phenyl)-benzamide;

(S)-3-Chloro-N-(4-(piperidin-3-yl)phenyl)benzamide;
(RS)-3,4-Dichloro-N-[4-(2-pyrrolidin-2-yl-ethyl)-phenyl]-benzamide;
(RS)—N-[4-(2-Pyrrolidin-2-yl-ethyl)-phenyl]-4-trifluoromethyl-benzamide;
(RS)-4-Fluoro-N-[4-(2-pyrrolidin-2-yl-ethyl)-phenyl]-benzamide;
(RS)-3-Chloro-N-[4-(2-pyrrolidin-2-yl-ethyl)-phenyl]-benzamide;
(RS)-4-Ethoxy-N-[4-(2-pyrrolidin-2-yl-ethyl)-phenyl]-benzamide;
(RS)-5-Chloro-pyrazine-2-carboxylic acid (4-piperidin-3-yl-phenyl)-amide;
(S)-6-Chloro-N-(4-(piperidin-3-yl)phenyl)nicotinamide;
(R)-5-Chloro-N-(4-(piperidin-3-yl)phenyl)picolinamide;
(S)-5-Chloro-N-(4-(piperidin-3-yl)phenyl)picolinamide;
(RS)-4-Chloro-N-(4-(2-(piperidin-2-yl)ethyl)phenyl)benzamide;
(RS)-5-Ethoxy-N-(4-(2-(pyrrolidin-2-yl)ethyl)phenyl)picolinamide;
(RS)—N-(4-(2-(Piperidin-2-yl)ethyl)phenyl)-4-(trifluoromethyl)benzamide;
(RS)-3,4-Dichloro-N-(4-(2-(piperidin-2-yl)ethyl)phenyl)benzamide;
(RS)-4-Ethynyl-N-(4-(2-(piperidin-2-yl)ethyl)phenyl)benzamide;
(RS)—N-(4-(Piperidin-3-yl)phenyl)-6-(2,2,2-trifluoroethoxy)nicotinamide;
(RS)-5-Ethoxy-pyridine-2-carboxylic acid (4-piperidin-3-yl-phenyl)-amide;
(RS)-4-Methyl-N-(4-(pyrrolidin-3-yl)phenyl)benzamide;
(RS)-4-Methyl-N-(4-(piperidin-3-yl)phenyl)benzamide;
(RS)-4-Methoxy-N-(4-(piperidin-3-yl)phenyl)benzamide;
(RS)—N-(4-(Morpholin-2-yl)phenyl)benzamide;
(RS)-4-Methyl-N-(4-(morpholin-2-yl)phenyl)benzamide;
(RS)-4-Methoxy-N-(4-(morpholin-2-yl)phenyl)benzamide;
(RS)—N-(4-(Piperidin-3-yl)phenyl)-5-(2,2,2-trifluoroethoxy)picolinamide;
(RS)-4-(benzyloxy)-N-(4-(morpholin-2-yl)phenyl)benzamide;
(RS)-6-chloro-N-(4-(morpholin-2-yl)phenyl)nicotinamide;
(RS)-2-(4-(6-cyanonicotinamido)phenyl)morpholin-4-ium chloride;
(R)-4-Methyl-N-(4-(morpholin-2-yl)phenyl)benzamide;
(S)-4-Methyl-N-(4-(morpholin-2-yl)phenyl)benzamide;
(RS)-4-Ethoxy-N-(4-(morpholin-2-yl)phenyl)benzamide;
(RS)-4-Ethyl-N-(4-(morpholin-2-yl)phenyl)benzamide;
(R)-4-Chloro-3-methoxy-N-(4-(piperidin-3-yl)phenyl)benzamide;
(S)-4-Chloro-3-methoxy-N-(4-(piperidin-3-yl)phenyl)benzamide;
(R)-3-Chloro-4-methoxy-N-(4-(piperidin-3-yl)phenyl)benzamide;
(S)-3-Chloro-4-methoxy-N-(4-(piperidin-3-yl)phenyl)benzamide;
(R)—N-(4-(Pyrrolidin-3-yl)phenyl)-6-(2,2,2-trifluoroethoxy)nicotinamide;
(S)—N-(4-(Pyrrolidin-3-yl)phenyl)-6-(2,2,2-trifluoroethoxy)nicotinamide;
(RS)-4-(4-Chlorophenoxy)-N-(4-(morpholin-2-yl)phenyl)benzamide;
(R)-6-Chloro-N-(4-(morpholin-2-yl)phenyl)nicotinamide;
(S)-6-Chloro-N-(4-(morpholin-2-yl)phenyl)nicotinamide;
(RS)-3-chloro-N-(4-(morpholin-2-yl)phenyl)benzamide;
(RS)-5-chloro-N-(4-(morpholin-2-yl)phenyl)nicotinamide;
(RS)-Methyl 4-((4-(4-(morpholin-2-yl)phenylcarbamoyl)phenoxy)methyl)benzoate;
(RS)-Methyl 2-chloro-4-(4-(4-(morpholin-2-yl)phenylcarbamoyl)phenoxy)benzoate;
(RS)-4-Cyclopropylmethoxy-N-(4-morpholin-2-yl-phenyl)-benzamide;
(RS)-4-(Methylthio)-N-(4-(morpholin-2-yl)phenyl)benzamide;
(RS)-2-Chloro-N-(4-(morpholin-2-yl)phenyl)isonicotinamide;
(RS)-5,6-Dichloro-N-(4-(morpholin-2-yl)phenyl)nicotinamide;
(RS)-4-(2-Chloromethyl-3-hydroxy-2-methyl-propoxy)-N-(4-morpholin-2-yl-phenyl)-benzamide;
(RS)-2,6-Dichloro-N-(4-(morpholin-2-yl)phenyl)isonicotinamide;
(RS)—N-(4-(Morpholin-2-yl)phenyl)-6-(2,2,2-trifluoroethoxy)nicotinamide;
(R)—N-(4-(Piperidin-3-yl)phenyl)-6-(2,2,2-trifluoroethoxy)nicotinamide;
(S)—N-(4-(Piperidin-3-yl)phenyl)-6-(2,2,2-trifluoroethoxy)nicotinamide;
(S)-3-Chloro-4-methyl-N-(4-(piperidin-3-yl)phenyl)benzamide;
(S)-4-Chloro-3-methyl-N-(4-(piperidin-3-yl)phenyl)benzamide;
(S)-3,4-Dimethyl-N-(4-(piperidin-3-yl)phenyl)benzamide;
(R)-4-Chloro-2-fluoro-N-(4-(morpholin-2-yl)phenyl)benzamide;
(S)-4-Chloro-2-fluoro-N-(4-(morpholin-2-yl)phenyl)benzamide;
(RS)—N-(4-(Morpholin-2-yl)phenyl)-2-phenylthiazole-5-carboxamide;
(RS)—N-(4-(Morpholin-2-yl)phenyl)-2-phenylthiazole-4-carboxamide;
(S)—N-(4-(Piperidin-3-yl)phenyl)-3-(trifluoromethyl)benzamide;
(S)-4-(Methylthio)-N-(4-(piperidin-3-yl)phenyl)benzamide;
(S)-4-(Ethylthio)-N-(4-(piperidin-3-yl)phenyl)benzamide;
5-Chloro-pyrazine-2-carboxylic acid ((S)-4-piperidin-3-yl-phenyl)-amide;
5-Chloro-pyrazine-2-carboxylic acid ((R)-4-piperidin-3-yl-phenyl)-amide;
(S)—N-(4-(Piperidin-3-yl)phenyl)-6-(trifluoromethyl)nicotinamide;
(S)-6-Methyl-N-(4-(piperidin-3-yl)phenyl)nicotinamide;
(S)-6-(Methylthio)-N-(4-(piperidin-3-yl)phenyl)nicotinamide;
(RS)-6-Ethoxy-N-(4-(morpholin-2-yl)phenyl)nicotinamide;
(RS)—N-(4-(Morpholin-2-yl)phenyl)-2-phenyloxazole-4-carboxamide;
(S)—N-(4-(Piperidin-3-yl)phenyl)-5-(2,2,2-trifluoroethoxy)pyrazine-2-carboxamide;
(S)-5-Bromo-N-(4-(piperidin-3-yl)phenyl)pyrazine-2-carboxamide 2,2,2-trifluoroacetate;
(S)-6-Bromo-N-(4-(piperidin-3-yl)phenyl)nicotinamide 2,2,2-trifluoroacetate;
(S)-3-Methyl-N-(4-(piperidin-3-yl)phenyl)benzamide;
(S)-5-(Methylthio)-N-(4-(piperidin-3-yl)phenyl)pyrazine-2-carboxamide;
(S)-3-(Methylthio)-N-(4-(piperidin-3-yl)phenyl)benzamide;
(R)-3,4-Dimethyl-N-(4-(piperidin-3-yl)phenyl)benzamide;
(R)—N-(4-(Piperidin-3-yl)phenyl)-3-(trifluoromethyl)benzamide;
(R)-3-Chloro-N-(4-(morpholin-2-yl)phenyl)benzamide;
(S)-3-Chloro-N-(4-(morpholin-2-yl)phenyl)benzamide;
(R)—N-(4-(Piperidin-3-yl)phenyl)-6-(trifluoromethyl)nicotinamide;

(R)-4-(Methylthio)-N-(4-(morpholin-2-yl)phenyl)benzamide;
(S)-4-(Methylthio)-N-(4-(morpholin-2-yl)phenyl)benzamide;
(R)—N-(4-(Morpholin-2-yl)phenyl)-6-(2,2,2-trifluoroethoxy)nicotinamide;
(S)—N-(4-(Morpholin-2-yl)phenyl)-6-(2,2,2-trifluoroethoxy)nicotinamide;
(R)-2,6-Dichloro-N-(4-(morpholin-2-yl)phenyl)isonicotinamide;
(S)-2,6-Dichloro-N-(4-(morpholin-2-yl)phenyl)isonicotinamide;
(RS)-2-Chloro-6-methyl-N-(4-(morpholin-2-yl)phenyl)isonicotinamide;
(R)-4-Ethoxy-N-(4-(morpholin-2-yl)phenyl)benzamide;
(S)-4-Ethoxy-N-(4-(morpholin-2-yl)phenyl)benzamide;
(RS)-3-Methyl-N-(4-(morpholin-2-yl)phenyl)benzamide;
(RS)—N-(4-(Morpholin-2-yl)phenyl)-6-(pyrrolidin-1-yl)nicotinamide;
(RS)—N-(4-(Morpholin-2-yl)phenyl)-2-(trifluoromethyl)isonicotinamide;
(S)-2,6-Dichloro-N-(4-(piperidin-3-yl)phenyl)isonicotinamide;
(S)-2-Chloro-6-methyl-N-(4-(piperidin-3-yl)phenyl)isonicotinamide;
(R)—N-(4-(Morpholin-2-yl)phenyl)-6-(trifluoromethyl)nicotinamide;
(S)—N-(4-(Morpholin-2-yl)phenyl)-6-(trifluoromethyl)nicotinamide;
(R)-2-Chloro-6-methyl-N-(4-(morpholin-2-yl)phenyl)isonicotinamide;
(S)-2-Chloro-6-methyl-N-(4-(morpholin-2-yl)phenyl)isonicotinamide;
(RS)—N-(4-(Morpholin-2-yl)phenyl)-2-(pyrazin-2-yl)thiazole-4-carboxamide;
(S)—N-(4-(Piperidin-3-yl)phenyl)-6-propylnicotinamide;
(S)-6-Ethyl-N-(4-(piperidin-3-yl)phenyl)nicotinamide;
(RS)—N-(4-(Morpholin-2-yl)phenyl)-1-phenyl-1H-pyrazole-3-carboxamide;
(RS)-2-Ethoxy-N-(4-(morpholin-2-yl)phenyl)isonicotinamide;
(S)-4-Chloro-2-iodo-N-(4-(morpholin-2-yl)phenyl)benzamide;
(S)—N-(4-(1,4-Oxazepan-2-yl)phenyl)-3-chlorobenzamide;
3-Chloro-N-(4-((2S,6S)-6-methylmorpholin-2-yl)phenyl)benzamide;
(R)-4-Chloro-N-(4-(morpholin-2-yl)benzyl)benzamide;
(R)-6-Chloro-N-(4-(morpholin-2-yl)benzyl)nicotinamide;
3-Chloro-N-[4-((2S,5S)-5-methyl-morpholin-2-yl)-phenyl]-benzamide; and
3-Chloro-N-[4-((2S,5R)-5-methyl-morpholin-2-yl)-phenyl]-benzamide.

A further embodiment of the invention provides compounds, wherein X is —(CHR")$_q$—O—, for example
(RS)-(4-Pyrrolidin-3-yl-phenyl)-carbamic acid phenyl ester;
(RS)-(4-Pyrrolidin-3-yl-phenyl)-carbamic acid 4-fluorophenyl ester;
(RS)-(4-Pyrrolidin-3-yl-phenyl)-carbamic acid 4-chlorophenyl ester;
(RS)-(4-Pyrrolidin-3-yl-phenyl)-carbamic acid 2-(4-fluorophenyl)-ethyl ester;
(RS)-(4-Pyrrolidin-3-yl-phenyl)-carbamic acid 4-fluorobenzyl ester;
(RS)-(4-Pyrrolidin-3-yl-phenyl)-carbamic acid 2-(4-chlorophenyl)-ethyl ester;
(RS)-(4-Pyrrolidin-3-yl-phenyl)-carbamic acid 2-(3-chlorophenyl)-ethyl ester;
(RS)-(4-Pyrrolidin-3-yl-phenyl)-carbamic acid 2-(4-trifluoromethyl-phenyl)-ethyl ester;
(RS)-(4-Pyrrolidin-3-yl-phenyl)-carbamic acid 2-(3-trifluoromethyl-phenyl)-ethyl ester;
(RS)-(4-Pyrrolidin-3-yl-phenyl)-carbamic acid 2-(2,5-difluoro-phenyl)-ethyl ester;
(RS)-(4-Pyrrolidin-3-yl-phenyl)-carbamic acid 2-(4-trifluoromethoxy-phenyl)-ethyl ester;
(RS)-(4-Pyrrolidin-3-yl-phenyl)-carbamic acid 2-(3,4-dichloro-phenyl)-ethyl ester;
(RS)-(4-Pyrrolidin-3-yl-phenyl)-carbamic acid (RS)-1-(4-chloro-phenyl)-ethyl ester;
(RS)-(4-Pyrrolidin-3-yl-phenyl)-carbamic acid 3-(4-chlorophenyl)-propyl ester;
(RS)-(4-Pyrrolidin-3-yl-phenyl)-carbamic acid indan-2-yl ester;
(RS)-(4-Pyrrolidin-3-yl-phenyl)-carbamic acid (RS)-1-(4-chloro-phenyl)-2,2,2-trifluoro-ethyl ester; and
(S)-2,3-Dihydro-1H-inden-2-yl-4-(piperidin-3-yl)phenyl-carbamate 2,2,2-trifluoroacetate.

A further embodiment of the invention provides compounds, wherein X is —O(CHR")$_q$—, for example
(S)-2-(4-Chlorophenoxy)-N-(4-(piperidin-3-yl)phenyl)acetamide and
(S)-4-chlorobenzyl 4-(piperidin-3-yl)phenylcarbamate.

A further embodiment of the invention are compounds, wherein X is —CHR"—, for example
(RS)-2-(4-Chloro-phenyl)-N-(4-pyrrolidin-3-yl-phenyl)-acetamide;
(RS)—N—((RS)-4-Pyrrolidin-3-yl-phenyl)-2-(3-trifluoromethyl-phenyl)-propionamide; and
(RS)—N-(4-Pyrrolidin-3-yl-phenyl)-2-(3-trifluoromethoxyphenyl)-propionamide.

A further embodiment of the invention provides compounds, wherein X is —CH$_2$CH$_2$—, for example
(RS)-3-(2-Chloro-phenyl)-N-(4-pyrrolidin-3-yl-phenyl)-propionamide and
(RS)-3-(4-Chloro-phenyl)-N-(4-piperidin-3-yl-phenyl)-propionamide.

Compounds of formula

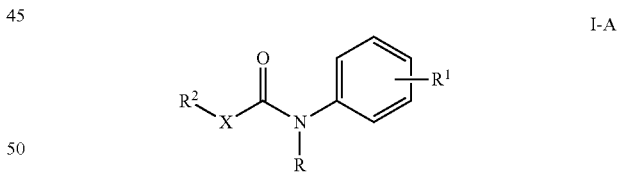

I-A wherein
R is hydrogen or lower alkyl;
$R^1$ is —(CH$_2$)$_n$—(O)$_o$-heterocycloalkyl, optionally substituted by lower alkyl, hydroxy, halogen, or by —(CH$_2$)$_p$-aryl;
n is 0, 1 or 2;
o is 0 or 1;
p is 0, 1 or 2;
$R^2$ is cycloalkyl, heterocycloalkyl, or is aryl or heteroaryl, wherein the aromatic rings are optionally substituted by one or two substituents, selected from lower alkyl, halogen, heteroaryl, CF$_3$, OCF$_3$, OCH$_2$CF$_3$, lower alkoxy, CH$_2$-lower alkoxy, lower alkynyl or cyano;
X is a bond, —NR'—, —CH$_2$NH—, —CHR"—, —(CH$_2$)$_q$—O— or —(CH$_2$)$_2$—;

R' is hydrogen or lower alkyl,
R" is hydrogen, lower alkyl, lower alkoxy,
q is 0, 1 or 2;
or a pharmaceutically suitable acid addition salt thereof are further an embodiment of the invention.

The present compounds of formula I and their pharmaceutically acceptable salts can be prepared by methods known in the art, for example, by processes described below, which process comprises a) cleaving off the N-protecting group from compounds of formula

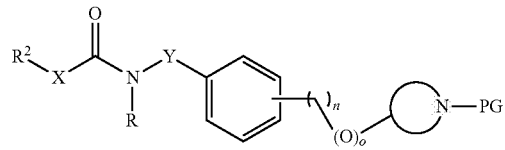

to obtain a compound of formula

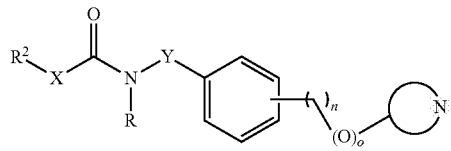

wherein

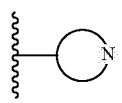

is a heterocyclic group selected from piperazinyl, piperidinyl, morpholinyl, pyrrolidinyl or thiomorpholinyl, PG is a N-protecting group selected from —C(O)O-tert-butyl and if desired, converting the compounds obtained into pharmaceutically acceptable acid addition salts, or b) reacting a compound of formula

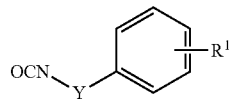

with a compound of formula

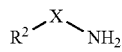

to obtain a compound of formula

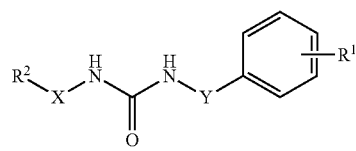

wherein X is a bond or —CH$_2$— and the other definitions are as described above, or if desired, converting the compounds obtained into pharmaceutically acceptable acid addition salts or c) reacting a compound of formula

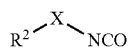

with a compound of formula

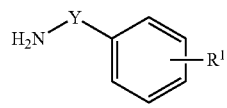

to obtain a compound of formula

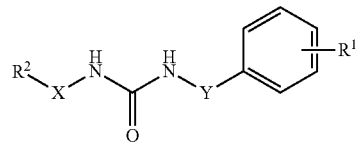

wherein the definitions are as described above, and if desired, converting the compounds obtained into pharmaceutically acceptable acid addition salts.

The preparation of compounds of formula I of the present invention can be carried out in sequential or convergent synthetic routes. Syntheses of the compounds of the invention are shown in the following schemes 1-17 and in the description of 323 specific examples. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in schemes 1 to 17, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

General Procedure

Scheme 1

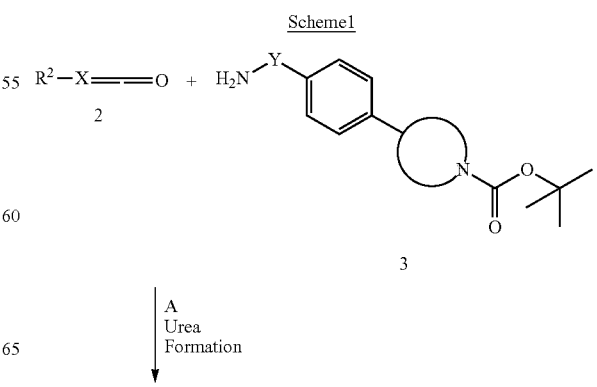

A
Urea Formation

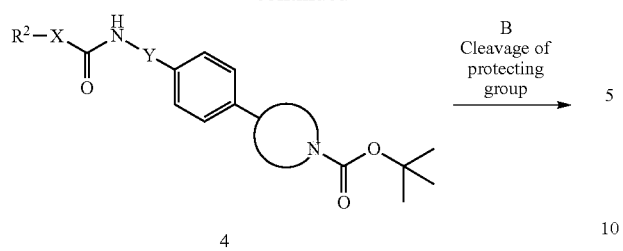

The substituents are as described above and X is N or —CH₂NH—.

Step A: Urea formation can be accomplished by a coupling reaction between an amine 3 and alkyl or aryl isocyanate compounds 2 in halogenated solvents such as dichloromethane or 1,2-dichloroethane or ethereal solvents such as diethyl ether, dioxane, THF, DME or TBME, optionally in the presence of a base such as triethylamine or N,N-diisopropylethylamine. Examples of appropriate amines 3 include N-protected pyrrolidine derivatives such as 3-a [CAS 908334-28-1] and 3-f [CAS 889947-54-0], piperidine derivatives such as 3-b [CAS 875798-79-1], 3-c [CAS 170011-57-1] and 3-g [CAS 908334-26-9], piperazine derivatives such as 3-d [CAS 170911-92-9] and morpholine derivatives such as 3-e [CAS 1002726-96-6]. Preferred conditions are in dichloromethane at room temperature for 3 hours.

Step B: Removal of the BOC N-protecting group can be effected with mineral acids such as HCl, $H_2SO_4$ or $H_3PO_4$ or organic acids such as $CF_3COOH$, $CHCl_2COOH$, HOAc or p-toluenesulfonic acid in solvents such as $CH_2Cl_2$, $CHCl_3$, THF, MeOH, EtOH or $H_2O$ at 0 to 80° C. Preferred conditions are 4N HCl in dioxane and THF at 60° C. overnight.

Scheme 2

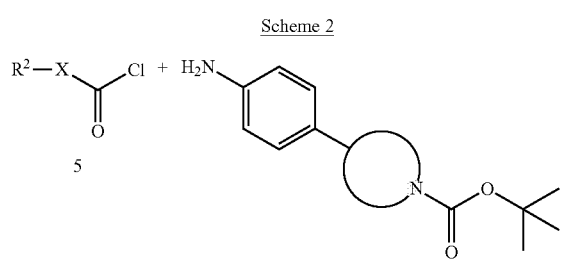

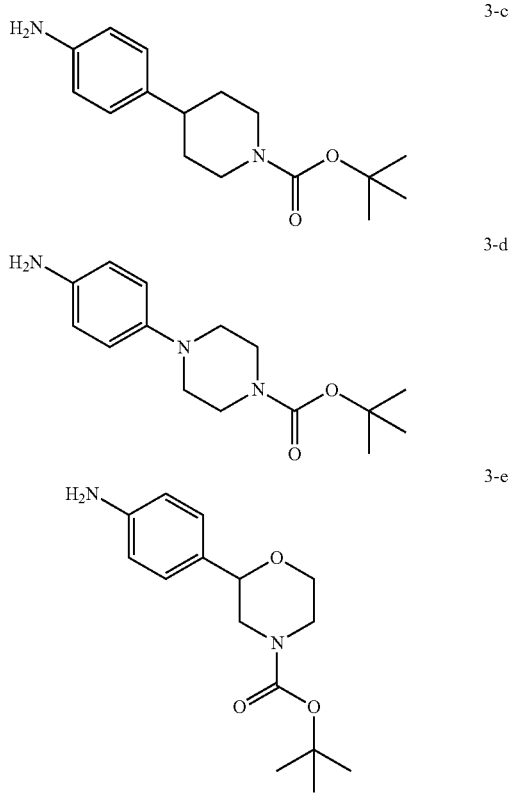

for example using:

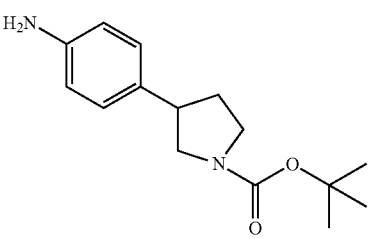

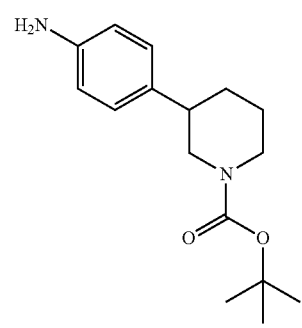

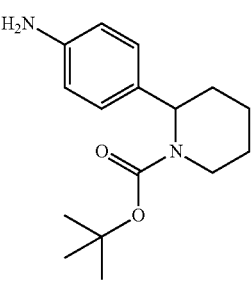

The substituents are as described above and X is a —O— or —CH₂O—.

Step A: Carbamate formation can be accomplished by a coupling reaction between an amine 3 and alkyl or aryl chloroformate compounds 5 in halogenated solvents such as dichloromethane or 1,2-dichloroethane or ethereal solvents such as diethyl ether, dioxane, THF, DME or TBME in the presence of a base such as triethylamine or N,N-diisopropylethylamine. Examples of appropriate amines 3 include N-protected pyrrolidine derivatives such as 3-a [CAS 908334-28-1] and 3-f [CAS 889947-54-0], piperidine derivatives such as 3-b [CAS 875798-79-1], 3-c [CAS 170011-57-1] and 3-g [CAS 908334-26-9], piperazine derivatives such as 3-d [CAS 170911-92-9] and morpholine derivatives such as 3-e [CAS 1002726-96-6]. Preferred conditions are triethylamine in THF at room temperature for 18 hours.

Step B: Removal of the BOC N-protecting group can be effected with mineral acids such as HCl, $H_2SO_4$ or $H_3PO_4$ or organic acids such as $CF_3COOH$, $CHCl_2COOH$, HOAc or p-toluenesulfonic acid in solvents such as $CH_2Cl_2$, $CHCl_3$, THF, MeOH, EtOH or $H_2O$ at 0 to 80° C. Preferred conditions are 4N HCl in dioxane and THF at 60° C. overnight.

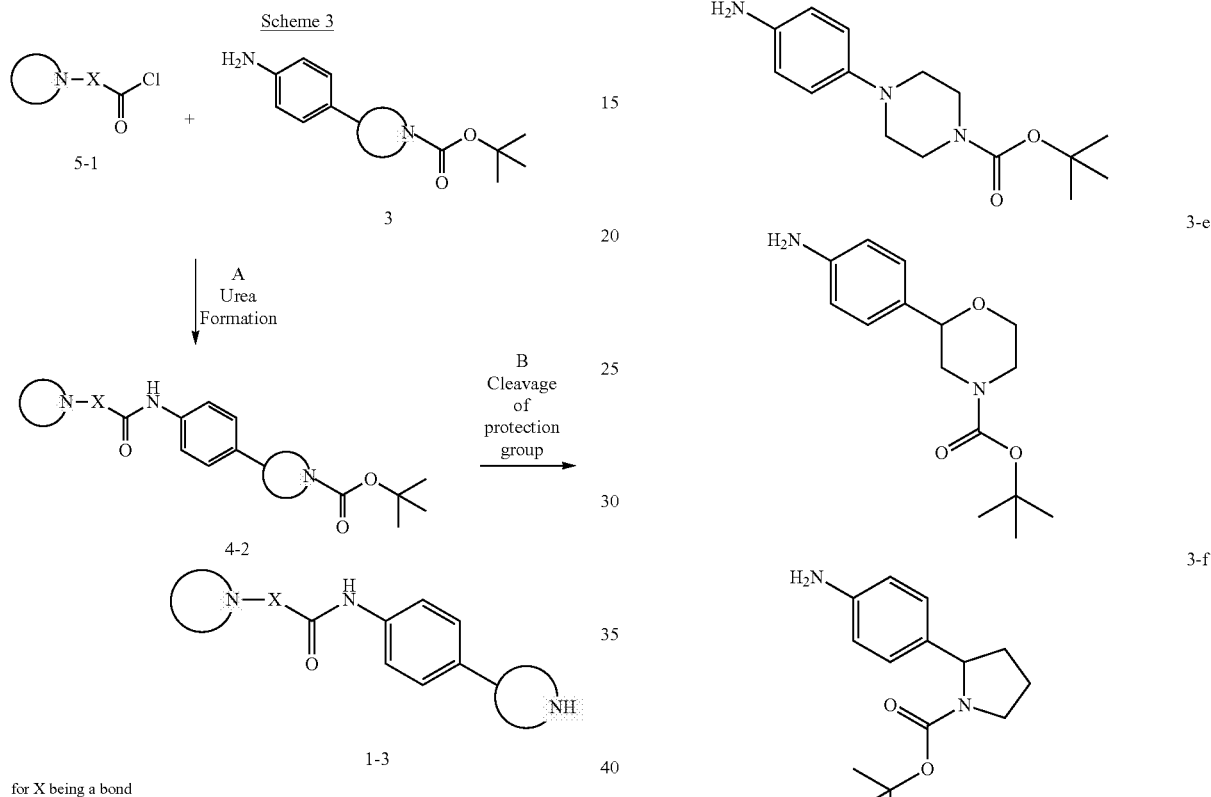

for X being a bond for example using:

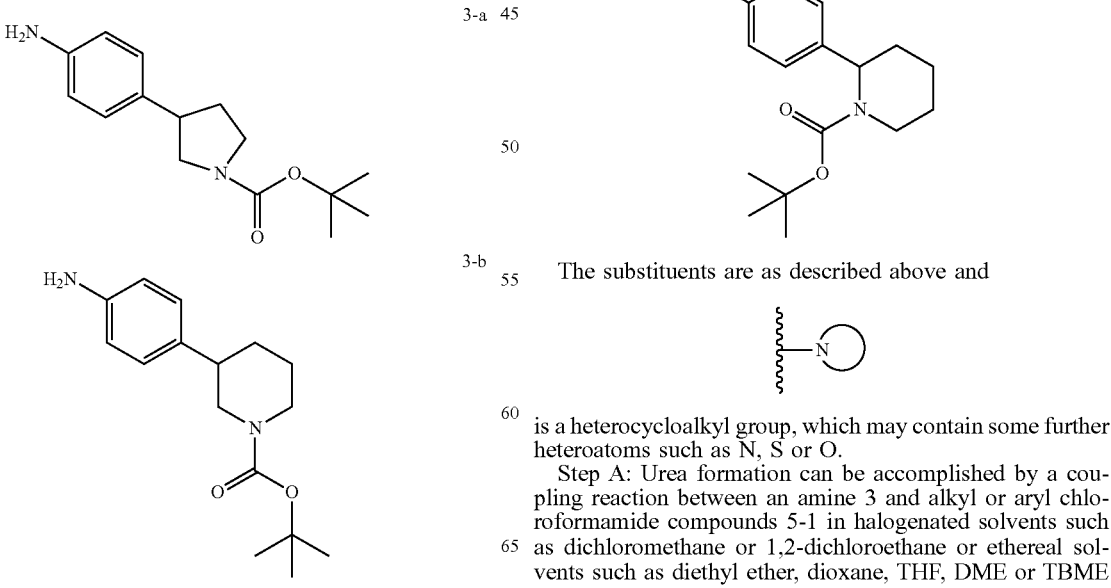

The substituents are as described above and is a heterocycloalkyl group, which may contain some further heteroatoms such as N, S or O.

Step A: Urea formation can be accomplished by a coupling reaction between an amine 3 and alkyl or aryl chloroformamide compounds 5-1 in halogenated solvents such as dichloromethane or 1,2-dichloroethane or ethereal solvents such as diethyl ether, dioxane, THF, DME or TBME in the presence of an organic base such as triethylamine or N,N-diisopropylethylamine. Examples of appropriate amines 3 include N-protected pyrrolidine derivatives such as 3-a [CAS 908334-28-1] and 3-f [CAS 889947-54-0], piperidine derivatives such as 3-b [CAS 875798-79-1], 3-c [CAS 170011-57-1] and 3-g [CAS 908334-26-9], piperazine derivatives such as 3-d [CAS 170911-92-9] and morpholine derivatives such as 3-e [CAS 1002726-96-6]. Preferred conditions are triethylamine in THF at room temperature for 18 hours.

Step B: Removal of the BOC N-protecting group can be effected with mineral acids such as HCl, $H_2SO_4$ or $H_3PO_4$ or organic acids such as $CF_3COOH$, $CHCl_2COOH$, HOAc or p-toluenesulfonic acid in solvents such as $CH_2Cl_2$, $CHCl_3$, THF, MeOH, EtOH or $H_2O$ at 0 to 80° C. Preferred conditions are 4N HCl in dioxane and THF at 60° C. overnight.

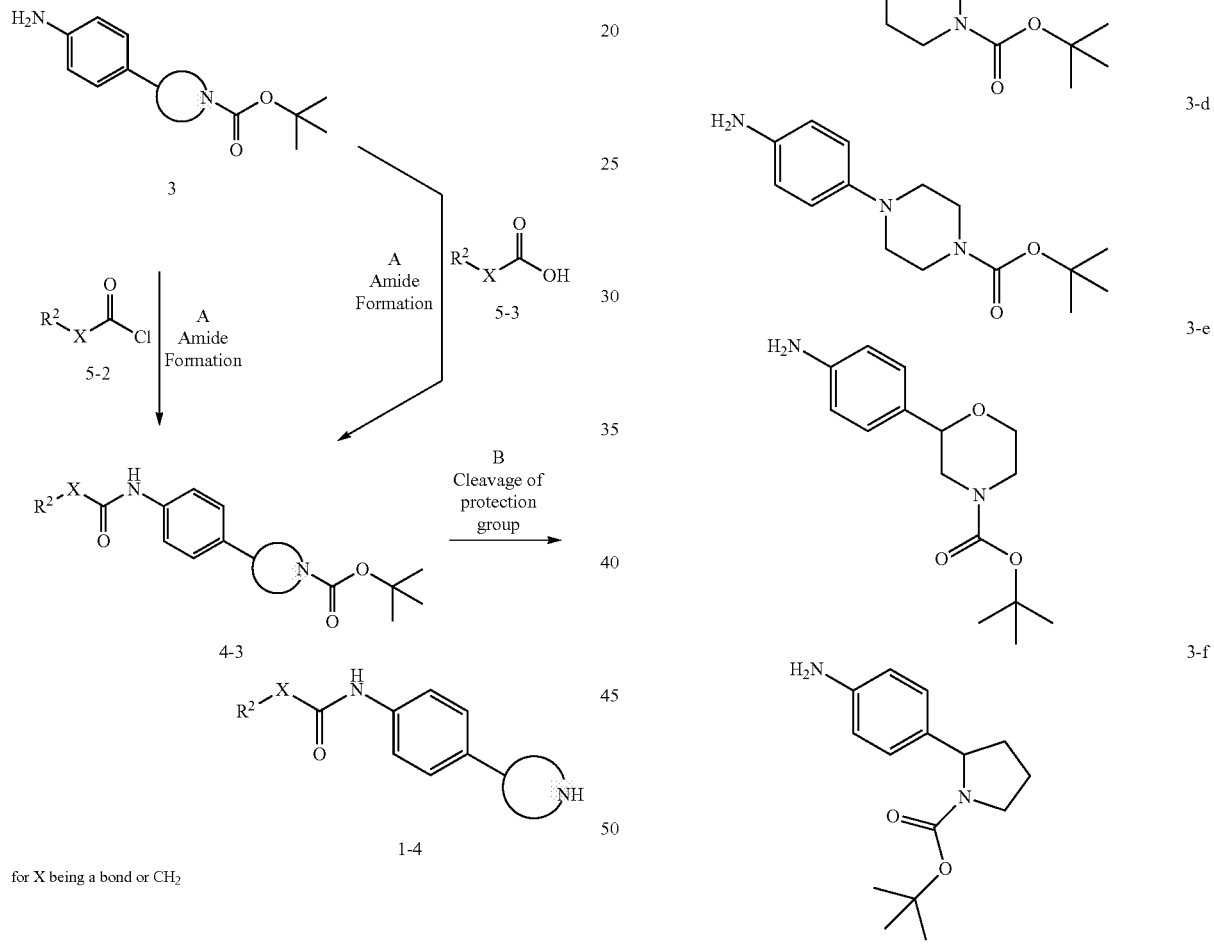

for X being a bond or $CH_2$ for example using:

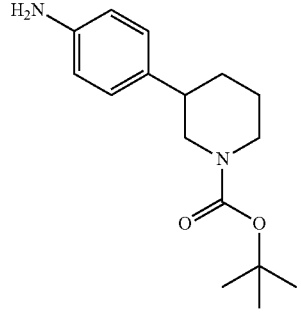
3-a

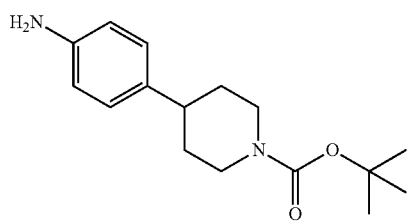
3-b

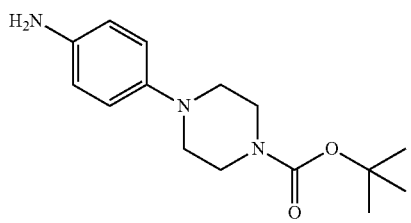
3-c

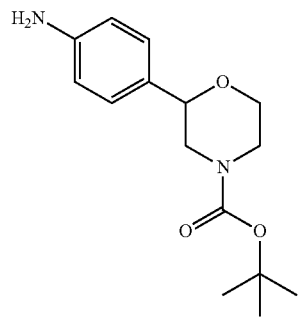
3-d

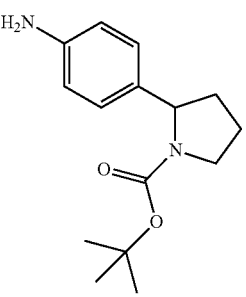
3-e

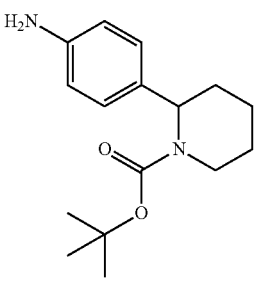
3-f 3-g

The substituents are as described above and X is a bond or —CH$_2$—.

Step A: Amide formation can be accomplished by a coupling reaction between an amine 3 and alkyl or aryl acid chloride compounds 5-2 in halogenated solvents such as dichloromethane or 1,2-dichloroethane or ethereal solvents such as diethyl ether, dioxane, THF, DME or TBME, in the presence of an organic base such as triethylamine or N,N-diisopropylethylamine. Examples of appropriate amines 3 include N-protected pyrrolidine derivatives such as 3-a [CAS 908334-28-1] and 3-f [CAS 889947-54-0], piperidine derivatives such as 3-b [CAS 875798-79-1], 3-c [CAS 170011-57-1] and 3-g [CAS 908334-26-9], piperazine derivatives such as 3-d [CAS 170911-92-9] and morpholine derivatives such as 3-e [CAS 1002726-96-6]. Preferred conditions are triethylamine in THF at room temperature for 18 hours.

Alternatively, amide formation can be accomplished by a coupling reaction between an amine 3 and carboxylic acids 5-3 in the presence of a coupling reagent such as DCC, EDC, TBTU or HATU in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF, DME or TBME. Preferred conditions are TBTU with N-methylmorpholine in THF at 50° C. for 18 hours.

Step B: Removal of the BOC N-protecting group can be effected with mineral acids such as HCl, H$_2$SO$_4$ or H$_3$PO$_4$ or organic acids such as CF$_3$COOH, CHCl$_2$COOH, HOAc or p-toluenesulfonic acid in solvents such as CH$_2$Cl$_2$, CHCl$_3$, THF, MeOH, EtOH or H$_2$O at 0 to 80° C. Preferred conditions are 4N HCl in dioxane and THF at 60° C. overnight.

for example using:

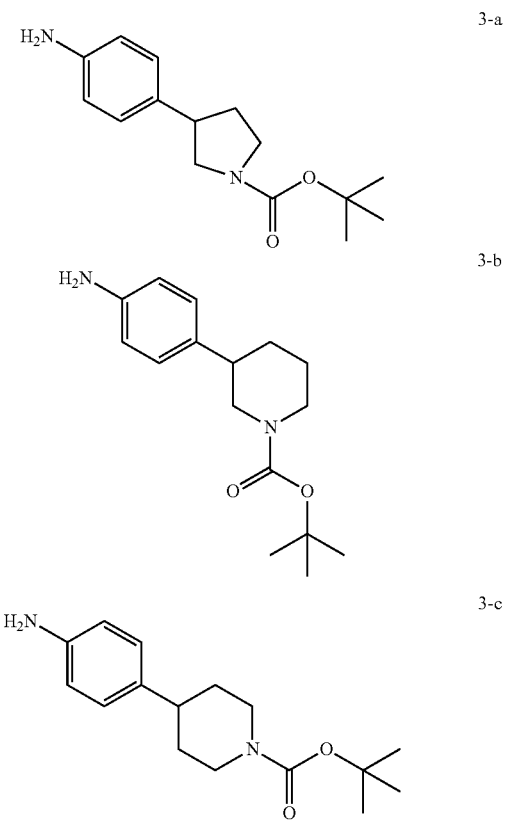

Scheme 5

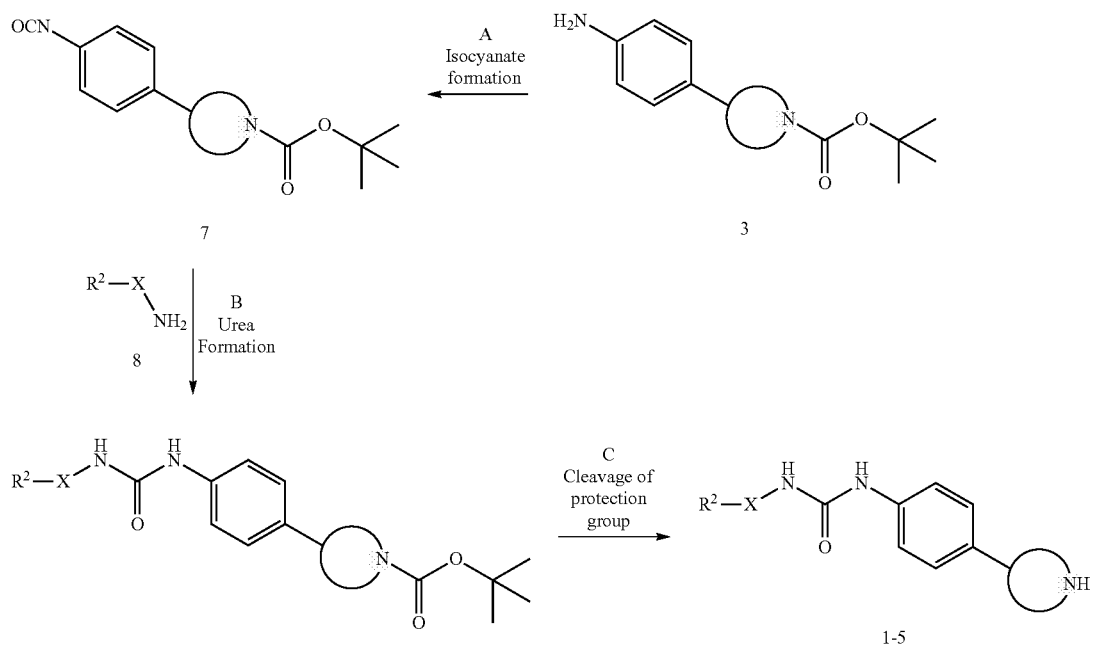

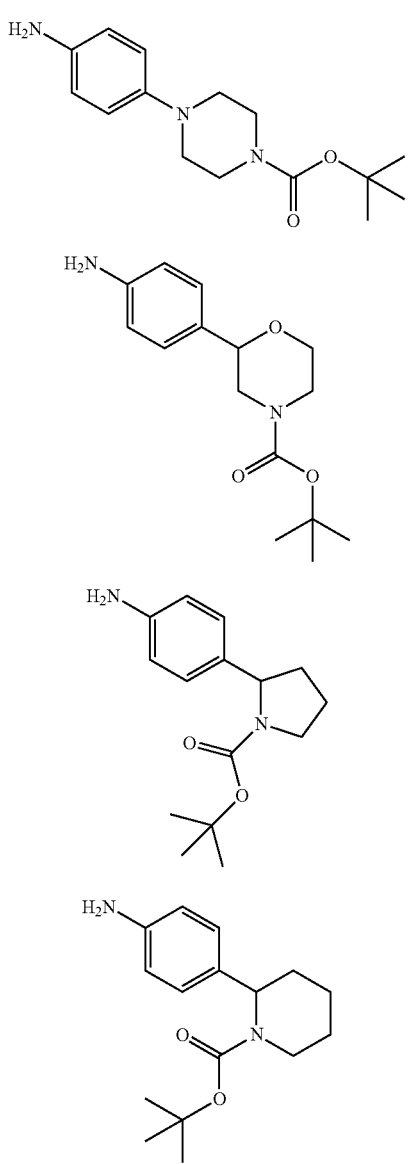

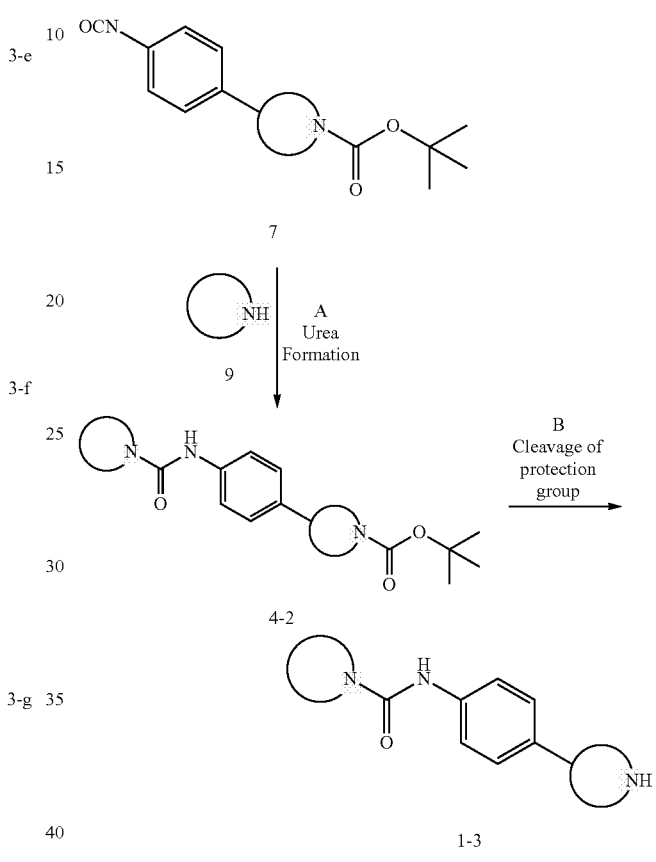

Scheme 6

4-2

1-3 for X being a bond for example using:

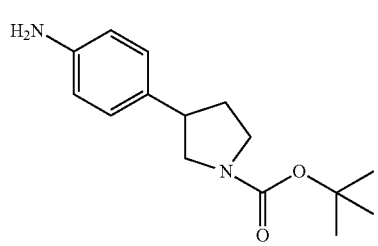

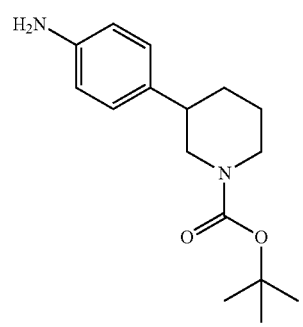

The substituents are as described above and X is a bond, —CHR' or —(CH$_2$)$_2$—.

Step A: Isocyanate formation can be accomplished by treatment of an amine 3 with triphosgen, diphosgen or phosgen in halogenated solvents such as dichloromethane or 1,2-dichloroethane in the presence of a base such as triethylamine or N,N-diisopropylethylamine. Examples of appropriate amines 3 include N-protected pyrrolidine derivatives such as 3-a [CAS 908334-28-1] and 3-f [CAS 889947-54-0], piperidine derivatives such as 3-b [CAS 875798-79-1], 3-c [CAS 170011-57-1] and 3-g [CAS 908334-26-9], piperazine derivatives such as 3-d [CAS 170911-92-9] and morpholine derivatives such as 3-e [CAS 1002726-96-6]. Preferred conditions are triphosgen and triethylamine in dichloromethane at 45° C. for 18 hours.

Step B: Urea formation can be accomplished by a coupling reaction between an isocyanate compound 7 and an amine 8 in halogenated solvents such as dichloromethane or 1,2-dichloroethane or ethereal solvents such as diethyl ether, dioxane, THF, DME or TBME, optionally in the presence of a base such as triethylamine or N,N-diisopropylethylamine. Preferred conditions are in dichloromethane at room temperature for 3 hours.

Step C: Removal of the BOC N-protecting group can be effected with mineral acids such as HCl, H$_2$SO$_4$ or H$_3$PO$_4$ or organic acids such as CF$_3$COOH, CHCl$_2$COOH, HOAc or p-toluenesulfonic acid in solvents such as CH$_2$Cl$_2$, CHCl$_3$, THF, MeOH, EtOH or H$_2$O at 0 to 80° C. Preferred conditions are 4N HCl in dioxane and THF at 60° C. overnight.

-continued

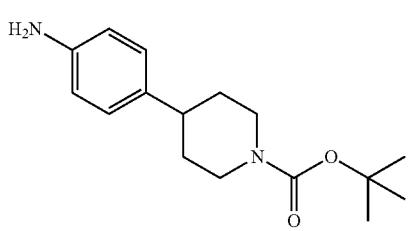
3-c

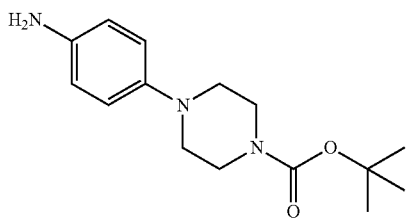
3-d

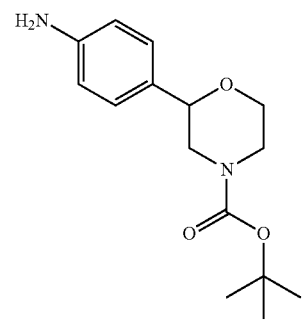
3-e

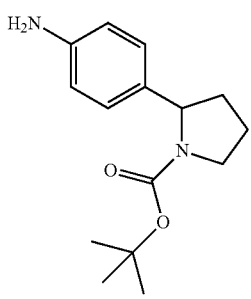
3-f

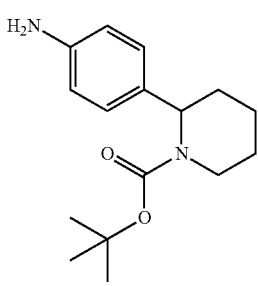
3-g

The substituents are as described above.

Step A: Urea formation can be accomplished by a coupling reaction between an isocyanate compound 7 (see scheme 5) and an amine 9 in halogenated solvents such as dichloromethane or 1,2-dichloroethane or ethereal solvents such as diethyl ether, dioxane, THF, DME or TBME, optionally in the presence of a base such as triethylamine or N,N-diisopropylethylamine. Preferred conditions are in dichloromethane at room temperature for 3 hours.

Step B: Removal of the BOC N-protecting group can be effected with mineral acids such as HCl, $H_2SO_4$ or $H_3PO_4$ or organic acids such as $CF_3COOH$, $CHCl_2COOH$, HOAc or p-toluenesulfonic acid in solvents such as $CH_2Cl_2$, $CHCl_3$, THF, MeOH, EtOH or $H_2O$ at 0 to 80° C. Preferred conditions are 4N HCl in dioxane and THF at 60° C. overnight.

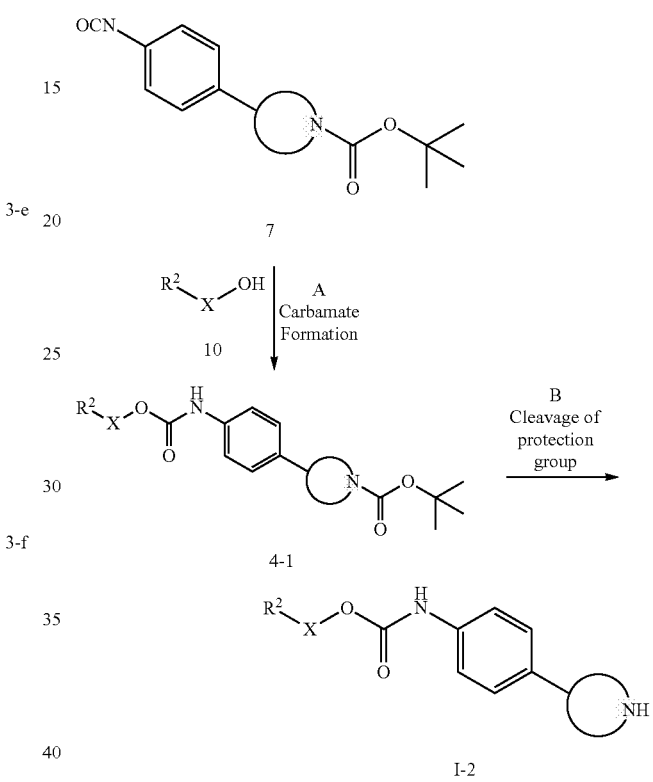

The substituents are as described above and X is a bond or —$CH_2$—.

Step A: Carbamate formation can be accomplished by a coupling reaction between an isocyanate compound 7 (see scheme 5) and an alcohol 10 in halogenated solvents such as dichloromethane or 1,2-dichloroethane or ethereal solvents such as diethyl ether, dioxane, THF, DME or TBME, optionally in the presence of a base such as triethylamine or N,N-diisopropylethylamine. Preferred conditions are N,N-diisopropylethylamine in THF at 110° C. for 18 hours.

Step B: Removal of the BOC N-protecting group can be effected with mineral acids such as HCl, $H_2SO_4$ or $H_3PO_4$ or organic acids such as $CF_3COOH$, $CHCl_2COOH$, HOAc or p-toluenesulfonic acid in solvents such as $CH_2Cl_2$, $CHCl_3$, THF, MeOH, EtOH or $H_2O$ at 0 to 80° C. Preferred conditions are 4N HCl in dioxane and THF at 60° C. overnight.

Scheme 8

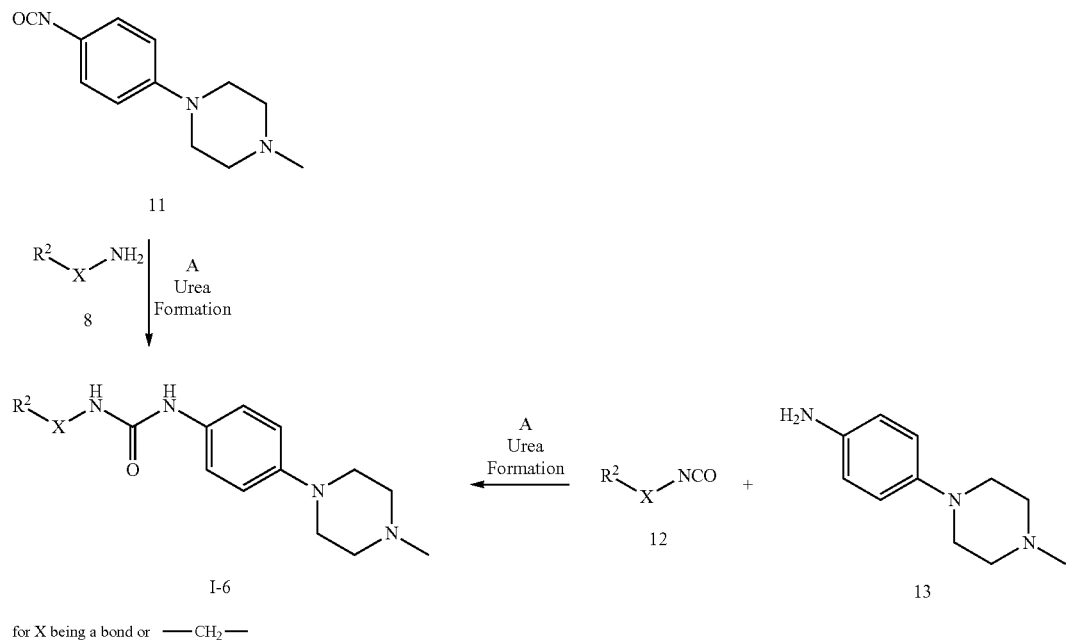

for X being a bond or —CH₂—

The substituents are as described above and X is a bond or —CH₂—.

Step A: Urea formation can be accomplished by a coupling reaction between isocynate 11 (CAS 879896-39-6) and alkyl or aryl amine 8 in halogenated solvents such as dichloromethane or 1,2-dichloroethane or ethereal solvents such as diethyl ether, dioxane, THF, DME or TBME, or polar organic solvents such as DMF, optionally in the presence of a base such as triethylamine or N,N-diisopropylethylamine. Preferred conditions are in DMF at room temperature for 18 hours.

Alternatively, urea formation can be accomplished by a coupling reaction between amine 13 (CAS 16153-81-4) and alkyl or aryl isocyanate compounds 12 in halogenated solvents such as dichloromethane or 1,2-dichloroethane or ethereal solvents such as diethyl ether, dioxane, THF, DME or TBME, or polar organic solvents such as DMF, optionally in the presence of a base such as triethylamine or N,N-diisopropylethylamine.

Preferred conditions are in DMF at room temperature for 2 hours.

Scheme 9

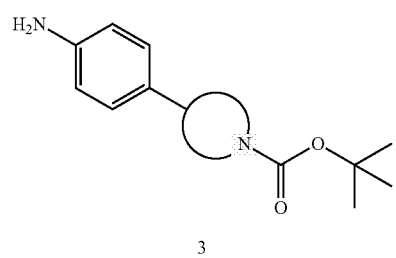

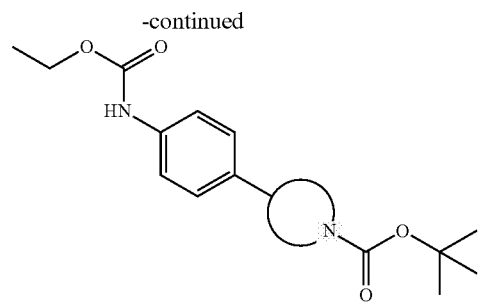

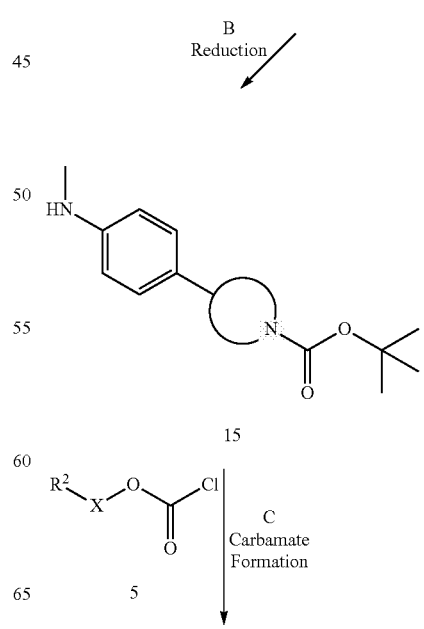

-continued

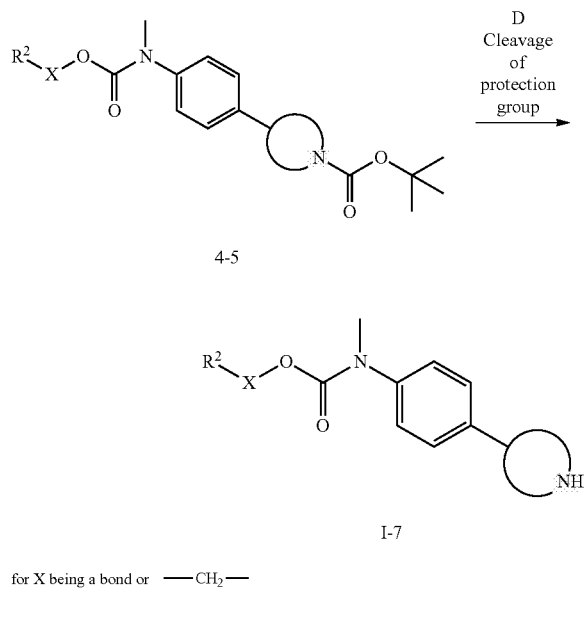

4-5 for X being a bond or —CH₂— for example using:

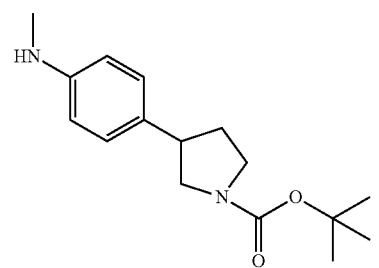

3-a

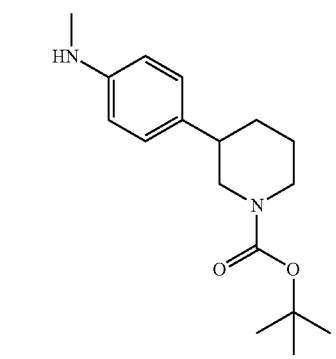

3-b

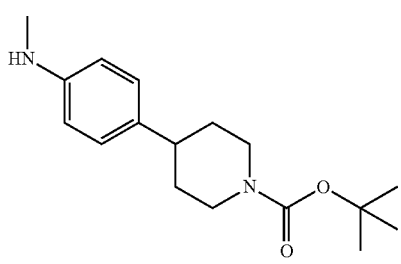

3-c

-continued

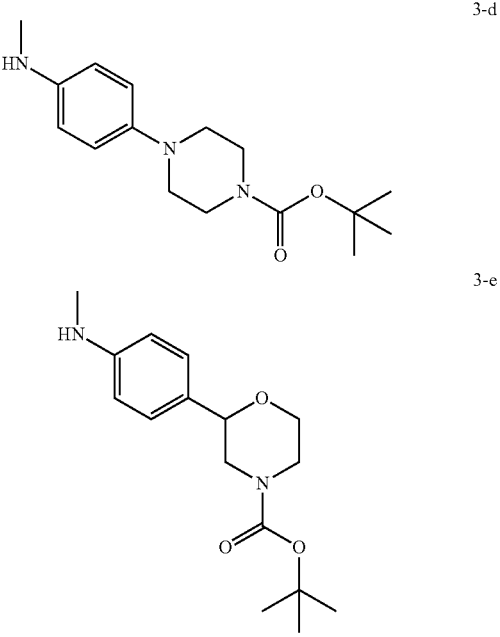

The substituents are as described above and X is a bond or —CH₂—.

Step A: Carbamate formation can be accomplished by treatment of an amine 3 with ethyl chloroformate in halogenated solvents such as dichloromethane or 1,2-dichloroethane or ethereal solvents such as diethyl ether, dioxane, THF, DME or TBME in the presence of a base such as triethylamine or N,N-diisopropylethylamine. Examples of appropriate amines 3 include N-protected pyrrolidine derivatives such as 3-a [CAS 908334-28-1], piperidine derivatives such as 3-b [CAS 875798-79-1] and 3-c [CAS 170011-57-1], piperazine derivatives such as 3-d [CAS 170911-92-9] and morpholine derivatives such as 3-e [CAS 1002726-96-6]. Preferred conditions are triethylamine in THF at room temperature for 18 hours.

Step B: Reduction can be accomplished by treatment of carbamate 14 with an aluminium hydride reducing agent such as Red-Al in an ethereal solvent such as THF or dioxane at temperatures between room temperature and the reflux temperature of the solvent. Preferred conditions are THF at room temperature for 5 hours and then at 50° C. for 15 minutes.

Step C: Carbamate formation can be accomplished by a coupling reaction between an amine 15 and alkyl or aryl chloroformate compounds 5 in halogenated solvents such as dichloromethane or 1,2-dichloroethane or ethereal solvents such as diethyl ether, dioxane, THF, DME or TBME in the presence of a base such as triethylamine or N,N-diisopropylethylamine. Preferred conditions are triethylamine in THF at room temperature for 18 hours.

Step D: Removal of the BOC N-protecting group can be effected with mineral acids such as HCl, $H_2SO_4$ or $H_3PO_4$ or organic acids such as $CF_3COOH$, $CHCl_2COOH$, HOAc or p-toluenesulfonic acid in solvents such as $CH_2Cl_2$, $CHCl_3$, THF, MeOH, EtOH or $H_2O$ at 0 to 80° C. Preferred conditions are 4N HCl in dioxane and THF at 60° C. overnight.

Scheme 10

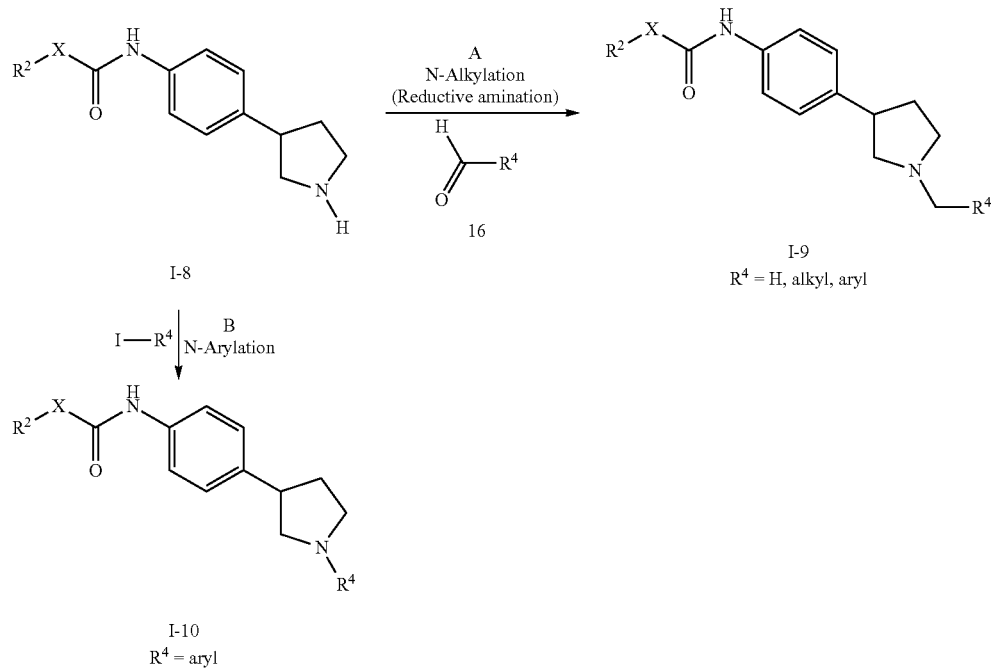

The substituents are as described above and X is a bond, —NR'—, —CH$_2$NH—, —CHR"—, —(CH$_2$)$_q$—O— or —(CH$_2$)$_2$—;

Step A: N-alkylation can be accomplished by a reduction amination reaction involving treatment of amine compounds I-8 with an aldehyde such as formaldehyde, acetaldehyde, benzaldehyde or phenylacetaldehyde in the presence of a Bronsted or Lewis acid so as to form the corresponding imine compound, with in situ treatment with a reducing agent such as sodium triacetoxyborohydride or sodium cyanoborohydride. Preferred conditions when using aqueous formaldehyde solution are zinc chloride, sodium acetate and sodium cyanoborohydride in methanol at 50° C. overnight. Preferred conditions when using acetaldehyde, benzaldehyde or phenylacetaldehyde are acetic acid, sodium acetate and sodium triacetoxyborohydride in 1,2-dichloroethane at 50° C. overnight.

Step B: N-arylation can be accomplished by treatment of amine compounds I-8 with aryl iodides in the presence of a metal catalyst, for instance using a copper-mediated Ullmann reaction or a palladium-catalysed Buchwald-Hartwig reaction. Preferred conditions are catalytic ferric oxide, catalytic L-proline and sodium tert-butoxide in DMSO at 135° C. overnight according to the procedure of Guo et al. (*Org. Lett.* 2008, 10, 4513-4516).

Scheme 11

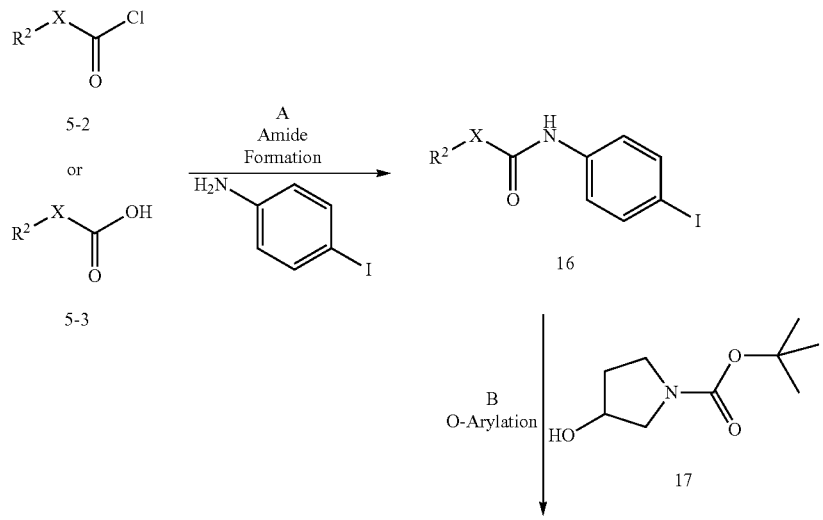

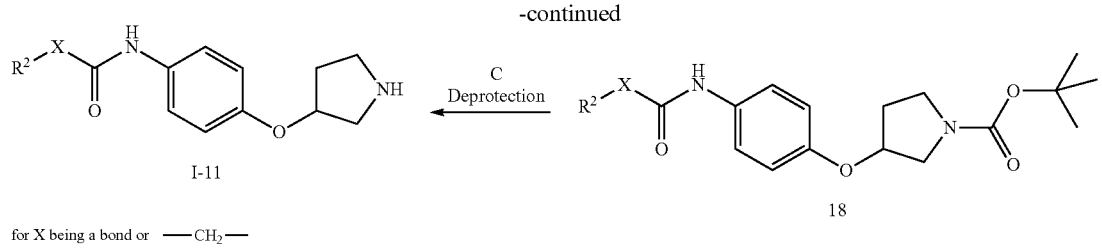

for X being a bond or —CH$_2$—

The substituents are as described above and X is a bond or —CH$_2$—.

Step A: Amide formation can be accomplished by a coupling reaction between aryl amine and an alkyl or aryl acid chloride 5-2 in halogenated solvents such as dichloromethane or 1,2-dichloroethane or ethereal solvents such as diethyl ether, dioxane, THF, DME or TBME, in the presence of an organic base such as triethylamine or N,N-diisopropylethylamine. Preferred conditions are triethylamine in THF at room temperature for 4 hours.

Alternatively, amide formation can be accomplished by a coupling reaction between aryl amine and carboxylic acids 5-3 in the presence of a coupling reagent such as DCC, EDC, TBTU or HATU in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF, DME or TBME. Preferred conditions are TBTU with N-methylmorpholine in THF at 50° C. for 18 hours.

Step B: O-arylation can be accomplished by treatment of aryl iodides 16 with hydroxypyrrolidine derivative 17 (CAS 103057-44-9) in the presence of a metal catalyst, for instance using a copper-mediated Ullmann reaction or a palladium-catalysed Buchwald-Hartwig reaction. Preferred conditions are catalytic copper(I) iodide, catalytic 1,10-phenanthroline and caesium carbonate in the absence of additional solvent at 130° C. overnight according to the procedure of Buchwald and co-workers (*Org. Lett.* 2002, 4, 973-976).

Step C: Removal of the BOC N-protecting group can be effected with mineral acids such as HCl, H$_2$SO$_4$ or H$_3$PO$_4$ or organic acids such as CF$_3$COOH, CHCl$_2$COOH, HOAc or p-toluenesulfonic acid in solvents such as CH$_2$Cl$_2$, CHCl$_3$, THF, MeOH, EtOH or H$_2$O at 0 to 80° C. Preferred conditions are 4N HCl in dioxane and THF at 60° C. overnight.

Scheme 12

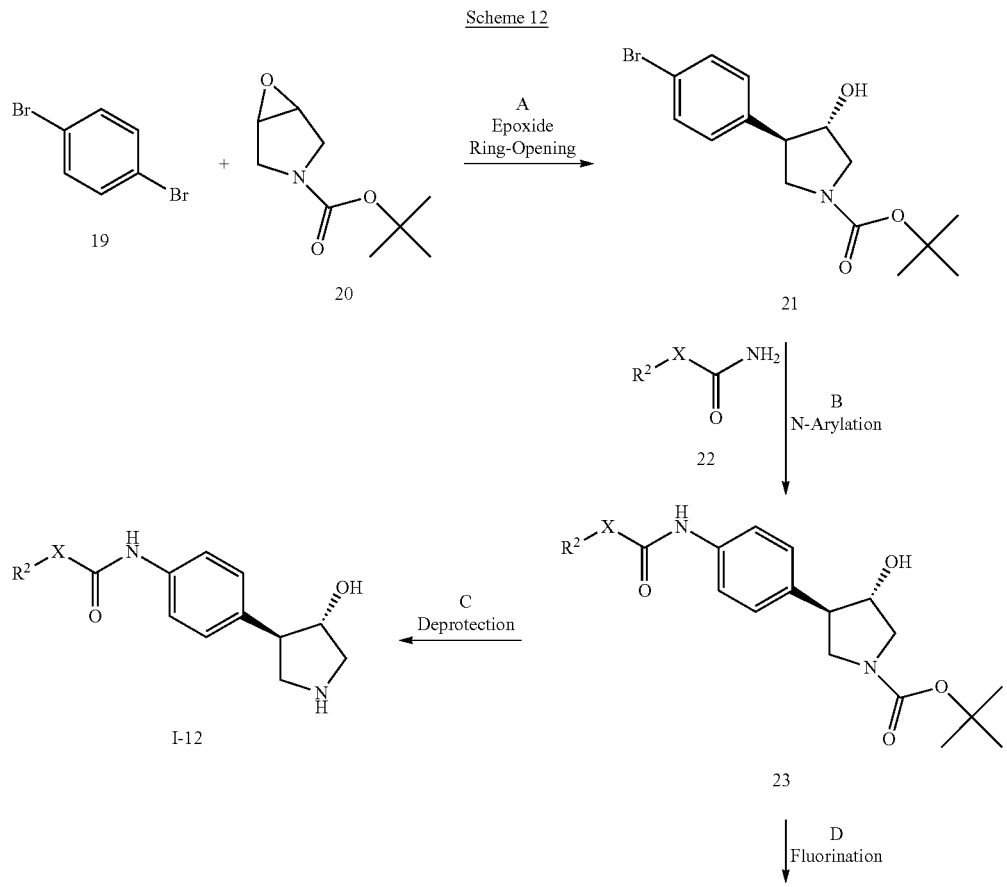

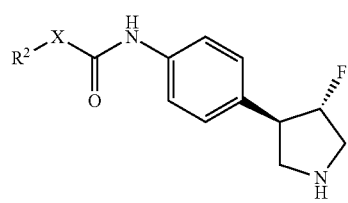

I-13

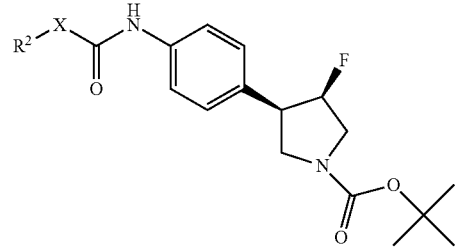

24 for X being a bond or —CH₂—

The substituents are as described above and X is a bond or —CH₂—.

Step A: Hydroxy pyrrolidine derivative 21 can be prepared by addition of 4-bromo-phenyllithium to epoxide 20 (CAS 114214-49-2) in the presence of a Lewis acid such as boron trifluoride etherate, whereby 4-bromo-phenyllithium can be first prepared in situ by treatment of 1,4-dibromobenzene 19 with a stoichiometric equivalent of n-butyllithium. The reaction can be carried out in ethereal organic solvents such as diethyl ether or THF, preferably at low temperature. Preferred conditions are THF at −78° C. for 30 min for 4-bromo-phenyllithium generation and then −78° C. for 2 hours for the epoxide-opening reaction.

Step B: N-arylation can be accomplished by treatment of aryl bromide 21 with amide compounds 22 in the presence of a metal catalyst, for instance using a copper-mediated Ullmann reaction or a palladium-catalysed Buchwald-Hartwig reaction. Preferred conditions are catalytic copper (I) iodide, catalytic N,N' dimethylethylenediamine and caesium carbonate in dioxane at 120° C. overnight according to the procedure of Buchwald and co-workers (*Org. Lett.* 2007, 9, 4749-4751).

Step C: Removal of the BOC N-protecting group can be effected with mineral acids such as HCl, H₂SO₄ or H₃PO₄ or organic acids such as CF₃COOH, CHCl₂COOH, HOAc or p-toluenesulfonic acid in solvents such as CH₂Cl₂, CHCl₃, THF, MeOH, EtOH or H₂O at 0 to 80° C. Preferred conditions are 4N HCl in dioxane and THF at 60° C. overnight.

Step D: Fluorination of alcohol 23 can be accomplished by treatment with a fluorinating reagent such as diethylaminosulphur trifluoride (DAST) in a non-protic organic solvent. Preferred conditions are DAST in a mixture of acetonitrile and 1,2-dichloroethane at a temperature between 0° C. and room temperature for 1 hour.

Step E: Removal of the BOC N-protecting group can be effected with mineral acids such as HCl, H₂SO₄ or H₃PO₄ or organic acids such as CF₃COOH, CHCl₂COOH, HOAc or p-toluenesulfonic acid in solvents such as CH₂Cl₂, CHCl₃, THF, MeOH, EtOH or H₂O at 0 to 80° C. Preferred conditions are 4N HCl in dioxane and THF at 60° C. overnight.

Scheme 13

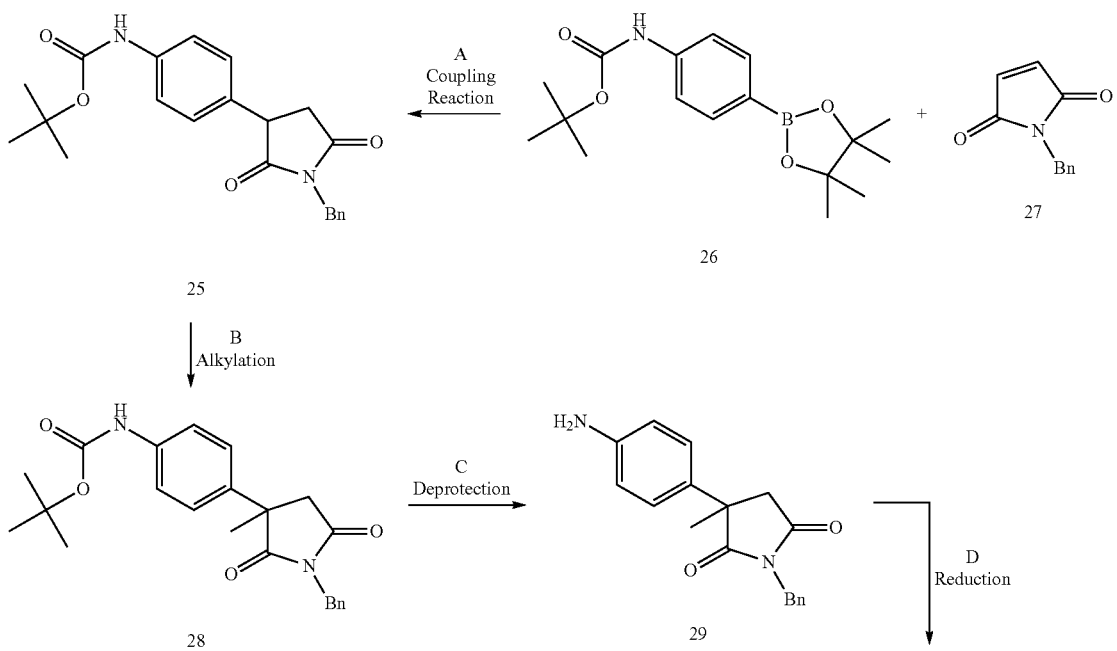

-continued

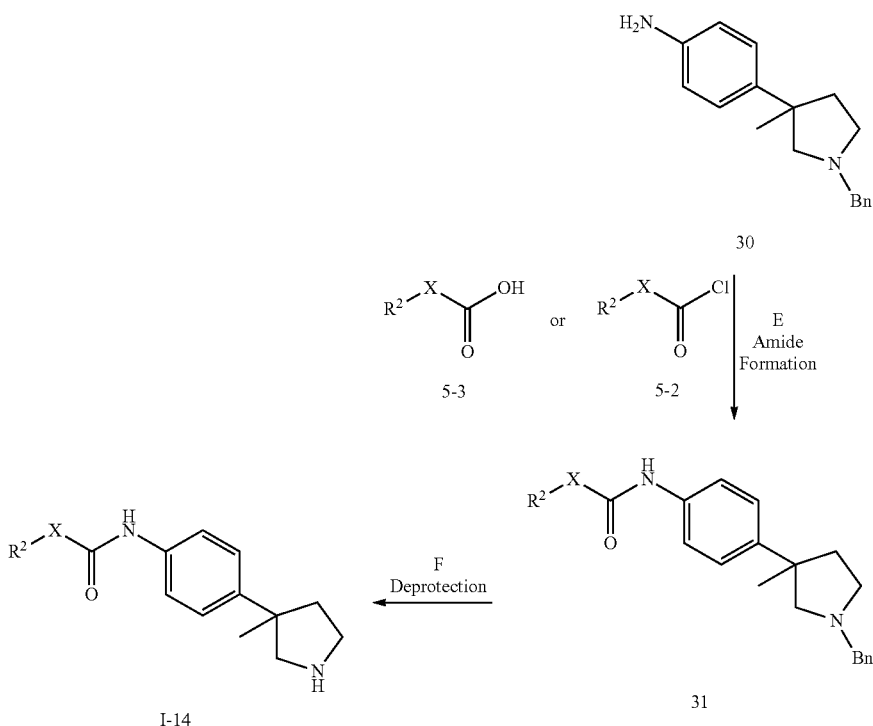

for X being a bond or —CH$_2$—

The substituents are as described above and X is a bond or —CH$_2$—.

Step A: Aryl pyrrolidindione 25 can be prepared using a metal-catalysed cross-coupling reaction, for instance using a rhodium-catalysed conjugate addition of aryl boronic ester 26 (CAS 330793-01-6) with maleiimide 27 (CAS 1631-26-1). Preferred conditions are catalytic [RhCl(cod)]$_2$, potassium hydroxide in aqueous dioxane at 90° C. for 5 minutes under microwave irradiation according to the procedure of Iyer et al. (*Tetrahedron. Lett.* 2007, 48, 4413-4418).

Step B: Alkylation can be accomplished by treatment with an alkyl bromide or alkyl iodide in the presence of an inorganic base such as sodium carbonate or caesium carbonate in a polar non-protic organic solvent such as DMF at a temperature between room temperature and the reflux temperature of the solvent. Preferred conditions are using methyl iodide and caesium carbonate in DMF at room temperature for 1 hour.

Step C: Removal of the BOC N-protecting group can be effected with mineral acids such as HCl, H$_2$SO$_4$ or H$_3$PO$_4$ or organic acids such as CF$_3$COOH, CHCl$_2$COOH, HOAc or p-toluenesulfonic acid in solvents such as CH$_2$Cl$_2$, CHCl$_3$, THF, MeOH, EtOH or H$_2$O at 0 to 80° C. Preferred conditions are 4N HCl in dioxane and THF at 60° C. overnight.

Step D: Reduction can be accomplished by treatment of carbamate 29 with an aluminium hydride reducing agent such as lithium aluminium hydride in an ethereal solvent such as THF or dioxane at temperatures between room temperature and the reflux temperature of the solvent. Preferred conditions are THF at 70° C. for 1 hour.

Step E: Amide formation can be accomplished by a coupling reaction between amine 30 and an alkyl or aryl acid chloride 5-2 in halogenated solvents such as dichloromethane or 1,2-dichloroethane or ethereal solvents such as diethyl ether, dioxane, THF, DME or TBME, in the presence of an organic base such as triethylamine or N,N-diisopropylethylamine. Preferred conditions are triethylamine in THF at room temperature for 3 hours.

Alternatively, amide formation can be accomplished by a coupling reaction between amine 30 and carboxylic acids 5-3 in the presence of a coupling reagent such as DCC, EDC, TBTU or HATU in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF, DME or TBME. Preferred conditions are TBTU with N-methylmorpholine in THF at 50° C. for 18 hours.

Step F: Removal of the benzyl protecting group can be effected by hydrogenation with hydrogen under normal or elevated pressure or by transfer hydrogenation using ammonium formate or cyclohexadiene as hydrogen source with a catalyst such as PtO$_2$, Pd—C or Raney nickel in solvents such as MeOH, EtOH, H$_2$O, dioxane, THF, HOAc, EtOAc CH$_2$Cl$_2$, CHCl$_3$, DMF or mixtures thereof. Preferred conditions are ammonium formate in the presence of palladium on charcoal in MeOH at 100° C. for 1 hour.

Scheme 14

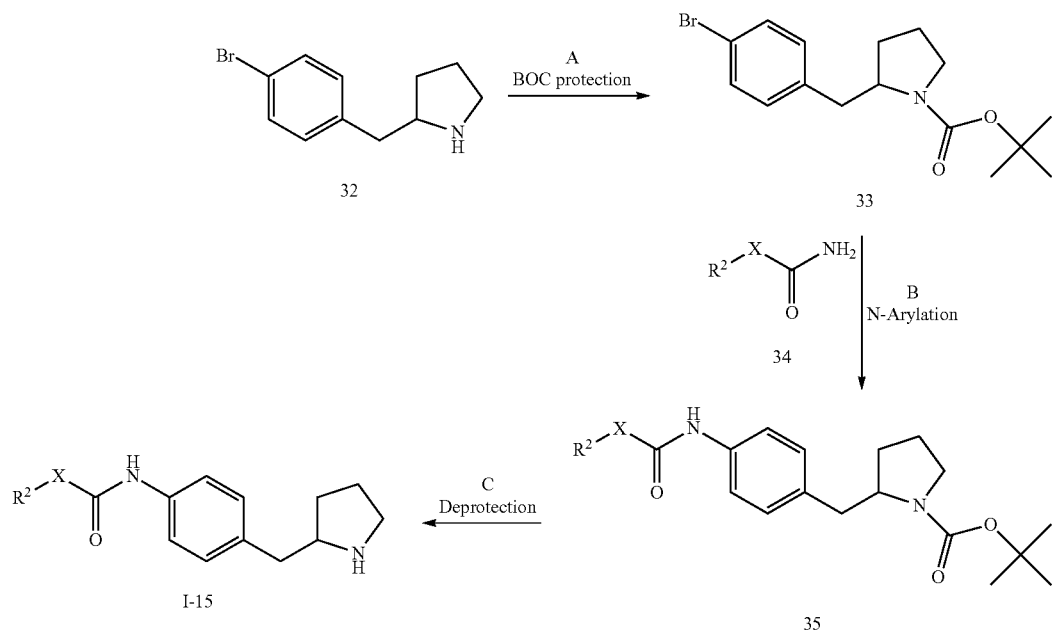

for X being a bond or —CH₂—

The substituents are as described above and X is a bond or —CH₂—.

Step A: Introduction of a BOC protecting group can be accomplished by treatment of benzyl-pyrrolidine derivative 32 (CAS 383127-68-2) with di-tert-butyl dicarbonate in the presence of an organic base such as N,N-diisopropylethylamine or triethylamine in non-protic solvents such as dichloromethane, 1,2-dichloroethane, dioxane, THF or DMF, or using inorganic bases such as sodium hydroxide or sodium carbonate in aqueous solvent systems such as water, aqueous ethanol or aqueous methanol. Preferred conditions are N,N-diisopropylethylamine in 1,2-dichloroethane at room temperature for 1 hour.

Step B: N-arylation can be accomplished by treatment of aryl bromide 33 with amide compounds 34 in the presence of a metal catalyst, for instance using a copper-mediated Ullmann reaction or a palladium-catalysed Buchwald-Hartwig reaction. Preferred conditions are catalytic copper (I) iodide, catalytic N,N' dimethylethylenediamine and caesium carbonate in dioxane at 120° C. overnight according to the procedure of Buchwald and co-workers (*Org. Lett.* 2007, 9, 4749-4751).

Step C: Removal of the BOC N-protecting group can be effected with mineral acids such as HCl, $H_2SO_4$ or $H_3PO_4$ or organic acids such as $CF_3COOH$, $CHCl_2COOH$, HOAc or p-toluenesulfonic acid in solvents such as $CH_2Cl_2$, $CHCl_3$, THF, MeOH, EtOH or $H_2O$ at 0 to 80° C. Preferred conditions are 4N HCl in dioxane and THF at 60° C. overnight.

Scheme 15

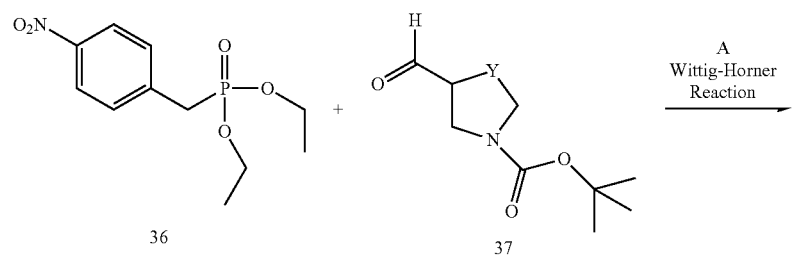

Y = —CH₂— or —CH₂CH₂—

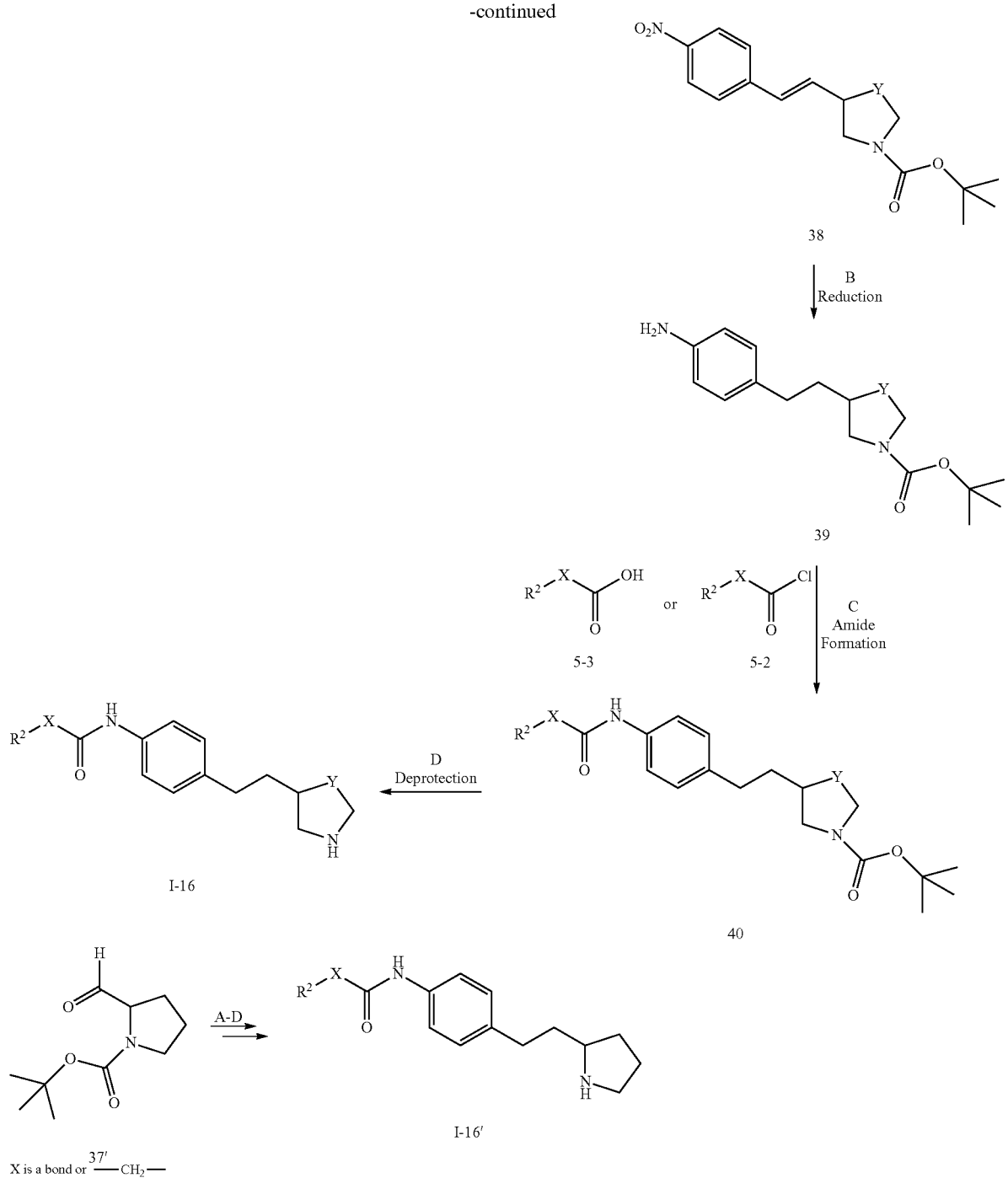

The substituents are as described above and X is a bond or —CH$_2$— and Y is —CH$_2$— or —CH$_2$CH$_2$—.

Step A: Wittig Horner reaction between benzyl-substituted phosphonic acid dialkyl ester 36 (CAS 2609-49-6) and an aldeyde 37 (for example (RS)-3-formyl-pyrrolidine-1-carboxylic acid tert-butyl ester [CAS 59379-02-1] or (RS)-3-formyl-piperidine-1-carboxylic acid tert-butyl ester [CAS 118156-93-7]) can be accomplished by using a base such as NaH, KOtBu, NaOMe, NaOEt, n-BuLi, LiHMDS, NaHMDS, KHMDS, LDA in a solvent such as THF, dioxane, acetonitrile, 1,2-dimethoxyethan, DMF, benzene, toluene or mixtures thereof at temperatures from −78° C.-80° C. for 15 min-8 hrs and if appropriate optional addition of a crown ether for ylide generation and then condensing the ylide with the carbonyl compound in the same solvent at temperature between 0 and 80° C. for 1-24 hrs. Alternatively, the base, the carbonyl compound and the base and the optional crown ether can be added to the reaction mixture at the same time without preformation of the ylide at temperatures from −78° C. to 80° C. Preferred conditions are ylide formation at −78° C. using LDA solution in hexane/THF as base and THF as solvent, reacting the phosphonic acid ester for 60 min at −78° C., and then condensation with the carbonyl component at −78° C. and then leaving to warm to room temperature overnight.

Step B: Simultaneous reduction of the alkene and the nitro function can be effected by hydrogenation with hydrogen under normal or elevated pressure or by transfer hydrogenation using ammonium formate or cyclohexadiene as hydrogen source with a catalyst such as $PtO_2$, Pd—C or Raney nickel in solvents such as MeOH, EtOH, $H_2O$, dioxane, THF, HOAc, EtOAc $CH_2Cl_2$, $CHCl_3$, DMF or mixtures thereof. Alternatively, the reduction of the alkene can be effected by Mg in MeOH or by $LiAlH_4$ in THF or diethylether. Preferred conditions are hydrogenation in the presence of Pd/C as catalyst with MeOH as solvent.

Step C: Amide formation can be accomplished by a coupling reaction between amine 39 and an alkyl or aryl acid chloride 5-2 in halogenated solvents such as dichloromethane or 1,2-dichloroethane or ethereal solvents such as diethyl ether, dioxane, THF, DME or TBME, in the presence of an organic base such as triethylamine or N,N-diisopropylethylamine. Preferred conditions are triethylamine in THF at room temperature for 3 hours. Alternatively, amide formation can be accomplished by a coupling reaction between amine 39 and carboxylic acids 5-3 in the presence of a coupling reagent such as DCC, EDC, TBTU or HATU in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF, DME or TBME. Preferred conditions are TBTU with N-methylmorpholine in THF at 50° C. for 18 hours.

Step D: Removal of the BOC N-protecting group can be effected with mineral acids such as HCl, $H_2SO_4$ or $H_3PO_4$ or organic acids such as $CF_3COOH$, $CHCl_2COOH$, HOAc or p-toluenesulfonic acid in solvents such as $CH_2Cl_2$, $CHCl_3$, THF, MeOH, EtOH or $H_2O$ at 0 to 80° C. Preferred conditions are 4N HCl in dioxane and THF at 60° C. overnight. In a similar manner, following steps A-D starting from aldeyde 37' ((RS)-2-formyl-pyrrolidine-1-carboxylic acid tert-butyl ester [CAS 117625-90-8]) instead of aldehyde 37 leads to product I-16' instead of I-16.

Scheme 16

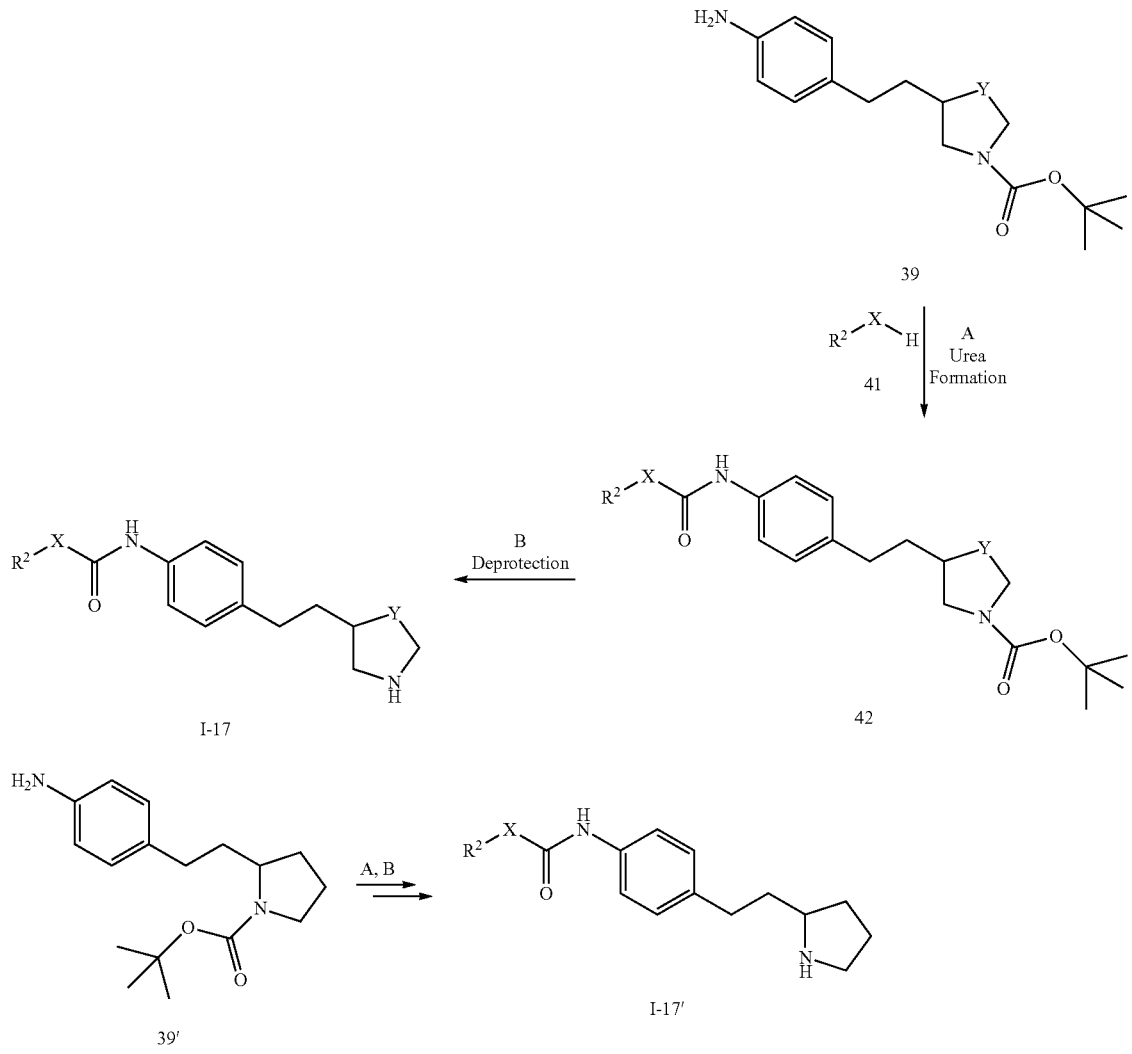

X is NH or —CH$_2$NH—

The substituents are as described above and X is —NH— or —CH$_2$NH—.

Step A: Urea formation can be accomplished by reaction of aryl amine 39 with triphosgene and with an alkyl or aryl amine 41 in halogenated solvents such as dichloromethane or 1,2-dichloroethane or ethereal solvents such as diethyl ether, dioxane, THF, DME or TBME, or polar organic solvents such as DMF, in the presence of a base such as triethylamine or N,N-diisopropylethylamine. Preferred conditions are triphosgene and triethylamine in dichloroethane at 80° C. for 18 h.

Step B: Removal of the BOC N-protecting group can be effected with mineral acids such as HCl, H$_2$SO$_4$ or H$_3$PO$_4$ or organic acids such as CF$_3$COOH, CHCl$_2$COOH, HOAc or p-toluenesulfonic acid in solvents such as CH$_2$Cl$_2$, CHCl$_3$, THF, MeOH, EtOH or H$_2$O at 0 to 80° C. Preferred conditions are 4 N HCl in dioxane and THF at 60° C. overnight. In a similar manner, following steps A and B starting from amine 39' instead of amine 39 leads to product I-17' instead of I-17.

N,N-diisopropylethylamine or triethylamine in non-protic solvents such as dichloromethane, 1,2-dichloroethane, dioxane, THF or DMF, or using inorganic bases such as sodium hydroxide or sodium carbonate in aqueous solvent systems such as water, aqueous ethanol or aqueous methanol. Examples of appropriate cyclic amines 43 include pyrrolidine derivatives such as 43-a [CAS 328546-98-1], piperidine derivatives such as 43-b [CAS 769944-72-1], and morpholine derivatives such as 43-c [CAS 83555-73-1]. Preferred conditions are N,N-diisopropylethylamine in THF at room temperature for 18 hours.

Step B: N-arylation can be accomplished by treatment of aryl bromide 44 with amide compounds 34 in the presence of a metal catalyst, for instance using a copper-mediated Ullmann reaction or a palladium-catalysed Buchwald-Hartwig reaction. Preferred conditions are catalytic copper (I) iodide, catalytic N,N' dimethylethylenediamine and caesium carbonate in dioxane in a sealed tube heated in a microwave oven at 180° C. for 2 hours according to a modification (microwave heating) of the procedure of Buchwald and co-workers (*Org. Lett.* 2007, 9, 4749-4751).

Scheme 17

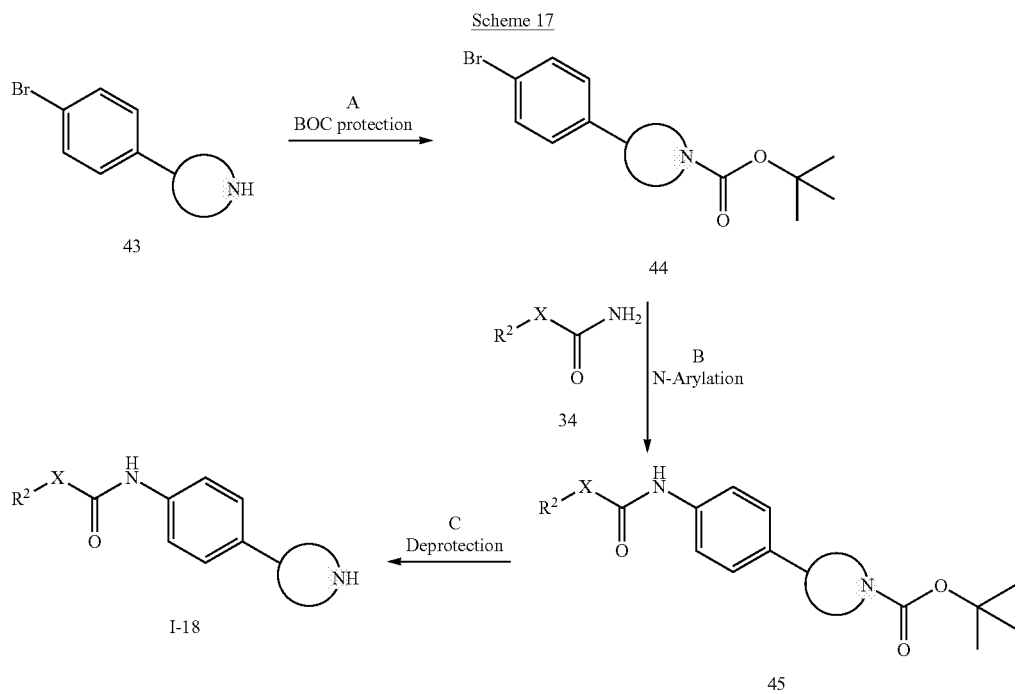

for example using:

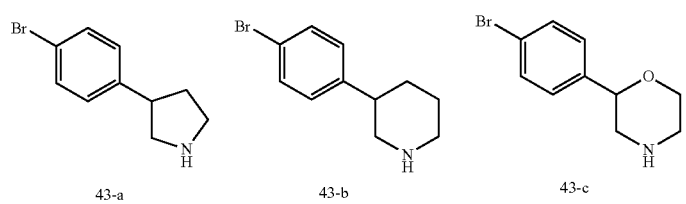

for X being a bond or —CH$_2$—

The substituents are as described above and X is a bond or —CH$_2$—.

Step A: Introduction of a BOC protecting group can be accomplished by treatment of a cyclic amine 43 with di-tert-butyl dicarbonate in the presence of an organic base such as Step C: Removal of the BOC N-protecting group can be effected with mineral acids such as HCl, H$_2$SO$_4$ or H$_3$PO$_4$ or organic acids such as CF$_3$COOH, CHCl$_2$COOH, HOAc or p-toluenesulfonic acid in solvents such as CH$_2$Cl$_2$, CHCl$_3$, THF, MeOH, EtOH or H$_2$O at 0 to 80° C. Preferred conditions are 4 N HCl in dioxane and THF at 60° C. overnight.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I are basic and can be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or can be brought out of solution with a less polar solvent.

The acid addition salts of the basic compounds of formula I can be converted to the corresponding free bases by treatment with at least a stoichiometric equivalent of a suitable base such as sodium or potassium hydroxide, potassium carbonate, sodium bicarbonate, ammonia, and the like.

Example 1

(RS)-1-(4-Butyl-2-methyl-phenyl)-3-(4-pyrrolidin-3-yl-phenyl)-urea; hydrochloride

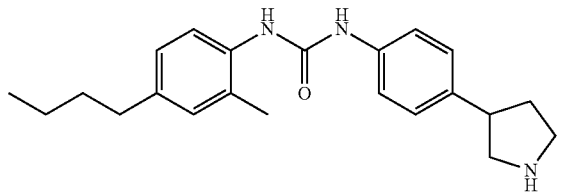 [SMILES: CCCCc1ccc(NC(=O)Nc2ccc(C3CCNC3)cc2)c(C)c1]

The title compound was obtained in analogy to example 6 using 4-butyl-2-methyl-phenyl isocyanate (CAS 306935-81-9) instead of phenyl isocyanate. White solid. MS (ISP): 352.4 ([M+H]$^+$).

Example 2

1-(3,4-Dichloro-phenyl)-3-[4-(4-methyl-piperazin-1-yl)-phenyl]-urea

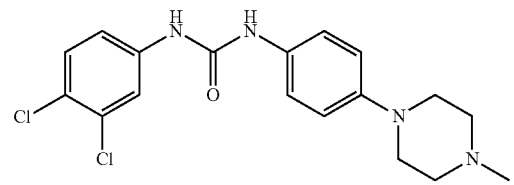 [SMILES: CN1CCN(c2ccc(NC(=O)Nc3ccc(Cl)c(Cl)c3)cc2)CC1]

To a stirred suspension of 4-(4-methyl-piperazin-1-yl)-phenylamine (195 mg, CAS 16153-81-4) in DMF (5 ml) was added 3,4-dichlorophenyl isocyanate (191 mgl, CAS 102-36-3) and stirring was continued at room temperature for 2 h. The mixture was then diluted with ethyl acetate (20 ml) and water (20 ml) whereupon a precipitate formed. The precipitate was collected by filtration, washing with ethyl acetate, and dried in vacuo to give 1-(3,4-dichloro-phenyl)-3-[4-(4-methyl-piperazin-1-yl)-phenyl]-urea (317 mg, 82%) as an off-white solid. MS (ISP): 381.1 ([$\{^{37}Cl\}$M−H]$^-$), 379.2 ([$\{^{37}Cl^{35}Cl\}$M−H]$^-$), 377.0 ([$\{^{35}Cl\}$M−H]$^-$).

Example 3

(RS)-1-(3,4-Dichloro-phenyl)-3-(4-pyrrolidin-3-yl-phenyl)-urea hydrochloride

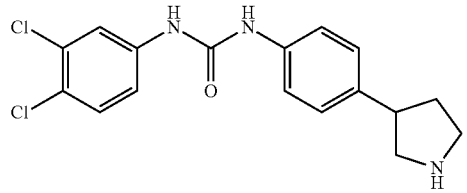 [SMILES: O=C(Nc1ccc(C2CCNC2)cc1)Nc1ccc(Cl)c(Cl)c1]

The title compound was obtained in analogy to example 6 using 3,4-dichloro-phenyl isocyanate (CAS 102-36-3) instead of phenyl isocyanate. White solid. MS (ISP): 352.1 ([$\{^{37}Cl\}$M−H]$^-$), 350.2 ([$\{^{37}Cl^{35}Cl\}$M−H]$^-$), 348.0 ([$\{^{35}Cl\}$M−H]$^-$).

Example 4

1-[4-(4-Methyl-piperazin-1-yl)-phenyl]-3-(4-oxazol-5-yl-phenyl)-urea

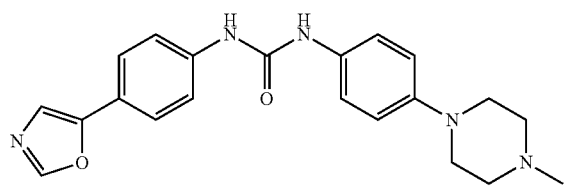 [SMILES: CN1CCN(c2ccc(NC(=O)Nc3ccc(-c4cnco4)cc3)cc2)CC1]

To a stirred suspension 1-(4-isocyanatophenyl)-4-methyl-piperazine (75 mg, CAS 879896-39-6) in DMF (2 ml) was added 4-(1,3-oxazol-5-yl)aniline (55 mg, CAS 1008-95-3) and stirring was continued at room temperature for 17 h. The mixture was then diluted with ethyl acetate (10 ml) and water (10 ml) whereupon a precipitate formed. The precipitate was collected by filtration, washing with ethyl acetate, and dried in vacuo to give 1-[4-(4-methyl-piperazin-1-yl)-phenyl]-3-(4-oxazol-5-yl-phenyl)-urea (41 mg, 31%) as a white solid. MS (ISP): 376.1 ([M−H]$^-$).

Example 5

(RS)-1-(4-Chloro-phenyl)-3-(4-pyrrolidin-3-yl-phenyl)-urea hydrochloride

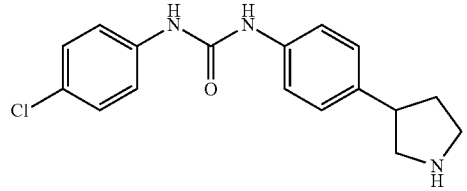

The title compound was obtained in analogy to example 6 using 4-chloro-phenyl isocyanate (CAS 104-12-1) instead of phenyl isocyanate. White solid. MS (ISP): 318.1 ([{$^{37}$Cl}M+H]$^+$), 316.1 ([{$^{35}$Cl}M+H]$^+$).

Example 6

(RS)-1-Phenyl-3-(4-pyrrolidin-3-yl-phenyl)-urea hydrochloride

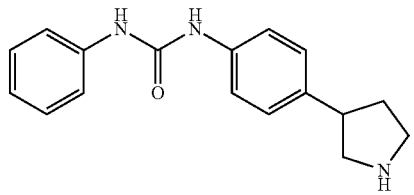 [SMILES: O=C(Nc1ccccc1)Nc1ccc(C2CCNC2)cc1]

a) (RS)-3-[4-(3-Phenyl-ureido)-phenyl]-pyrrolidine-1-carboxylic acid tert-butyl ester To a stirred suspension of (RS)-tert-butyl 3-(4-aminophenyl)pyrrolidine-1-carboxylate (70 mg, CAS 908334-28-1) in dichloromethane (2.5 ml) was added phenyl isocyanate (0.03 ml) and stirring was continued at room temperature for 3 h. The mixture was then concentrated in vacuo and the residue was purified by column chromatography (SiO$_2$; gradient: heptane/EtOAc) to give (RS)-3-[4-(3-phenyl-ureido)-phenyl]-pyrrolidine-1-carboxylic acid tert-butyl ester (102 mg, quant.) as a light yellow solid. MS (ISP): 404.3 ([M+Na]$^+$), 399.2 ([M+NH$_4$]$^+$), 382.2 ([M+H]$^+$), 326.3 ([M+H—C$_4$H$_8$]$^+$).

b) (RS)-1-Phenyl-3-(4-pyrrolidin-3-yl-phenyl)-urea hydrochloride

To a stirred solution of (RS)-3-[4-(3-phenyl-ureido)-phenyl]-pyrrolidine-1-carboxylic acid tert-butyl ester (92 mg) in THF (2 ml) was added dropwise a solution of hydrogen chloride in dioxane (0.60 ml, 4 M solution) and the mixture was heated at 60° C. overnight. The mixture was then cooled to 0° C. and diluted with diethyl ether (5 ml). The ensuing crystals were collected by filtration, washing with diethyl ether, and were dried in vacuo at 60° C. to afford (RS)-1-phenyl-3-(4-pyrrolidin-3-yl-phenyl)-urea hydrochloride (52 mg, 68%) as a white crystalline solid. MS (ISP): 282.2 ([M+H]$^+$).

Example 7

(RS)-1-(2,4-Dichloro-phenyl)-3-(4-pyrrolidin-3-yl-phenyl)-urea hydrochloride

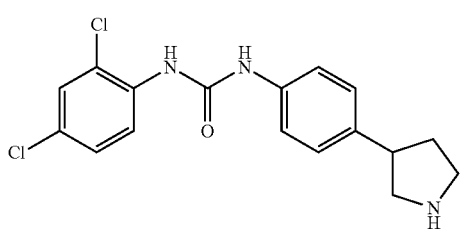 [SMILES: O=C(Nc1ccc(C2CCNC2)cc1)Nc1ccc(Cl)cc1Cl]

The title compound was obtained in analogy to example 6 using 2,4-dichloro-phenyl isocyanate (CAS 2612-57-9) instead of phenyl isocyanate. White solid. MS (ISP): 354.1 ([{$^{37}$Cl}M+H]$^+$), 352.1 ([{$^{37}$Cl$^{35}$Cl}M+H]$^+$), 350.1 ([{$^{35}$Cl}M+H]$^+$).

Example 8

(RS)-1-(3-Chloro-phenyl)-3-(4-pyrrolidin-3-yl-phenyl)-urea hydrochloride

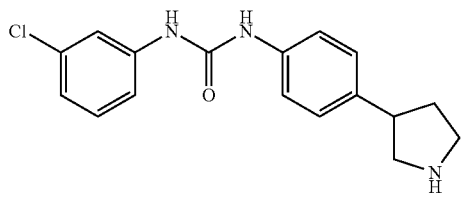 [SMILES: O=C(Nc1ccc(C2CCNC2)cc1)Nc1cccc(Cl)c1]

The title compound was obtained in analogy to example 6 using 3-chloro-phenyl isocyanate (CAS 2909-38-8) instead of phenyl isocyanate. White solid. MS (ISP): 318.1 ([{$^{37}$Cl}M+H]$^+$), 316.1 ([{$^{35}$Cl}M+H]$^+$).

Example 9

(RS)-1-Benzyl-3-(4-pyrrolidin-3-yl-phenyl)-urea hydrochloride

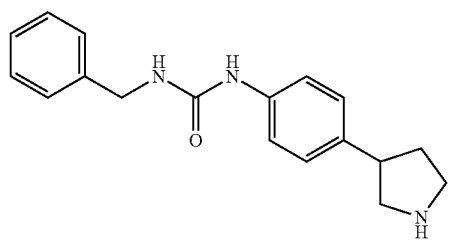 [SMILES: O=C(NCc1ccccc1)Nc1ccc(C2CCNC2)cc1]

The title compound was obtained in analogy to example 6 using benzyl isocyanate instead of phenyl isocyanate. Off-white solid. MS (ISP): 296.2 ([M+H]$^+$).

Example 10

(RS)-1-Cyclohexyl-3-(4-pyrrolidin-3-yl-phenyl)-urea hydrochloride

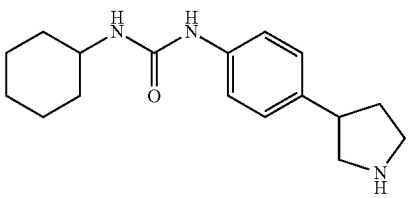 [SMILES: O=C(Nc1ccc(C2CCNC2)cc1)NC1CCCCC1]

The title compound was obtained in analogy to example 6 using cyclohexyl isocyanate instead of phenyl isocyanate. Off-white solid. MS (ISP): 288.2 ([M+H]$^+$).

Example 11

(RS)-(4-Pyrrolidin-3-yl-phenyl)-carbamic acid phenyl ester hydrochloride

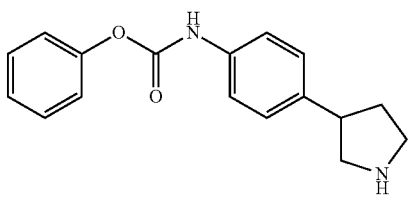 [SMILES: O=C(Nc1ccc(C2CCNC2)cc1)Oc1ccccc1]

a) (RS)-3-(4-Phenoxycarbonylamino-phenyl)-pyrrolidine-1-carboxylic acid tert-butyl ester To a stirred suspension of (RS)-tert-butyl 3-(4-aminophenyl)pyrrolidine-1-carboxylate (80 mg, CAS 908334-28-1) in THF (2 ml) were added sequentially triethylamine (0.05 ml) and phenyl chloroformate (0.04 ml) and stirring was continued at room temperature for 18 h. The mixture was then concentrated in vacuo and the residue was purified by column chromatography (SiO$_2$; gradient: heptane/EtOAc) to give (RS)-3-(4-phenoxycarbonylamino-phenyl)-pyrrolidine-1-carboxylic acid tert-butyl ester (102 mg, 87%) as a white solid. MS (ISP): 405.3 ([M+Na]$^+$), 400.1 ([M+NH$_4$]$^+$), 327.2 ([M+H—C$_4$H$_8$]$^+$).

b) (RS)-(4-Pyrrolidin-3-yl-phenyl)-carbamic acid phenyl ester hydrochloride To a stirred solution of (RS)-3-(4-phenoxycarbonylamino-phenyl)-pyrrolidine-1-carboxylic acid tert-butyl ester (98 mg) in THF (2 ml) was added dropwise a solution of hydrogen chloride in dioxane (0.64 ml, 4 M solution) and the mixture was heated at 60° C. overnight. The mixture was then cooled to 0° C. and diluted with diethyl ether (5 ml). The ensuing crystals were collected by filtration, washing with diethyl ether, and were dried in vacuo at 60° C. to afford (RS)-(4-pyrrolidin-3-yl-phenyl)-carbamic acid phenyl ester hydrochloride (52 mg, 68%) as a white crystalline solid. MS (ISP): 283.1 ([M+H]$^+$).

Example 12

(RS)-2-Phenyl-N-(4-pyrrolidin-3-yl-phenyl)-acetamide hydrochloride

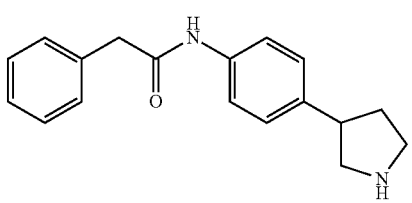 [SMILES: O=C(Cc1ccccc1)Nc1ccc(C2CCNC2)cc1]

a) (RS)-3-(4-Phenylacetylamino-phenyl)-pyrrolidine-1-carboxylic acid tert-butyl ester To a stirred suspension of (RS)-tert-butyl 3-(4-aminophenyl)pyrrolidine-1-carboxylate (80 mg, CAS 908334-28-1) in THF (2 ml) were added sequentially triethylamine (0.05 ml) and phenylacetyl chloride (0.04 ml) and stirring was continued at room temperature for 18 h. The mixture was then concentrated in vacuo and the residue was purified by column chromatography (SiO$_2$; gradient: heptane/EtOAc) to give (RS)-3-(4-phenylacetylamino-phenyl)-pyrrolidine-1-carboxylic acid tert-butyl ester (95 mg, 82%) as a white solid. MS (ISP): 403.2 ([M+Na]$^+$), 398.2 ([M+NH$_4$]$^+$), 325.3 ([M+H—C$_4$H$_8$]$^+$).

b) (RS)-2-Phenyl-N-(4-pyrrolidin-3-yl-phenyl)-acetamide hydrochloride

To a stirred solution of (RS)-3-(4-phenylacetylamino-phenyl)-pyrrolidine-1-carboxylic acid tert-butyl ester (91 mg) in THF (2 ml) was added dropwise a solution of hydrogen chloride in dioxane (0.60 ml, 4 M solution) and the mixture was heated at 60° C. overnight. The mixture was then cooled to 0° C. and diluted with diethyl ether (5 ml). The ensuing crystals were collected by filtration, washing with diethyl ether, and were dried in vacuo at 60° C. to afford (RS)-2-Phenyl-N-(4-pyrrolidin-3-yl-phenyl)-acetamide hydrochloride (63 mg, 83%) as an off-white crystalline solid. MS (ISP): 281.2 ([M+H]$^+$).

Example 13

(RS)—N-(4-Pyrrolidin-3-yl-phenyl)-benzamide hydrochloride

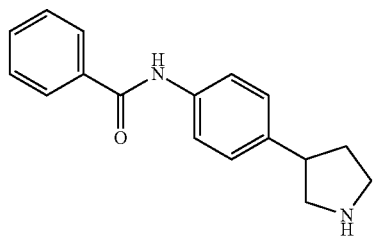 [SMILES: O=C(Nc1ccc(C2CCNC2)cc1)c1ccccc1]

The title compound was obtained in analogy to example 12 using benzoyl chloride instead of phenylacetyl chloride. White solid. MS (ISP): 267.1 ([M+H]$^+$).

Example 14

(RS)-1-Methyl-1-phenyl-3-(4-pyrrolidin-3-yl-phenyl)-urea

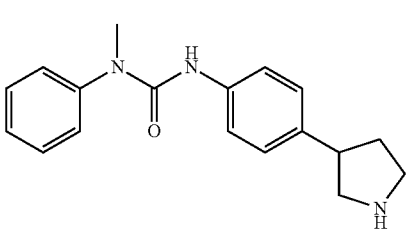 [SMILES: CN(C(=O)Nc1ccc(C2CCNC2)cc1)c1ccccc1]

The title compound was obtained in analogy to example 11 using N-methyl-N-phenylcarbamoyl chloride instead of phenyl chloroformate. Colourless oil. MS (ISP): 296.3 ([M+H]$^+$).

Example 15

(RS)-(4-Pyrrolidin-3-yl-phenyl)-carbamic acid 4-fluoro-phenyl ester hydrochloride

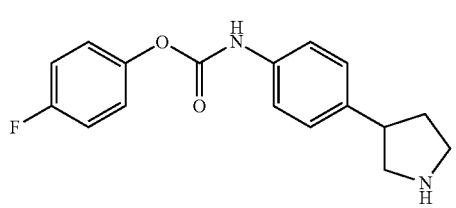 [SMILES: O=C(Nc1ccc(C2CCNC2)cc1)Oc1ccc(F)cc1]

The title compound was obtained in analogy to example 11 using 4-fluoro-phenyl chloroformate instead of phenyl chloroformate. White solid. MS (ISP): 301.1 ([M+H]$^+$).

Example 16

(RS)-4-Chloro-N-(4-pyrrolidin-3-yl-phenyl)-benzamide hydrochloride

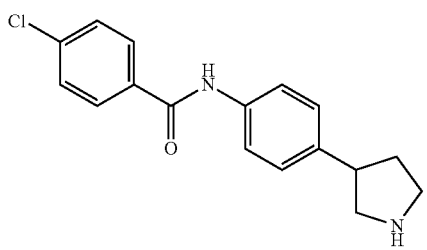 [SMILES: O=C(Nc1ccc(C2CCNC2)cc1)c1ccc(Cl)cc1]

The title compound was obtained in analogy to example 12 using 4-chloro-benzoyl chloride instead of phenylacetyl chloride. White solid. MS (ISP): 303.1 ([{$^{37}$Cl}M+H]$^+$), 301.1 ([{$^{35}$Cl}M+H]$^+$).

Example 17

(RS)-2-(4-Chloro-phenyl)-N-(4-pyrrolidin-3-yl-phenyl)-acetamide hydrochloride

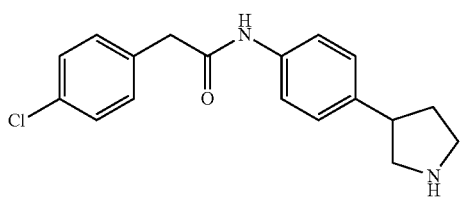 [SMILES: O=C(Cc1ccc(Cl)cc1)Nc1ccc(C2CCNC2)cc1]

The title compound was obtained in analogy to example 12 using 4-chloro-phenylacetyl chloride instead of phenylacetyl chloride. White solid. MS (ISP): 317.1 ([{$^{37}$Cl}M+H]$^+$), 315.1 ([{$^{35}$Cl}M+H]$^+$).

Example 18

(RS)—N-(4-Pyrrolidin-3-yl-phenyl)-4-trifluoromethyl-benzamide hydrochloride

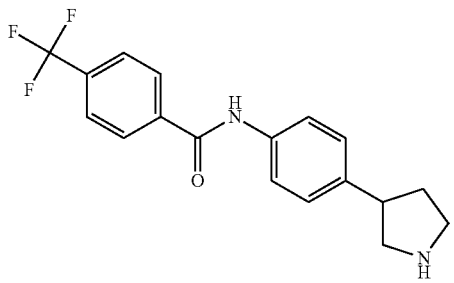 [SMILES: O=C(Nc1ccc(C2CCNC2)cc1)c1ccc(C(F)(F)F)cc1]

The title compound was obtained in analogy to example 12 using 4-trifluoromethyl-benzoyl chloride instead of phenylacetyl chloride. White solid. MS (ISP): 335.1 ([M+H]$^+$).

Example 19

(RS)-2,4-Dichloro-N-(4-pyrrolidin-3-yl-phenyl)-benzamide hydrochloride

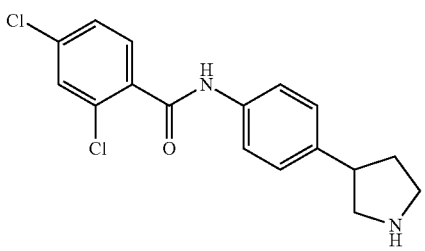 [SMILES: O=C(Nc1ccc(C2CCNC2)cc1)c1ccc(Cl)cc1Cl]

The title compound was obtained in analogy to example 12 using 2,4-dichloro-benzoyl chloride instead of phenylacetyl chloride. Off-white solid. MS (ISP): 339.1 ([{$^{37}$Cl}M+H]$^+$), 337.1 ([{$^{37}$Cl$^{35}$Cl}M+H]$^+$), 335.1 ([{$^{35}$Cl}M+H]$^+$).

Example 20

(RS)-3-Chloro-N-(4-pyrrolidin-3-yl-phenyl)-benzamide hydrochloride

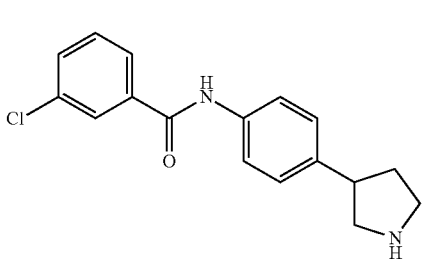 [SMILES: O=C(Nc1ccc(C2CCNC2)cc1)c1cccc(Cl)c1]

The title compound was obtained in analogy to example 12 using 3-chloro-benzoyl chloride instead of phenylacetyl chloride. Off-white solid. MS (ISP): 303.1 ([{$^{37}$Cl}M+H]$^+$), 301.1 ([{$^{35}$Cl}M+H]$^+$).

Example 21

(RS)-Morpholine-4-carboxylic acid (4-pyrrolidin-3-yl-phenyl)-amide hydrochloride

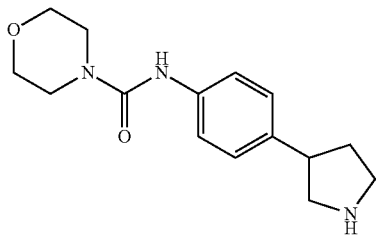 [SMILES: O=C(Nc1ccc(C2CCNC2)cc1)N1CCOCC1]

The title compound was obtained in analogy to example 11 using 4-morpholinecarbonyl chloride instead of phenyl chloroformate. Off-white solid. MS (ISP): 276.2 ([M+H]$^+$).

Example 22

(RS)-Methyl-(4-pyrrolidin-3-yl-phenyl)-carbamic acid phenyl ester

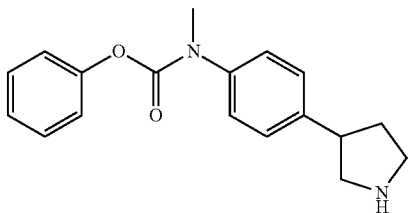 [SMILES: CN(C(=O)Oc1ccccc1)c1ccc(C2CCNC2)cc1]

a) (RS)-3-(4-Ethoxycarbonylamino-phenyl)-pyrrolidine-1-carboxylic acid tert-butyl ester The title compound was obtained in analogy to example 11(a) using ethyl chloroformate instead of phenyl chloroformate. White solid. MS (ISP): 357.2 ([M+Na]$^+$), 352.2 ([M+NH$_4$]$^+$), 279.2 ([M+H—C$_4$H$_8$]$^+$).

b) (RS)-3-(4-Methylamino-phenyl)-pyrrolidine-1-carboxylic acid tert-butyl ester

To a stirred solution of (RS)-3-(4-ethoxycarbonylamino-phenyl)-pyrrolidine-1-carboxylic acid tert-butyl ester (690 mg) in THF (9 ml) was added dropwise a solution of Red-Al (1.77 ml, 3.5 M solution in toluene) and the mixture was then stirred at room temperature for 5 h and at 50° C. for 15 min. The mixture was then cooled to 0° C. and quenched by dropwise addition of 1 M aq. sodium hydroxide solution. The mixture was diluted with ethyl acetate and was then washed with saturated brine. The organic phase was separated, dried over Na$_2$SO$_4$ and concentrated in vacuo. The residue was purified by column chromatography (SiO$_2$; gradient: heptane/EtOAc) to afford (RS)-3-(4-methylamino-phenyl)-pyrrolidine-1-carboxylic acid tert-butyl ester (580 mg, quant) as a colourless oil. MS (ISP): 299.4 ([M+Na]$^+$), 221.3 ([M+H—C$_4$H$_8$]$^+$).

c) (RS)-3-[4-(Methyl-phenoxycarbonyl-amino)-phenyl]-pyrrolidine-1-carboxylic acid tert-butyl ester The title compound was obtained in analogy to example 11(a) using (RS)-3-(4-methylamino-phenyl)-pyrrolidine-1-carboxylic acid tert-butyl ester instead of (RS)-tert-butyl 3-(4-aminophenyl)pyrrolidine-1-carboxylate. Colourless oil. MS (ISP): 419.3 ([M+Na]$^+$), 414.3 ([M+NH$_4$]$^+$), 341.2 ([M+H—C$_4$H$_8$]$^+$).

d) (RS)-Methyl-(4-pyrrolidin-3-yl-phenyl)-carbamic acid phenyl ester

The title compound was obtained in analogy to example 11(b) using (RS)-3-[4-(methyl-phenoxycarbonyl-amino)-phenyl]-pyrrolidine-1-carboxylic acid tert-butyl ester instead of (RS)-3-(4-phenoxycarbonylamino-phenyl)-pyrrolidine-1-carboxylic acid tert-butyl ester. Colourless oil. MS (ISP): 297.3 ([M+NH$_4$]$^+$).

Example 23

(RS)-(4-Pyrrolidin-3-yl-phenyl)-carbamic acid 4-chloro-phenyl ester hydrochloride

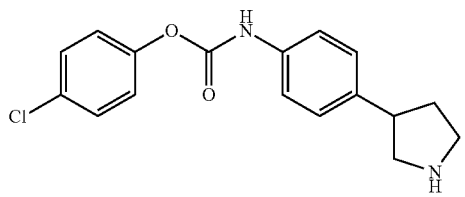 [SMILES: O=C(Nc1ccc(C2CCNC2)cc1)Oc1ccc(Cl)cc1]

The title compound was obtained in analogy to example 11 using 4-chloro-phenyl chloroformate instead of phenyl chloroformate. White solid. MS (ISP): 319.1 ([{$^{37}$Cl}M+H]$^+$), 317.2 ([{$^{35}$Cl}M+H]$^+$).

Example 24

(RS)—N-(4-Pyrrolidin-3-yl-phenyl)-2-(4-trifluoromethyl-phenyl)-acetamide

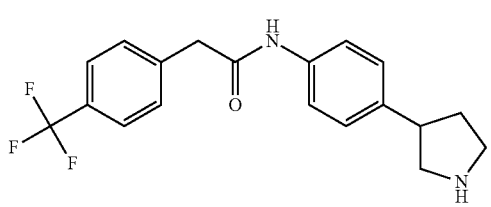 [SMILES: O=C(Cc1ccc(C(F)(F)F)cc1)Nc1ccc(C2CCNC2)cc1]

The title compound was obtained in analogy to example 12 using 4-trifluoromethyl-phenylacetyl chloride instead of phenylacetyl chloride. Colourless oil. MS (ISP): 349.2 ([M+H]$^+$).

Example 25

(RS)-2-Phenyl-N—((RS)-4-pyrrolidin-3-yl-phenyl)-propionamide

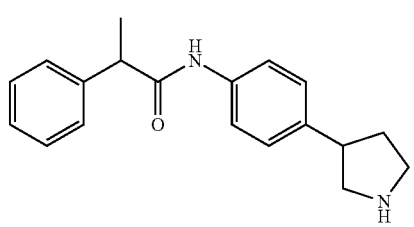 [SMILES: CC(C(=O)Nc1ccc(C2CCNC2)cc1)c1ccccc1]

The title compound was obtained in analogy to example 12 using 2-phenyl-propionyl chloride instead of phenylacetyl chloride. Colourless oil. MS (ISP): 295.3 ([M+H]$^+$).

Example 26

(RS)-1-(6-Chloro-pyridin-3-yl)-3-(4-pyrrolidin-3-yl-phenyl)-urea hydrochloride

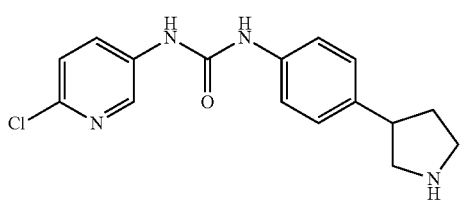

The title compound was obtained in analogy to example 6 using 2-chloro-5-isocyanatopyridine (CAS 125117-96-6) instead of phenyl isocyanate. Off-white solid. MS (ISP): 319.1 ([{$^{37}$Cl}M+H]$^+$), 317.2 ([{$^{35}$Cl}M+H]$^+$).

Example 27

(RS)-1-(4-Pyrrolidin-3-yl-phenyl)-3-(4-trifluoromethyl-phenyl)-urea hydrochloride

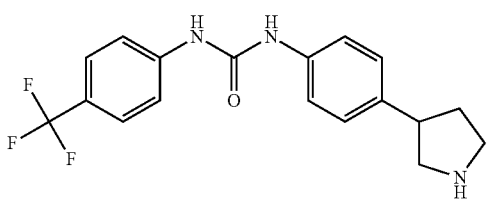

The title compound was obtained in analogy to example 6 using 4-trifluoromethyl-phenyl isocyanate instead of phenyl isocyanate. Off-white solid. MS (ISP): 250.2 ([M+H]$^+$).

Example 28

(RS)-Piperidine-1-carboxylic acid (4-pyrrolidin-3-yl-phenyl)-amide

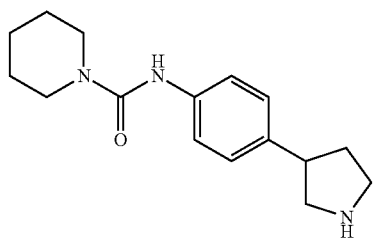 [SMILES: O=C(Nc1ccc(C2CCNC2)cc1)N1CCCCC1]

The title compound was obtained in analogy to example 11 using 1-piperidinecarbonyl chloride instead of phenyl chloroformate. Colourless amorphous solid. MS (ISP): 274.3 ([M+H]$^+$).

Example 29

(R)-2-Phenyl-N—((RS)-4-pyrrolidin-3-yl-phenyl)-propionamide

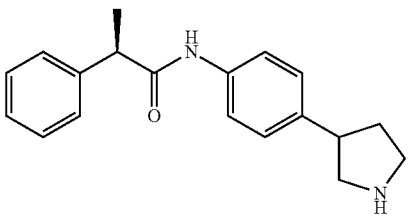 [SMILES: C[C@@H](C(=O)Nc1ccc(C2CCNC2)cc1)c1ccccc1]

a) (RS)-3-[4-((R)-2-Phenyl-propionylamino)-phenyl]-pyrrolidine-1-carboxylic acid tert-butyl ester To a stirred suspension of (RS)-tert-butyl 3-(4-aminophenyl)pyrrolidine-1-carboxylate (70 mg, CAS 908334-28-1) in THF (2 ml) were added sequentially N-methylmorpholine (0.12 ml), TBTU (171 mg) and (R)-2-phenylpropionic acid (60 mg) and the mixture was heated at 50° C. for 18 h. The mixture was then concentrated in vacuo and the residue was purified by column chromatography (SiO$_2$; gradient: heptane/EtOAc) to give (RS)-3-[4-((R)-2-phenyl-propionylamino)-phenyl]-pyrrolidine-1-carboxylic acid tert-butyl ester (107 mg, quant.) as a colourless oil. MS (ISP): 417.3 ([M+Na]$^+$), 412.3 ([M+NH$_4$]$^+$), 395.2 ([M+H]$^+$), 339.2 ([M+H—C$_4$H$_8$]$^+$).

b) (R)-2-Phenyl-N—((RS)-4-pyrrolidin-3-yl-phenyl)-propionamide

To a stirred solution of (RS)-3-[4-((R)-2-phenyl-propionylamino)-phenyl]-pyrrolidine-1-carboxylic acid tert-butyl ester (100 mg) in THF (2 ml) was added dropwise a solution of hydrogen chloride in dioxane (0.95 ml, 4 M solution) and the mixture was heated at 60° C. overnight. The mixture was then cooled to 0° C. and made basic by addition of 5 M aq. sodium hydroxide solution. The mixture was diluted with ethyl acetate/THF (1:1) and the phases were then separated.

The organic layer was dried over MgSO4, filtered and concentrated in vacuo. The residue was purified by column chromatography (SiO$_2$; gradient: heptane/EtOAc) to afford (R)-2-phenyl-N—((RS)-4-pyrrolidin-3-yl-phenyl)-propionamide (63 mg, 83%) as an amorphous colourless solid. MS (ISP): 295.2 ([M+H]$^+$).

Example 30

(S)-2-Phenyl-N—((RS)-4-pyrrolidin-3-yl-phenyl)-propionamide

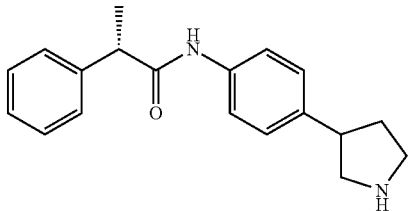 [SMILES: C[C@H](C(=O)Nc1ccc(C2CCNC2)cc1)c1ccccc1]

The title compound was obtained in analogy to example 29 using (S)-2-phenylpropionic acid instead of (R)-2-phenylpropionic acid. Off-white solid. MS (ISP): 295.2 ([M+H]$^+$).

Example 31

(RS)-3-(2-Chloro-phenyl)-N-(4-pyrrolidin-3-yl-phenyl)-propionamide

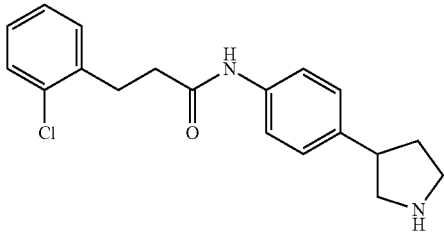 [SMILES: O=C(CCc1ccccc1Cl)Nc1ccc(C2CCNC2)cc1]

The title compound was obtained in analogy to example 29 using 3-(2-chloro-phenyl)propionic acid instead of (R)-2-phenylpropionic acid. Colourless amorphous solid. MS (ISP): 331.1 ([$\{^{37}Cl\}$M+H]$^+$), 329.1 ([$\{^{35}Cl\}$M+H]$^+$).

Example 32

(RS)-4-Chloro-N-[4-(1-methyl-pyrrolidin-3-yl)-phenyl]-benzamide

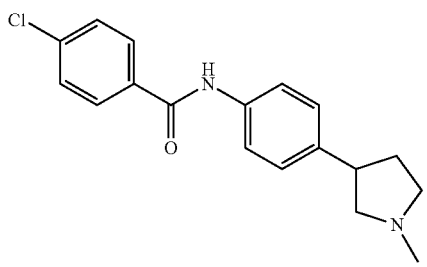 [SMILES: CN1CCC(c2ccc(NC(=O)c3ccc(Cl)cc3)cc2)C1]

To a stirred suspension of (RS)-4-chloro-N-(4-pyrrolidin-3-yl-phenyl)-benzamide hydrochloride (100 mg, Example 16) in methanol (5 ml) were added sequentially sodium acetate (24 mg), formaldehyde (0.11 ml, 37% aqueous solution), zinc chloride (162 mg) and sodium cyanoborohydride (65 mg) and the mixture was heated at 50° C. overnight. The mixture was then cooled to room temperature and made basic by dropwise addition of 25% aq. ammonia solution. The mixture was then concentrated in vacuo and the residue was purified by column chromatography (Isolute® Flash-NH$_2$ from Separtis; gradient: heptane/ethyl acetate/methanol) to afford (RS)-4-chloro-N-[4-(1-methyl-pyrrolidin-3-yl)-phenyl]-benzamide (80 mg, 86%) as a white solid. MS (ISP): 317.2 ([$\{^{37}Cl\}$M+H]$^+$), 315.2 ([$\{^{35}Cl\}$M+H]$^+$).

Example 33

(RS)-4-Chloro-N-[4-(1-ethyl-pyrrolidin-3-yl)-phenyl]-benzamide

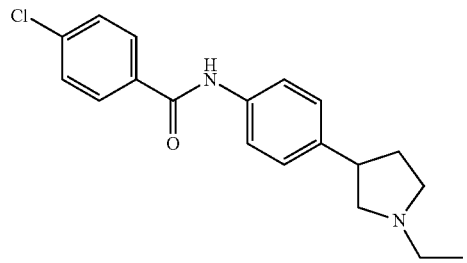 [SMILES: CCN1CCC(c2ccc(NC(=O)c3ccc(Cl)cc3)cc2)C1]

To a stirred suspension of (RS)-4-chloro-N-(4-pyrrolidin-3-yl-phenyl)-benzamide hydrochloride (100 mg, Example 16) in 1,2-dichloroethane (6 ml) were added sequentially sodium acetate (24 mg), acetaldehyde (0.08 ml), acetic acid (0.02 ml) and sodium triacetoxyborohydride (189 mg) and the mixture was heated at 50° C. overnight. The mixture was then cooled to room temperature and made basic by dropwise addition of 25% aq. ammonia solution. The mixture was then concentrated in vacuo and the residue was purified by column chromatography (Isolute® Flash-NH$_2$ from Separtis; gradient: heptane/ethyl acetate/methanol) to afford (RS)-4-chloro-N-[4-(1-ethyl-pyrrolidin-3-yl)-phenyl]-benzamide (86 mg, 88%) as an off-white solid. MS (ISP): 331.3 ([$\{^{37}Cl\}$M+H]$^+$), 329.3 ([$\{^{35}Cl\}$M+H]$^+$).

Example 34

(RS)—N-[4-(1-Benzyl-pyrrolidin-3-yl)-phenyl]-4-chloro-benzamide

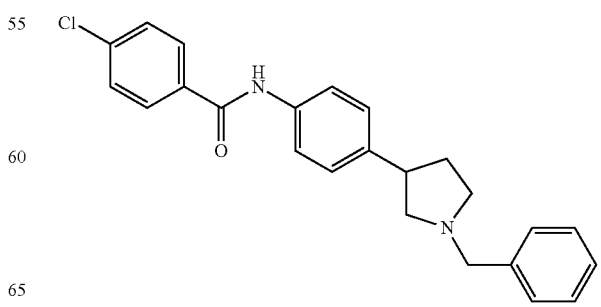

The title compound was obtained in analogy to example 33 using benzaldehyde instead of acetaldehyde. White solid. MS (ISP): 393.2 ([{$^{37}$Cl}M+H]$^+$), 391.2 ([{$^{35}$Cl}M+H]$^+$).

Example 35

(RS)—N-[4-(1-Benzyl-pyrrolidin-3-yl)-phenyl]-4-chloro-benzamide

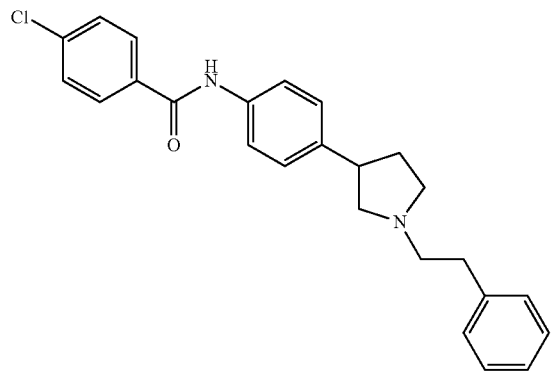 [SMILES: O=C(Nc1ccc(C2CCN(CCc3ccccc3)C2)cc1)c1ccc(Cl)cc1]

The title compound was obtained in analogy to example 33 using phenylacetaldehyde instead of acetaldehyde. Colourless oil. MS (ISP): 407.4 ([{$^{37}$Cl}M+H]$^+$), 405.4 ([{$^{35}$Cl}M+H]$^+$).

Example 36

(RS)-4-Chloro-N-[4-(1-phenyl-pyrrolidin-3-yl)-phenyl]-benzamide

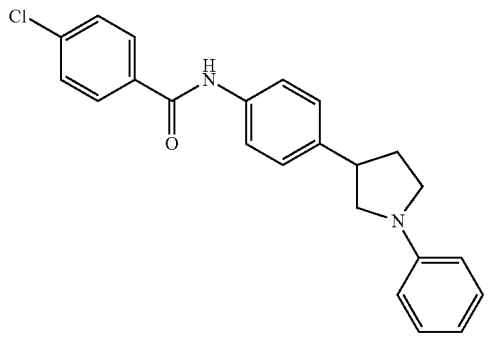 [SMILES: O=C(Nc1ccc(C2CCN(c3ccccc3)C2)cc1)c1ccc(Cl)cc1]

To a stirred solution of (RS)-4-chloro-N-(4-pyrrolidin-3-yl-phenyl)-benzamide hydrochloride (200 mg, Example 16) in DMSO (3 ml) were added sequentially iodobenzene (242 mg), ferric oxide (19 mg), L-proline (27 mg) and sodium tert-butoxide (171 mg) and the mixture was heated at 135° C. overnight. The mixture was then cooled to room temperature and diluted with ethyl acetate. The mixture was washed sequentially with water and with saturated brine and then the organic phase was separated, dried over sodium sulphate and concentrated in vacuo. The residue was purified by column chromatography (SiO$_2$; gradient: heptane/EtOAc) to give (RS)-4-chloro-N-[4-(1-phenyl-pyrrolidin-3-yl)-phenyl]-benzamide (28 mg, 13%) as a light yellow solid. MS (ISP): 407.4 ([{$^{37}$Cl}M+H]$^+$), 405.4 ([{$^{35}$Cl}M+H]$^+$).

Example 37

(RS)-2-(4-Chloro-phenyl)-N—((RS)-4-pyrrolidin-3-yl-phenyl)-propionamide

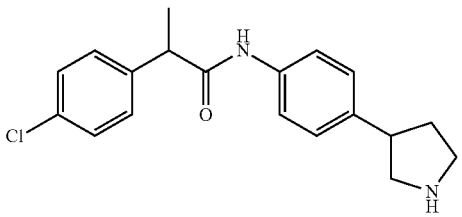 [SMILES: CC(C(=O)Nc1ccc(C2CCNC2)cc1)c1ccc(Cl)cc1]

The title compound was obtained in analogy to example 29 using 4-chloro-alpha-methylphenylacetic acid instead of (R)-2-phenylpropionic acid. Yellow oil. MS (ISP): 331.1 ([{$^{37}$Cl}M+H]$^+$), 329.2 ([{$^{35}$Cl}M+H]$^+$).

Example 38

(RS)-2-Phenyl-N—((RS)-4-pyrrolidin-3-yl-phenyl)-butyramide

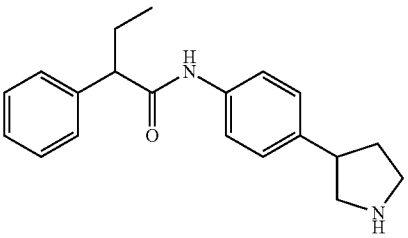 [SMILES: CCC(C(=O)Nc1ccc(C2CCNC2)cc1)c1ccccc1]

The title compound was obtained in analogy to example 29 using (RS)-2-phenylbutyric acid instead of (R)-2-phenylpropionic acid. Yellow oil. MS (ISP): 309.2 ([M+H]$^+$).

Example 39

(RS)-4-Chloro-N-[4-(pyrrolidin-3-yloxy)-phenyl]-benzamide hydrochloride

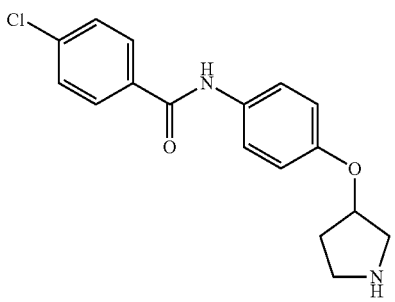 [SMILES: O=C(Nc1ccc(OC2CCNC2)cc1)c1ccc(Cl)cc1]

a) 4-Chloro-N-(4-iodo-phenyl)-benzamide

To a stirred suspension of 4-iodoaniline (1.50 g) in THF (20 ml) were added sequentially triethylamine (1.90 ml) and 4-chlorobenzoyl chloride (0.88 ml) and stirring was continued at room temperature for 4 h. The mixture was then diluted with ethyl acetate and washed sequentially with 0.5 N aq. sodium hydroxide solution, saturated brine, 0.5 N aq. hydrochloric acid and finally with saturated brine. The organic phase was separated, dried over Na$_2$SO$_4$ and concentrate in vacuo to afford 4-chloro-N-(4-iodo-phenyl)-benzamide (2.55 g, quant.) as a light brown solid. MS (EI): 359 ({$^{37}$Cl}M$^+$), 357 ($^{35}$Cl}M$^+$), 141 ([{$^{37}$Cl}M-IC$_6$H$_4$NH]$^+$), 139 ([$^{35}$Cl}M-IC$_6$H$_4$NH]$^+$).

b) (RS)-3-[4-(4-Chloro-benzoylamino)-phenoxy]-pyrrolidine-1-carboxylic acid tert-butyl ester A stirred suspension of 4-chloro-N-(4-iodo-phenyl)-benzamide (500 mg), 1-BOC-3-hydroxypyrrolidine (2.10 g, CAS 103057-44-9), copper(I) iodide (27 mg), 1-10-phenanthroline (50 mg) and caesium carbonate (0.91 g) was heated at 130° C. overnight. The mixture was then cooled to room temperature and diluted with ethyl acetate. The mixture was washed sequentially with water and with saturated brine. The phases were then separated and the organic layer was dried over sodium sulphate, filtered and concentrated in vacuo. The residue was purified by column chromatography (SiO$_2$; gradient: heptane/EtOAc) to afford (RS)-3-[4-(4-chloro-benzoylamino)-phenoxy]-pyrrolidine-1-carboxylic acid tert-butyl ester (47 mg, 8%) as a light brown solid. MS (ISP): 436.2 ([{$^{37}$Cl}M+NH$_4$]$^+$), 434.4 ([{$^{35}$Cl}M+NH$_4$]$^+$), 363.1 ([{$^{37}$Cl}M+H—C$_4$H$_8$]$^+$), 361.2 ([{$^{35}$Cl}M+H—C$_4$H$_8$]$^+$).

c) (RS)-4-Chloro-N-[4-(pyrrolidin-3-yloxy)-phenyl]-benzamide hydrochloride

To a stirred solution of (RS)-3-[4-(4-chloro-benzoylamino)-phenoxy]-pyrrolidine-1-carboxylic acid tert-butyl ester (45 mg) in THF (2 ml) was added dropwise a solution of hydrogen chloride in dioxane (0.40 ml, 4 M solution) and the mixture was heated at 60° C. overnight. The mixture was then cooled to 0° C. and diluted with diethyl ether (5 ml). The ensuing crystals were collected by filtration, washing with diethyl ether, and were dried in vacuo at 60° C. to afford (RS)-4-chloro-N-[4-(pyrrolidin-3-yloxy)-phenyl]-benzamide hydrochloride (31 mg, 81%) as a light brown crystalline solid. MS (ISP): 319.1 ([{$^{37}$Cl}M+H]$^+$), 317.2 ([{$^{35}$Cl}M+H]$^+$).

Example 40

(RS)—N-[4-(1-Benzyl-3-methyl-pyrrolidin-3-yl)-phenyl]-4-chloro-benzamide

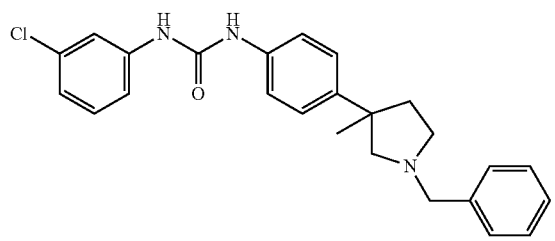 [SMILES: CC1(c2ccc(NC(=O)Nc3cccc(Cl)c3)cc2)CCN(Cc2ccccc2)C1]

a) (RS)-[4-(1-Benzyl-2,5-dioxo-pyrrolidin-3-yl)-phenyl]-carbamic acid tert-butyl ester A stirred suspension of 4-(BOC-amino)benzeneboronic acid pinacol ester (4.40 g, CAS 330793-01-6), N-benzyl-maleimide (2.84 g, CAS 1631-26-1), potassium hydroxide powder (0.77 g) and [RhCl(cod)]$_2$ (0.27 g) in dioxane (48 ml) and water (8 ml) in a sealed tube was heated at 90° C. for 5 minutes under microwave irradiation. The mixture was then cooled to room temperature and filtered through celite. The filtrate was concentrated in vacuo and the residue was purified by column chromatography (SiO$_2$; gradient: heptane/EtOAc) to give (RS)-[4-(1-benzyl-2,5-dioxo-pyrrolidin-3-yl)-phenyl]-carbamic acid tert-butyl ester (3.83 g, 73%) as an off-white solid. MS (ISP): 398.2 ([M+NH$_4$]$^+$), 325.3 ([M+H—C$_4$H$_8$]$^+$).

b) (RS)-[4-(1-Benzyl-3-methyl-2,5-dioxo-pyrrolidin-3-yl)-phenyl]-carbamic acid tert-butyl ester To a stirred suspension of (RS)-[4-(1-benzyl-2,5-dioxo-pyrrolidin-3-yl)-phenyl]-carbamic acid tert-butyl ester (3.80 g) and caesium carbonate (9.76 g) in DMF (20 ml) at 0° C. was added dropwise a solution of methyl iodide (0.50 ml) in DMF (2 ml) and the mixture was then stirred at room temperature for 1 hour. The mixture was then diluted with ethyl acetate and the resulting mixture was washed sequentially with water and with saturated brine. The phases were separated and the organic phase was dried over sodium sulphate and concentrated in vacuo. The residue was purified by column chromatography (SiO$_2$; gradient: heptane/EtOAc) to give (RS)-[4-(1-benzyl-3-methyl-2,5-dioxo-pyrrolidin-3-yl)-phenyl]-carbamic acid tert-butyl ester (0.95 g, 24%) as a yellow solid. MS (ISP): 412.4 ([M+NH$_4$]$^+$), 339.3 ([M+H—C$_4$H$_8$]$^+$).

c) (RS)-3-(4-Amino-phenyl)-1-benzyl-3-methyl-pyrrolidine-2,5-dione

To a stirred solution of (RS)-[4-(1-benzyl-3-methyl-2,5-dioxo-pyrrolidin-3-yl)-phenyl]-carbamic acid tert-butyl ester (0.94 g) in THF (15 ml) was added dropwise a solution of hydrogen chloride in dioxane (8.9 ml, 4 M solution) and the mixture was heated at 60° C. overnight. The mixture was then cooled to 0° C. and diluted with ethyl acetate. The mixture was then made basic by addition of 5 M aq. sodium hydroxide solution. The phases were then separated and the organic layer was washed with saturated brine. The phases were then separated and the organic layer was dried over sodium sulphate, filtered and concentrated in vacuo. The residue was purified by column chromatography (SiO$_2$; gradient: heptane/EtOAc) to afford (RS)-3-(4-amino-phenyl)-1-benzyl-3-methyl-pyrrolidine-2,5-dione (0.57 g, 81%) as a yellow solid. MS (ISP): 295.3 ([M+H]$^+$).

d) (RS)-4-(1-Benzyl-3-methyl-pyrrolidin-3-yl)-phenylamine

To a stirred solution of (RS)-3-(4-amino-phenyl)-1-benzyl-3-methyl-pyrrolidine-2,5-dione (0.56 g) in THF (20 ml) was added portionwise lithium aluminium hydride (0.29 g) and the mixture was then stirred at 70° C. for 1 hour. The mixture was then cooled to 0° C. and quenched by dropwise addition of 4 M aq. hydrochloric acid. The mixture was then made basic by addition of 5 N aq. sodium hydroxide solution and subsequently diluted with ethyl acetate/THF (2:1) and then washed with saturated brine. The organic phase was separated, dried over Na$_2$SO$_4$ and concentrated in vacuo to afford (RS)-4-(1-benzyl-3-methyl-pyrrolidin-3-yl)-phenylamine (424 mg, 84%) as a yellow oil. MS (ISP): 267.2 ([M+H]$^+$).

e) (RS)—N-[4-(1-Benzyl-3-methyl-pyrrolidin-3-yl)-phenyl]-4-chloro-benzamide

To a stirred suspension of ((RS)-4-(1-benzyl-3-methyl-pyrrolidin-3-yl)-phenylamine (420 mg) in THF (5 ml) were added sequentially triethylamine (0.55 ml) and 4-chlorobenzoyl chloride (0.30 ml) and stirring was continued at room temperature for 3 h. The mixture was then diluted with ethyl acetate and then washed sequentially with water and with saturated brine. The organic phase was separated, dried over $Na_2SO_4$ and concentrate in vacuo. The residue was purified by column chromatography (Isolute® Flash-$NH_2$ from Separtis; gradient: heptane/ethyl acetate/methanol) to afford (RS)—N-[4-(1-benzyl-3-methyl-pyrrolidin-3-yl)-phenyl]-4-chloro-benzamide (262 mg, 41%) as an off-white solid. MS (ISP): 407.4 ($[\{^{37}Cl\}M+H]^+$), 405.4 ($[\{^{35}Cl\}M+H]^+$).

Example 41

(RS)—N-[4-(3-Methyl-pyrrolidin-3-yl)-phenyl]-benzamide

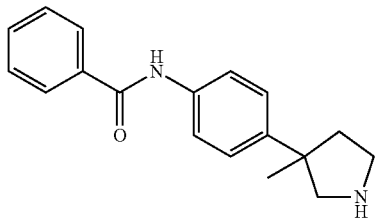 [SMILES: CC1(c2ccc(NC(=O)c3ccccc3)cc2)CCNC1]

To a stirred suspension of (RS)—N-[4-(1-benzyl-3-methyl-pyrrolidin-3-yl)-phenyl]-4-chloro-benzamide (36 mg) in methanol (2 ml) were added ammonium formate (90 mg) and palladium on charcoal (19 mg, 10 wt %) and the mixture was heated at 100° C. for 1 hours. The mixture was then cooled to room temperature, filtered through celite and the filtrate was concentrated in vacuo. The residue was taken up in ethyl acetate and the resulting solution was washed with saturated brine. The organic phase was then separated, dried over sodium sulphate and concentrated in vacuo. The residue was purified by column chromatography (Isolute® Flash-$NH_2$ from Separtis; gradient: heptane/dichloromethane/methanol) to give (RS)—N-[4-(3-methyl-pyrrolidin-3-yl)-phenyl]-benzamide (12 mg, 48%) as a yellow solid. MS (ISP): 281.2 ($[M+H]^+$).

Example 42

(RS)-5-Chloro-pyridine-2-carboxylic acid (4-pyrrolidin-3-yl-phenyl)-amide hydrochloride

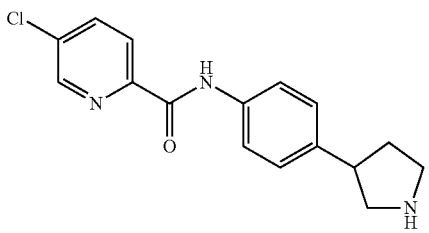 [SMILES: O=C(Nc1ccc(C2CCNC2)cc1)c1ccc(Cl)cn1]

The title compound was obtained in analogy to example 29 using 5-chloro-2-pyridinecarboxylic acid (CAS 86873-60-1) instead of (R)-2-phenylpropionic acid. White solid. MS (ISP): 304.1 ($[\{^{37}Cl\}M+H]^+$), 302.2 ($[\{^{35}Cl\}M+H]^+$).

Example 43

(RS)-6-Chloro-pyridine-3-carboxylic acid (4-pyrrolidin-3-yl-phenyl)-amide hydrochloride

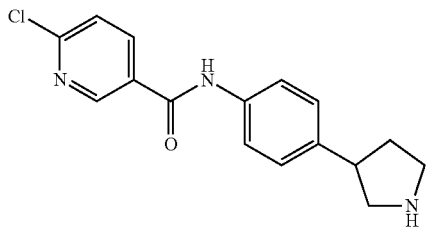 [SMILES: O=C(Nc1ccc(C2CCNC2)cc1)c1ccc(Cl)nc1]

The title compound was obtained in analogy to example 29 using 6-chloronicotinic acid (CAS 5326-23-8) instead of (R)-2-phenylpropionic acid. White solid. MS (ISP): 304.1 ($[\{^{37}Cl\}M+H]^+$), 302.2 ($[\{^{35}Cl\}M+H]^+$).

Example 44

(RS)-1-(5-Chloro-pyridin-2-yl)-3-(4-pyrrolidin-3-yl-phenyl)-urea hydrochloride

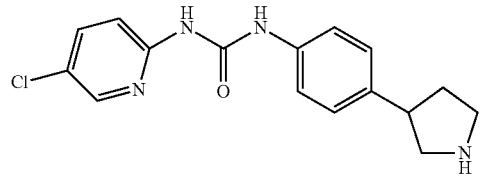 [SMILES: O=C(Nc1ccc(C2CCNC2)cc1)Nc1ccc(Cl)cn1]

The title compound was obtained in analogy to example 6 using 5-chloro-2-isocyanatopyridine (CAS 95735-68-5) instead of phenyl isocyanate. Off-white solid. MS (ISP): 319.1 ($[\{^{37}Cl\}M+H]^+$), 317.2 ($[\{^{35}Cl\}M+H]^+$).

Example 45

(RS)-(4-Pyrrolidin-3-yl-phenyl)-carbamic acid 4,4-difluoro-cyclohexyl ester

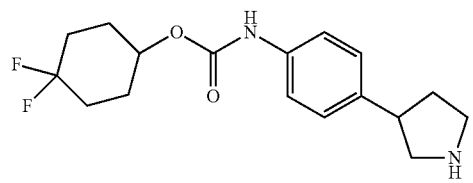

a) (RS)-3-(4-Isocyanato-phenyl)-pyrrolidine-1-carboxylic acid tert-butyl ester

To a stirred solution of (RS)-tert-butyl 3-(4-aminophenyl) pyrrolidine-1-carboxylate (500 mg, CAS 908334-28-1) in dichloromethane (8 ml) were added sequentially triethylamine (0.53 ml) and triphosgene (209 mg) and the mixture was heated at 45° C. for 18 h. The mixture was then concentrated in vacuo and the residue was resuspended in diethyl ether (15 ml) and stirred at room temperature for 5 min. The ensuing crystals were removed by filtration and the filtrate was concentrated in vacuo to afford (RS)-3-(4-isocyanato-phenyl)-pyrrolidine-1-carboxylic acid tert-butyl ester (600 mg, quant.) as a yellow oil which was used in the next step without further purification.

b) (RS)-3-[4-(4,4-Difluoro-cyclohexyloxycarbo-nylamino)-phenyl]-pyrrolidine-1-carboxylic acid tert-butyl ester To a stirred suspension of (RS)-3-(4-isocyanato-phenyl)-pyrrolidine-1-carboxylic acid tert-butyl ester (110 mg) in THF (1 ml) were added sequentially N,N-diisopropylethyl-amine (0.13 ml) and 4,4-difluorocyclohexanol (68 mg, CAS 22419-35-8) and the mixture was heated at 110° C. for 18 h. The mixture was then concentrated in vacuo and the residue was purified by column chromatography (SiO$_2$; gradient: heptane/EtOAc) to give (RS)-3-[4-(4,4-difluoro-cyclohexy-loxycarbonylamino)-phenyl]-pyrrolidine-1-carboxylic acid tert-butyl ester (20 mg, 12%) as an off-white solid. MS (ISP): 447.4 ([M+Na]$^+$), 442.4 ([M+NH$_4$]$^+$), 369.2 ([M+H—C$_4$H$_8$]$^+$).

c) (RS)-(4-Pyrrolidin-3-yl-phenyl)-carbamic acid 4,4-difluoro-cyclohexyl ester

To a stirred solution of (RS)-3-[4-(4,4-difluoro-cyclo-hexyloxycarbonylamino)-phenyl]-pyrrolidine-1-carboxylic acid tert-butyl ester (20 mg) in THF (2 ml) was added dropwise a solution of hydrogen chloride in dioxane (0.18 ml, 4 M solution) and the mixture was heated at 60° C. overnight. The mixture was then cooled to 0° C. and made basic by addition of 5 M aq. sodium hydroxide solution. The mixture was diluted with ethyl acetate/THF (1:1) and the phases were then separated. The organic layer was dried over MgSO4, filtered and concentrated in vacuo. The residue was purified by column chromatography (Isolute® Flash-NH$_2$ from Separtis; gradient: heptane/dichlorometh-ane/methanol) to afford (RS)-(4-pyrrolidin-3-yl-phenyl)-carbamic acid 4,4-difluoro-cyclohexyl ester (10 mg, 65%) as an amorphous yellow solid. MS (ISP): 325.4 ([M+H]$^+$).

Example 46

(RS)-(4-Pyrrolidin-3-yl-phenyl)-carbamic acid 2-(4-fluoro-phenyl)-ethyl ester

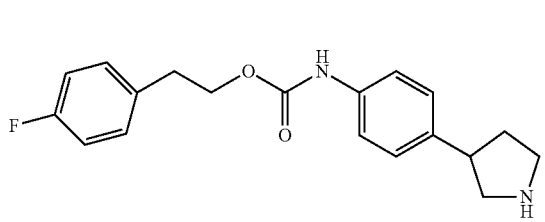 [SMILES: O=C(Nc1ccc(C2CCNC2)cc1)OCCc1ccc(F)cc1]

The title compound was obtained in analogy to example 45 using 4-fluoro-phenylethyl alcohol instead of 4,4-difluo-rocyclohexanol. Yellow amorphous solid. MS (ISP): 329.3 ([M+H]$^+$).

Example 47

(RS)-(4-Pyrrolidin-3-yl-phenyl)-carbamic acid 4-fluoro-benzyl ester hydrochloride

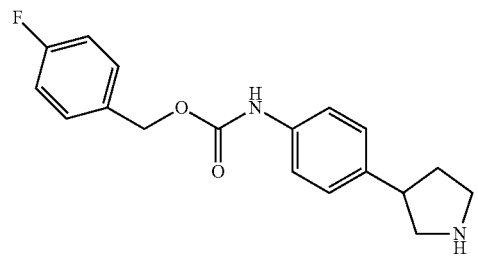 [SMILES: O=C(Nc1ccc(C2CCNC2)cc1)OCc1ccc(F)cc1]

The title compound was obtained in analogy to example 45 using 4-fluoro-benzyl alcohol instead of 4,4-difluorocy-clohexanol. White solid. MS (ISP): 351.2 ([M+H]$^+$).

Example 48

(S)-2-Methoxy-2-phenyl-N—((RS)-4-pyrrolidin-3-yl-phenyl)-acetamide

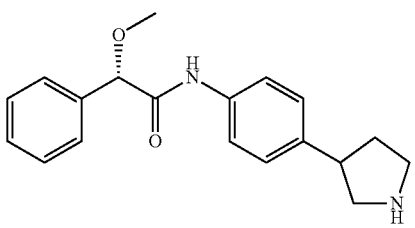 [SMILES: CO[C@H](C(=O)Nc1ccc(C2CCNC2)cc1)c1ccccc1]

The title compound was obtained in analogy to example 29 using (S)-alpha-methoxyphenylacetic acid (CAS 26164-26-1) instead of (R)-2-phenylpropionic acid. Yellow oil. MS (ISP): 311.3 ([M+H]$^+$).

Example 49

(R)-2-Methoxy-2-phenyl-N—((RS)-4-pyrrolidin-3-yl-phenyl)-acetamide

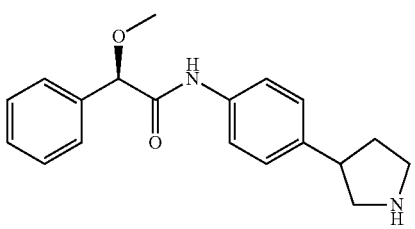 [SMILES: CO[C@@H](C(=O)Nc1ccc(C2CCNC2)cc1)c1ccccc1]

The title compound was obtained in analogy to example 29 using (R)-alpha-methoxyphenylacetic acid (CAS 3966-32-3) instead of (R)-2-phenylpropionic acid. Colourless oil. MS (ISP): 311.3 ([M+H]$^+$).

Example 50

(RS)-2-(4-Bromo-phenyl)-2-methoxy-N—((RS)-4-pyrrolidin-3-yl-phenyl)-acetamide

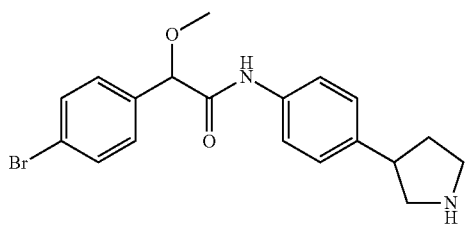

The title compound was obtained in analogy to example 29 using (RS)-(4-bromo-phenyl)-methoxy-acetic acid (CAS 16053-90-0) instead of (R)-2-phenylpropionic acid. Colourless amorphous solid. MS (ISP): 391.1 ([{$^{81}$Br}M+H]$^+$), 389.0 ([{$^{79}$Br}M+H]$^+$).

Example 51

(RS)-4-Methoxymethyl-N-(4-pyrrolidin-3-yl-phenyl)-benzamide hydrochloride

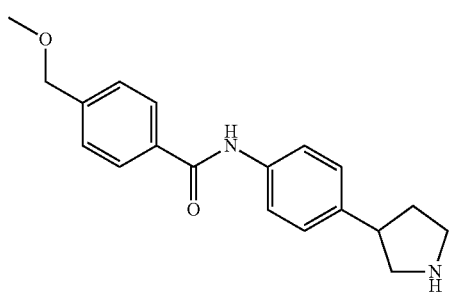 [SMILES: COCc1ccc(C(=O)Nc2ccc(C3CCNC3)cc2)cc1]

The title compound was obtained in analogy to example 29 using 4-methoxymethyl-benzoic acid (CAS 67003-50-3) instead of (R)-2-phenylpropionic acid. Off-white solid. MS (ISP): 311.3 ([M+H]$^+$).

Example 52

(RS)-4-Ethoxy-N-(4-pyrrolidin-3-yl-phenyl)-benzamide hydrochloride

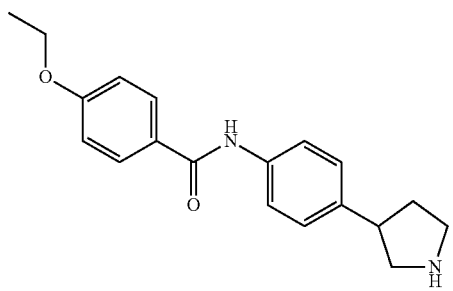 [SMILES: CCOc1ccc(C(=O)Nc2ccc(C3CCNC3)cc2)cc1]

The title compound was obtained in analogy to example 29 using 4-ethoxy-benzoic acid (CAS 619-86-3) instead of (R)-2-phenylpropionic acid. Off-white solid. MS (ISP): 311.3 ([M+H]$^+$).

Example 53

(RS)-4-Propyl-N-(4-pyrrolidin-3-yl-phenyl)-benzamide hydrochloride

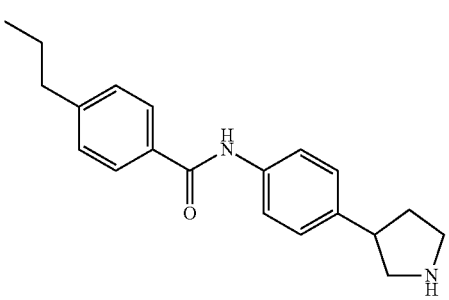 [SMILES: CCCc1ccc(C(=O)Nc2ccc(C3CCNC3)cc2)cc1]

The title compound was obtained in analogy to example 29 using 4-propyl-benzoic acid (CAS 2438-05-3) instead of (R)-2-phenylpropionic acid. White solid. MS (ISP): 309.2 ([M+H]$^+$).

Example 54

(RS)-4-Ethynyl-N-(4-pyrrolidin-3-yl-phenyl)-benzamide hydrochloride

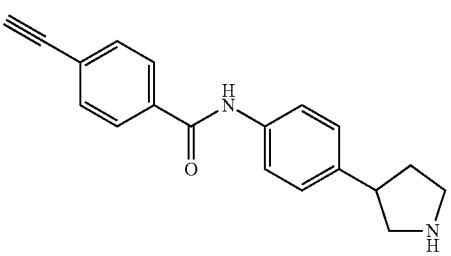 [SMILES: C#Cc1ccc(C(=O)Nc2ccc(C3CCNC3)cc2)cc1]

The title compound was obtained in analogy to example 29 using 4-ethynyl-benzoic acid (CAS 10602-00-3) instead of (R)-2-phenylpropionic acid. White solid. MS (ISP): 291.2 ([M+H]$^+$).

Example 55

(RS)-4-Cyano-N-(4-pyrrolidin-3-yl-phenyl)-benzamide hydrochloride

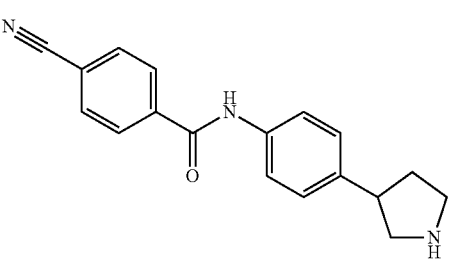 [SMILES: N#Cc1ccc(C(=O)Nc2ccc(C3CCNC3)cc2)cc1]

The title compound was obtained in analogy to example 29 using 4-cyano-benzoic acid (CAS 619-65-8) instead of (R)-2-phenylpropionic acid. White solid. MS (ISP): 292.1 ([M+H]$^+$).

Example 56

(RS)-3,4-Dichloro-N-(4-pyrrolidin-3-yl-phenyl)-benzamide hydrochloride

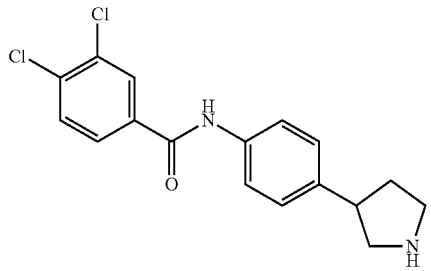 [SMILES: O=C(Nc1ccc(C2CCNC2)cc1)c1ccc(Cl)c(Cl)c1]

The title compound was obtained in analogy to example 29 using 3,4-dichloro-benzoic acid instead of (R)-2-phenylpropionic acid. White solid. MS (ISP): 339.2 ([{$^{37}$Cl}M+H]$^+$), 337.2 ([{$^{37}$Cl$^{35}$Cl}M+H]$^+$), 335.1 ([{$^{35}$Cl}M+H]$^+$).

Example 57

4-Chloro-N-(4-piperidin-4-yl-phenyl)-benzamide hydrochloride

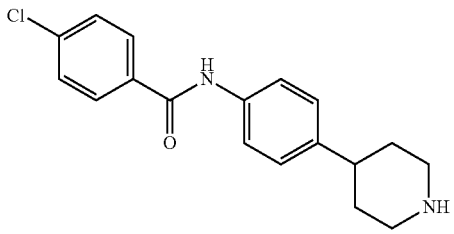 [SMILES: O=C(Nc1ccc(C2CCNCC2)cc1)c1ccc(Cl)cc1]

The title compound was obtained in analogy to example 29 using tert-butyl 4-(4-aminophenyl)-1-piperidinecarboxylate (CAS 170011-57-1) instead of (RS)-tert-butyl 3-(4-aminophenyl)pyrrolidine-1-carboxylate and 4-chloro-benzoic acid instead of (R)-2-phenylpropionic acid. Off-white solid. MS (ISP): 317.1 ([{$^{37}$Cl}M+H]$^+$), 315.1 ([{$^{35}$Cl}M+H]$^+$).

Example 58

(RS)-4-Chloro-N-(4-piperidin-3-yl-phenyl)-benzamide hydrochloride

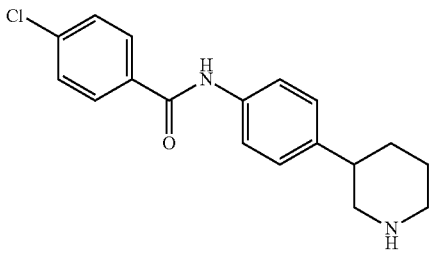 [SMILES: O=C(Nc1ccc(C2CCCNC2)cc1)c1ccc(Cl)cc1]

The title compound was obtained in analogy to example 29 using (RS)-tert-butyl 3-(4-aminophenyl)-1-piperidinecarboxylate (CAS 875798-79-1) instead of (RS)-tert-butyl 3-(4-aminophenyl)pyrrolidine-1-carboxylate and 4-chlorobenzoic acid instead of (R)-2-phenylpropionic acid. Off-white solid. MS (ISP): 317.1 ([{$^{37}$Cl}M+H]$^+$), 315.1 ([{$^{35}$Cl}M+H]$^+$).

Example 59

4-Chloro-N-(4-piperazin-1-yl-phenyl)-benzamide hydrochloride

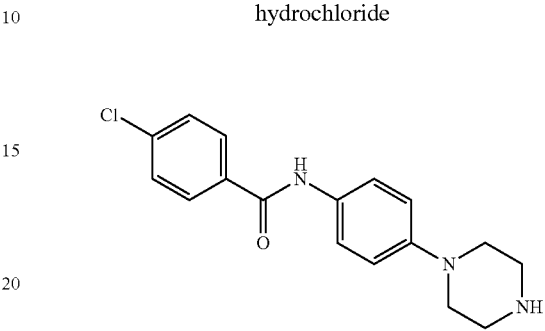

The title compound was obtained in analogy to example 29 using tert-butyl 4-(4-aminophenyl)-1-piperazinecarboxylate (CAS 170911-92-9) instead of (RS)-tert-butyl 3-(4-aminophenyl)pyrrolidine-1-carboxylate and 4-chloro-benzoic acid instead of (R)-2-phenylpropionic acid. Off-white solid. MS (ISP): 318.1 ([{$^{37}$Cl}M+H]$^+$), 316.1 ([{$^{35}$Cl}M+H]$^+$).

Example 60

(RS)-2-(4-Chloro-phenyl)-2-methoxy-N—((RS)-4-pyrrolidin-3-yl-phenyl)-acetamide

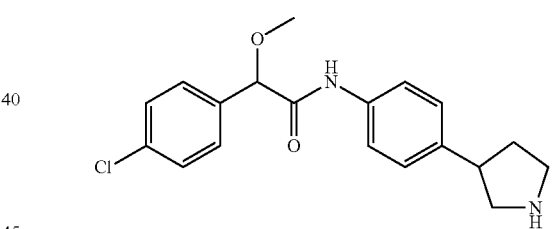

The title compound was obtained in analogy to example 29 using (4-chloro-phenyl)-methoxy-acetic acid (CAS 4674-24-2) instead of (R)-2-phenylpropionic acid. Yellow solid. MS (ISP): 347.2 ([{$^{37}$Cl}M+H]$^+$), 345.1 ([{$^{35}$Cl}M+H]$^+$).

Example 61

(RS)—N—((RS)-4-Pyrrolidin-3-yl-phenyl)-2-(3-trifluoromethyl-phenyl)-propionamide

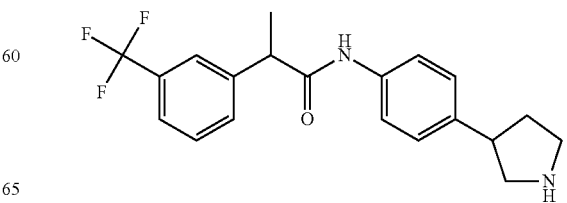

The title compound was obtained in analogy to example 29 using (RS)-2-(3-trifluoromethyl-phenyl)-propionic acid (CAS 68718-08-1) instead of (R)-2-phenylpropionic acid. Colourless amorphous solid. MS (ISP): 363.3 (M+H)$^+$.

Example 62

(RS)—N-(4-Pyrrolidin-3-yl-phenyl)-2-(3-trifluoromethoxy-phenyl)-propionamide

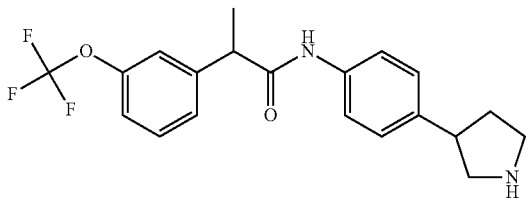 [SMILES: CC(C(=O)Nc1ccc(C2CCNC2)cc1)c1cccc(OC(F)(F)F)c1]

The title compound was obtained in analogy to example 29 using (RS)-2-(3-trifluoromethoxy-phenyl)-propionic acid instead of (R)-2-phenylpropionic acid. Yellow amorphous solid. MS (ISP): 379.3 (M+H)$^+$.

Example 63

4-Chloro-N-[4-((3RS,4SR)-4-hydroxy-pyrrolidin-3-yl)-phenyl]-benzamide hydrochloride

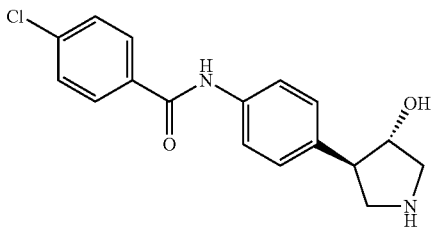 [SMILES: O=C(Nc1ccc([C@@H]2CNC[C@H]2O)cc1)c1ccc(Cl)cc1]

a) (3RS,4SR)-3-(4-Bromo-phenyl)-4-hydroxy-pyrrolidine-1-carboxylic acid tert-butyl ester To a stirred solution of 1,4-dibromobenzene (3.49 g) in dry THF (30 ml) under an argon atmosphere at −78° C. was added dropwise n-butyllithium solution (9.25 ml, 1.6 M solution in hexane) and stirring continued for 30 min. Boron trifluoride etherate (1.86 ml) was then added dropwise and stirring continued for a further 10 min. A solution of (1R,5S)-6-oxa-3-aza-bicyclo[3.1.0]hexane-3-carboxylic acid tert-butyl ester (1.37 g, CAS 114214-49-2) in THF (4 ml) was then added dropwise and the mixture was stirred at −78° C. for a further 2 h before being quenched by dropwise addition of aqueous sodium bicarbonate solution (20 ml). The mixture was allowed to warm to room temperature and was then diluted with ethyl acetate/THF (1:1). The mixture was washed with saturated brine and then the phases were separated and the organic phase was dried over sodium sulphate, filtered and concentrated in vacuo. The residue was purified by column chromatography (SiO$_2$; gradient: heptane/EtOAc) to give (3RS,4SR)-3-(4-bromo-phenyl)-4-hydroxy-pyrrolidine-1-carboxylic acid tert-butyl ester as a colourless amorphous solid. MS (ISP): 344.0 ([$^{81}$Br}M+H]$^+$), 342.0 ([$^{79}$Br}M+H]$^+$), 288.0 ([$^{81}$Br}M+H—C$_4$H$_8$]$^+$), 286.0 ([$^{79}$Br}M+H—C$_4$H$_8$]$^+$).

b) (3RS,4SR)-3-[4-(4-Chloro-benzoylamino)-phenyl]-4-hydroxy-pyrrolidine-1-carboxylic acid tert-butyl ester A stirred suspension of (3RS,4SR)-3-(4-bromo-phenyl)-4-hydroxy-pyrrolidine-1-carboxylic acid tert-butyl ester (810 mg), 4-chlorobenzamide (552 mg), caesium carbonate (1.54 g), N,N'-dimethylethylenediamine (0.06 ml) and copper(I) iodide (45 mg) in dioxane (8 ml) under an atmosphere of argon in a sealed tube was heated at 120° C. for 18 h. The mixture was then cooled to room temperature, filtered through celite and the filtrate was concentrated in vacuo. The residue was taken up in ethyl acetate and the resulting solution was washed sequentially with water and with saturated brine. The organic phase was then separated, dried over sodium sulphate and concentrated in vacuo. The residue was purified by column chromatography (SiO$_2$; gradient: heptane/EtOAc) to give (3RS,4SR)-3-[4-(4-chloro-benzoylamino)-phenyl]-4-hydroxy-pyrrolidine-1-carboxylic acid tert-butyl ester (800 mg, 81%) as a white solid. MS (ISP): 441.3 ([$^{37}$Cl}M+Na]$^+$), 439.3 ([$^{35}$Cl}M+Na]$^+$), 363.1 ([$^{37}$Cl}M+H—C$_4$H$_8$]$^+$), 361.2 ([$^{35}$Cl}M+H—C$_4$H$_8$]$^+$).

c) 4-Chloro-N-[4-((3RS,4SR)-4-hydroxy-pyrrolidin-3-yl)-phenyl]-benzamide hydrochloride To a stirred solution of (3RS,4SR)-3-[4-(4-chloro-benzoylamino)-phenyl]-4-hydroxy-pyrrolidine-1-carboxylic acid tert-butyl ester (47 mg) in THF (1.5 ml) was added dropwise a solution of hydrogen chloride in dioxane (0.42 ml, 4 M solution) and the mixture was heated at 60° C. overnight. The mixture was then cooled to 0° C. and the ensuing crystals were collected by filtration, washing once with THF and once with diethyl ether, and were dried in vacuo at 60° C. to afford 4-chloro-N-[4-((3RS,4SR)-4-hydroxy-pyrrolidin-3-yl)-phenyl]-benzamide hydrochloride (31 mg, 81%) as a white crystalline solid. MS (ISP): 319.0 ([$^{37}$Cl}M+H]$^+$), 317.1 ([$^{35}$Cl}M+H]$^+$).

Example 64

(RS)-2-(3-Benzoyl-phenyl)-N—((RS)-4-pyrrolidin-3-yl-phenyl)-propionamide

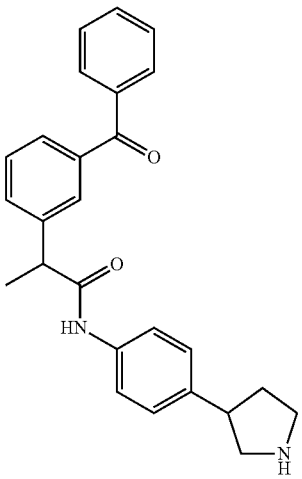 [SMILES: CC(C(=O)Nc1ccc(C2CCNC2)cc1)c1cccc(C(=O)c2ccccc2)c1]

The title compound was obtained in analogy to example 29 using (RS)-ketoprofen (CAS 22071-15-4) instead of (R)-2-phenylpropionic acid. White solid. MS (ISP): 399.2 (M+H)$^+$.

Example 65

(RS)-2-(3-Methoxy-phenyl)-N-(4-pyrrolidin-3-yl-phenyl)-acetamide hydrochloride

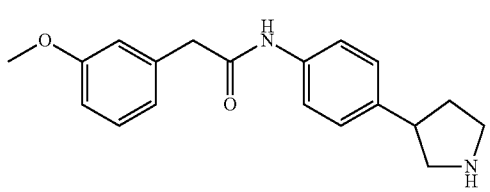 [SMILES: COc1cccc(CC(=O)Nc2ccc(C3CCNC3)cc2)c1]

The title compound was obtained in analogy to example 29 using 3-methoxy-phenylacetic acid instead of (R)-2-phenylpropionic acid. White solid. MS (ISP): 311.2 (M+H)$^+$).

Example 66

(RS)-2-(3-Cyano-phenyl)-N-(4-pyrrolidin-3-yl-phenyl)-acetamide

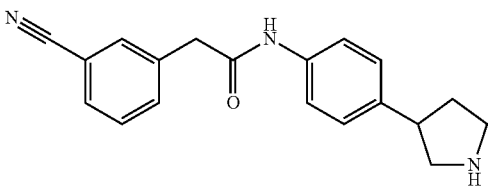 [SMILES: N#Cc1cccc(CC(=O)Nc2ccc(C3CCNC3)cc2)c1]

The title compound was obtained in analogy to example 29 using 3-cyano-phenylacetic acid instead of (R)-2-phenylpropionic acid. Colourless oil. MS (ISP): 306.2 (M+H)$^+$).

Example 67

(RS)-2-(3-Methoxy-phenyl)-N—((RS)-4-pyrrolidin-3-yl-phenyl)-propionamide

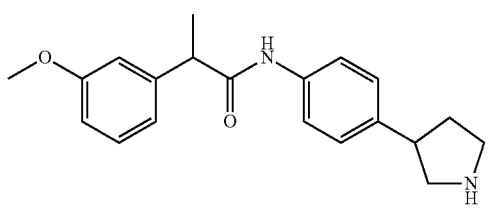 [SMILES: COc1cccc(C(C)C(=O)Nc2ccc(C3CCNC3)cc2)c1]

The title compound was obtained in analogy to example 29 using 2-(3-methoxy-phenyl)-propionic acid (CAS 3146-60-9) instead of (R)-2-phenylpropionic acid. Yellow oil. MS (ISP): 325.2 (M+H)$^+$).

Example 68

(RS)-2-(3-Cyano-phenyl)-N—((RS)-4-pyrrolidin-3-yl-phenyl)-propionamide

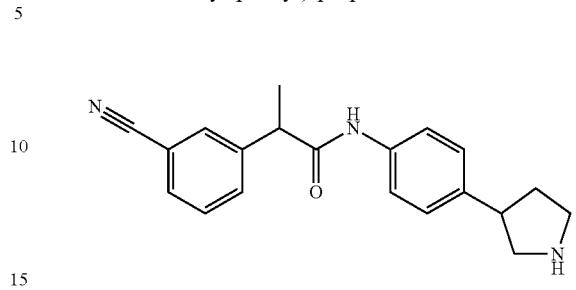

The title compound was obtained in analogy to example 29 using 2-(3-cyano-phenyl)-propionic acid instead of (R)-2-phenylpropionic acid. Yellow oil. MS (ISP): 320.2 (M+H)$^+$).

Example 69

4-Chloro-N-[4-((3RS,4RS)-4-fluoro-pyrrolidin-3-yl)-phenyl]-benzamide hydrochloride

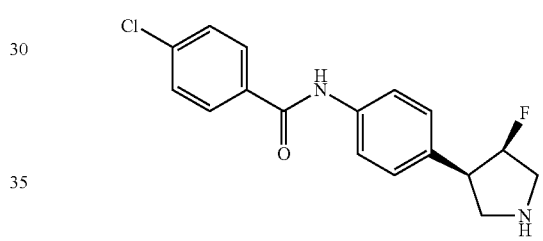

a) (3RS,4RS)-3-[4-(4-Chloro-benzoylamino)-phenyl]-4-fluoro-pyrrolidine-1-carboxylic acid tert-butyl ester To a stirred suspension of (3RS,4SR)-3-[4-(4-chloro-benzoylamino)-phenyl]-4-hydroxy-pyrrolidine-1-carboxylic acid tert-butyl ester (730 mg, example 63(b)) in dichloroethane (15 ml) and acetonitrile (15 ml) at 0° C. was added dropwise diethylaminosulphur trifluoride (0.46 ml) and the mixture was then stirred at room temperature for 1 h. The mixture was then concentrated in vacuo and the residue was purified by column chromatography (SiO$_2$; gradient: heptane/EtOAc) to give (3RS,4RS)-3-[4-(4-chloro-benzoylamino)-phenyl]-4-fluoro-pyrrolidine-1-carboxylic acid tert-butyl ester (112 mg, 15%) as a white solid. MS (ISP): 438.4 ([{$^{37}$Cl}M+NH$_4$]$^+$), 436.3 ([{$^{35}$Cl}M+NH$_4$]$^+$), 365.1 ([{$^{37}$Cl}M+H—C$_4$H$_8$]$^+$), 363.0 ([{$^{35}$Cl}M+H—C$_4$H$_8$]$^+$).

b) 4-Chloro-N-[4-((3RS,4RS)-4-fluoro-pyrrolidin-3-yl)-phenyl]-benzamide hydrochloride To a stirred solution of (3RS,4RS)-3-[4-(4-chloro-benzoylamino)-phenyl]-4-fluoro-pyrrolidine-1-carboxylic acid tert-butyl ester (110 mg) in THF (2 ml) was added dropwise a solution of hydrogen chloride in dioxane (0.98 ml, 4 M solution) and the mixture was heated at 60° C. overnight. The mixture was then cooled to 0° C. and diluted with ethyl acetate. The ensuing crystals were collected by filtration, washing twice with ethyl acetate and twice with diethyl ether, and then dried in vacuo at 60° C. to afford 4-chloro-N-[4-((3RS,4RS)-4-fluoro-pyrrolidin-3-yl)-phenyl]-benzamide hydrochloride (81 mg, 87%) as a white crystalline solid. MS (ISP): 321.1 ([{$^{37}$Cl}M+H]$^+$), 319.1 ([{$^{35}$Cl}M+H]$^+$).

Example 70

(RS)-4-Chloro-N-[3-(pyrrolidin-3-yloxy)-phenyl]-benzamide

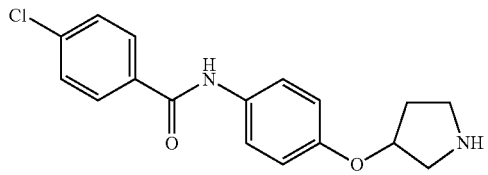 [SMILES: O=C(Nc1ccc(OC2CCNC2)cc1)c1ccc(Cl)cc1]

The title compound was obtained in analogy to example 39 using 3-iodoaniline instead of 4-iodoaniline. Light yellow gum. MS (ISP): 319.2 ([{$^{37}$Cl}M+H]$^+$), 317.2 ([{$^{35}$Cl}M+H]$^+$).

Example 71

(RS)-4-Chloro-N-(4-morpholin-2-yl-phenyl)-benzamide hydrochloride

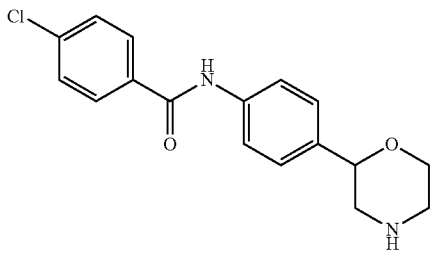

The title compound was obtained in analogy to example 29 using (RS)-tert-butyl 2-(4-aminophenyl)morpholine-4-carboxylate (CAS 1002726-96-6) instead of (RS)-tert-butyl 3-(4-aminophenyl)pyrrolidine-1-carboxylate and 4-chloro-benzoic acid instead of (R)-2-phenylpropionic acid. White solid. MS (ISP): 319.0 ([{$^{37}$Cl}M+H]$^+$), 317.2 ([{$^{35}$Cl}M+H]$^+$).

Example 72

(RS)-4-Chloro-N-(3-morpholin-2-yl-phenyl)-benzamide hydrochloride

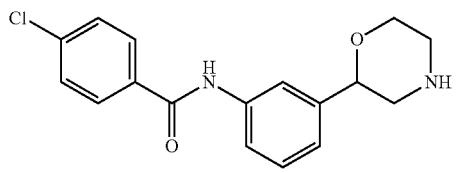 [SMILES: O=C(Nc1cccc(C2CNCCO2)c1)c1ccc(Cl)cc1]

The title compound was obtained in analogy to example 29 using (RS)-tert-butyl 2-(3-aminophenyl)morpholine-4-carboxylate instead of (RS)-tert-butyl 3-(4-aminophenyl)pyrrolidine-1-carboxylate and 4-chloro-benzoic acid instead of (R)-2-phenylpropionic acid. Colourless amorphous solid. MS (ISP): 319.1 ([{$^{37}$Cl}M+H]$^+$), 317.2 ([{$^{35}$Cl}M+H]$^+$).

Example 73

(RS)-6-Pyrazol-1-yl-N-(4-pyrrolidin-3-yl-phenyl)-nicotinamide hydrochloride

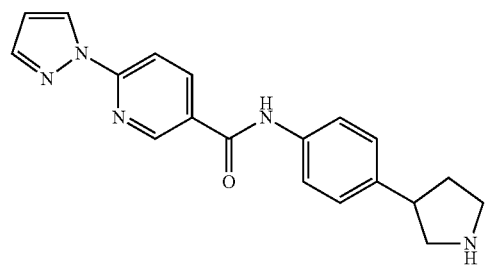 [SMILES: O=C(Nc1ccc(C2CCNC2)cc1)c1ccc(-n2cccn2)nc1]

The title compound was obtained in analogy to example 29 using 6-pyrazol-1-ylnicotinic acid (CAS 253315-22-9) instead of (R)-2-phenylpropionic acid. Light brown solid. MS (ISP): 334.2 (M+H]$^+$).

Example 74

(RS)-6-Chloro-N-(4-piperidin-3-yl-phenyl)-nicotinamide hydrochloride

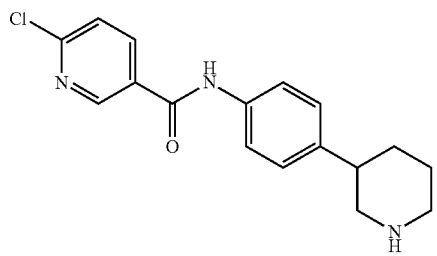

The title compound was obtained in analogy to example 29 using (RS)-tert-butyl 3-(4-aminophenyl)-1-piperidinecarboxylate (CAS 875798-79-1) instead of (RS)-tert-butyl 3-(4-aminophenyl)pyrrolidine-1-carboxylate and 6-chloro-nicotinic acid (CAS 5326-23-8) instead of (R)-2-phenylpropionic acid. White solid. MS (ISP): 318.2 ([{$^{37}$Cl}M+H]$^+$), 316.2 ([{$^{35}$Cl}M+H]$^+$).

Example 75

(RS)-3,5-Difluoro-pyridine-2-carboxylic acid (4-pyrrolidin-3-yl-phenyl)-amide hydrochloride

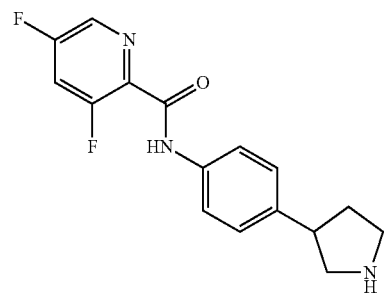 [SMILES: O=C(Nc1ccc(C2CCNC2)cc1)c1ncc(F)cc1F]

The title compound was obtained in analogy to example 29 using 3,5-difluoropicolinic acid (CAS 745784-04-7)

instead of (R)-2-phenylpropionic acid. White solid. MS (ISP): 304.1 (M+H]+).

Example 76

(RS)-1H-Benzoimidazole-2-carboxylic acid (4-pyrrolidin-3-yl-phenyl)-amide hydrochloride

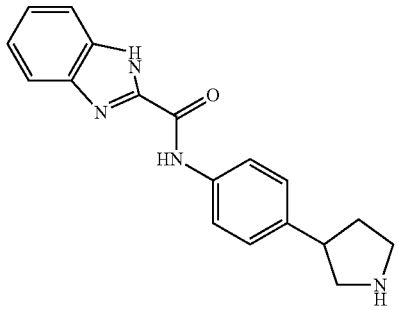 [SMILES: O=C(Nc1ccc(C2CCNC2)cc1)c1nc2ccccc2[nH]1]

The title compound was obtained in analogy to example 29 using 1H-benzimidazole-2-carboxylic acid (CAS 2849-93-6) instead of (R)-2-phenylpropionic acid. White solid. MS (ISP): 307.2 (M+H]+).

Example 77

(RS)-4-Chloro-2-fluoro-N-(4-pyrrolidin-3-yl-phenyl)-benzamide hydrochloride

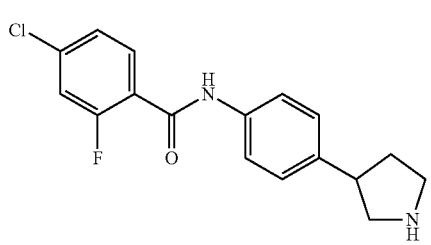 [SMILES: O=C(Nc1ccc(C2CCNC2)cc1)c1ccc(Cl)cc1F]

The title compound was obtained in analogy to example 29 using 4-chloro-2-fluoro-benzoic acid instead of (R)-2-phenylpropionic acid. White solid. MS (ISP): 321.1 ([$^{37}$Cl]M+H]+), 319.1 ([$^{35}$Cl]M+H]+).

Example 78

(RS)-5-Chloro-pyridine-2-carboxylic acid (4-piperidin-3-yl-phenyl)-amide hydrochloride

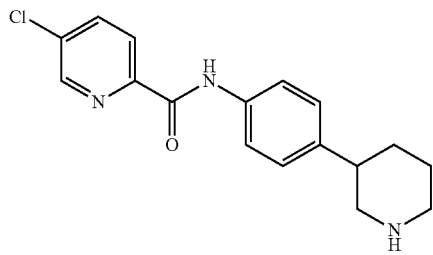 [SMILES: O=C(Nc1ccc(C2CCCNC2)cc1)c1ccc(Cl)cn1]

The title compound was obtained in analogy to example 29 using (RS)-tert-butyl 3-(4-aminophenyl)-1-piperidinecarboxylate (CAS 875798-79-1) instead of (RS)-tert-butyl 3-(4-aminophenyl)pyrrolidine-1-carboxylate and 5-chloropicolinic acid (CAS 86873-60-1) instead of (R)-2-phenylpropionic acid. Light yellow solid. MS (ISP): 318.3 ([$^{37}$Cl]M+H]+), 316.2 ([$^{35}$Cl]M+H]+).

Example 79

(RS)-1-(6-Chloro-pyridin-3-yl)-3-(4-piperidin-3-yl-phenyl)-urea hydrochloride

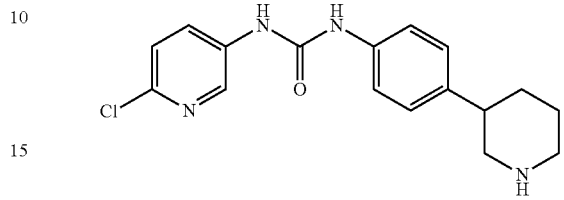

The title compound was obtained in analogy to example 6 using (RS)-tert-butyl 3-(4-aminophenyl)-1-piperidinecarboxylate (CAS 875798-79-1) instead of (RS)-tert-butyl 3-(4-aminophenyl)pyrrolidine-1-carboxylate and 2-chloro-5-isocyanatopyridine (CAS 125117-96-6) instead of phenyl isocyanate. Off-white solid. MS (ISP): 333.1 ([$^{37}$Cl]M+H]+), 331.1 ([$^{35}$Cl]M+H]+).

Example 80

(RS)-4-Chloro-N-[4-(4-methyl-morpholin-2-yl)-phenyl]-benzamide

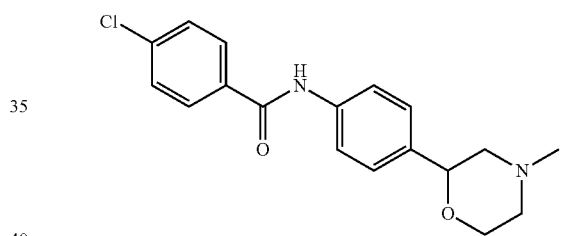

The title compound was obtained in analogy to example 32 using 4-chloro-N-(4-morpholin-2-yl-phenyl)-benzamide hydrochloride (example 71) instead of (RS)-4-chloro-N-(4-pyrrolidin-3-yl-phenyl)-benzamide hydrochloride. White solid. MS (ISP): 333.2 ([$^{37}$Cl]M+H]+), 331.1 ([$^{35}$Cl]M+H]+).

Example 81

(RS)-1-(4-Pyrrolidin-3-yl-phenyl)-3-quinolin-8-yl-urea

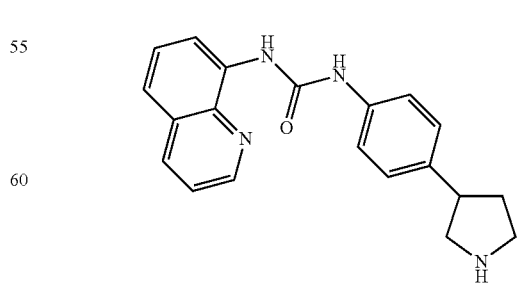

The title compound was obtained in analogy to example 6 using 8-aminoquinoline (CAS 578-66-5) instead of (RS)- tert-butyl 3-(4-aminophenyl)pyrrolidine-1-carboxylate and (RS)-3-(4-isocyanato-phenyl)-pyrrolidine-1-carboxylic acid tert-butyl ester (Example 45a) instead of phenyl isocyanate. Off-white solid. MS (ISP): 333.2 ([M+H]$^+$).

Example 82

(RS)-3-Fluoro-pyridine-2-carboxylic acid (4-pyrrolidin-3-yl-phenyl)-amide hydrochloride

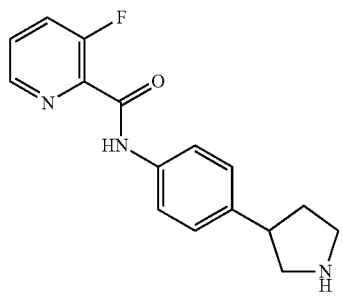 [SMILES: O=C(Nc1ccc(C2CCNC2)cc1)c1ncccc1F]

The title compound was obtained in analogy to example 29 using 3-fluoro-pyridine-2-carboxylic acid (CAS 152126-31-3) instead of (R)-2-phenylpropionic acid. Light yellow solid. MS (ISP): 286.2 ([M+H]$^+$).

Example 83

(RS)-1-(5-Chloro-pyridin-2-yl)-3-(4-piperidin-3-yl-phenyl)-urea hydrochloride

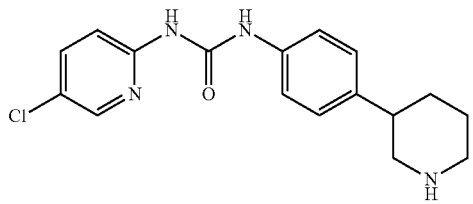 [SMILES: O=C(Nc1ccc(C2CCCNC2)cc1)Nc1ccc(Cl)cn1]

The title compound was obtained in analogy to example 6 using (RS)-tert-butyl 3-(4-aminophenyl)-1-piperidinecarboxylate (CAS 875798-79-1) instead of (RS)-tert-butyl 3-(4-aminophenyl)pyrrolidine-1-carboxylate and 5-chloro-2-isocyanatopyridine (CAS 95735-68-5) instead of phenyl isocyanate. Off-white solid. MS (ISP): 333.3 ([{$^{37}$Cl}M+H]$^+$), 331.2 ([{$^{35}$Cl}M+H]$^+$).

Example 84

(RS)-Quinoline-2-carboxylic acid (4-pyrrolidin-3-yl-phenyl)-amide hydrochloride

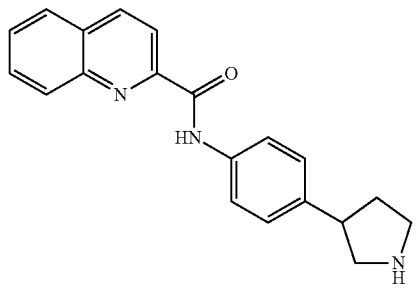 [SMILES: O=C(Nc1ccc(C2CCNC2)cc1)c1ccc2ccccc2n1]

The title compound was obtained in analogy to example 29 using quinaldic acid (CAS 93-10-7) instead of (R)-2-phenylpropionic acid. Yellow solid. MS (ISP): 318.2 ([M+H]$^+$).

Example 85

(RS)-Isoquinoline-1-carboxylic acid (4-pyrrolidin-3-yl-phenyl)-amide hydrochloride

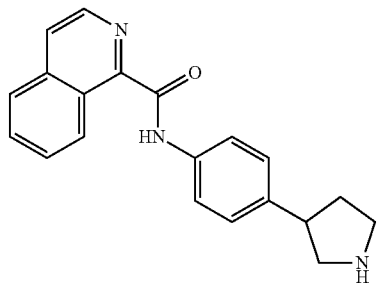 [SMILES: O=C(Nc1ccc(C2CCNC2)cc1)c1nccc2ccccc12]

The title compound was obtained in analogy to example 29 using 1-isoquinoline carboxylic acid (CAS 486-73-7) instead of (R)-2-phenylpropionic acid. White solid. MS (ISP): 318.2 ([M+H]$^+$).

Example 86

(RS)-4-Chloro-pyridine-2-carboxylic acid (4-pyrrolidin-3-yl-phenyl)-amide hydrochloride

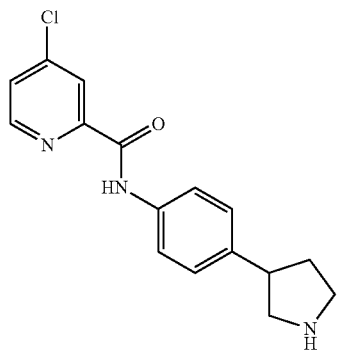 [SMILES: O=C(Nc1ccc(C2CCNC2)cc1)c1cc(Cl)ccn1]

The title compound was obtained in analogy to example 29 using 4-chloropicolinic acid (CAS 5470-22-4) instead of (R)-2-phenylpropionic acid. White solid. MS (ISP): 304.1 ([{$^{37}$Cl}M+H]$^+$), 302.1 ([{$^{35}$Cl}M+H]$^+$).

Example 87

(RS)-5-Bromo-pyridine-2-carboxylic acid (4-pyrrolidin-3-yl-phenyl)-amide hydrochloride

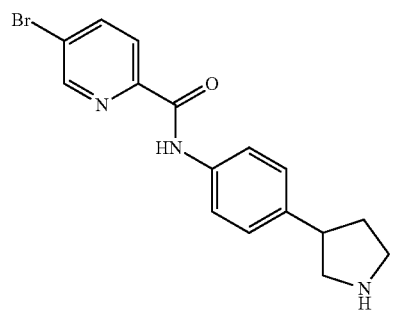 [SMILES: O=C(Nc1ccc(C2CCNC2)cc1)c1ccc(Br)cn1]

The title compound was obtained in analogy to example 29 using 5-bromo-pyridine-2-carboxylic acid (CAS 30766-

Example 88

(RS)-2-Fluoro-4-methoxy-N-(4-pyrrolidin-3-yl-phenyl)-benzamide hydrochloride

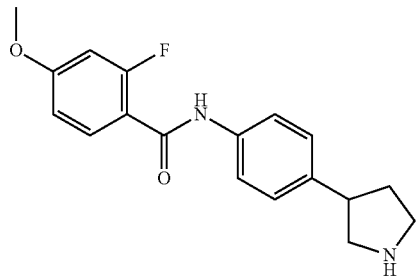 [SMILES: COc1ccc(C(=O)Nc2ccc(C3CCNC3)cc2)c(F)c1]

The title compound was obtained in analogy to example 29 using 2-fluoro-4-methoxy-benzoic acid (CAS 394-42-3) instead of (R)-2-phenylpropionic acid. White solid. MS (ISP): 315.1 ([M+H]$^+$).

Example 89

(RS)—N-(4-Pyrrolidin-3-yl-phenyl)-6-(2,2,2-trifluoro-ethoxy)-nicotinamide hydrochloride

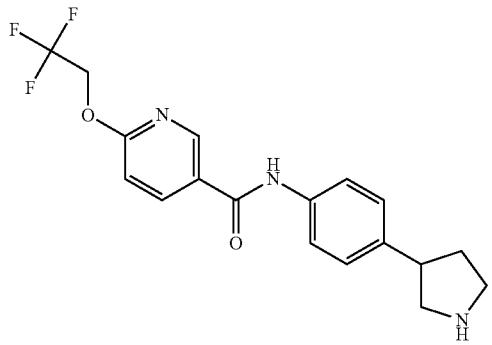

The title compound was obtained in analogy to example 29 using 6-(2,2,2-trifluoro-ethoxy)-nicotinic acid (CAS 175204-90-7) instead of (R)-2-phenylpropionic acid. White solid. MS (ISP): 366.2 ([M+H]$^+$).

Example 90

(RS)-4-Methoxy-quinoline-2-carboxylic acid (4-pyrrolidin-3-yl-phenyl)-amide hydrochloride

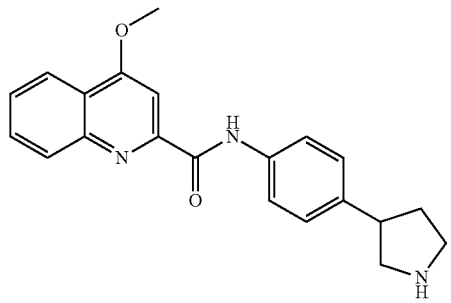 [SMILES: COc1cc(C(=O)Nc2ccc(C3CCNC3)cc2)nc2ccccc12]

The title compound was obtained in analogy to example 29 using 4-methoxy-2-quinolinecarboxylic acid (CAS 15733-83-2) instead of (R)-2-phenylpropionic acid. Yellow solid. MS (ISP): 348.2 ([M+H]$^+$).

Example 91

(RS)-6-Methoxy-quinoline-2-carboxylic acid (4-pyrrolidin-3-yl-phenyl)-amide hydrochloride

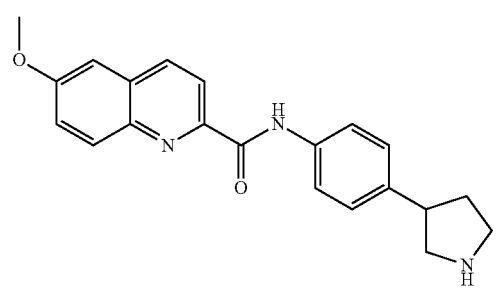 [SMILES: COc1ccc2nc(C(=O)Nc3ccc(C4CCNC4)cc3)ccc2c1]

The title compound was obtained in analogy to example 29 using 6-methoxy-quinoline-2-carboxylic acid (CAS 75433-99-7) instead of (R)-2-phenylpropionic acid. Yellow solid. MS (ISP): 348.2 ([M+H]$^+$).

Example 92

(RS)-3-Chloro-N-(4-piperidin-3-yl-phenyl)-benzamide hydrochloride

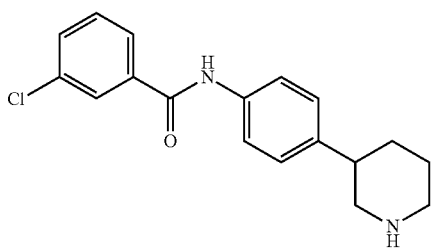

The title compound was obtained in analogy to example 29 using (RS)-tert-butyl 3-(4-aminophenyl)-1-piperidinecarboxylate (CAS 875798-79-1) instead of (RS)-tert-butyl 3-(4-aminophenyl)pyrrolidine-1-carboxylate and 3-chlorobenzoic acid (CAS 535-80-8) instead of (R)-2-phenylpropionic acid. White solid. MS (ISP): 317.2 ([{$^{37}$Cl}M+H]$^+$), 315.2 ([{$^{35}$Cl}M+H]$^+$).

Example 93

(RS)-Thieno[2,3-c]pyridine-7-carboxylic acid (4-pyrrolidin-3-yl-phenyl)-amide hydrochloride

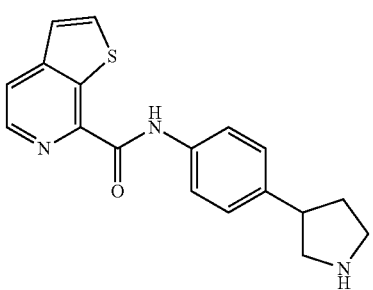 [SMILES: O=C(Nc1ccc(C2CCNC2)cc1)c1nccc2ccsc12]

The title compound was obtained in analogy to example 29 using thieno[2,3-c]pyridine-7-carboxylic acid (CAS 852532-64-0) instead of (R)-2-phenylpropionic acid. Yellow solid. MS (ISP): 324.2 ([M+H]$^+$).

Example 94

(RS)-5-Methoxy-pyridine-2-carboxylic acid (4-pyrrolidin-3-yl-phenyl)-amide hydrochloride

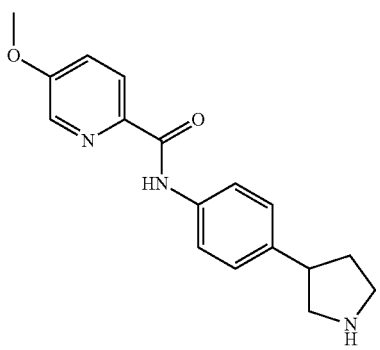 [SMILES: COc1ccc(C(=O)Nc2ccc(C3CCNC3)cc2)nc1]

The title compound was obtained in analogy to example 29 using 5-methoxy-pyridine-2-carboxylic acid (CAS 29082-92-6) instead of (R)-2-phenylpropionic acid. White solid. MS (ISP): 298.2 ([M+H]$^+$).

Example 95

(RS)-2,6-Dimethoxy-N-(4-pyrrolidin-3-yl-phenyl)-nicotinamide

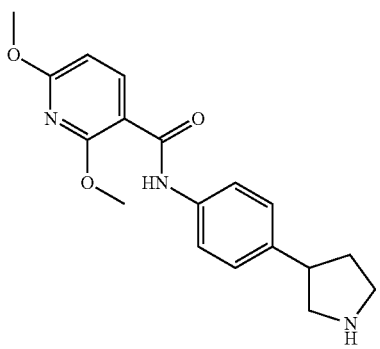 [SMILES: COc1ccc(C(=O)Nc2ccc(C3CCNC3)cc2)c(OC)n1]

The title compound was obtained in analogy to example 29 using 2,6-dimethoxy-nicotinic acid (CAS 16727-43-8) instead of (R)-2-phenylpropionic acid. Light yellow oil. MS (ISP): 328.2 ([M+H]$^+$).

Example 96

(RS)-3,4-Dichloro-N-(4-piperidin-3-yl-phenyl)-benzamide hydrochloride

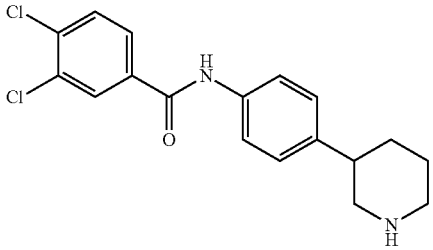 [SMILES: O=C(Nc1ccc(C2CCCNC2)cc1)c1ccc(Cl)c(Cl)c1]

The title compound was obtained in analogy to example 29 using (RS)-tert-butyl 3-(4-aminophenyl)-1-piperidinecarboxylate (CAS 875798-79-1) instead of (RS)-tert-butyl 3-(4-aminophenyl)pyrrolidine-1-carboxylate and 3,4-dichloro-benzoic acid (CAS 51-44-5) instead of (R)-2-phenylpropionic acid. White solid. MS (ISP): 353.2 ([$\{^{37}Cl\}$M+H]$^+$), 351.3 ([$\{^{37}Cl^{35}Cl\}$M+H]$^+$), 349.2 ([$\{^{35}Cl\}$M+H]$^+$).

Example 97

(RS)-4-Ethoxy-N-(4-piperidin-3-yl-phenyl)-benzamide hydrochloride

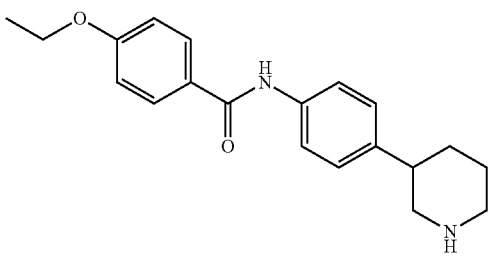 [SMILES: CCOc1ccc(C(=O)Nc2ccc(C3CCCNC3)cc2)cc1]

The title compound was obtained in analogy to example 29 using (RS)-tert-butyl 3-(4-aminophenyl)-1-piperidinecarboxylate (CAS 875798-79-1) instead of (RS)-tert-butyl 3-(4-aminophenyl)pyrrolidine-1-carboxylate and 4-ethoxy-benzoic acid (CAS 619-86-3) instead of (R)-2-phenylpropionic acid. White solid. MS (ISP): 325.4 ([M+H]$^+$).

Example 98

(RS)—N-(4-Piperidin-3-yl-phenyl)-4-trifluoromethyl-benzamide hydrochloride

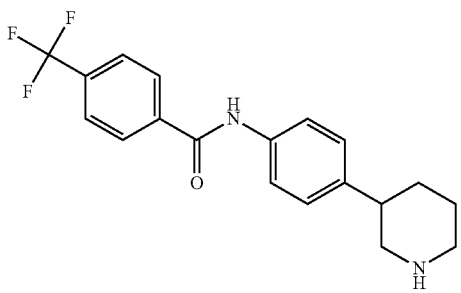 [SMILES: O=C(Nc1ccc(C2CCCNC2)cc1)c1ccc(C(F)(F)F)cc1]

The title compound was obtained in analogy to example 29 using (RS)-tert-butyl 3-(4-aminophenyl)-1-piperidinecarboxylate (CAS 875798-79-1) instead of (RS)-tert-butyl 3-(4-aminophenyl)pyrrolidine-1-carboxylate and 4-trifluoromethyl-benzoic acid (CAS 455-24-3) instead of (R)-2-phenylpropionic acid. White solid. MS (ISP): 349.2 ([M+H]$^+$).

Example 99

(RS)-2,4-Dichloro-N-(4-piperidin-3-yl-phenyl)-benzamide hydrochloride

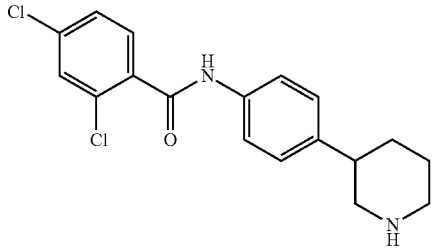 [SMILES: O=C(Nc1ccc(C2CCCNC2)cc1)c1ccc(Cl)cc1Cl]

The title compound was obtained in analogy to example 29 using (RS)-tert-butyl 3-(4-aminophenyl)-1-piperidinecarboxylate (CAS 875798-79-1) instead of (RS)-tert-butyl 3-(4-aminophenyl)pyrrolidine-1-carboxylate and 2,4-dichloro-benzoic acid (CAS 50-84-0) instead of (R)-2-phenylpropionic acid. White solid. MS (ISP): 353.2 ([{$^{37}$Cl}M+H]$^+$) 351.3 ([{$^{37}$Cl$^{35}$Cl}M+H]$^+$), 349.2 ([{$^{35}$Cl}M+H]$^+$).

Example 100

(RS)-4-Chloro-2-fluoro-N-(4-piperidin-3-yl-phenyl)-benzamide hydrochloride

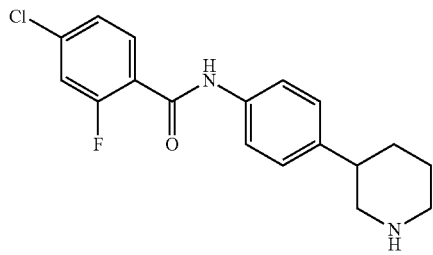 [SMILES: O=C(Nc1ccc(C2CCCNC2)cc1)c1ccc(Cl)cc1F]

The title compound was obtained in analogy to example 29 using (RS)-tert-butyl 3-(4-aminophenyl)-1-piperidinecarboxylate (CAS 875798-79-1) instead of (RS)-tert-butyl 3-(4-aminophenyl)pyrrolidine-1-carboxylate and 4-chloro-2-fluoro-benzoic acid (CAS 446-30-0) instead of (R)-2-phenylpropionic acid. White solid. MS (ISP): 335.3 ([{$^{37}$Cl}M+H]$^+$), 333.3 ([{$^{35}$Cl}M+H]$^+$).

Example 101

(RS)-3-(4-Chloro-phenyl)-N-(4-piperidin-3-yl-phenyl)-propionamide hydrochloride

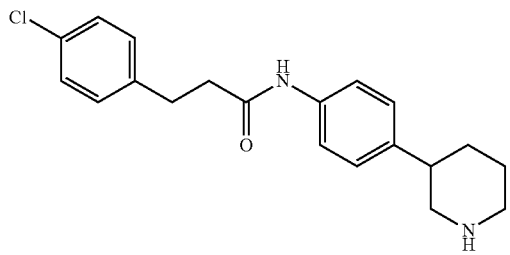 [SMILES: O=C(CCc1ccc(Cl)cc1)Nc1ccc(C2CCCNC2)cc1]

The title compound was obtained in analogy to example 29 using (RS)-tert-butyl 3-(4-aminophenyl)-1-piperidinecarboxylate (CAS 875798-79-1) instead of (RS)-tert-butyl 3-(4-aminophenyl)pyrrolidine-1-carboxylate and 3-(4-chloro-phenyl)-propionic acid (CAS 2019-34-3) instead of (R)-2-phenylpropionic acid. White solid. MS (ISP): 345.2 ([{$^{37}$Cl}M+H]$^+$), 343.2 ([{$^{35}$Cl}M+H]$^+$).

Example 102

(RS)-2-(4-Chloro-phenyl)-N-(4-piperidin-3-yl-phenyl)-acetamide hydrochloride

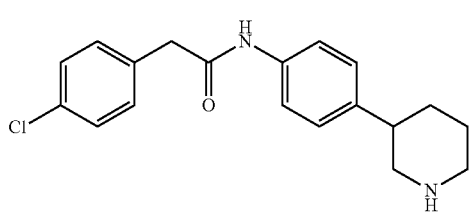 [SMILES: O=C(Cc1ccc(Cl)cc1)Nc1ccc(C2CCCNC2)cc1]

The title compound was obtained in analogy to example 29 using (RS)-tert-butyl 3-(4-aminophenyl)-1-piperidin-ecarboxylate (CAS 875798-79-1) instead of (RS)-tert-butyl 3-(4-aminophenyl)pyrrolidine-1-carboxylate and 3-(4-chloro-phenyl)-acetic acid (CAS 1878-66-6) instead of (R)-2-phenylpropionic acid. Off-white solid. MS (ISP): 331.2 ([{$^{37}$Cl}M+H]$^+$), 329.3 ([{$^{35}$Cl}M+H]$^+$).

Example 103

(RS)-2-(4-Chloro-phenyl)-N—((RS)-4-piperidin-3-yl-phenyl)-propionamide

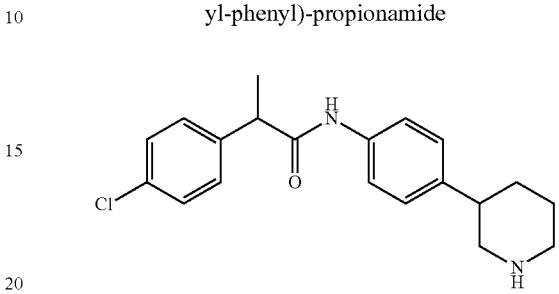

The title compound was obtained in analogy to example 29 using (RS)-tert-butyl 3-(4-aminophenyl)-1-piperidinecarboxylate (CAS 875798-79-1) instead of (RS)-tert-butyl 3-(4-aminophenyl)pyrrolidine-1-carboxylate and 2-(4-chloro-phenyl)-propionic acid (CAS 938-95-4) instead of (R)-2-phenylpropionic acid. White solid. MS (ISP): 345.2 ([{$^{37}$Cl}M+H]$^+$), 343.3 ([{$^{35}$Cl}M+H]$^+$).

Example 104

(RS)—N—((RS)-4-Piperidin-3-yl-phenyl)-2-(3-trifluoromethyl-phenyl)-propionamide

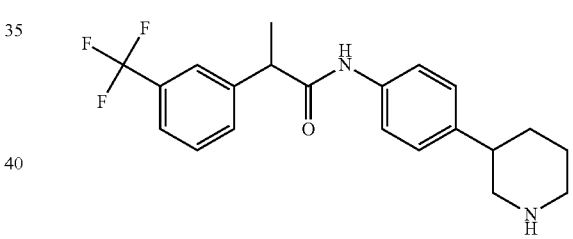

The title compound was obtained in analogy to example 29 using (RS)-tert-butyl 3-(4-aminophenyl)-1-piperidinecarboxylate (CAS 875798-79-1) instead of (RS)-tert-butyl 3-(4-aminophenyl)pyrrolidine-1-carboxylate and 2-(3-trifluoromethyl-phenyl)-propionic acid (CAS 68718-08-1) instead of (R)-2-phenylpropionic acid. White solid. MS (ISP): 377.4 ([M+H]$^+$).

Example 105

(RS)—N—((RS)-4-Piperidin-3-yl-phenyl)-2-(3-trifluoromethoxy-phenyl)-propionamide

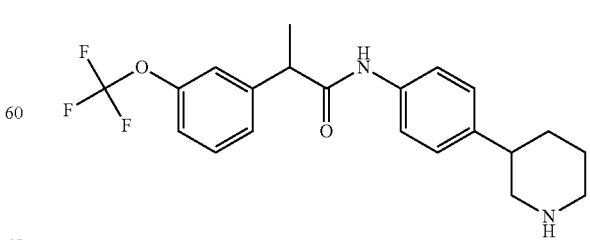

The title compound was obtained in analogy to example 29 using (RS)-tert-butyl 3-(4-aminophenyl)-1-piperidinecarboxylate (CAS 875798-79-1) instead of (RS)-tert-butyl 3-(4-aminophenyl)pyrrolidine-1-carboxylate and 2-(3-trifluoromethoxy-phenyl)-propionic acid instead of (R)-2-phenylpropionic acid. Colourless gum. MS (ISP): 393.2 ([M+H]+).

Example 106

(RS)-3,5-Difluoro-pyridine-2-carboxylic acid (4-piperidin-3-yl-phenyl)-amide hydrochloride

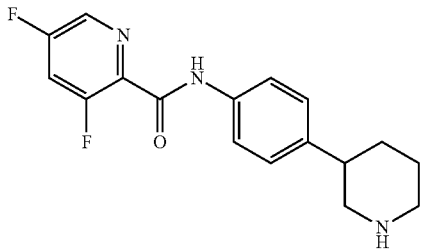 [SMILES: O=C(Nc1ccc(C2CCCNC2)cc1)c1ncc(F)cc1F]

The title compound was obtained in analogy to example 29 using (RS)-tert-butyl 3-(4-aminophenyl)-1-piperidinecarboxylate (CAS 875798-79-1) instead of (RS)-tert-butyl 3-(4-aminophenyl)pyrrolidine-1-carboxylate and 3,5-difluoropyridine-2-carboxylic acid (CAS 745784-04-7) instead of (R)-2-phenylpropionic acid. Off-white solid. MS (ISP): 318.3 ([M+H]+).

Example 107

(RS)-4-Chloro-N-(4-pyrrolidin-2-ylmethyl-phenyl)-benzamide hydrochloride

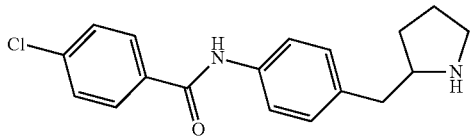 [SMILES: O=C(Nc1ccc(CC2CCCN2)cc1)c1ccc(Cl)cc1]

a) (RS)-2-(4-Bromo-benzyl)-pyrrolidine-1-carboxylic acid tert-butyl ester

To a stirred solution of (RS)-2-(4-bromo-benzyl)-pyrrolidine (1.00 g, CAS 383127-68-2) in 1,2-dichloroethane (10 ml) were added sequentially N,N-diisopropylethylamine (0.79 ml) and di-tert-butyl dicarbonate (1.02 g) and the mixture was stirred at room temperature for 1 hours. The mixture was diluted with dichloromethane and washed sequentially with water, dilute aq. hydrochloric acid, saturated aq. sodium bicarbonate solution and saturated brine. The organic phase was then dried over sodium sulphate, filtered and concentrated in vacuo to afford (RS)-2-(4-bromo-benzyl)-pyrrolidine-1-carboxylic acid tert-butyl ester (1.41 g, quant.) as a light yellow viscous oil. MS (ISP): 342.1 ([{$^{81}$Br}M+H]+), 340.2 ([{$^{79}$Br}M+H]+), 286.1 ([{$^{81}$Br}M+H—C$_4$H$_8$]+), 284.2 ([{$^{79}$Br}M+H—C$_4$H$_8$]+).

b) (RS)-2-[4-(4-Chloro-benzoylamino)-benzyl]-pyrrolidine-1-carboxylic acid tert-butyl ester A stirred suspension of (RS)-2-(4-bromo-benzyl)-pyrrolidine-1-carboxylic acid tert-butyl ester (400 mg), 4-chlorobenzamide (280 mg), caesium carbonate (766 mg), N,N'-dimethyl-ethylenediamine (0.04 ml) and copper(I) iodide (23 mg) in dioxane (3 ml) under an atmosphere of argon in a sealed tube was heated at 120° C. for 18 h. The mixture was then cooled to room temperature, filtered through celite and the filtrate was concentrated in vacuo. The residue was taken up in ethyl acetate and the resulting solution was washed sequentially with water and with saturated brine. The organic phase was then separated, dried over sodium sulphate and concentrated in vacuo. The residue was purified by column chromatography (SiO$_2$; gradient: heptane/EtOAc) to give (RS)-2-[4-(4-chloro-benzoylamino)-benzyl]-pyrrolidine-1-carboxylic acid tert-butyl ester (19 mg, 4%) as a light yellow gum. MS (ISP): 417.3 ([{$^{37}$Cl}M+H]+), 415.3 ([{$^{35}$Cl}M+H]+), 361.1 ([{$^{37}$Cl}M+H—C$_4$H$_8$]+), 359.1 ([{$^{35}$Cl}M+H—C$_4$H$_8$]+).

c) (RS)-4-Chloro-N-(4-pyrrolidin-2-ylmethyl-phenyl)-benzamide hydrochloride

To a stirred solution of (RS)-2-[4-(4-chloro-benzoylamino)-benzyl]-pyrrolidine-1-carboxylic acid tert-butyl ester (16 mg) in THF (1.5 ml) was added dropwise a solution of hydrogen chloride in dioxane (0.14 ml, 4 M solution) and the mixture was heated at 60° C. overnight. The mixture was then cooled to 0° C. and the ensuing crystals were collected by filtration, washing once with ethyl acetate and once with diethyl ether, and were dried in vacuo at 60° C. to afford (RS)-4-chloro-N-(4-pyrrolidin-2-ylmethyl-phenyl)-benzamide hydrochloride (3 mg, 22%) as an off-white crystalline solid. MS (ISP): 317.1 ([{$^{37}$Cl}M+H]+), 315.1 ([{$^{35}$Cl}M+H]+).

Example 108

(RS)-1-Chloro-isoquinoline-3-carboxylic acid (4-pyrrolidin-3-yl-phenyl)-amide hydrochloride

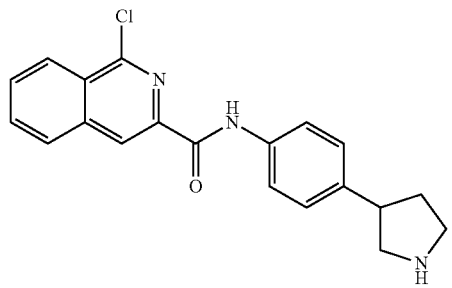 [SMILES: O=C(Nc1ccc(C2CCNC2)cc1)c1cc2ccccc2c(Cl)n1]

The title compound was obtained in analogy to example 29 using 1-chloro-isoquinoline-3-carboxylic acid (CAS 1049606-80-5) instead of (R)-2-phenylpropionic acid. White solid. MS (ISP): 354.2 ([{$^{37}$Cl}M+H]+), 352.2 ([{$^{35}$Cl}M+H]+).

Example 109

(RS)-4-Chloro-N-[4-(2-pyrrolidin-3-yl-ethyl)-phenyl]-benzamide hydrochloride

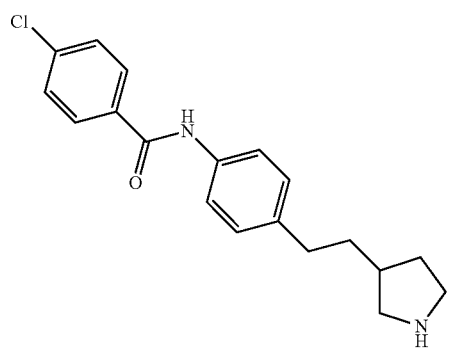 [SMILES: O=C(Nc1ccc(CCC2CCNC2)cc1)c1ccc(Cl)cc1]

a) (RS)-3-[(E)-2-(4-Nitro-phenyl)-vinyl]-pyrrolidine-1-carboxylic acid tert-butyl ester To a stirred solution of N,N-diisopropylamine (3.36 ml) in tetrahydrofuran (20 ml) at −78° C. was added dropwise a solution of n-butyllithium (14.9 ml, 1.6 M in hexane) and the reaction mixture was then warmed to 0° C. for 15 min. After re-cooling to −78° C., a solution of diethyl (4-nitrobenzyl) phosphonate (5.00 g, CAS 2609-49-6) in tetrahydrofuran (10 ml) was added dropwise. The mixture was stirred at −78° C. for 60 min and then a solution of (RS)-3-formyl-pyrrolidine-1-carboxylic acid tert-butyl ester (4.01 g, CAS 59379-02-1) in tetrahydrofuran (10 ml) was added dropwise over 30 min. The mixture was then allowed to warm to room temperature and stirring continued at room temperature for 18 hours. The mixture was then diluted with ethyl acetate and acidified to pH 6 by addition of aqueous hydrochloric acid (1 N). The mixture was washed sequentially with water and with saturated brine, dried over $Na_2SO_4$ and concentrated in vacuo. The residue was purified by column chromatography (SiO2, heptane/EtOAc gradient) to yield (RS)-3-[(E)-2-(4-nitro-phenyl)-vinyl]-pyrrolidine-1-carboxylic acid tert-butyl ester (3.39 g, 58%) as a yellow oil.

b) (RS)-3-[2-(4-Amino-phenyl)-ethyl]-pyrrolidine-1-carboxylic acid tert-butyl ester To a solution of (RS)-3-formyl-pyrrolidine-1-carboxylic acid tert-butyl ester (3.39 g) in methanol (250 ml) was added palladium on charcoal (10%, 340 mg). The mixture was stirred vigorously under an atmosphere of hydrogen for 7 hours. The catalyst was filtered off and the filtrate was evaporated. The crude product was purified by column chromatography (SiO2, heptane/EtOAc gradient) to give (RS)-3-[2-(4-amino-phenyl)-ethyl]-pyrrolidine-1-carboxylic acid tert-butyl ester (2.44 g, 79%) as a yellow oil. MS (ISP): 291.2 ([M+H]$^+$).

c) (RS)-3-{2-[4-(4-Chloro-benzoylamino)-phenyl]-ethyl}-pyrrolidine-1-carboxylic acid tert-butyl ester To a stirred suspension of (RS)-3-[2-(4-amino-phenyl)-ethyl]-pyrrolidine-1-carboxylic acid tert-butyl ester (100 mg) in THF (5 ml) were added sequentially N-methylmorpholine (0.15 ml), TBTU (221 mg) and 4-chloro-benzoic acid (70 mg) and the mixture was heated at 50° C. for 18 h. The mixture was then concentrated in vacuo and the residue was purified by column chromatography (SiO$_2$; gradient: heptane/EtOAc) to give (RS)-3-{2-[4-(4-chloro-benzoylamino)-phenyl]-ethyl}-pyrrolidine-1-carboxylic acid tert-butyl ester (131 mg, 89%) as a white solid. MS (ISP):): 431.3 ([{$^{37}$Cl}M+H]$^+$), 429.3 ([{$^{35}$Cl}M+H]$^+$), 375.5 ([{$^{37}$Cl}M+H—C$_4$H$_8$]$^+$), 373.2 ([{$^{35}$Cl}M+H—C$_4$H$_8$]$^+$).

d) (RS)-4-Chloro-N-[4-(2-pyrrolidin-3-yl-ethyl)-phenyl]-benzamide hydrochloride To a stirred solution of (RS)-3-{2-[4-(4-chloro-benzoylamino)-phenyl]-ethyl}-pyrrolidine-1-carboxylic acid tert-butyl ester (130 mg) in THF (3 ml) was added dropwise a solution of hydrogen chloride in dioxane (1.14 ml, 4 M solution) and the mixture was heated at 60° C. overnight. The mixture was then cooled to 0° C. and the ensuing crystals were collected by filtration, washing with ethyl acetate, and were dried in vacuo at 60° C. to afford (RS)-4-chloro-N-[4-(2-pyrrolidin-3-yl-ethyl)-phenyl]-benzamide hydrochloride (111 mg, quant.) as an off-white crystalline solid. MS (ISP): 331.3 ([{$^{37}$Cl}M+H]$^+$), 329.1 ([{$^{35}$Cl}M+H]$^+$).

Example 110

(RS)-4-Chloro-N-[4-(2-piperidin-3-yl-ethyl)-phenyl]-benzamide hydrochloride

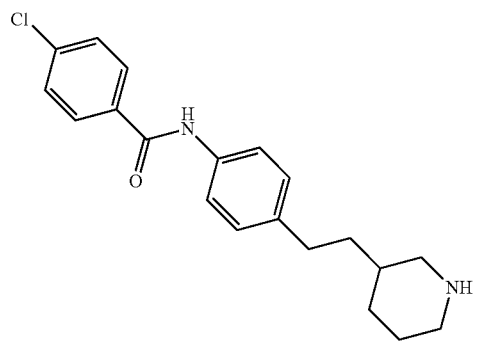

The title compound was obtained in analogy to example 109 using (RS)-3-formyl-piperidine-1-carboxylic acid tert-butyl ester (CAS 118156-93-7) instead of (RS)-3-formyl-pyrrolidine-1-carboxylic acid tert-butyl ester. Off-white solid. MS (ISP): 345.2 ([{$^{37}$Cl}M+H]$^+$), 343.2 ([{$^{35}$Cl}M+H]$^+$).

Example 111

(RS)-2-(3-Chloro-phenyl)-N—((RS)-4-piperidin-3-yl-phenyl)-propionamide

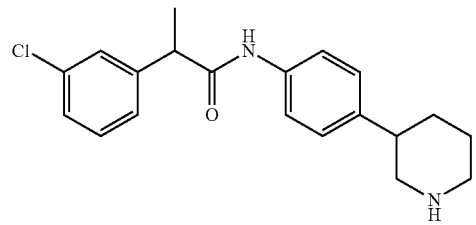 [SMILES: CC(C(=O)Nc1ccc(C2CCCNC2)cc1)c1cccc(Cl)c1]

The title compound was obtained in analogy to example 29 using (RS)-tert-butyl 3-(4-aminophenyl)-1-piperidinecarboxylate (CAS 875798-79-1) instead of (RS)-tert-butyl 3-(4-aminophenyl)pyrrolidine-1-carboxylate and 2-(3-chloro-phenyl)-propionic acid (14161-84-3) instead of (R)-2-phenylpropionic acid. Colourless gum. MS (ISP): 345.2 ([{$^{37}$Cl}M+H]$^+$), 343.2 ([{$^{35}$Cl}M+H]$^+$).

Example 112

4-Chloro-N—((S)-4-piperidin-3-yl-phenyl)-benzamide

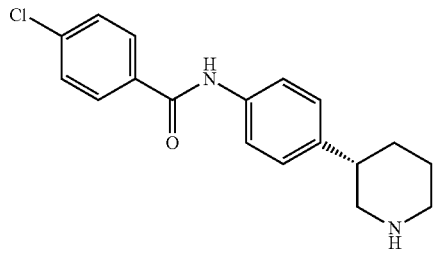 [SMILES: O=C(Nc1ccc([C@@H]2CCCNC2)cc1)c1ccc(Cl)cc1]

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 4-chloroben-

Example 113

4-Chloro-N—((R)-4-piperidin-3-yl-phenyl)-benzamide

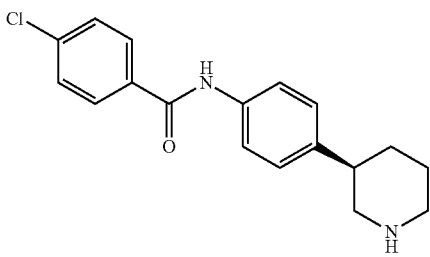 [SMILES: O=C(Nc1ccc([C@H]2CCCNC2)cc1)c1ccc(Cl)cc1]

The title compound was obtained in analogy to example 29 using (R)-tert-butyl 3-(4-aminophenyl)piperidine-1-carboxylate (example 150a) instead of (RS)-tert-butyl 3-(4-aminophenyl)pyrrolidine-1-carboxylate and 4-chlorobenzoic acid (CAS 74-11-3) instead of (R)-2-phenylpropionic acid. White solid. MS (ISP): 317.3 ([{$^{37}$Cl}M+H]$^+$), 315.2 ([{$^{35}$Cl}M+H]$^+$).

Example 114

(RS)-1-(5-Chloro-pyridin-2-yl)-3-[4-(2-pyrrolidin-3-yl-ethyl)-phenyl]-urea hydrochloride

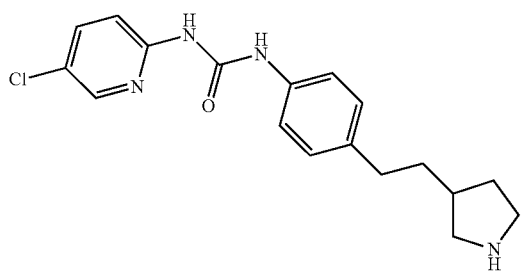 [SMILES: O=C(Nc1ccc(CCC2CCNC2)cc1)Nc1ccc(Cl)cn1]

a) (RS)-3-(2-{4-[3-(5-Chloro-pyridin-2-yl)-ureido]-phenyl}-ethyl)-pyrrolidine-1-carboxylic acid tert-butyl ester To a stirred suspension of (RS)-3-[2-(4-amino-phenyl)-ethyl]-pyrrolidine-1-carboxylic acid tert-butyl ester (100 mg, Example 109(b)) in dichloroethane (3 ml) were added sequentially triethylamine (0.10 ml) and triphosgene (38 mg) and the mixture was heated at 80° C. for 30 min. To the resulting mixture was added 2-amino-5-chloropyridine (44 mg, CAS 1072-98-6) and the mixture was heated at 80° C. for 18 h. The mixture was then cooled to room temperature and concentrated in vacuo. The residue was purified by column chromatography (SiO$_2$; gradient: heptane/EtOAc) to give (RS)-3-(2-{4-[3-(5-chloro-pyridin-2-yl)-ureido]-phenyl}-ethyl)-pyrrolidine-1-carboxylic acid tert-butyl ester (89 mg, 58%) as a white solid. MS (ISP): 447.4 ([{$^{37}$Cl}M+H]$^+$), 445.4 ([{$^{35}$Cl}M+H]$^+$), 391.2 ([{$^{37}$Cl}M+H—C$_4$H$_8$]$^+$), 389.1 ([{$^{35}$Cl}M+H—C$_4$H$_8$]$^+$).

b) (RS)-1-(5-Chloro-pyridin-2-yl)-3-[4-(2-pyrrolidin-3-yl-ethyl)-phenyl]-urea hydrochloride To a stirred solution of (RS)-3-(2-{4-[3-(5-chloro-pyridin-2-yl)-ureido]-phenyl}-ethyl)-pyrrolidine-1-carboxylic acid tert-butyl ester (85 mg) in THF (2 ml) was added dropwise a solution of hydrogen chloride in dioxane (0.72 ml, 4 M solution) and the mixture was heated at 60° C. overnight. The mixture was then cooled to 0° C. and the ensuing crystals were collected by filtration, washing twice with ethyl acetate, and were dried in vacuo at 60° C. to afford (RS)-1-(5-chloro-pyridin-2-yl)-3-[4-(2-pyrrolidin-3-yl-ethyl)-phenyl]-urea hydrochloride (74 mg, quant.) as a white crystalline solid. MS (ISP): 347.2 ([{$^{37}$Cl}M+H]$^+$), 345.2 ([{$^{35}$Cl}M+H]$^+$).

Example 115

(RS)-1-(5-Chloro-pyridin-2-yl)-3-[4-(2-piperidin-3-yl-ethyl)-phenyl]-urea hydrochloride

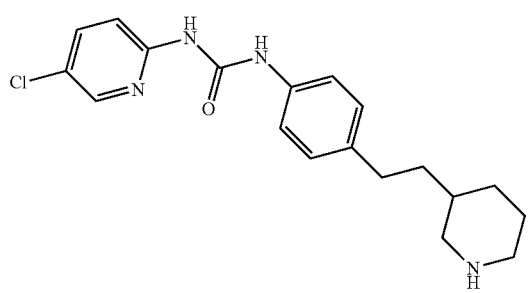 [SMILES: O=C(Nc1ccc(CCC2CCCNC2)cc1)Nc1ccc(Cl)cn1]

The title compound was obtained in analogy to example 109 step (b) and example 114 using (RS)-3-formyl-piperidine-1-carboxylic acid tert-butyl ester (CAS 118156-93-7) instead of (RS)-3-formyl-pyrrolidine-1-carboxylic acid tert-butyl ester. White solid. MS (ISP): 361.2 ([{$^{37}$Cl}M+H]$^+$), 359.2 ([{$^{35}$Cl}M+H]$^+$).

Example 116

(RS)-1-(4-Chloro-phenyl)-3-[4-(2-pyrrolidin-3-yl-ethyl)-phenyl]-urea hydrochloride

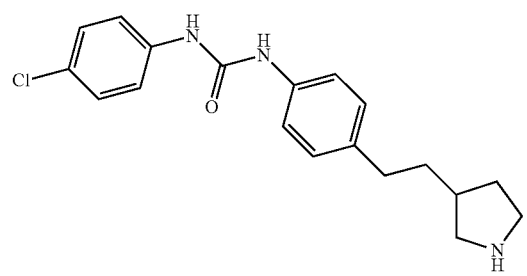 [SMILES: O=C(Nc1ccc(Cl)cc1)Nc1ccc(CCC2CCNC2)cc1]

The title compound was obtained in analogy to example 114 using 4-chloro-aniline (CAS 106-47-8) instead of 2-amino-5-chloropyridine. White solid. MS (ISP): 346.1 ([{$^{37}$Cl}M+H]$^+$), 344.2 ([{$^{35}$Cl}M+H]$^+$).

Example 117

(RS)-5-Chloro-pyridine-2-carboxylic acid [4-(2-pyrrolidin-3-yl-ethyl)-phenyl]-amide hydrochloride

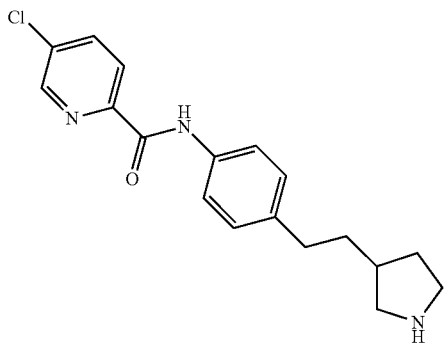 [SMILES: O=C(Nc1ccc(CCC2CCNC2)cc1)c1ccc(Cl)cn1]

The title compound was obtained in analogy to example 109 using 5-chloro-pyridine-2-carboxylic acid (CAS 86873-60-1) instead of 4-chloro-benzoic acid. Yellow solid. MS (ISP): 332.2 ($[\{^{37}Cl\}M+H]^+$), 330.2 ($[\{^{35}Cl\}M+H]^+$).

Example 118

(RS)-5-Chloro-pyridine-2-carboxylic acid [4-(2-piperidin-3-yl-ethyl)-phenyl]-amide hydrochloride

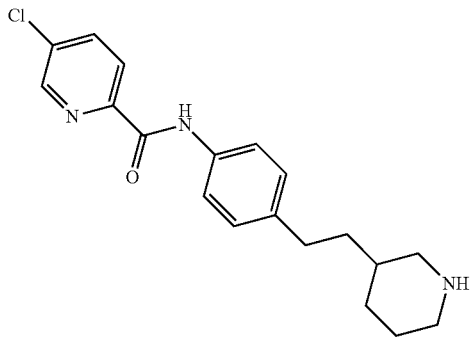 [SMILES: O=C(Nc1ccc(CCC2CCCNC2)cc1)c1ccc(Cl)cn1]

The title compound was obtained in analogy to example 109 using (RS)-3-formyl-piperidine-1-carboxylic acid tert-butyl ester (CAS 118156-93-7) instead of (RS)-3-formyl-pyrrolidine-1-carboxylic acid tert-butyl ester and 5-chloro-pyridine-2-carboxylic acid (CAS 86873-60-1) instead of 4-chloro-benzoic acid. Yellow solid. MS (ISP): 346.1 ($[\{^{37}Cl\}M+H]^+$), 344.2 ($[\{^{35}Cl\}M+H]^+$).

Example 119

(RS)-1-(4-Chloro-phenyl)-3-[4-(2-piperidin-3-yl-ethyl)-phenyl]-urea hydrochloride

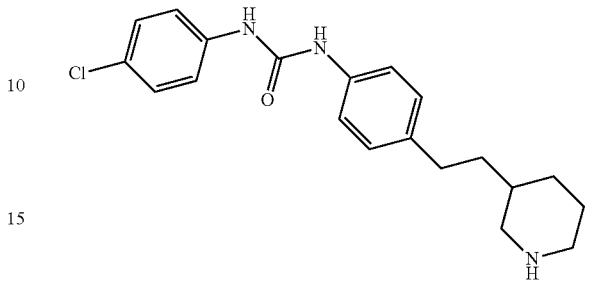

The title compound was obtained in analogy to example 109 step (b) and example 114 using (RS)-3-formyl-piperidine-1-carboxylic acid tert-butyl ester (CAS 118156-93-7) instead of (RS)-3-formyl-pyrrolidine-1-carboxylic acid tert-butyl ester and 4-chloro-aniline (CAS 106-47-8) instead of 2-amino-5-chloropyridine. White solid. MS (ISP): 360.2 ($[\{^{37}Cl\}M+H]^+$), 358.2 ($[\{^{35}Cl\}M+H]^+$).

Example 120

(RS)-(4-Pyrrolidin-3-yl-phenyl)-carbamic acid 2-(4-chloro-phenyl)-ethyl ester

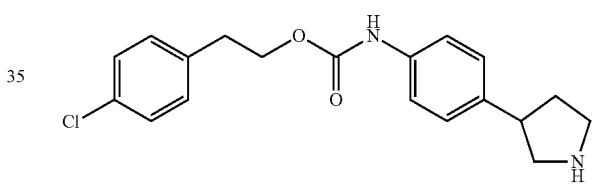

a) (RS)-3-{4-[2-(4-Chloro-phenyl)-ethoxycarbonylamino]-phenyl}-pyrrolidine-1-carboxylic acid tert-butyl ester To a stirred solution of (RS)-tert-butyl 3-(4-aminophenyl)pyrrolidine-1-carboxylate (100 mg, CAS 908334-28-1) in dichloroethane (4 ml) were added sequentially triethylamine (0.62 ml) and triphosgene (44 mg) and the mixture was heated at 80° C. for 1 h. To the resulting mixture was added 4-chlorophenethyl alcohol (0.06 ml, CAS 1875-88-3) and the mixture was heated at 100° C. for 18 h. The mixture was then cooled to room temperature and diluted with dichloromethane. The mixture was washed with water, then the phases were separated and the organic phase was dried over sodium sulphate and concentrated in vacuo. The residue was purified by column chromatography ($SiO_2$; gradient: heptane/EtOAc) to give (RS)-3-{4-[2-(4-chloro-phenyl)-ethoxycarbonylamino]-phenyl}-pyrrolidine-1-carboxylic acid tert-butyl ester (104 mg, 63%) as an orange solid. MS (ISP): 464.3 ($[\{^{37}Cl\}M+NH_4]^+$), 462.3 ($[\{^{35}Cl\}M+NH_4]^+$). 391.2 ($[\{^{37}Cl\}M+H-C_4H_8]^+$), 389.2 ($[\{^{35}Cl\}M+H-C_4H_8]^+$).

b) (RS)-(4-Pyrrolidin-3-yl-phenyl)-carbamic acid 2-(4-chloro-phenyl)-ethyl ester To a stirred solution of (RS)-3-{4-[2-(4-chloro-phenyl)-ethoxycarbonylamino]-phenyl}-pyrrolidine-1-carboxylic acid tert-butyl ester (100 mg) in THF (2 ml) was added dropwise a solution of hydrogen chloride in dioxane (0.84 ml, 4 M solution) and the mixture was heated at 60° C. overnight. The mixture was then cooled to 0° C. and made basic by addition of 1 M aq. sodium hydroxide solution. The mixture was extracted twice with ethyl acetate and the combined organic phases were dried over sodium sulphate, filtered and concentrated in vacuo. The residue was purified by column chromatography (Isolute® Flash-NH$_2$ from Separtis; gradient: heptane/ethyl acetate/methanol) to afford (RS)-(4-pyrrolidin-3-yl-phenyl)-carbamic acid 2-(4-chloro-phenyl)-ethyl ester (38 mg, 49%) as a colourless gum. MS (ISP): 347.1 ([{$^{37}$Cl}M+H]$^+$), 345.2 ([{$^{35}$Cl}M+H]$^+$).

Example 121

(RS)-(4-Pyrrolidin-3-yl-phenyl)-carbamic acid 2-(3-chloro-phenyl)-ethyl ester

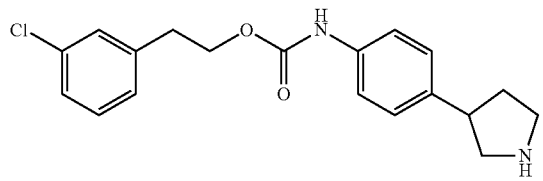 [SMILES: O=C(Nc1ccc(C2CCNC2)cc1)OCCc1cccc(Cl)c1]

The title compound was obtained in analogy to example 120 using 3-chlorophenethyl alcohol instead of 4-chloro-phenethyl alcohol. Colourless gum. MS (ISP): 347.1 ([{$^{37}$Cl}M+H]$^+$), 345.2 ([{$^{35}$Cl}M+H]$^+$).

Example 122

(RS)-(4-Pyrrolidin-3-yl-phenyl)-carbamic acid 2-(4-trifluoromethyl-phenyl)-ethyl ester

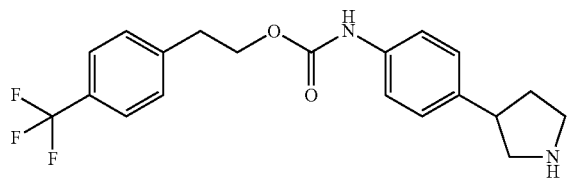 [SMILES: O=C(Nc1ccc(C2CCNC2)cc1)OCCc1ccc(C(F)(F)F)cc1]

The title compound was obtained in analogy to example 120 using 4-(trifluoromethyl)phenethyl alcohol instead of 4-chlorophenethyl alcohol. Colourless gum. MS (ISP): 379.3 ([M+H]$^+$).

Example 123

(RS)-(4-Pyrrolidin-3-yl-phenyl)-carbamic acid 2-(3-trifluoromethyl-phenyl)-ethyl ester

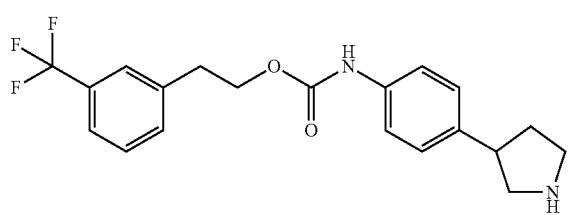 [SMILES: O=C(Nc1ccc(C2CCNC2)cc1)OCCc1cccc(C(F)(F)F)c1]

The title compound was obtained in analogy to example 120 using 3-(trifluoromethyl)phenethyl alcohol instead of 4-chlorophenethyl alcohol. Colourless gum. MS (ISP): 379.3 ([M+H]$^+$).

Example 124

(RS)-(4-Pyrrolidin-3-yl-phenyl)-carbamic acid 2-(2,5-difluoro-phenyl)-ethyl ester

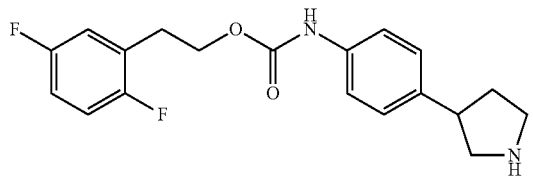 [SMILES: O=C(Nc1ccc(C2CCNC2)cc1)OCCc1cc(F)ccc1F]

The title compound was obtained in analogy to example 120 using 2,5-difluoro-phenethyl alcohol instead of 4-chlorophenethyl alcohol. Colourless gum. MS (ISP): 347.2 ([M+H]$^+$).

Example 125

(RS)-(4-Pyrrolidin-3-yl-phenyl)-carbamic acid 2-(4-trifluoromethoxy-phenyl)-ethyl ester

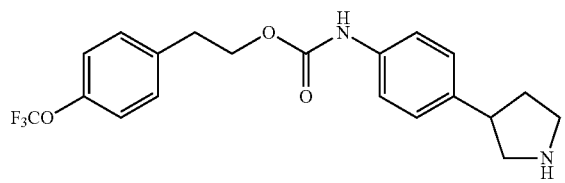 [SMILES: O=C(Nc1ccc(C2CCNC2)cc1)OCCc1ccc(OC(F)(F)F)cc1]

The title compound was obtained in analogy to example 120 using 4-(trifluoromethoxy)-phenethyl alcohol instead of 4-chlorophenethyl alcohol. Light yellow gum. MS (ISP): 395.2 ([M+H]$^+$).

Example 126

(RS)-(4-Pyrrolidin-3-yl-phenyl)-carbamic acid 2-(3,4-dichloro-phenyl)-ethyl ester

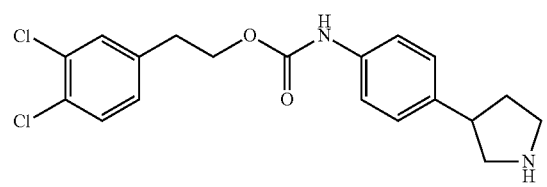 [SMILES: O=C(Nc1ccc(C2CCNC2)cc1)OCCc1ccc(Cl)c(Cl)c1]

The title compound was obtained in analogy to example 120 using 3,4-dichlorophenethyl alcohol instead of 4-chlorophenethyl alcohol. Orange gum. MS (ISP): 383.1 ([{$^{37}$Cl}M+H]$^+$), 381.2 ([{$^{37}$Cl$^{35}$Cl}M+H]$^+$), 379.3 ([{$^{35}$Cl}M+H]$^+$).

Example 127

(RS)-(4-Pyrrolidin-3-yl-phenyl)-carbamic acid (RS)-1-(4-chloro-phenyl)-ethyl ester

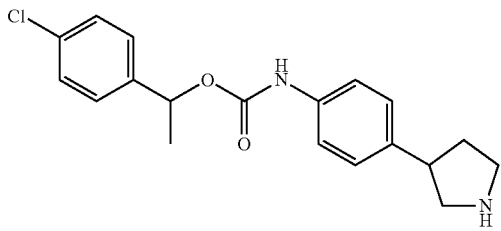 [SMILES: CC(OC(=O)Nc1ccc(C2CCNC2)cc1)c1ccc(Cl)cc1]

The title compound was obtained in analogy to example 120 using 3-chlorophenethyl alcohol instead of 4-chlorophenethyl alcohol. Amorphous colourless solid. MS (ISP): 347.1 ([{$^{37}$Cl}M+H]$^+$), 345.2 ([{$^{35}$Cl}M+H]$^+$).

Example 128

(RS)-(4-Pyrrolidin-3-yl-phenyl)-carbamic acid 3-(4-chloro-phenyl)-propyl ester

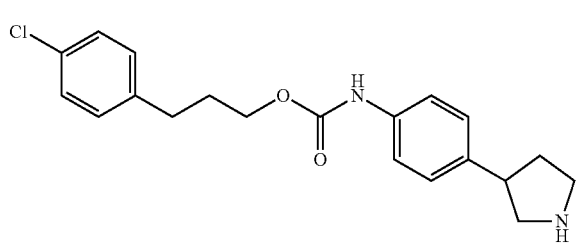 [SMILES: O=C(Nc1ccc(C2CCNC2)cc1)OCCCc1ccc(Cl)cc1]

The title compound was obtained in analogy to example 120 using 3-(4-chlorophenyl)propan-1-ol instead of 4-chlorophenethyl alcohol. Off-white solid. MS (ISP): 361.2 ([{$^{37}$Cl}M+H]$^+$), 359.2 ([{$^{35}$Cl}M+H]$^+$).

Example 129

(RS)-(4-Pyrrolidin-3-yl-phenyl)-carbamic acid indan-2-yl ester

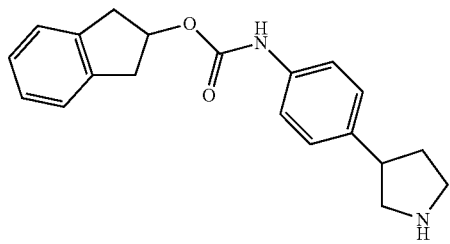 [SMILES: O=C(Nc1ccc(C2CCNC2)cc1)OC1Cc2ccccc2C1]

The title compound was obtained in analogy to example 120 using 2-indanol instead of 4-chlorophenethyl alcohol. Off-white solid. MS (ISP): 323.3 ([M+H]$^+$).

Example 130

(RS)-(4-Pyrrolidin-3-yl-phenyl)-carbamic acid (RS)-1-(4-chloro-phenyl)-2,2,2-trifluoro-ethyl ester

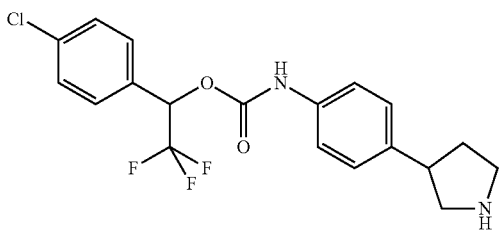 [SMILES: O=C(Nc1ccc(C2CCNC2)cc1)OC(c1ccc(Cl)cc1)C(F)(F)F]

The title compound was obtained in analogy to example 120 using 1-(4-chlorophenyl)-2,2,2-trifluoroethanol instead of 4-chlorophenethyl alcohol. Off-white solid. MS (ISP): 401.2 ([{$^{37}$Cl}M+H]$^+$), 399.2 ([{$^{35}$Cl}M+H]$^+$).

Example 131

(RS)-(4-Pyrrolidin-3-yl-phenyl)-carbamic acid (RS)-3,3,3-trifluoro-1-methyl-propyl ester

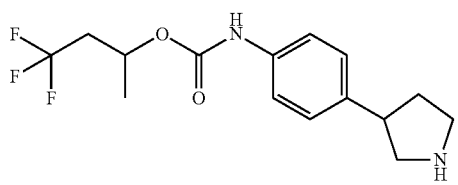 [SMILES: CC(CC(F)(F)F)OC(=O)Nc1ccc(C2CCNC2)cc1]

The title compound was obtained in analogy to example 120 using 4,4,4-trifluoro-2-butanol instead of 4-chlorophenethyl alcohol. Amorphous brown solid. MS (ISP): 317.3 ([M+H]$^+$).

Example 132

(RS)-3-Fluoro-pyridine-2-carboxylic acid [4-(2-pyrrolidin-3-yl-ethyl)-phenyl]-amide hydrochloride

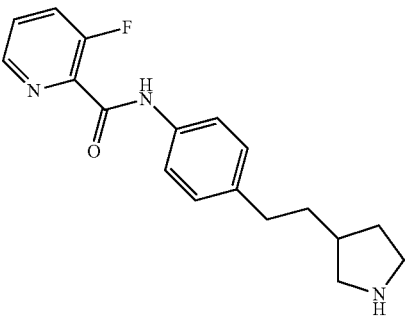 [SMILES: O=C(Nc1ccc(CCC2CCNC2)cc1)c1ncccc1F]

The title compound was obtained in analogy to example 109 using 3-fluoro-pyridine-2-carboxylic acid (CAS 152126-31-3) instead of 4-chloro-benzoic acid. Yellow solid. MS (ISP): 314.1 ([M+H]$^+$).

Example 133

(RS)-3,5-Difluoro-pyridine-2-carboxylic acid [4-(2-pyrrolidin-3-yl-ethyl)-phenyl]-amide hydrochloride

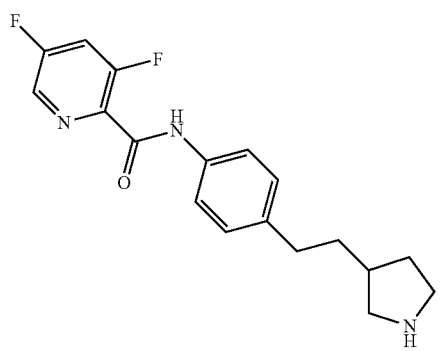 [SMILES: O=C(Nc1ccc(CCC2CCNC2)cc1)c1ncc(F)cc1F]

The title compound was obtained in analogy to example 109 using 3,5-difluoro-pyridine-2-carboxylic acid (CAS 745784-04-7) instead of 4-chloro-benzoic acid. Yellow solid. MS (ISP): 332.2 ([M+H]$^+$).

Example 134

(RS)-3-Fluoro-pyridine-2-carboxylic acid [4-(2-piperidin-3-yl-ethyl)-phenyl]-amide hydrochloride

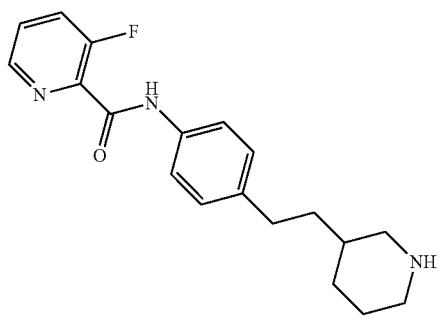 [SMILES: O=C(Nc1ccc(CCC2CCCNC2)cc1)c1ncccc1F]

The title compound was obtained in analogy to example 109 using (RS)-3-formyl-piperidine-1-carboxylic acid tert-butyl ester (CAS 118156-93-7) instead of (RS)-3-formyl-pyrrolidine-1-carboxylic acid tert-butyl ester and 3-fluoro-pyridine-2-carboxylic acid (CAS 152126-31-3) instead of 4-chloro-benzoic acid. Yellow solid. MS (ISP): 328.3 ([M+H]$^+$).

Example 135

(RS)-3,5-Difluoro-pyridine-2-carboxylic acid [4-(2-piperidin-3-yl-ethyl)-phenyl]-amide hydrochloride

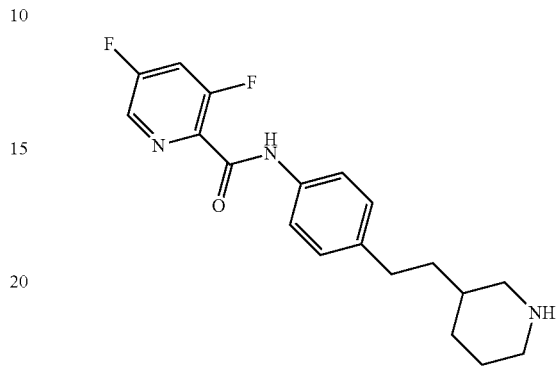

The title compound was obtained in analogy to example 109 using (RS)-3-formyl-piperidine-1-carboxylic acid tert-butyl ester (CAS 118156-93-7) instead of (RS)-3-formyl-pyrrolidine-1-carboxylic acid tert-butyl ester and 3,5-difluoro-pyridine-2-carboxylic acid (CAS 745784-04-7) instead of 4-chloro-benzoic acid. Yellow solid. MS (ISP): 346.1 ([M+H]$^+$).

Example 136

(RS)-4-Chloro-N-[4-(pyrrolidine-3-carbonyl)-phenyl]-benzamide hydrochloride

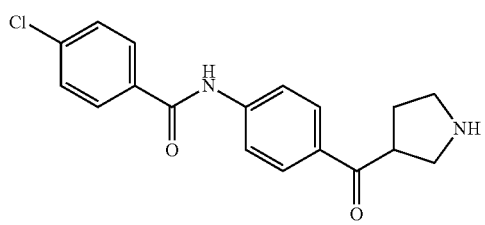 [SMILES: O=C(Nc1ccc(C(=O)C2CCNC2)cc1)c1ccc(Cl)cc1]

The title compound was obtained in analogy to example 141 using (RS)-3-(4-bromo-benzoyl)-pyrrolidine-1-carboxylic acid tert-butyl ester (CAS 960402-23-7) instead of (RS)-tert-butyl 2-(4-bromophenyl)morpholine-4-carboxylate and 4-chloro-benzamide (CAS 619-56-7) instead of 5-trifluoromethyl-pyridine-2-carboxylic acid amide. Light brown solid. MS (ISP): 331.2 ([{$^{37}$Cl}M+H]$^+$), 329.3 ([{$^{35}$Cl}M+H]$^+$).

Example 137

(RS)—N-(4-Piperidin-3-yl-phenyl)-4-propyl-benzamide hydrochloride

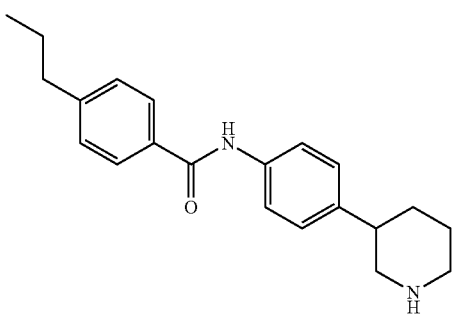 [SMILES: CCCc1ccc(C(=O)Nc2ccc(C3CCCNC3)cc2)cc1]

The title compound was obtained in analogy to example 29 using (RS)-tert-butyl 3-(4-aminophenyl)-1-piperidinecarboxylate (CAS 875798-79-1) instead of (RS)-tert-butyl 3-(4-aminophenyl)pyrrolidine-1-carboxylate and 4-n-propyl-benzoic acid (CAS 2438-05-3) instead of (R)-2-phenylpropionic acid. White solid. MS (ISP): 323.2 ([M+H]$^+$).

Example 138

(RS)-5-Trifluoromethyl-pyridine-2-carboxylic acid (4-piperidin-3-yl-phenyl)-amide hydrochloride

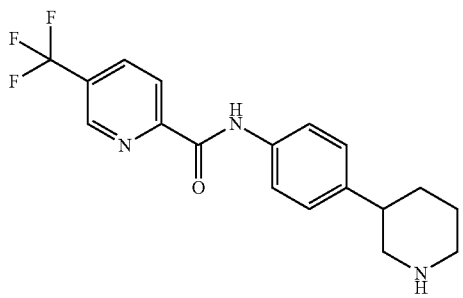 [SMILES: O=C(Nc1ccc(C2CCCNC2)cc1)c1ccc(C(F)(F)F)cn1]

The title compound was obtained in analogy to example 29 using (RS)-tert-butyl 3-(4-aminophenyl)-1-piperidinecarboxylate (CAS 875798-79-1) instead of (RS)-tert-butyl 3-(4-aminophenyl)pyrrolidine-1-carboxylate and 5-trifluoromethyl-2-pyridine-carboxylic acid (CAS 80194-69-0) instead of (R)-2-phenylpropionic acid. White solid. MS (ISP): 350.2 ([M+H]$^+$).

Example 139

(RS)-5-Trifluoromethyl-pyridine-2-carboxylic acid (4-pyrrolidin-3-yl-phenyl)-amide hydrochloride

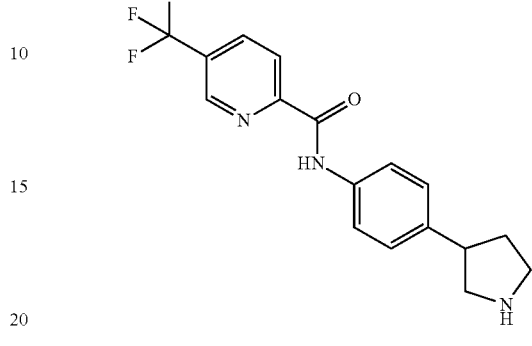

The title compound was obtained in analogy to example 29 using 5-trifluoromethyl-2-pyridine-carboxylic acid (CAS 80194-69-0) instead of (R)-2-phenylpropionic acid. White solid. MS (ISP): 336.2 ([M+H]$^+$).

Example 140

(RS)-4-Chloro-N-(6-pyrrolidin-3-yl-pyridin-3-yl)-benzamide

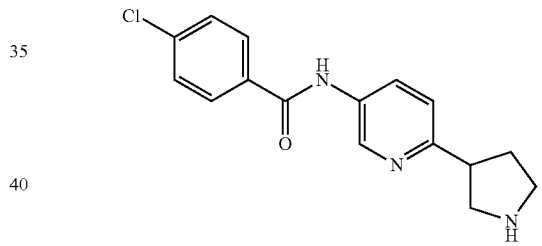

(a) (RS)-2-[1-(4-Methoxy-benzyl)-pyrrolidin-3-yl]-5-nitro-pyridine

To a stirred solution of 5-nitro-2-vinyl-pyridine (400 mg, CAS 119836-85-0) and (4-methoxy-benzyl)-methoxymethyl-trimethylsilanylmethyl-amine (1.43 g, CAS 433289-59-9) in dichloromethane at 0° C. was added a solution of trifluoroacetic acid (0.02 ml) in dichloromethane (0.3 ml). The mixture was warmed to room temperature and stirred for 2 hours. The mixture was then washed sequentially with sat. aq. sodium bicarbonate solution and with saturated brine. The organic phase was dried over sodium sulphate and concentrated in vacuo. The residue was purified by flash chromatography (SiO2, heptane/EtOAc gradient) to afford (RS)-2-[1-(4-methoxy-benzyl)-pyrrolidin-3-yl]-5-nitro-pyridine (592 mg, 71%) as an orange viscous oil. MS (ISP): 314.2 ([M+H]$^+$).

(b) (RS)-6-[1-(4-Methoxy-benzyl)-pyrrolidin-3-yl]-pyridin-3-ylamine

To a solution of (RS)-2-[1-(4-methoxy-benzyl)-pyrrolidin-3-yl]-5-nitro-pyridine (586 mg) in methanol (2 ml) was added palladium on charcoal (10%, 99 mg). The mixture was stirred under an atmosphere of hydrogen for 1 hour. The mixture was filtered through celite to remove the catalyst, washing the filter with dichloromethane, and the filtrate was concentrated in vacuo to afford (RS)-6-[1-(4-methoxy-benzyl)-pyrrolidin-3-yl]-pyridin-3-ylamine (532 mg, quant.) as a red viscous oil. MS (ISP): 284.3 ([M+H]$^+$).

(c) (RS)-4-Chloro-N-{6-[1-(4-methoxy-benzyl)-pyrrolidin-3-yl]-pyridin-3-yl}-benzamide The title compound was obtained in analogy to example 29 step (a) using (RS)-6-[1-(4-methoxy-benzyl)-pyrrolidin-3-yl]-pyridin-3-ylamine instead of (RS)-tert-butyl 3-(4-aminophenyl)pyrrolidine-1-carboxylate and 4-chlorobenzoic acid (CAS 74-11-3) instead of (R)-2-phenylpropionic acid. Orange gum. MS (ISP): 424.2 ([{$^{37}$Cl}M+H]$^+$), 422.2 ([{$^{35}$Cl}M+H]$^+$).

(d) (RS)-4-Chloro-N-(6-pyrrolidin-3-yl-pyridin-3-yl)-benzamide

To a stirred solution of (RS)-4-chloro-N-{6-[1-(4-methoxy-benzyl)-pyrrolidin-3-yl]-pyridin-3-yl}-benzamide in dichloromethane (10 ml) at 0° C. were added sequentially pyridine (0.24 ml) and triphosgene (455 mg) and the resulting mixture was allowed to warm to room temperature while stirring was continued overnight. The mixture was then concentrated in vacuo and the residue was taken up in dioxane (5 ml) and water (5 ml). Two drops of concentrated hydrochloric acid were added and the resulting mixture was then heated at 70° C. for 18 h. The reaction mixture was then cooled to room temperature and quenched by addition of saturated aq. sodium bicarbonate solution. The mixture was extracted twice with ethyl acetate and the combined organic phases were dried over sodium sulphate and concentrated in vacuo. The residue was purified by flash chromatography (Isolute® Flash-NH$_2$ from Separtis; gradient: heptane/EtOAc/MeOH 100:0:0 to 0:80:20) to afford (RS)-4-chloro-N-(6-pyrrolidin-3-yl-pyridin-3-yl)-benzamide (18 mg, 8%) as an orange gum. MS (ISP): 304.1 ([{$^{37}$Cl}M+H]$^+$), 302.1 ([{$^{35}$Cl}M+H]$^+$).

Example 141

(RS)-5-Trifluoromethyl-pyridine-2-carboxylic acid (4-morpholin-2-yl-phenyl)-amide hydrochloride

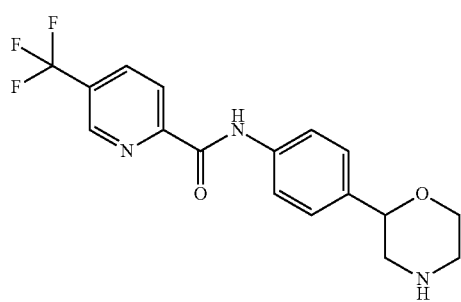 [SMILES: O=C(Nc1ccc(C2CNCCO2)cc1)c1ccc(C(F)(F)F)cn1]

a) (RS)-tert-Butyl 2-(4-bromophenyl)morpholine-4-carboxylate

To a stirred solution of (RS)-2-(4-bromo-phenyl)-morpholine (1.00 g, CAS 83555-73-1) in THF (12 ml) were added sequentially N,N-diisopropylethylamine (0.84 ml) and di-tert-butyl dicarbonate (1.08 g) and the mixture was stirred at room temperature for 18 hours. The mixture was concentrated in vacuo and the residue was purified by column chromatography (SiO$_2$; gradient: heptane/EtOAc) to afford (RS)-tert-butyl 2-(4-bromophenyl)morpholine-4-carboxylate (1.30 g, 92%) as a colourless oil. MS (ISP): 344.2 ([{$^{81}$Br}M+H]$^+$), 342.2 ([{$^{79}$Br}M+H]$^+$), 288.1 ([{$^{81}$Br}M+H—C$_4$H$_8$]$^+$), 286.1 ([{$^{79}$Br}M+H—C$_4$H$_8$]$^+$).

b) (RS)-2-{4-[(5-Trifluoromethyl-pyridine-2-carbonyl)-amino]-phenyl}-morpholine-4-carboxylic acid tert-butyl ester A stirred suspension of (RS)-tert-butyl 2-(4-bromophenyl)morpholine-4-carboxylate (500 mg), 5-trifluoromethyl-pyridine-2-carboxylic acid amide (389 mg, CAS 22245-86-9), caesium carbonate (952 mg), N,N'-dimethylethylenediamine (0.04 ml) and copper(I) iodide (28 mg) in dioxane (10 ml) under an argon atmosphere in a sealed tube was heated in a microwave oven at 180° C. for 2 h. The mixture was cooled to room temperature, filtered through celite and the filtrate was concentrated in vacuo. The residue was purified by column chromatography (SiO$_2$; gradient: heptane/EtOAc) to give (RS)-2-{4-[(5-trifluoromethyl-pyridine-2-carbonyl)-amino]-phenyl}-morpholine-4-carboxylic acid tert-butyl ester (366 mg, 55%) as a white solid. MS (ISP): 469.2 ([M+NH$_4$]$^+$), 396.0 ([M+H—C$_4$H$_8$]$^+$).

c) (RS)-5-Trifluoromethyl-pyridine-2-carboxylic acid (4-morpholin-2-yl-phenyl)-amide hydrochloride To a stirred solution of (RS)-2-{4-[(5-trifluoromethyl-pyridine-2-carbonyl)-amino]-phenyl}-morpholine-4-carboxylic acid tert-butyl ester (360 mg) in THF (3 ml) was added dropwise a solution of hydrogen chloride in dioxane (2.99 ml, 4 M solution) and the mixture was heated at 60° C. overnight. The mixture was then cooled to 0° C. and the ensuing crystals were collected by filtration, washing twice with ethyl acetate, and were dried in vacuo at 60° C. to afford (RS)-5-trifluoromethyl-pyridine-2-carboxylic acid (4-morpholin-2-yl-phenyl)-amide hydrochloride (263 mg, 85%) as a white crystalline solid. MS (ISP): 352.3 ([M+H]$^+$).

Example 142

(RS)-4-Chloro-N-[4-(2-pyrrolidin-2-yl-ethyl)-phenyl]-benzamide hydrochloride

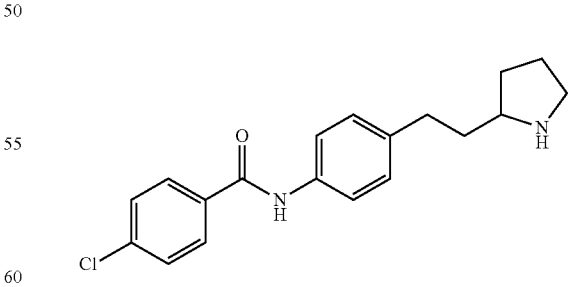

The title compound was obtained in analogy to example 109 using (RS)-2-formyl-pyrrolidine-1-carboxylic acid tert-butyl ester (CAS 117625-90-8) instead of (RS)-3-formyl-pyrrolidine-1-carboxylic acid tert-butyl ester. Off-white solid. MS (ISP): 331.1 ([{$^{37}$Cl}M+H]$^+$), 329.3 ([{$^{35}$Cl}M+H]$^+$).

Example 143

4-Chloro-N—((R)-4-morpholin-2-yl-phenyl)-benzamide hydrochloride

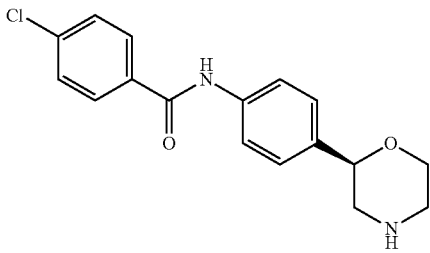

The title compound was obtained in analogy to example 141 using (R)-tert-butyl 2-(4-bromophenyl)morpholine-4-carboxylate (example 207b) instead of (RS)-tert-butyl 2-(4-bromophenyl)morpholine-4-carboxylate and 4-chloro-benzamide (CAS 619-56-7) instead of 5-trifluoromethyl-pyridine-2-carboxylic acid amide. White solid. MS (ISP): 319.2 ($[\{^{37}Cl\}M+H]^+$), 317.2 ($[\{^{35}Cl\}M+H]^+$).

Example 144

4-Chloro-N—((S)-4-morpholin-2-yl-phenyl)-benzamide hydrochloride

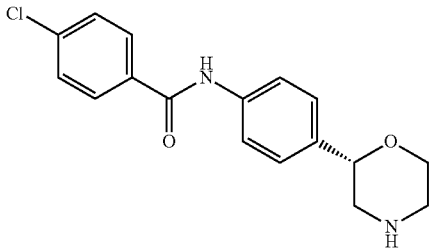

The title compound was obtained in analogy to example 141 using (S)-tert-butyl 2-(4-bromophenyl)morpholine-4-carboxylate (example 208b) instead of (RS)-tert-butyl 2-(4-bromophenyl)morpholine-4-carboxylate and 4-chloro-benzamide (CAS 619-56-7) instead of 5-trifluoromethyl-pyridine-2-carboxylic acid amide. White solid. MS (ISP): 319.2 ($[\{^{37}Cl\}M+H]^+$), 317.2 ($[\{^{35}Cl\}M+H]^+$).

Example 145

(RS)-4-Chloro-N-[4-(pyrrolidin-3-yloxymethyl)-phenyl]-benzamide hydrochloride

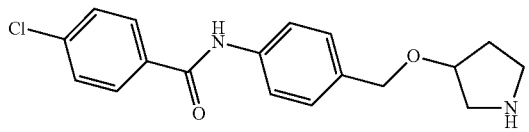 [SMILES: O=C(Nc1ccc(COC2CCNC2)cc1)c1ccc(Cl)cc1]

(a) (RS)-3-(4-Amino-benzyloxy)-pyrrolidine-1-carboxylic acid tert-butyl ester

To a solution of (RS)-3-(4-nitro-benzyloxy)-pyrrolidine-1-carboxylic acid tert-butyl ester (70 mg, CAS 1121634-39-6) in methanol (5 ml) was added palladium on charcoal (10%, 12 mg). The mixture was stirred vigorously under an atmosphere of hydrogen for 18 hours. The catalyst was filtered off and the filtrate was evaporated. The crude product was purified by column chromatography (SiO2, heptane/EtOAc gradient) to give (RS)-3-(4-amino-benzyloxy)-pyrrolidine-1-carboxylic acid tert-butyl ester (33 mg, 52%) as a light yellow viscous oil. MS (ISP): 315.2 ($[M+Na]^+$).

(b) (RS)-4-Chloro-N-[4-(pyrrolidin-3-yloxymethyl)-phenyl]-benzamide hydrochloride The title compound was obtained in analogy to example 29 using (RS)-3-(4-amino-benzyloxy)-pyrrolidine-1-carboxylic acid tert-butyl ester instead of (RS)-tert-butyl 3-(4-aminophenyl)pyrrolidine-1-carboxylate and 4-chlorobenzoic acid (CAS 74-11-3) instead of (R)-2-phenylpropionic acid. Off-white solid. MS (ISP): 333.1 ($[\{^{37}Cl\}M+H]^+$), 331.1 ($[\{^{35}Cl\}M+H]^+$).

Example 146

(RS)-4-Chloro-2-fluoro-N-(4-morpholin-2-yl-phenyl)-benzamide hydrochloride

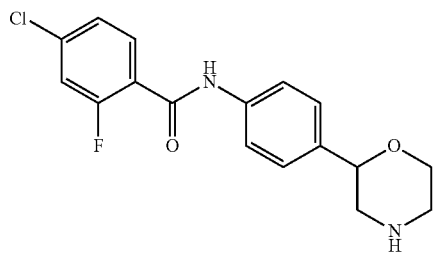

The title compound was obtained in analogy to example 141 using 4-chloro-2-fluoro-benzamide (CAS 104326-93-4) instead of 5-trifluoromethyl-pyridine-2-carboxylic acid amide. White solid. MS (ISP): 337.3 ($[\{^{37}Cl\}M+H]^+$), 335.3 ($[\{^{35}Cl\}M+H]^+$).

Example 147

(RS)-3,4-Dichloro-N-(4-morpholin-2-yl-phenyl)-benzamide hydrochloride

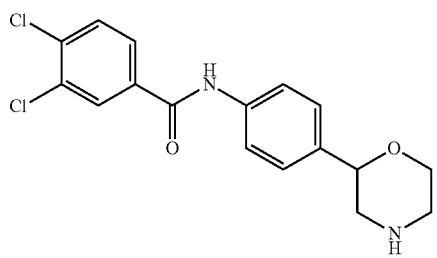 [SMILES: O=C(Nc1ccc(C2CNCCO2)cc1)c1ccc(Cl)c(Cl)c1]

The title compound was obtained in analogy to example 141 using 3,4-dichloro-benzamide (CAS 2670-38-4) instead of 5-trifluoromethyl-pyridine-2-carboxylic acid amide. White solid. MS (ISP): 355.3 ($[\{^{37}Cl\}M+H]^+$), 353.2 ($[\{^{37}Cl^{35}Cl\}M+H]^+$), 351.3 ($[\{^{35}Cl\}M+H]^+$).

Example 148

(RS)-5-Chloro-pyridine-2-carboxylic acid (4-morpholin-2-yl-phenyl)-amide hydrochloride

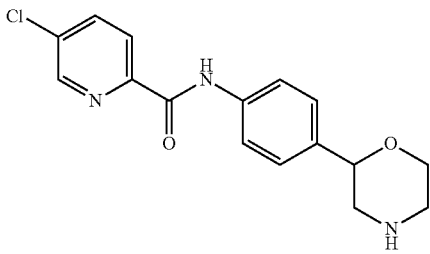 [SMILES: O=C(Nc1ccc(C2CNCCO2)cc1)c1ccc(Cl)cn1]

The title compound was obtained in analogy to example 141 using 5-chloro-pyridine-2-carboxylic acid amide (CAS 370104-72-6) instead of 5-trifluoromethyl-pyridine-2-carboxylic acid amide. Off-white solid. MS (ISP): 320.1 ([$\{^{37}Cl\}$M+H]$^+$), 318.2 ([$\{^{35}Cl\}$M+H]$^+$).

Example 149

(RS)-4-Chloro-N-(4-pyrrolidin-3-ylmethyl-phenyl)-benzamide hydrochloride

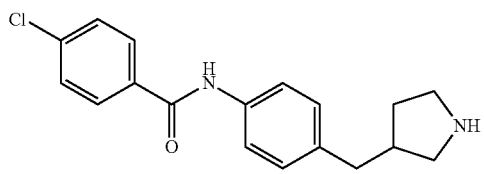 [SMILES: O=C(Nc1ccc(CC2CCNC2)cc1)c1ccc(Cl)cc1]

The title compound was obtained in analogy to example 107 using (RS)-3-(4-bromo-benzyl)-pyrrolidine (CAS 1158764-56-7) instead of (RS)-2-(4-bromo-benzyl)-pyrrolidine. Light brown solid. MS (ISP): 317.2 ([$\{^{37}Cl\}$M+H]$^+$), 315.1 ([$\{^{35}Cl\}$M+H]$^+$).

Example 150

3,4-Dichloro-N—((R)-4-piperidin-3-yl-phenyl)-benzamide hydrochloride

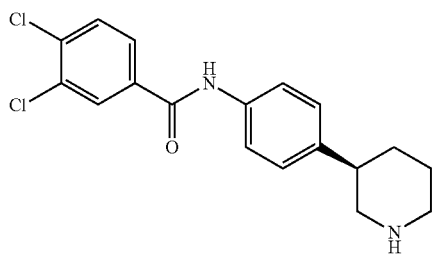 [SMILES: O=C(Nc1ccc([C@H]2CCCNC2)cc1)c1ccc(Cl)c(Cl)c1]

(a) (R)-tert-Butyl 3-(4-aminophenyl)piperidine-1-carboxylate & (S)-tert-Butyl 3-(4-aminophenyl)piperidine-1-carboxylate The enantiomers of (RS)-tert-butyl 3-(4-aminophenyl)piperidine-1-carboxylate (6.00 g, CAS 875798-79-1) were separated using chiral HPLC (column: Chiralpak AD, 5×50 cm; eluent: 10% ethanol/heptane; pressure: 15 bar; flow rate: 35 ml/min) affording:

(+)-(R)-tert-Butyl 3-(4-aminophenyl)piperidine-1-carboxylate (2.72 g, white solid)
Retention time=62 min
(−)-(S)-tert-Butyl 3-(4-aminophenyl)piperidine-1-carboxylate (2.65 g, white solid)
Retention time=88 min (b) 3,4-Dichloro-N—((R)-4-piperidin-3-yl-phenyl)-benzamide hydrochloride The title compound was obtained in analogy to example 29 using (R)-tert-butyl 3-(4-aminophenyl)piperidine-1-carboxylate (example 150a) instead of (RS)-tert-butyl 3-(4-aminophenyl)pyrrolidine-1-carboxylate and 3,4-dichlorobenzoic acid (CAS 51-44-5) instead of (R)-2-phenylpropionic acid. White solid. MS (ISP): 353.2 ([$\{^{37}Cl\}$M+H]$^+$), 351.3 ([$\{^{37}Cl^{35}Cl\}$M+H]$^+$), 349.2 ([$\{^{35}Cl\}$M+H]$^+$).

Example 151

(R)-3-Chloro-N-(4-(piperidin-3-yl)phenyl)benzamide hydrochloride

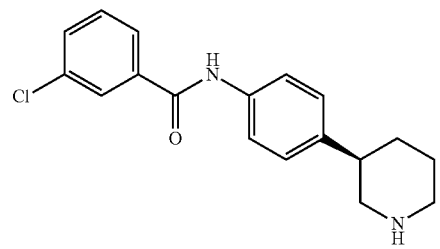 [SMILES: O=C(Nc1ccc([C@H]2CCCNC2)cc1)c1cccc(Cl)c1]

The title compound was obtained in analogy to example 29 using (R)-tert-butyl 3-(4-aminophenyl)piperidine-1-carboxylate (example 150a) instead of (RS)-tert-butyl 3-(4-aminophenyl)pyrrolidine-1-carboxylate and 3-chlorobenzoic acid (CAS 535-80-8) instead of (R)-2-phenylpropionic acid. White solid. MS (ISP): 317.3 ([$\{^{37}Cl\}$M+H]$^+$), 315.1 ([$\{^{35}Cl\}$M+H]$^+$).

Example 152

3,4-Dichloro-N—((S)-4-piperidin-3-yl-phenyl)-benzamide hydrochloride

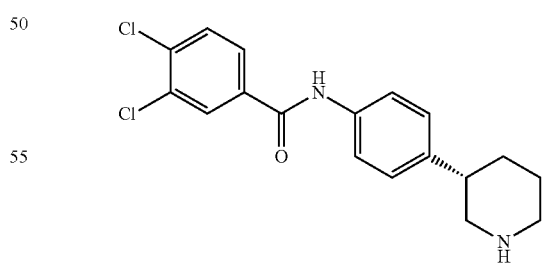

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 3,4-dichlorobenzoic acid (CAS 51-44-5) instead of (R)-2-phenylpropionic acid. White solid. MS (ISP): 353.2 ([$\{^{37}Cl\}$M+H]$^+$), 351.3 ([$\{^{37}Cl^{35}Cl\}$M+H]$^+$), 349.2 ([$\{^{35}Cl\}$M+H]$^+$).

Example 153

(S)-3-Chloro-N-(4-(piperidin-3-yl)phenyl)benzamide hydrochloride

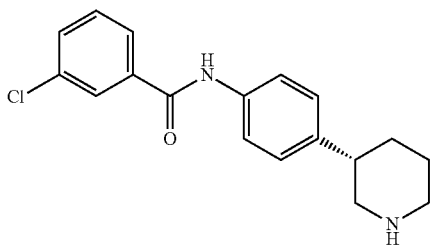 [SMILES: O=C(Nc1ccc([C@@H]2CCCNC2)cc1)c1cccc(Cl)c1]

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 3-chlorobenzoic acid (CAS 535-80-8) instead of (R)-2-phenylpropionic acid. White solid. MS (ISP): 317.2 ([{$^{37}$Cl}M+H]$^+$), 315.2 ([{$^{35}$Cl}M+H]$^+$).

Example 154

(RS)-3,4-Dichloro-N-[4-(2-pyrrolidin-2-yl-ethyl)-phenyl]-benzamide hydrochloride

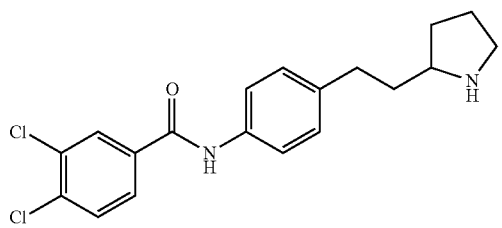 [SMILES: O=C(Nc1ccc(CCC2CCCN2)cc1)c1ccc(Cl)c(Cl)c1]

The title compound was obtained in analogy to example 109 using (RS)-2-formyl-pyrrolidine-1-carboxylic acid tert-butyl ester (CAS 117625-90-8) instead of (RS)-3-formyl-pyrrolidine-1-carboxylic acid tert-butyl ester and 3,4-dichlorobenzoic acid (CAS 51-44-5) instead of 4-chlorobenzoic acid. Off-white solid. MS (ISP): 367.1 ([{$^{37}$Cl}M+H]$^+$), 365.2 ([{$^{37}$Cl$^{35}$Cl}M+H]$^+$), 363.2 ([{$^{35}$Cl}M+H]$^+$).

Example 155

(RS)—N-[4-(2-Pyrrolidin-2-yl-ethyl)-phenyl]-4-trifluoromethyl-benzamide hydrochloride

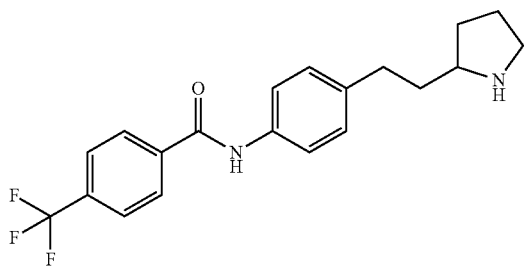 [SMILES: O=C(Nc1ccc(CCC2CCCN2)cc1)c1ccc(C(F)(F)F)cc1]

The title compound was obtained in analogy to example 109 using (RS)-2-formyl-pyrrolidine-1-carboxylic acid tert-butyl ester (CAS 117625-90-8) instead of (RS)-3-formyl-pyrrolidine-1-carboxylic acid tert-butyl ester and 4-(trifluoromethyl)benzoic acid (CAS 455-24-3) instead of 4-chlorobenzoic acid. White solid. MS (ISP): 363.3 ([M+H]$^+$).

Example 156

(RS)-4-Fluoro-N-[4-(2-pyrrolidin-2-yl-ethyl)-phenyl]-benzamide hydrochloride

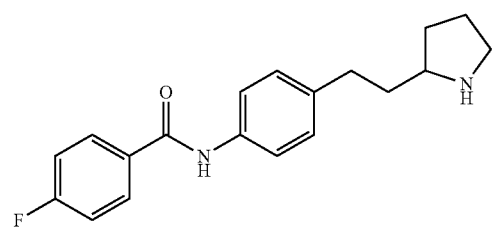 [SMILES: O=C(Nc1ccc(CCC2CCCN2)cc1)c1ccc(F)cc1]

The title compound was obtained in analogy to example 109 using (RS)-2-formyl-pyrrolidine-1-carboxylic acid tert-butyl ester (CAS 117625-90-8) instead of (RS)-3-formyl-pyrrolidine-1-carboxylic acid tert-butyl ester and 4-fluorobenzoic acid (CAS 456-22-4) instead of 4-chlorobenzoic acid. White solid. MS (ISP): 313.3 ([M+H]$^+$).

Example 157

(RS)-3-Chloro-N-[4-(2-pyrrolidin-2-yl-ethyl)-phenyl]-benzamide

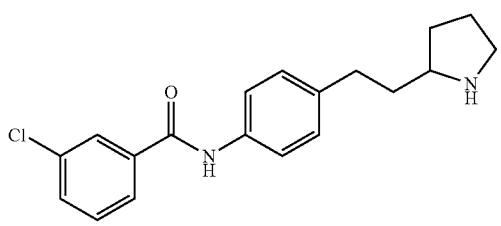 [SMILES: O=C(Nc1ccc(CCC2CCCN2)cc1)c1cccc(Cl)c1]

The title compound was obtained in analogy to example 109 using (RS)-2-formyl-pyrrolidine-1-carboxylic acid tert-butyl ester (CAS 117625-90-8) instead of (RS)-3-formyl-pyrrolidine-1-carboxylic acid tert-butyl ester and 3-chlorobenzoic acid (CAS 535-80-8) instead of 4-chlorobenzoic acid. Off-white solid. MS (ISP): 331.2 ([{$^{37}$Cl}M+H]$^+$), 329.3 ([{$^{35}$Cl}M+H]$^+$).

Example 158

(RS)-4-Ethoxy-N-[4-(2-pyrrolidin-2-yl-ethyl)-phenyl]-benzamide hydrochloride

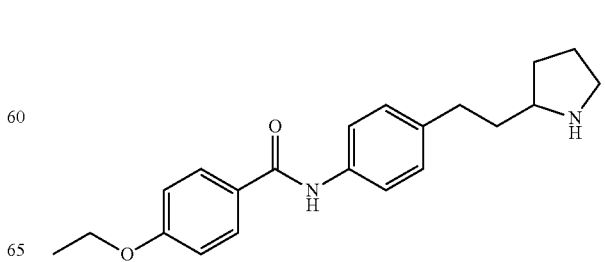

The title compound was obtained in analogy to example 109 using (RS)-2-formyl-pyrrolidine-1-carboxylic acid tert-butyl ester (CAS 117625-90-8) instead of (RS)-3-formyl-pyrrolidine-1-carboxylic acid tert-butyl ester and 4-ethoxy-benzoic acid (CAS 619-86-3) instead of 4-chlorobenzoic acid. White solid. MS (ISP): 313.3 ([M+H]$^+$).

Example 159

(RS)-4-Chloro-N-(4-piperidin-2-yl-phenyl)-benzamide hydrochloride

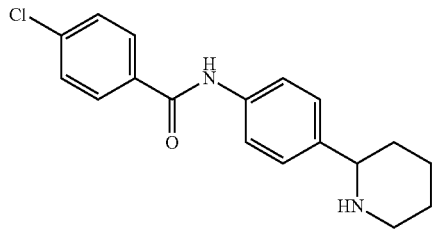 [SMILES: O=C(Nc1ccc(C2CCCCN2)cc1)c1ccc(Cl)cc1]

The title compound was obtained in analogy to example 29 using (RS)-tert-butyl 2-(4-aminophenyl)-1-piperidinecarboxylate (CAS 908334-26-9) instead of (RS)-tert-butyl 3-(4-aminophenyl)pyrrolidine-1-carboxylate and 4-chlorobenzoic acid (CAS 74-11-3) instead of (R)-2-phenylpropionic acid. White solid. MS (ISP): 317.2 ([$^{37}$Cl}M+H]$^+$), 315.1 ([$^{35}$Cl}M+H]$^+$).

Example 160

(RS)-5-Chloro-pyrazine-2-carboxylic acid (4-piperidin-3-yl-phenyl)-amide hydrochloride

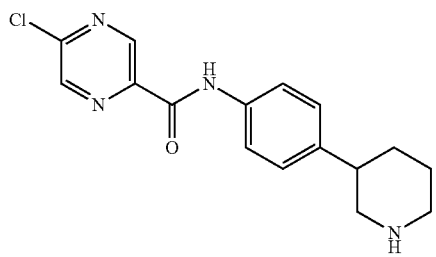

The title compound was obtained in analogy to example 29 using (RS)-tert-butyl 3-(4-aminophenyl)-1-piperidinecarboxylate (CAS 875798-79-1) instead of (RS)-tert-butyl 3-(4-aminophenyl)pyrrolidine-1-carboxylate and 5-chloro-pyrazine-2-carboxylic acid (CAS 36070-80-1) instead of (R)-2-phenylpropionic acid. White solid. MS (ISP): 319.2 ([$^{37}$Cl}M+H]$^+$), 317.2 ([$^{35}$Cl}M+H]$^+$).

Example 161

(R)-6-Chloro-N-(4-(piperidin-3-yl)phenyl)nicotinamide hydrochloride

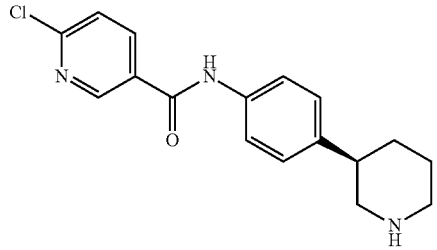 [SMILES: O=C(Nc1ccc([C@H]2CCCNC2)cc1)c1ccc(Cl)nc1]

The title compound was obtained in analogy to example 29 using (R)-tert-butyl 3-(4-aminophenyl)piperidine-1-carboxylate (example 150a) instead of (RS)-tert-butyl 3-(4-aminophenyl)pyrrolidine-1-carboxylate and 6-chloro-nicotinic acid (CAS 5326-23-8) instead of (R)-2-phenylpropionic acid. White solid. MS (ISP): 318.2 ([$^{37}$Cl}M+H]$^+$), 316.2 ([$^{35}$Cl}M+H]$^+$).

Example 162

(S)-6-Chloro-N-(4-(piperidin-3-yl)phenyl)nicotinamide hydrochloride

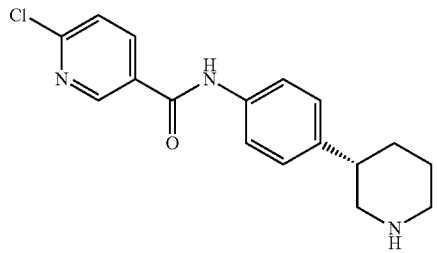 [SMILES: O=C(Nc1ccc([C@@H]2CCCNC2)cc1)c1ccc(Cl)nc1]

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 6-chloro-nicotinic acid (CAS 5326-23-8) instead of (R)-2-phenylpropionic acid. Off-white solid. MS (ISP): 318.2 ([$^{37}$Cl}M+H]$^+$), 316.2 ([$^{35}$Cl}M+H]$^+$).

Example 163

(RS)-5-Chloro-N-(4-(pyrrolidin-3-yl)phenyl)pyrazine-2-carboxamide hydrochloride

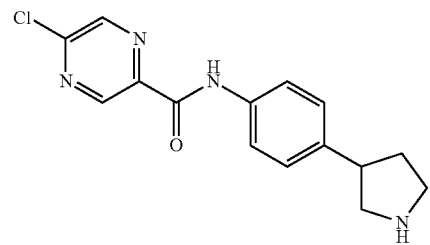 [SMILES: O=C(Nc1ccc(C2CCNC2)cc1)c1cnc(Cl)cn1]

The title compound was obtained in analogy to example 29 using 5-chloro-pyrazine-2-carboxylic acid (CAS 36070-80-1) instead of (R)-2-phenylpropionic acid. White solid. MS (ISP): 305.2 ([{$^{37}$Cl}M+H]$^+$), 303.3 ([{$^{35}$Cl}M+H]$^+$).

Example 164

(RS)-5-Chloro-N-(4-(2-(pyrrolidin-2-yl)ethyl)phenyl)pyrazine-2-carboxamide hydrochloride

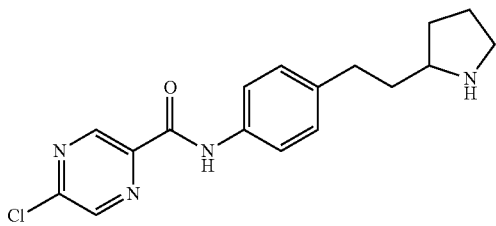 [SMILES: O=C(Nc1ccc(CCC2CCCN2)cc1)c1cnc(Cl)cn1]

The title compound was obtained in analogy to example 109 using (RS)-2-formyl-pyrrolidine-1-carboxylic acid tert-butyl ester (CAS 117625-90-8) instead of (RS)-3-formyl-pyrrolidine-1-carboxylic acid tert-butyl ester and 5-chloro-pyrazine-2-carboxylic acid (CAS 36070-80-1) instead of 4-chlorobenzoic acid. White solid. MS (ISP): 333.3 ([{$^{37}$Cl}M+H]$^+$), 331.2 ([{$^{35}$Cl}M+H]$^+$).

Example 165

(RS)-5-Cyano-N-(4-(pyrrolidin-3-yl)phenyl)picolinamide hydrochloride

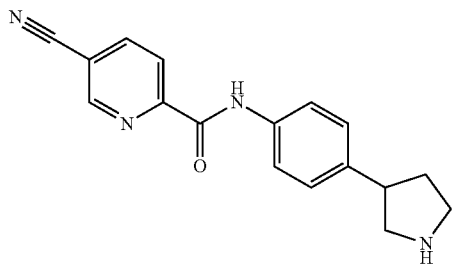 [SMILES: N#Cc1ccc(C(=O)Nc2ccc(C3CCNC3)cc2)nc1]

The title compound was obtained in analogy to example 29 using 5-cyanopicolinic acid (CAS 53234-55-2) instead of (R)-2-phenylpropionic acid. Light brown solid. MS (ISP): 293.2 ([M+H]$^+$).

Example 166

(RS)-5-Fluoro-N-(4-(2-(pyrrolidin-2-yl)ethyl)phenyl)picolinamide hydrochloride

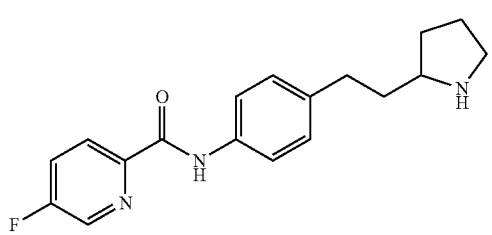

The title compound was obtained in analogy to example 109 using (RS)-2-formyl-pyrrolidine-1-carboxylic acid tert-butyl ester (CAS 117625-90-8) instead of (RS)-3-formyl-pyrrolidine-1-carboxylic acid tert-butyl ester and 5-fluoro-pyridine-2-carboxylic acid (CAS 107504-08-5) instead of 4-chlorobenzoic acid. Yellow solid. MS (ISP): 314.2 ([M+H]$^+$).

Example 167

(R)-5-Chloro-N-(4-(piperidin-3-yl)phenyl)picolinamide hydrochloride

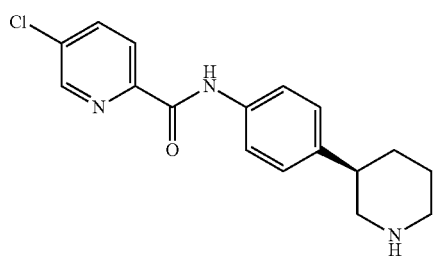 [SMILES: O=C(Nc1ccc([C@H]2CCCNC2)cc1)c1ccc(Cl)cn1]

The title compound was obtained in analogy to example 29 using (R)-tert-butyl 3-(4-aminophenyl)piperidine-1-carboxylate (example 150a) instead of (RS)-tert-butyl 3-(4-aminophenyl)pyrrolidine-1-carboxylate and 5-chloro-picolinic acid (CAS 86873-60-1) instead of (R)-2-phenylpropionic acid. White solid. MS (ISP): 318.2 ([{$^{37}$Cl}M+H]$^+$), 316.1 ([{$^{35}$Cl}M+H]$^+$).

Example 168

(S)-5-Chloro-N-(4-(piperidin-3-yl)phenyl)picolinamide hydrochloride

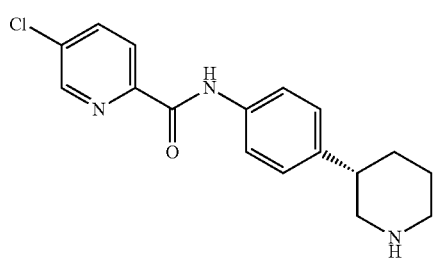 [SMILES: O=C(Nc1ccc([C@@H]2CCCNC2)cc1)c1ccc(Cl)cn1]

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 5-chloro-picolinic acid (CAS 86873-60-1) instead of (R)-2-phenylpropionic acid. White solid. MS (ISP): 318.2 ([{$^{37}$Cl}M+H]$^+$), 316.2 ([{$^{35}$Cl}M+H]$^+$).

Example 169

(RS)-4-Chloro-N-(4-(2-(piperidin-2-yl)ethyl)phenyl)benzamide hydrochloride

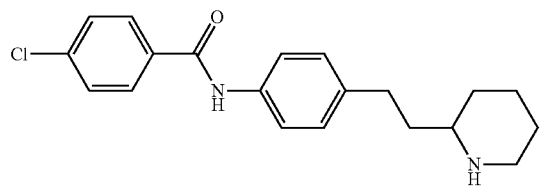 [SMILES: O=C(Nc1ccc(CCC2CCCCN2)cc1)c1ccc(Cl)cc1]

The title compound was obtained in analogy to example 109 using (RS)-2-formyl-piperidine-1-carboxylic acid tert-butyl ester (CAS 157634-02-1) instead of (RS)-3-formyl-pyrrolidine-1-carboxylic acid tert-butyl ester. White solid. MS (ISP): 345.2 ([{$^{37}$Cl}M+H]$^+$), 343.2 ([{$^{35}$Cl}M+H]$^+$).

Example 170

(RS)-4-Fluoro-N-(4-(2-(piperidin-2-yl)ethyl)phenyl)benzamide hydrochloride

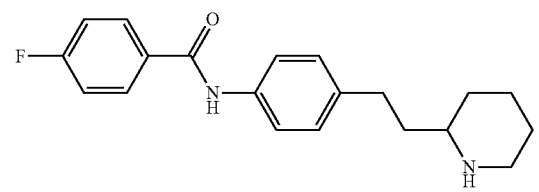 [SMILES: O=C(Nc1ccc(CCC2CCCCN2)cc1)c1ccc(F)cc1]

The title compound was obtained in analogy to example 109 using (RS)-2-formyl-piperidine-1-carboxylic acid tert-butyl ester (CAS 157634-02-1) instead of (RS)-3-formyl-pyrrolidine-1-carboxylic acid tert-butyl ester and 4-fluorobenzoic acid (CAS 456-22-4) instead of 4-chlorobenzoic acid. White solid. MS (ISP): 327.2 ([M+H]$^+$).

Example 171

(RS)-5-Chloro-N-(4-(2-(piperidin-2-yl)ethyl)phenyl)picolinamide hydrochloride

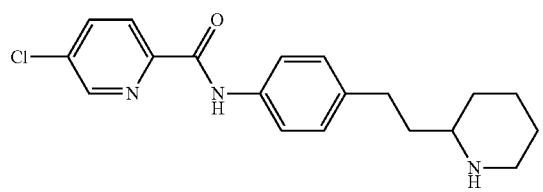 [SMILES: O=C(Nc1ccc(CCC2CCCCN2)cc1)c1ccc(Cl)cn1]

The title compound was obtained in analogy to example 109 using (RS)-2-formyl-piperidine-1-carboxylic acid tert-butyl ester (CAS 157634-02-1) instead of (RS)-3-formyl-pyrrolidine-1-carboxylic acid tert-butyl ester and 5-chloro-pyridine-2-carboxylic acid (CAS 86873-60-1) instead of 4-chlorobenzoic acid. Yellow solid. MS (ISP): 346.1 ([{$^{37}$Cl}M+H]$^+$), 344.2 ([{$^{35}$Cl}M+H]$^+$).

Example 172

(RS)-5-Ethoxy-N-(4-(2-(pyrrolidin-2-yl)ethyl)phenyl)picolinamide hydrochloride

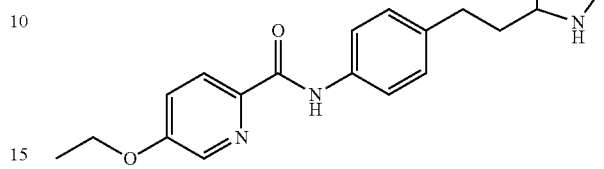

The title compound was obtained in analogy to example 109 using (RS)-2-formyl-pyrrolidine-1-carboxylic acid tert-butyl ester (CAS 117625-90-8) instead of (RS)-3-formyl-pyrrolidine-1-carboxylic acid tert-butyl ester and 5-ethoxy-pyridine-2-carboxylic acid (CAS 98353-08-3) instead of 4-chlorobenzoic acid. Light yellow solid. MS (ISP): 340.2 ([M+H]$^+$).

Example 173

(RS)-6-Chloro-N-(4-(2-(piperidin-2-yl)ethyl)phenyl)nicotinamide hydrochloride

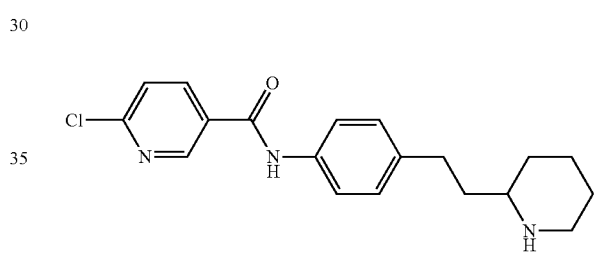

The title compound was obtained in analogy to example 109 using (RS)-2-formyl-piperidine-1-carboxylic acid tert-butyl ester (CAS 157634-02-1) instead of (RS)-3-formyl-pyrrolidine-1-carboxylic acid tert-butyl ester and 6-chloro-pyridine-3-carboxylic acid (CAS 5326-23-8) instead of 4-chlorobenzoic acid. Yellow solid. MS (ISP): 346.2 ([{$^{37}$Cl}M+H]$^+$), 344.2 ([{$^{35}$Cl}M+H]$^+$).

Example 174

(RS)-5-Chloro-N-(4-(2-(piperidin-2-yl)ethyl)phenyl)pyrazine-2-carboxamide hydrochloride

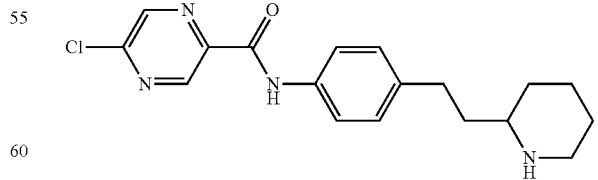

The title compound was obtained in analogy to example 109 using (RS)-2-formyl-piperidine-1-carboxylic acid tert-butyl ester (CAS 157634-02-1) instead of (RS)-3-formyl-pyrrolidine-1-carboxylic acid tert-butyl ester and 5-chloro-pyrazine-2-carboxylic acid (CAS 36070-80-1) instead of 4-chlorobenzoic acid. White solid. MS (ISP): 347.1 ([{$^{37}$Cl}M+H]$^+$), 345.1 ([{$^{35}$Cl}M+H]$^+$).

Example 175

(RS)—N-(4-(2-(Piperidin-2-yl)ethyl)phenyl)-4-(trifluoromethyl)benzamide hydrochloride

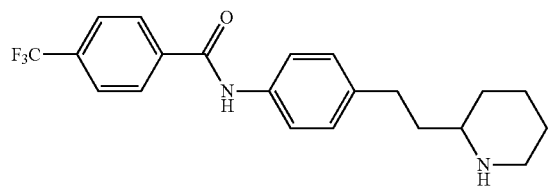 [SMILES: O=C(Nc1ccc(CCC2CCCCN2)cc1)c1ccc(C(F)(F)F)cc1]

The title compound was obtained in analogy to example 109 using (RS)-2-formyl-piperidine-1-carboxylic acid tert-butyl ester (CAS 157634-02-1) instead of (RS)-3-formyl-pyrrolidine-1-carboxylic acid tert-butyl ester and 4-(trifluoromethyl)benzoic acid (CAS 455-24-3) instead of 4-chlorobenzoic acid. White solid. MS (ISP): 377.2 ([M+H]$^+$).

Example 176

(RS)-3,4-Dichloro-N-(4-(2-(piperidin-2-yl)ethyl)phenyl)benzamide hydrochloride

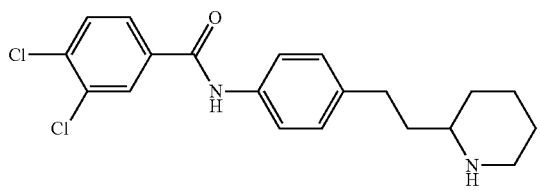 [SMILES: O=C(Nc1ccc(CCC2CCCCN2)cc1)c1ccc(Cl)c(Cl)c1]

The title compound was obtained in analogy to example 109 using (RS)-2-formyl-piperidine-1-carboxylic acid tert-butyl ester (CAS 157634-02-1) instead of (RS)-3-formyl-pyrrolidine-1-carboxylic acid tert-butyl ester and 3,4-dichlorobenzoic acid (CAS 51-44-5) instead of 4-chlorobenzoic acid. White solid. MS (ISP): 381.1 ([{$^{37}$Cl}M+H]$^+$), 379.1 ([{$^{37}$Cl$^{35}$Cl}M+H]$^+$), 377.1 ([{$^{35}$Cl}M+H]$^+$).

Example 177

(RS)-4-Ethynyl-N-(4-(2-(piperidin-2-yl)ethyl)phenyl)benzamide hydrochloride

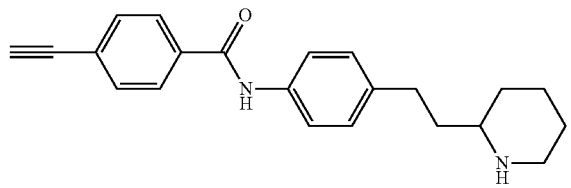 [SMILES: C#Cc1ccc(C(=O)Nc2ccc(CCC3CCCCN3)cc2)cc1]

The title compound was obtained in analogy to example 109 using (RS)-2-formyl-piperidine-1-carboxylic acid tert-butyl ester (CAS 157634-02-1) instead of (RS)-3-formyl-pyrrolidine-1-carboxylic acid tert-butyl ester and 4-(ethynyl)benzoic acid (CAS 10602-00-3) instead of 4-chlorobenzoic acid. White solid. MS (ISP): 333.2 ([M+H]$^+$).

Example 178

(RS)—N-(4-(Piperidin-3-yl)phenyl)-6-(2,2,2-trifluoroethoxy)nicotinamide hydrochloride

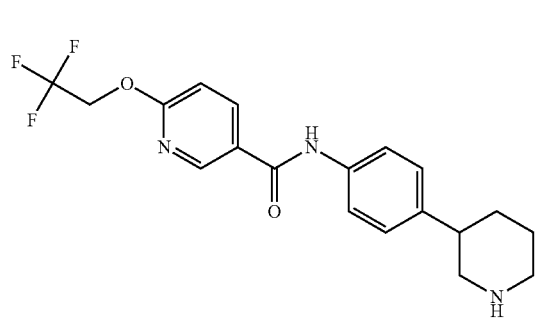 [SMILES: O=C(Nc1ccc(C2CCCNC2)cc1)c1ccc(OCC(F)(F)F)nc1]

The title compound was obtained in analogy to example 29 using (RS)-tert-butyl 3-(4-aminophenyl)-1-piperidinecarboxylate (CAS 875798-79-1) instead of (RS)-tert-butyl 3-(4-aminophenyl)pyrrolidine-1-carboxylate and 6-(2,2,2-trifluoro-ethoxy)-nicotinic acid (CAS 175204-90-7) instead of (R)-2-phenylpropionic acid. White solid. MS (ISP): 380.3 ([M+H]$^+$).

Example 179

(RS)-5-Ethoxy-pyridine-2-carboxylic acid (4-piperidin-3-yl-phenyl)-amide; hydrochloride

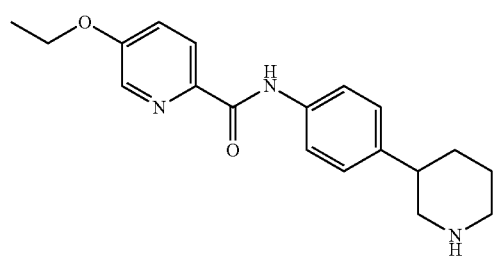 [SMILES: CCOc1ccc(C(=O)Nc2ccc(C3CCCNC3)cc2)nc1]

The title compound was obtained in analogy to example 29 using (RS)-tert-butyl 3-(4-aminophenyl)-1-piperidinecarboxylate (CAS 875798-79-1) instead of (RS)-tert-butyl 3-(4-aminophenyl)pyrrolidine-1-carboxylate and 5-ethoxy-pyridine-2-carboxylic acid (CAS 98353-08-3) instead of (R)-2-phenylpropionic acid. Off-white solid. MS (ISP): 326.3 ([M+H]$^+$).

Example 180

(RS)-5-Fluoro-N-(4-(piperidin-3-yl)phenyl)picolinamide hydrochloride

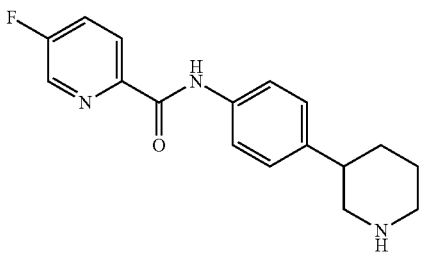 [SMILES: O=C(Nc1ccc(C2CCCNC2)cc1)c1ccc(F)cn1]

The title compound was obtained in analogy to example 29 using (RS)-tert-butyl 3-(4-aminophenyl)-1-piperidinecarboxylate (CAS 875798-79-1) instead of (RS)-tert-butyl 3-(4-aminophenyl)pyrrolidine-1-carboxylate and 5-fluoropyridine-2-carboxylic acid (CAS 107504-08-5) instead of (R)-2-phenylpropionic acid. Light yellow solid. MS (ISP): 300.3 ([M+H]$^+$).

Example 181

(RS)-4-Chloro-N-(5-(pyrrolidin-3-yl)pyridin-2-yl)benzamide hydrochloride

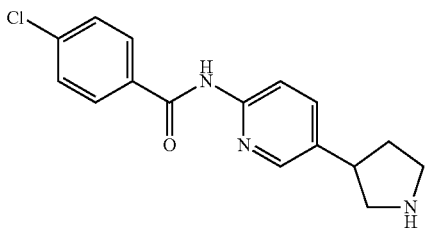 [SMILES: O=C(Nc1ccc(C2CCNC2)cn1)c1ccc(Cl)cc1]

(a) tert-Butyl 3-(6-aminopyridin-3-yl)-2,5-dihydro-1H-pyrrole-1-carboxylate To a solution of 3-trifluoromethanesulfonyloxy-2,5-dihydro-pyrrole-1-carboxylic acid tert-butyl ester (395 mg, CAS 630121-86-7) in THF (10 ml) under an argon atmosphere at room temperature were added potassium carbonate (434 mg), 5-(4,4,5,5-tetramethyl-1,3,2-dioxaborolan-2-yl)pyridin-2-amine (329 mg, CAS 827614-64-2), tetrakis(triphenyl-phosphine)palladium(0) (14.4 mg) and water (200 µl). The reaction mixture was heated to 70° C. and stirred for 16 h. The reaction mixture was poured into sat. aq. NaHCO3 solution and extracted with ether. The phases were separated and the organic layer was washed with sat. brine, then dried over Na2SO4 and concentrated in vacuo. The crude material was purified by flash chromatography (Isolute® Flash-NH$_2$ from Separtis; gradient: 0% to 100% EtOAc in heptane, then 0% to 10% MeOH in EtOAc) to afford tert-butyl 3-(6-aminopyridin-3-yl)-2,5-dihydro-1H-pyrrole-1-carboxylate (325 mg, 46%) as a light yellow solid. MS (ISP): 262.2 ([M+H]$^+$), 206.1 ([M+H—C$_4$H$_8$]$^+$).

(b) (RS)-tert-Butyl 3-(6-aminopyridin-3-yl)pyrrolidine-1-carboxylate

To a solution of tert-butyl 3 (6-aminopyridin-3-yl)-2,5-dihydro-1H-pyrrole-1-carboxylate (145 mg) in methanol (12 ml) was added palladium on charcoal (10%, 12 mg). The mixture was stirred vigorously under an atmosphere of hydrogen for 48 hours. The catalyst was filtered off and the filtrate was evaporated to give (RS)-tert-butyl 3-(6-aminopyridin-3-yl)pyrrolidine-1-carboxylate (167 mg, quant.) as a light yellow solid. MS (ISP): 264.2 ([M+H]$^+$), 208.2 ([M+H—C$_4$H$_8$]$^+$).

(c) (RS)-4-Chloro-N-(5-(pyrrolidin-3-yl)pyridin-2-yl)benzamide hydrochloride The title compound was obtained in analogy to example 29 using (RS)-tert-butyl 3-(6-aminopyridin-3-yl)pyrrolidine-1-carboxylate instead of (RS)-tert-butyl 3-(4-aminophenyl)pyrrolidine-1-carboxylate and 4-chloro-benzoic acid (CAS 74-11-3) instead of (R)-2-phenylpropionic acid. Off-white solid. MS (ISP): 304.2 ([{$^{37}$Cl}M+H]$^+$), 302.3 ([{$^{35}$Cl}M+H]$^+$).

Example 182

(RS)-4-Methyl-N-(4-(pyrrolidin-3-yl)phenyl)benzamide hydrochloride

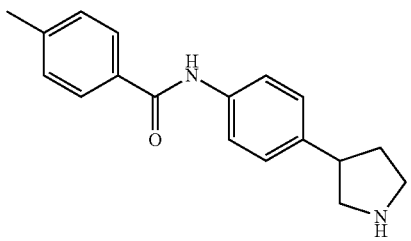 [SMILES: Cc1ccc(C(=O)Nc2ccc(C3CCNC3)cc2)cc1]

The title compound was obtained in analogy to example 29 using 4-methylbenzoic acid (CAS 99-94-5) instead of (R)-2-phenylpropionic acid. Off-white solid. MS (ISP): 281.3 ([M+H]$^+$).

Example 183

(RS)-4-Methoxy-N-(4-(pyrrolidin-3-yl)phenyl)benzamide hydrochloride

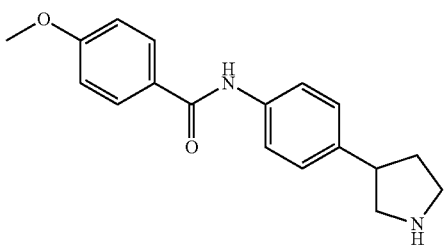 [SMILES: COc1ccc(C(=O)Nc2ccc(C3CCNC3)cc2)cc1]

The title compound was obtained in analogy to example 29 using 4-methoxybenzoic acid (CAS 100-09-4) instead of (R)-2-phenylpropionic acid. Off-white solid. MS (ISP): 297.4 ([M+H]$^+$).

Example 184

(RS)—N-(4-(piperidin-3-yl)phenyl)benzamide hydrochloride

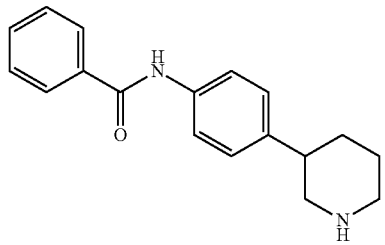 [SMILES: O=C(Nc1ccc(C2CCCNC2)cc1)c1ccccc1]

The title compound was obtained in analogy to example 29 using (RS)-tert-butyl 3-(4-aminophenyl)-1-piperidinecarboxylate (CAS 875798-79-1) instead of (RS)-tert-butyl 3-(4-aminophenyl)pyrrolidine-1-carboxylate and benzoic acid (CAS 65-85-0) instead of (R)-2-phenylpropionic acid. White solid. MS (ISP): 281.3 ([M+H]$^+$).

Example 185

(RS)-4-Methyl-N-(4-(piperidin-3-yl)phenyl)benzamide hydrochloride

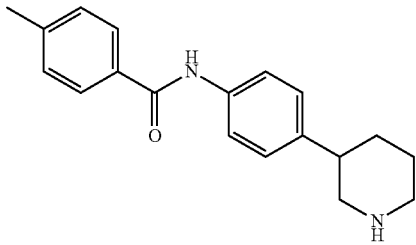 [SMILES: Cc1ccc(C(=O)Nc2ccc(C3CCCNC3)cc2)cc1]

The title compound was obtained in analogy to example 29 using (RS)-tert-butyl 3-(4-aminophenyl)-1-piperidinecarboxylate (CAS 875798-79-1) instead of (RS)-tert-butyl 3-(4-aminophenyl)pyrrolidine-1-carboxylate and 4-methylbenzoic acid (CAS 99-94-5) instead of (R)-2-phenylpropionic acid. White solid. MS (ISP): 295.3 ([M+H]$^+$).

Example 186

(RS)-4-Methoxy-N-(4-(piperidin-3-yl)phenyl)benzamide hydrochloride

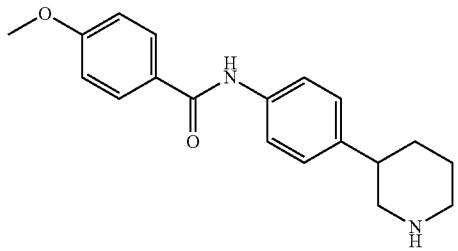 [SMILES: COc1ccc(C(=O)Nc2ccc(C3CCCNC3)cc2)cc1]

The title compound was obtained in analogy to example 29 using (RS)-tert-butyl 3-(4-aminophenyl)-1-piperidinecarboxylate (CAS 875798-79-1) instead of (RS)-tert-butyl 3-(4-aminophenyl)pyrrolidine-1-carboxylate and 4-methoxybenzoic acid (CAS 100-09-4) instead of (R)-2-phenylpropionic acid. Off-white solid. MS (ISP): 311.3 ([M+H]$^+$).

Example 187

(RS)-4-Chloro-N-(5-(piperidin-3-yl)pyridin-2-yl)benzamide hydrochloride

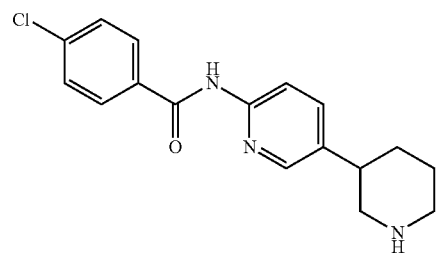 [SMILES: O=C(Nc1ccc(C2CCCNC2)cn1)c1ccc(Cl)cc1]

The title compound was obtained in analogy to example 181 using 5-trifluoromethanesulfonyloxy-3,6-dihydro-2H-pyridine-1-carboxylic acid tert-butyl ester (CAS 180691-65-0) instead of 3-trifluoromethanesulfonyloxy-2,5-dihydro-pyrrole-1-carboxylic acid tert-butyl ester. Off-white solid. MS (ISP): 318.3 ([$\{^{37}Cl\}$M+H]$^+$), 316.2 ([$\{^{35}Cl\}$M+H]$^+$).

Example 188

(RS)—N-(4-(Morpholin-2-yl)phenyl)benzamide hydrochloride

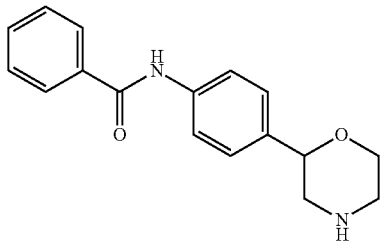 [SMILES: O=C(Nc1ccc(C2CNCCO2)cc1)c1ccccc1]

The title compound was obtained in analogy to example 141 using benzamide (CAS 55-21-0) instead of 5-trifluoromethyl-pyridine-2-carboxylic acid amide. White solid. MS (ISP): 283.3 ([M+H]$^+$).

Example 189

(RS)-4-Methyl-N-(4-(morpholin-2-yl)phenyl)benzamide hydrochloride

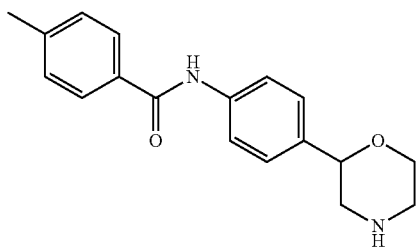

The title compound was obtained in analogy to example 141 using 4-methyl-benzamide (CAS 619-55-6) instead of 5-trifluoromethyl-pyridine-2-carboxylic acid amide. White solid. MS (ISP): 297.4 ([M+H]+).

Example 190

(RS)-4-Methoxy-N-(4-(morpholin-2-yl)phenyl)benzamide hydrochloride

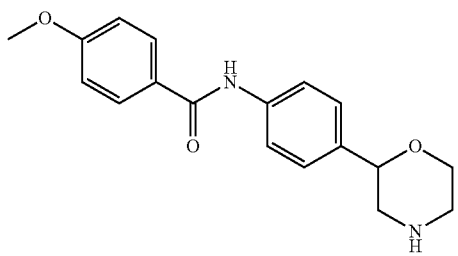

The title compound was obtained in analogy to example 141 using 4-methoxy-benzamide (CAS 3424-93-9) instead of 5-trifluoromethyl-pyridine-2-carboxylic acid amide. White solid. MS (ISP): 313.3 ([M+H]+).

Example 191

(RS)—N-(4-(Piperidin-3-yl)phenyl)-5-(2,2,2-trifluoroethoxy)picolinamide hydrochloride

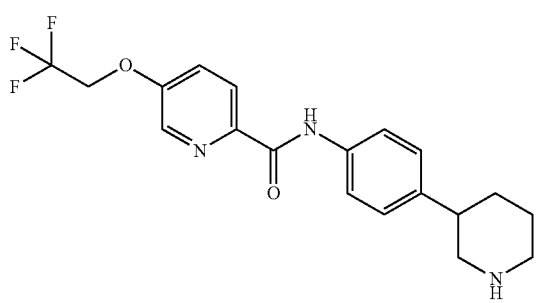 [SMILES: O=C(Nc1ccc(C2CCCNC2)cc1)c1ccc(OCC(F)(F)F)cn1]

The title compound was obtained in analogy to example 29 using (RS)-tert-butyl 3-(4-aminophenyl)-1-piperidinecarboxylate (CAS 875798-79-1) instead of (RS)-tert-butyl 3-(4-aminophenyl)pyrrolidine-1-carboxylate and 5-(2,2,2-trifluoro-ethoxy)-pyridine-2-carboxylic acid (CAS 881409-53-6) instead of (R)-2-phenylpropionic acid. Light yellow solid. MS (ISP): 380.3 ([M+H]+).

Example 192

(RS)-4-(benzyloxy)-N-(4-(morpholin-2-yl)phenyl)benzamide hydrochloride

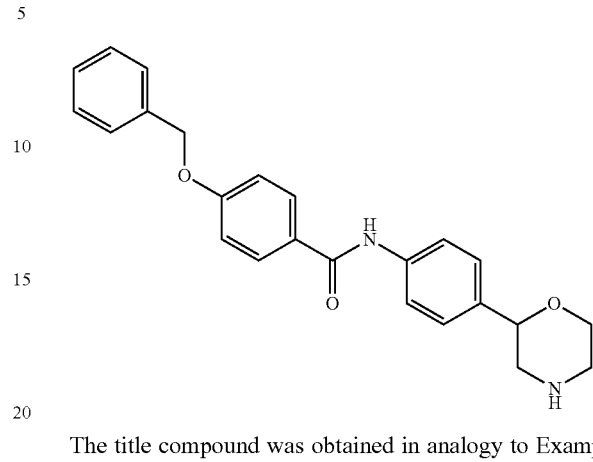

The title compound was obtained in analogy to Example 141 using 4-benzyloxy-benzamide (CAS-56442-43-4) instead of 5-trifluoromethyl-pyridine-2-carboxylic acid amide. White solid. MS (ISP): 389.3 ([M+H]+).

Example 193

(RS)-6-chloro-N-(4-(morpholin-2-yl)phenyl)nicotinamide hydrochloride

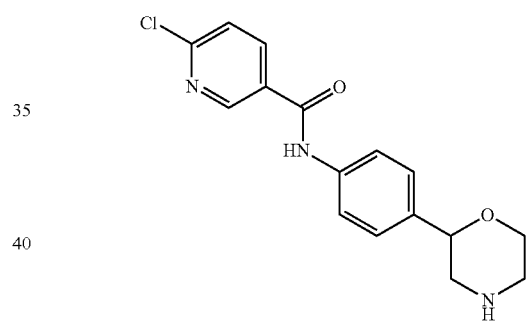

The title compound was obtained in analogy to example 141 using 6-chloro nicotinamide (CAS-6271-78-9) instead of 5-trifluoromethyl-pyridine-2-carboxylic acid amide. White solid. MS (ISP): 318.0 ([M+H]+).

Example 194

(RS)-2-(4-(6-cyanonicotinamido)phenyl)morpholin-4-ium chloride

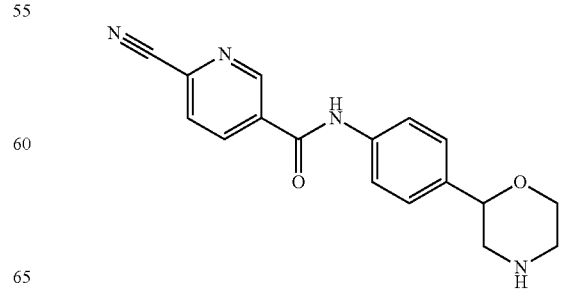

The title compound was obtained in analogy to Example 141 using 6-cyano-nicotinamide (CAS-14178-45-1) instead of 5-trifluoromethyl-pyridine-2-carboxylic acid amide. Off-white solid. MS (ISP): 309.2 ([M+H]⁺).

Example 195

(R)-4-Methyl-N-(4-(morpholin-2-yl)phenyl)benzamide hydrochloride

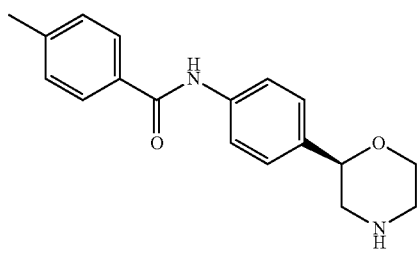 [SMILES: Cc1ccc(C(=O)Nc2ccc([C@@H]3CNCCO3)cc2)cc1]

The title compound was obtained in analogy to example 141 using (R)-tert-butyl 2-(4-bromophenyl)morpholine-4-carboxylate (example 207b) instead of (RS)-tert-butyl 2-(4-bromophenyl)morpholine-4-carboxylate and 4-methyl-benzamide (CAS 619-55-6) instead of 5-trifluoromethyl-pyridine-2-carboxylic acid amide. White solid. MS (ISP): 297.3 ([M+H]⁺).

Example 196

(S)-4-Methyl-N-(4-(morpholin-2-yl)phenyl)benzamide hydrochloride

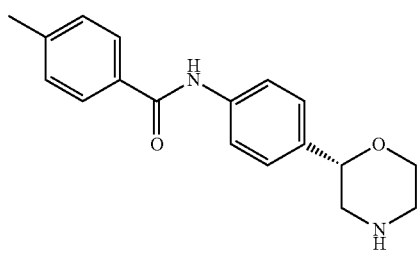 [SMILES: Cc1ccc(C(=O)Nc2ccc([C@H]3CNCCO3)cc2)cc1]

The title compound was obtained in analogy to example 141 using (S)-tert-butyl 2-(4-bromophenyl)morpholine-4-carboxylate (example 208b) instead of (RS)-tert-butyl 2-(4-bromophenyl)morpholine-4-carboxylate and 4-methyl-benzamide (CAS 619-55-6) instead of 5-trifluoromethyl-pyridine-2-carboxylic acid amide. White solid. MS (ISP): 297.3 ([M+H]⁺).

Example 197

(RS)-4-Ethoxy-N-(4-(morpholin-2-yl)phenyl)benzamide hydrochloride

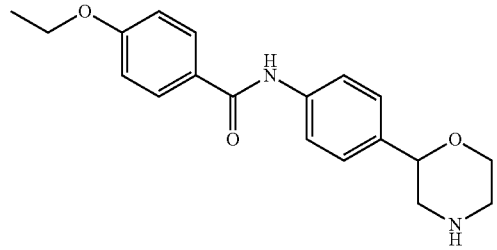 [SMILES: CCOc1ccc(C(=O)Nc2ccc(C3CNCCO3)cc2)cc1]

The title compound was obtained in analogy to example 141 using 4-ethoxy-benzamide (CAS-55836-71-0) instead of 5-trifluoromethyl-pyridine-2-carboxylic acid amide. White solid. MS (ISP): 327.3 ([M+H]⁺).

Example 198

(RS)-4-Ethyl-N-(4-(morpholin-2-yl)phenyl)benzamide hydrochloride

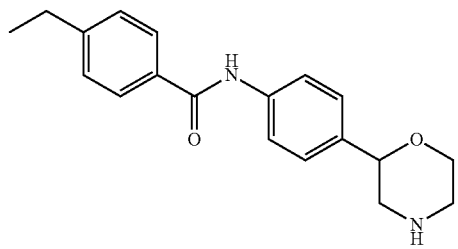 [SMILES: CCc1ccc(C(=O)Nc2ccc(C3CNCCO3)cc2)cc1]

The title compound was obtained in analogy to Example 141 using 4-ethyl-benzamide (CAS-33695-58-8) instead of 5-trifluoromethyl-pyridine-2-carboxylic acid amide. White solid. MS (ISP): 311.3 ([M+H]⁺).

Example 199

(RS)-4-Hydroxy-N-(4-(morpholin-2-yl)phenyl)benzamide hydrochloride

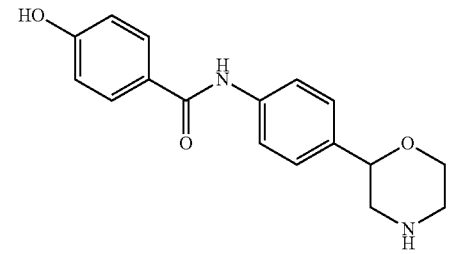 [SMILES: O=C(Nc1ccc(C2CNCCO2)cc1)c1ccc(O)cc1]

a) (RS)-tert-butyl 2-(4-(4-hydroxybenzamido)phenyl)morpholine-4-carboxylate (RS)-tert-butyl 2-(4-(4-(benzyloxy)benzamido)phenyl) morpholine-4-carboxylate (31 mg, 63 μmol, intermediate from example 192) was dissolved in methanol (15 ml) and treated with 10% Pd/C (10 mg) and hydrogenated for 1.5 h at rt. The catalyst was then removed by filtration and the solvent removed in vacuo, leading to 25 mg tert-butyl 2-(4-(4-hydroxybenzamido)phenyl)morpholine-4-carboxylate (MS (ISP): 343.2 ([M+H]$^+$)), which was used directly in the next step.

b) (RS)-4-hydroxy-N-(4-(morpholin-2-yl)phenyl) benzamide hydrochloride (RS)-tert-butyl 2-(4-(4-hydroxybenzamido)phenyl)morpholine-4-carboxylate (24 mg, 60.2 μmol) was dissolved in THF (0.85 ml) and treated with 4 M HCl in dioxane (0.23 ml, 0.9 mmol). After 3.5 h stirring at 60° C., the mixture was cooled to rt, diluted with ethyl acetate and the ensuing crystals were collected by filtration, washing with ethyl acetate and diethylether, and were dried in high vacuo to afford (RS)-4-hydroxy-N-(4-(morpholin-2-yl)phenyl)benzamide hydrochloride (19 mg, 94%) as a white crystalline solid. MS (ISP): 299.3 ([M+H]$^+$).

Example 200

(R)-4-Chloro-3-methoxy-N-(4-(piperidin-3-yl)phenyl)benzamide hydrochloride

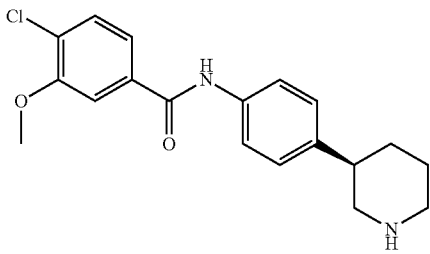 [SMILES: COc1cc(C(=O)Nc2ccc([C@H]3CCCNC3)cc2)ccc1Cl]

The title compound was obtained in analogy to example 29 using (R)-tert-butyl 3-(4-aminophenyl)piperidine-1-carboxylate (example 150a) instead of (RS)-tert-butyl 3-(4-aminophenyl)pyrrolidine-1-carboxylate and 4-chloro-3-methoxy benzoic acid (CAS 85740-98-3) instead of (R)-2-phenylpropionic acid. White solid. MS (ISP): 347.2 ([{$^{37}$Cl}M+H]$^+$), 345.2 ([{$^{35}$Cl}M+H]$^+$).

Example 201

(S)-4-Chloro-3-methoxy-N-(4-(piperidin-3-yl)phenyl)benzamide hydrochloride

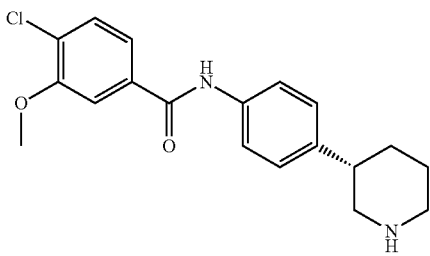 [SMILES: COc1cc(C(=O)Nc2ccc([C@@H]3CCCNC3)cc2)ccc1Cl]

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 4-chloro-3-methoxy benzoic acid (CAS 85740-98-3) instead of (R)-2-phenylpropionic acid. White solid. MS (ISP): 347.1 ([{$^{37}$Cl}M+H]$^+$), 345.2 ([{$^{35}$Cl}M+H]$^+$).

Example 202

(R)-3-Chloro-4-methoxy-N-(4-(piperidin-3-yl)phenyl)benzamide hydrochloride

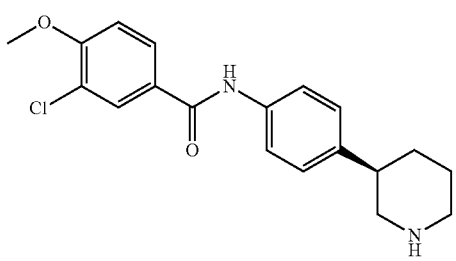 [SMILES: COc1ccc(C(=O)Nc2ccc([C@H]3CCCNC3)cc2)cc1Cl]

The title compound was obtained in analogy to example 29 using (R)-tert-butyl 3-(4-aminophenyl)piperidine-1-carboxylate (example 150a) instead of (RS)-tert-butyl 3-(4-aminophenyl)pyrrolidine-1-carboxylate and 3-chloro-4-methoxy benzoic acid (CAS 37908-96-6) instead of (R)-2-phenylpropionic acid. White solid. MS (ISP): 347.2 ([{$^{37}$Cl}M+H]$^+$), 345.2 ([{$^{35}$Cl}M+H]$^+$).

Example 203

(S)-3-Chloro-4-methoxy-N-(4-(piperidin-3-yl)phenyl)benzamide hydrochloride

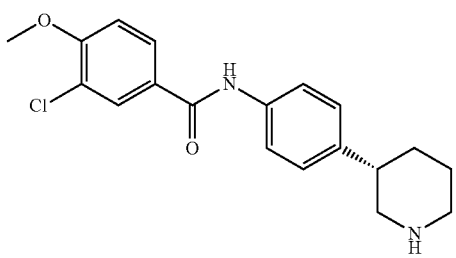 [SMILES: COc1ccc(C(=O)Nc2ccc([C@@H]3CCCNC3)cc2)cc1Cl]

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 3-chloro-4-methoxy benzoic acid (CAS 37908-96-6) instead of (R)-2-phenylpropionic acid. White solid. MS (ISP): 347.3 ([{$^{37}$Cl}M+H]$^+$), 345.2 ([{$^{35}$Cl}M+H]$^+$).

Example 204

(R)—N-(4-(Pyrrolidin-3-yl)phenyl)-6-(2,2,2-trifluoroethoxy)nicotinamide hydrochloride

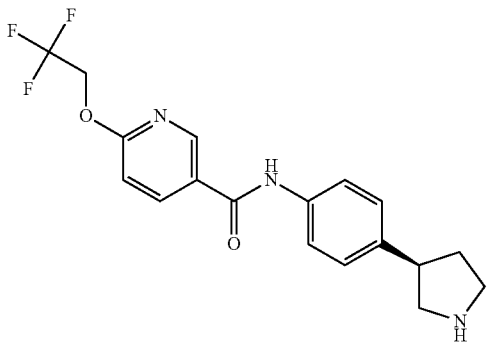 [SMILES: O=C(Nc1ccc([C@H]2CCNC2)cc1)c1ccc(OCC(F)(F)F)nc1]

a) (RS)-3-(4-{[6-(2,2,2-Trifluoro-ethoxy)-pyridine-3-carbonyl]-amino}-phenyl)-pyrrolidine-1-carboxylic acid tert-butyl ester The title compound was obtained in analogy to example 29 step (a) using 6-(2,2,2-trifluoroethoxy)nicotinic acid (CAS 175204-90-7) instead of (R)-2-phenylpropionic acid. White solid. MS (ISP): 466.2 ([M+H]$^+$), 410.2 ([M+H—$C_4H_8$]$^+$).

b) (R)-3-(4-{[6-(2,2,2-Trifluoro-ethoxy)-pyridine-3-carbonyl]-amino}-phenyl)-pyrrolidine-1-carboxylic acid tert-butyl ester & (S)-3-(4-{[6-(2,2,2-Trifluoro-ethoxy)-pyridine-3-carbonyl]-amino}-phenyl)-pyrrolidine-1-carboxylic acid tert-butyl ester The enantiomers of (RS)-3-(4-{[6-(2,2,2-trifluoro-ethoxy)-pyridine-3-carbonyl]-amino}-phenyl)-pyrrolidine-1-carboxylic acid tert-butyl ester (310 mg) were separated using chiral HPLC (column: Chiralpak AD, 5×50 cm; eluent: 25% isopropanol/heptane; pressure: 15 bar; flow rate: 35 ml/min) affording:
(+)-(R)-3-(4-{[6-(2,2,2-Trifluoro-ethoxy)-pyridine-3-carbonyl]-amino}-phenyl)-pyrrolidine-1-carboxylic acid tert-butyl ester (139 mg, white solid)
Retention time=60 min
(−)-(S)-3-(4-{[6-(2,2,2-Trifluoro-ethoxy)-pyridine-3-carbonyl]-amino}-phenyl)-pyrrolidine-1-carboxylic acid tert-butyl ester (138 mg, white solid)
Retention time=81 min c) (R)—N-(4-(Pyrrolidin-3-yl)phenyl)-6-(2,2,2-trifluoroethoxy)nicotinamide hydrochloride To a stirred solution of (R)-3-(4-{[6-(2,2,2-trifluoroethoxy)-pyridine-3-carbonyl]-amino}-phenyl)-pyrrolidine-1-carboxylic acid tert-butyl ester (135 mg, example 204b) in THF (3 ml) was added dropwise a solution of hydrogen chloride in dioxane (1.09 ml, 4 M solution) and the mixture was heated at 60° C. overnight. The mixture was then cooled to 0° C. and the ensuing crystals were collected by filtration, washing twice with ethyl acetate, and were dried in vacuo at 60° C. to afford (R)—N-(4-(pyrrolidin-3-yl)phenyl)-6-(2,2,2-trifluoroethoxy)nicotinamide hydrochloride (113 mg, 97%) as a white crystalline solid. MS (ISP): 366.1 ([M+H]$^+$).

Example 205

(S)—N-(4-(Pyrrolidin-3-yl)phenyl)-6-(2,2,2-trifluoroethoxy)nicotinamide hydrochloride

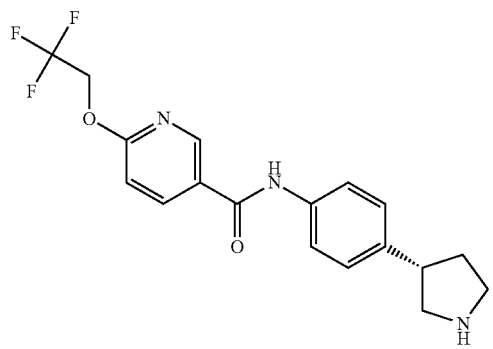

The title compound was obtained in analogy to example 204 step (c) using (S)-3-(4-{[6-(2,2,2-trifluoro-ethoxy)-pyridine-3-carbonyl]-amino}-phenyl)-pyrrolidine-1-carboxylic acid tert-butyl ester (example 204b) instead of (R)-3-(4-{[6-(2,2,2-trifluoro-ethoxy)-pyridine-3-carbonyl]-amino}-phenyl)-pyrrolidine-1-carboxylic acid tert-butyl ester. White solid. MS (ISP): 366.1 ([M+H]$^+$).

Example 206

(RS)-4-(4-Chlorophenoxy)-N-(4-(morpholin-2-yl)phenyl)benzamide hydrochloride

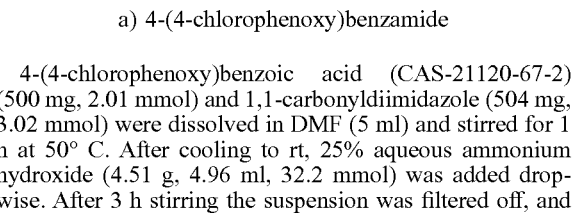

a) 4-(4-chlorophenoxy)benzamide 4-(4-chlorophenoxy)benzoic acid (CAS-21120-67-2) (500 mg, 2.01 mmol) and 1,1-carbonyldiimidazole (504 mg, 3.02 mmol) were dissolved in DMF (5 ml) and stirred for 1 h at 50° C. After cooling to rt, 25% aqueous ammonium hydroxide (4.51 g, 4.96 ml, 32.2 mmol) was added dropwise. After 3 h stirring the suspension was filtered off, and the solid washed with ethyl acetate and diethylether and dried under high vacuo leading to 500 mg white solid MS (ISP): 248.1 ([M+H]$^+$).

b) (RS)-4-(4-chlorophenoxy)-N-(4-(morpholin-2-yl)phenyl)benzamide hydrochloride The title compound was obtained in analogy to Example 141 using 4-(4-chlorophenoxy)benzamide instead of 5-trifluoromethyl-pyridine-2-carboxylic acid amide. White solid. MS (ISP): 409.2 ([M+H]$^+$).

Example 207

(R)-6-Chloro-N-(4-(morpholin-2-yl)phenyl)nicotinamide hydrochloride

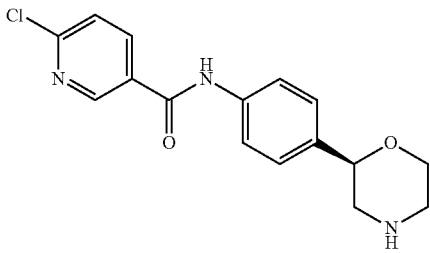 [SMILES: O=C(Nc1ccc([C@@H]2CNCCO2)cc1)c1ccc(Cl)nc1]

a) (R)-2-(4-Bromophenyl)morpholine

The enantiomers of (RS)-2-(4-bromo-phenyl)-morpholine (2.27 g, CAS-1131220-82-0) were separated using chiral HPLC (column: Chiralpak IA, 8×32 cm; eluent: n-heptane/ethanol (1:11) containing 0.1% DEA) affording:
(S)-2-(4-Bromo-phenyl)-morpholine: collected from 7.6 min to 9.4 min.
Yield 0.97 g (42.9%) with 97.4% ee
(R)-2-(4-Bromo-phenyl)-morpholine: collected from 9.8 min to 13.9 min
Yield 0.99 g (43.6%) with 97.4% ee b) (R)-tert-butyl 2-(4-bromophenyl)morpholine-4-carboxylate (R)-2-(4-Bromophenyl)morpholine (6 g, 24.8 mmol) and N,N-diisopropylethylamine (3.84 g, 5.19 ml, 29.7 mmol) in THF (60 ml) were treated with di-tert-butyl dicarbonate (6.49 g, 29.7 mmol). The reaction mixture was stirred for 17 h at rt, concentrated in vacuo, diluted with ethyl acetate, washed with 1 M-aq. citric acid, dried over magnesium sulfate, filtered and concentrated in vacuo. The crude material was crystallized from heptane/ethyl acetate to afford 8.48 g (87%) (R)-tert-butyl 2-(4-bromophenyl)morpholine-4-carboxylate as a white solid. MS (ISP): 3-(4.1 ([M+H]$^+$).

c) (R)-tert-butyl 2-(4-(diphenylmethyleneamino)phenyl)morpholine-4-carboxylate (R)-tert-butyl 2-(4-bromophenyl)morpholine-4-carboxylate (5.4 g, 15.8 mmol), diphenylmethanimine (3.43 g, 3.17 ml, 18.9 mmol), BINAP (737 mg, 1.18 mmol) and Pd$_2$(dba)$_3$ (361 mg, 0.39 mmol) were dissolved under argon in dry and de-aerated toluene (108 ml) and treated with sodium tert-butoxide (2.12 g, 22.1 mmol). The dark brown mixture was stirred at 90° C. for 18 h. The yellow/brown reaction mixture was diluted with toluene (100 ml), cooled to rt and extracted twice with water. The organic layer was separated, dried over magnesium sulfate and concentrated in vacuo. The crude product was diluted with 50 ml hexane, stirred for 1 h and filtered off, leading to a yellow solid (7.4 g) which was purified by column chromatography (50 g silicagel, 5% to 15% ethylacetate/heptane). The combined and concentrated fractions were suspended in hexane, stirred for 17 h, filtered off and dried in high vacuo, to yield 6.15 g (86%) yellow solid. MS (ISP): 443.4 ([M+H]$^+$).

d) (R)-tert-butyl 2-(4-aminophenyl)morpholine-4-carboxylate

A suspension of (R)-tert-butyl 2-(4-(diphenylmethyleneamino)phenyl)morpholine-4-carboxylate (6 g, 13.6 mmol), ammonium formate (12.8 g, 203 mmol) and Pd/C 5% (721 mg, 0.339 mmol) in methanol (103 ml) was stirred at 60° C. for 2 h. The reaction mixture was filtered and concentrated. The residue was dissolved in ethyl acetate and water. The organic phase was extracted twice with 0.5M HCl. The combined aqueous phases were basified with 2M-NaOH and extracted twice with dichloromethane. The organic phases were dried over magnesium sulfate, filtered and dried in vacuo, to yield 3.04 g off-white solid. MS (ISP): 279.1 ([M+H]$^+$).

e) (R)-6-Chloro-N-(4-(morpholin-2-yl)phenyl)nicotinamide hydrochloride

The title compound was obtained in analogy to Example 29 using (R)-tert-butyl 2-(4-aminophenyl)morpholine-4-carboxylate instead of (RS)-tert-butyl 3-(4-aminophenyl)pyrrolidine-1-carboxylate, 6-chloro-nicotinic acid (CAS-5326-23-8) instead of (R)-2-phenylpropionic acid, and HBTU instead of TBTU (17 h at rt). White solid. MS (ISP): 318.1 ([M+H]$^+$).

Example 208

(S)-6-Chloro-N-(4-(morpholin-2-yl)phenyl)nicotinamide hydrochloride

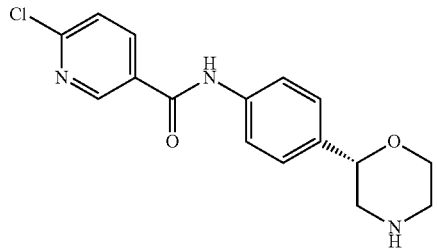 [SMILES: O=C(Nc1ccc([C@H]2CNCCO2)cc1)c1ccc(Cl)nc1]

a) (S)-2-(4-Bromophenyl)morpholine

The enantiomers of (RS)-2-(4-bromo-phenyl)-morpholine (2.27 g, CAS-1131220-82-0) were separated using chiral HPLC (column: Chiralpak IA, 8×32 cm; eluent: n-heptane/ethanol (1:11) containing 0.1% DEA) affording:
(S)-2-(4-Bromo-phenyl)-morpholine: collected from 7.6 min to 9.4 min.
Yield 0.97 g (42.9%) with 97.4% ee
(R)-2-(4-Bromo-phenyl)-morpholine: collected from 9.8 min to 13.9 min
Yield 0.99 g (43.6%) with 97.4% ee b) (S)-tert-butyl 2-(4-bromophenyl)morpholine-4-carboxylate (S)-2-(4-Bromo-phenyl)-morpholine (36.3 g, 150 mmol) and N,N-diisopropylethylamine (23.3 g, 31.4 ml, 180 mmol) in THF (360 ml) were treated with di-tert-butyl dicarbonate (39.3 g, 180 mmol). The reaction mixture was stirred for 17 h at rt, concentrated in vacuo, diluted with ethyl acetate, washed with 1 M-aq. citric acid (2×100 ml), dried over magnesium sulfate, filtered and concentrated in vacuo. The crude material was crystallized from hexane to afford 47.1 g (92%) (S)-tert-butyl 2-(4-bromophenyl)morpholine-4-carboxylate as an off-white solid. MS (ISP): 3-(4.1 ([M+H]$^+$).

c) (S)-tert-butyl 2-(4-(diphenylmethyleneamino)phenyl)morpholine-4-carboxylate (S)-tert-butyl 2-(4-bromophenyl)morpholine-4-carboxylate (47 g, 137 mmol), diphenylmethanimine (29.9 g, 27.6 m, 165 mmol), BINAP (6.41 g, 10.3 mmol) and Pd$_2$(dba)$_3$ (3.14 g, 3.43 mmol) were dissolved under Argon in dry and de-aerated toluene (940 ml) and treated with sodium tert-butoxide (18.5 g, 192 mmol). The dark brown mixture was stirred at 90° C. for 18 h. The yellow/brown reaction mixture was diluted with toluene (700 ml), cooled to rt and extracted twice with water. The organic layer was separated, dried over magnesium sulfate and concentrated in vacuo. The crude product was diluted with 300 ml hexane, stirred for 1 h and filtered off, leading to an orange solid (68 g) which was purified by column chromatography (1.3 kg silicagel, 20% ethylacetate/heptane). The combined and concentrated fractions were suspended in hexane, stirred for 17 h, filtered off and dried in high vacuo, to yield 54.1 g (89%) yellow solid. MS (ISP): 443.3 ([M+H]$^+$).

d) (S)-tert-butyl 2-(4-aminophenyl)morpholine-4-carboxylate

A suspension of (S)-tert-butyl 2-(4-(diphenylmethyleneamino)phenyl)morpholine-4-carboxylate (54.1 g, 122 mmol), ammonium formate (116 g, 1.83 mol) and Pd/C 5% (6.5 g, 3.06 mmol) in methanol (930 ml) was stirred at 60° C. for 2 h. The reaction mixture was filtered and concentrated. The residue was dissolved in ethyl acetate and water. The organic phase was extracted twice with 0.5 M aq. HCl. The combined aqueous phases were basified with 2 M aq. NaOH and extracted twice with dichloromethane. The organic phases were dried over magnesium sulfate, filtered and dried in vacuo, to yield 31.95 g off-white solid. MS (ISP): 279.1 ([M+H]$^+$).

e) (S)-6-chloro-N-(4-(morpholin-2-yl)phenyl)nicotinamide hydrochloride

The title compound was obtained in analogy to Example 29 using (S)-tert-butyl 2-(4-aminophenyl)morpholine-4-carboxylate (CAS-1002726-96-6) instead of (RS)-tert-butyl 3-(4-aminophenyl)pyrrolidine-1-carboxylate, 6-chloronicotinic acid (CAS-5326-23-8) instead of (R)-2-phenylpropionic acid and HBTU instead of TBTU (17 h at rt). White solid. MS (ISP): 318.1 ([M+H]$^+$).

Example 209

(RS)-3-chloro-N-(4-(morpholin-2-yl)phenyl)benzamide hydrochloride

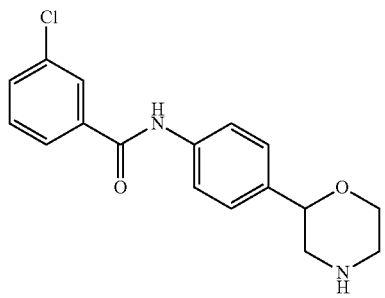 [SMILES: O=C(Nc1ccc(C2CNCCO2)cc1)c1cccc(Cl)c1]

The title compound was obtained in analogy to Example 29 using (RS)-tert-butyl 2-(4-aminophenyl)morpholine-4-carboxylate (CAS-1002726-96-6) instead of (RS)-tert-butyl 3-(4-aminophenyl)pyrrolidine-1-carboxylate, 3-chloro-benzoic acid instead of (R)-2-phenylpropionic acid and HBTU instead of TBTU (17 h at rt). White solid. MS (ISP): 317.1 ([M+H]$^+$).

Example 210

(RS)-5-chloro-N-(4-(morpholin-2-yl)phenyl)nicotinamide hydrochloride

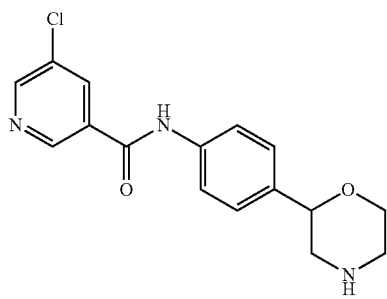 [SMILES: O=C(Nc1ccc(C2CNCCO2)cc1)c1cncc(Cl)c1]

The title compound was obtained in analogy to Example 29 using (RS)-tert-butyl 2-(4-aminophenyl)morpholine-4-carboxylate (CAS-1002726-96-6) instead of (RS)-tert-butyl 3-(4-aminophenyl)pyrrolidine-1-carboxylate, 5-chloronicotinic acid instead of (R)-2-phenylpropionic acid and HBTU instead of TBTU (17 h at rt). White solid. MS (ISP): 318.1 ([M+H]$^+$).

Example 211

(RS)-Methyl 4-((4-(4-(morpholin-2-yl)phenylcarbamoyl)phenoxy)methyl)benzoate hydrochloride

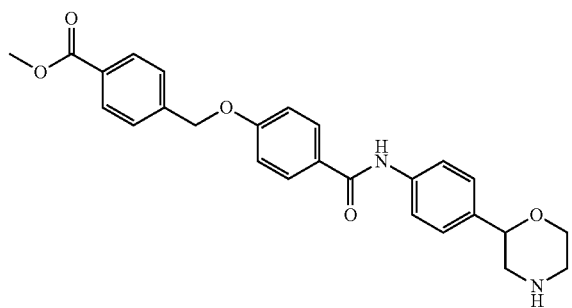 [SMILES: COC(=O)c1ccc(COc2ccc(C(=O)Nc3ccc(C4CNCCO4)cc3)cc2)cc1]

a) (RS)-tert-butyl 2-(4-(4-(4-(methoxycarbonyl)benzyloxy)benzamido)phenyl)morpholine-4-carboxylate (RS)-tert-butyl 2-(4-(4-hydroxybenzamido)phenyl)morpholine-4-carboxylate (100 mg, 0.25 mmol, example 199a), methyl 4-(bromomethyl)benzoate (129 mg, 0.565 mmol), potassium carbonate (78 mg, 0.565 mmol) and potassium iodide (6.2 mg, 0.037 mmol) were combined with acetone (6 ml) to give a light brown suspension. The reaction mixture was stirred at 60° C. for 17 h. The crude reaction mixture was concentrated in vacuo, combined with water and extracted with dichloromethane (3×). The organic layers were dried over magnesium sulfate and concentrated in vacuo. The crude material was combined with methanol (15 ml), stirred for 15 minutes under reflux, cooled down to rt and filtered off, to yield 99 mg white solid. MS (ISP): 547.2 ([M+H]$^+$).

b) (RS)-Methyl 4-((4-(4-(morpholin-2-yl)phenylcarbamoyl)phenoxy)methyl)benzoate hydrochloride The title compound was obtained in analogy to Example 29 (step b) starting from (RS)-tert-butyl 2-(4-(4-(4-(methoxycarbonyl)benzyloxy)benzamido)phenyl)morpholine-4-carboxylate. White solid. MS (ISP): 447.2 ([M+H]$^+$).

Example 212

(RS)-4-((4-(4-(morpholin-2-yl)phenylcarbamoyl)phenoxy)methyl)benzoic acid hydrochloride

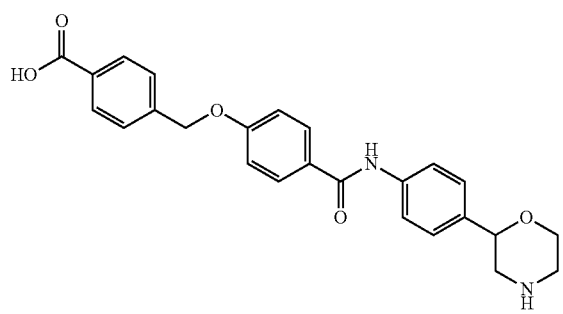 [SMILES: O=C(O)c1ccc(COc2ccc(C(=O)Nc3ccc(C4CNCCO4)cc3)cc2)cc1]

(RS)-Methyl 4-((4-(4-(morpholin-2-yl)phenylcarbamoyl)phenoxy)methyl)benzoate hydrochloride (40 mg, 0.083 mmol, example 211) was suspended in THF (1 ml) and methanol (0.25 ml) and 1 M aq. LiOH (0.207 ml, 0.207 mmol) was added. The solution was stirred for 17 h at rt, concentrated in vacuo, suspended in water (2 ml) and acidified with 1 M aq. HCl. The precipitate was filtered off and dried under high vacuum, to yield 30 mg white solid. MS (ISP): 433.2 ([M+H]$^+$).

Example 213

(RS)-Methyl 2-chloro-4-(4-(4-(morpholin-2-yl)phenylcarbamoyl)phenoxy)benzoate hydrochloride

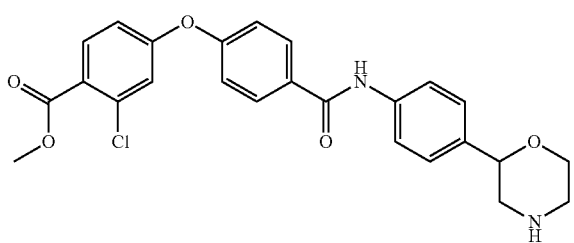 [SMILES: COC(=O)c1ccc(Oc2ccc(C(=O)Nc3ccc(C4CNCCO4)cc3)cc2)cc1Cl]

a) (RS)-tert-butyl 2-(4-(4-(3-chloro-4-(methoxycarbonyl)phenoxy)benzamido)phenyl)morpholine-4-carboxylate (RS)-tert-butyl 2-(4-(4-hydroxybenzamido)phenyl)morpholine-4-carboxylate (150 mg, 1.13 mmol, Example 199a), 3-chloro-4-(methoxycarbonyl)phenylboronic acid (CAS-603122-82-3) (242 mg, 1.13 mmol), copper (II) acetate (205 mg, 1.13 mmol) and pyridine (149 mg, 1.88 mmol) were combined with dichloromethane (3 ml) to give a blue suspension. The reaction mixture was stirred for 40 h, filtered through celite and concentrated. The residue was dissolved in dichloromethane, absorbed on SiO$_2$ and chromatographed (20 g silica gel, 10 to 35% ethyl acetate in heptane, leading to 70 mg colorless amorphous solid. MS (ISP): 567.3 ([M+H]$^+$).

b) (RS)-Methyl 2-chloro-4-(4-(4-(morpholin-2-yl)phenylcarbamoyl)phenoxy)benzoate hydrochloride The title compound was obtained in analogy to example 29 (Step b) starting from (RS)-tert-butyl 2-(4-(4-(3-chloro-4-(methoxycarbonyl)phenoxy)benzamido)phenyl)morpholine-4-carboxylate. White solid. MS (ISP): 467.3 ([M+H]$^+$).

Example 214

(RS)-4-Cyclopropylmethoxy-N-(4-morpholin-2-yl-phenyl)-benzamide hydrochloride

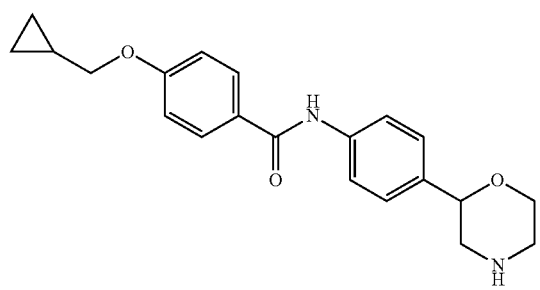 [SMILES: O=C(Nc1ccc(C2CNCCO2)cc1)c1ccc(OCC2CC2)cc1]

a) (RS)-tert-butyl 2-(4-(4-(cyclopropylmethoxy)benzamido)phenyl)morpholine-4-carboxylate (RS)-tert-butyl 2-(4-(4-hydroxybenzamido)phenyl)morpholine-4-carboxylate (60 mg, 0.15 mmol, Example 199a), (bromomethyl)cyclopropane (47 mg, 0.339 mmol), potassium carbonate (47 mg, 0.339 mmol) and potassium iodide (3.7 mg, 0.023 mmol) were combined with acetone (4 ml) to give a light brown suspension. The reaction mixture was stirred at 60° C. for 17 h. The crude reaction mixture was concentrated in vacuo, combined with water and extracted with dichloromethane (3×). The organic layers were dried over magnesium sulfate and concentrated in vacuo. The crude material was combined with methanol (5 ml), stirred for 15 minutes and filtered off, to yield 48 mg white solid. MS (ISP): 453.3 ([M+H]$^+$).

b) (RS)-4-Cyclopropylmethoxy-N-(4-morpholin-2-yl-phenyl)-benzamide hydrochloride The title compound was obtained in analogy to example 29 (Step b) starting from (RS)-tert-butyl 2-(4-(4-(cyclopropylmethoxy)benzamido)phenyl)morpholine-4-carboxylate. White solid. MS (ISP): 353.3 ([M+H]$^+$).

Example 215

(RS)-2-Chloro-4-(4-(4-(morpholin-2-yl)phenylcarbamoyl)phenoxy)benzoic acid hydrochloride

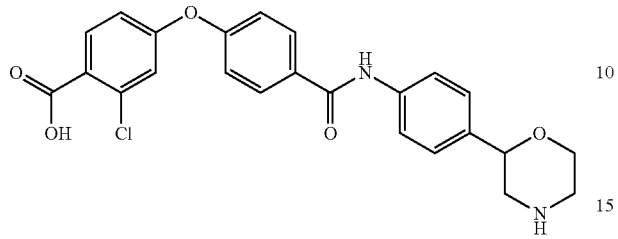

The title compound was obtained in analogy to Example 212 using (RS)-methyl 4-((4-(4-(morpholin-2-yl)phenylcarbamoyl)phenoxy)methyl)benzoate hydrochloride. White solid. MS (ISP): 453.2 ([M+H]$^+$).

Example 216

(RS)-4-(Methylthio)-N-(4-(morpholin-2-yl)phenyl)benzamide hydrochloride

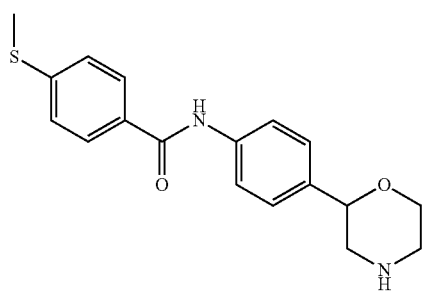 [SMILES: CSc1ccc(C(=O)Nc2ccc(C3CNCCO3)cc2)cc1]

The title compound was obtained in analogy to Example 29 using (RS)-tert-butyl 2-(4-aminophenyl)morpholine-4-carboxylate (CAS-1002726-96-6) instead of (RS)-tert-butyl 3-(4-aminophenyl)pyrrolidine-1-carboxylate, 4-(methylthio)benzoic acid instead of (R)-2-phenylpropionic acid and HBTU instead of TBTU (17 h at rt). White solid. MS (ISP): 329.1 ([M+H]$^+$).

Example 217

(RS)-2-Methyl-N-(4-(morpholin-2-yl)phenyl)thiazole-4-carboxamide hydrochloride

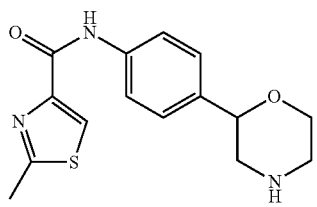 [SMILES: Cc1nc(C(=O)Nc2ccc(C3CNCCO3)cc2)cs1]

The title compound was obtained in analogy to Example 141 using 2-methylthiazole-4-carboxamide (CAS-31825-95-3) instead of 5-trifluoromethyl-pyridine-2-carboxylic acid amide. Yellow solid. MS (ISP): 304.2 ([M+H]$^+$).

Example 218

(RS)-2-Chloro-N-(4-(morpholin-2-yl)phenyl)isonicotinamide hydrochloride

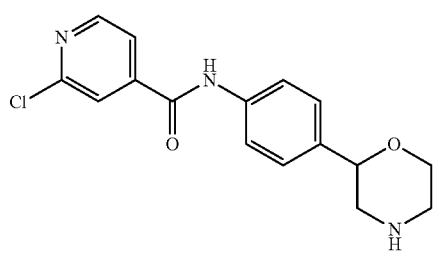 [SMILES: O=C(Nc1ccc(C2CNCCO2)cc1)c1ccnc(Cl)c1]

The title compound was obtained in analogy to Example 29 using (RS)-tert-butyl 2-(4-aminophenyl)morpholine-4-carboxylate (CAS-1002726-96-6) instead of (RS)-tert-butyl 3-(4-aminophenyl)pyrrolidine-1-carboxylate, 2-chloroisonicotinic acid instead of (R)-2-phenylpropionic acid and HBTU instead of TBTU (17 h at rt). White solid. MS (ISP): 318.1 ([M+H]$^+$).

Example 219

(RS)-5,6-Dichloro-N-(4-(morpholin-2-yl)phenyl)nicotinamide hydrochloride

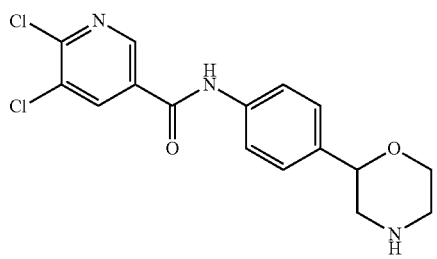 [SMILES: O=C(Nc1ccc(C2CNCCO2)cc1)c1cnc(Cl)c(Cl)c1]

The title compound was obtained in analogy to Example 29 using (RS)-tert-butyl 2-(4-aminophenyl)morpholine-4-carboxylate (CAS-1002726-96-6) instead of (RS)-tert-butyl 3-(4-aminophenyl)pyrrolidine-1-carboxylate, 5,6-dichloronicotinic acid instead of (R)-2-phenylpropionic acid and HBTU instead of TBTU (17 h at rt). White solid. MS (ISP): 352.1 ([M+H]$^+$).

Example 220

(RS)-4-(2-Chloromethyl-3-hydroxy-2-methyl-propoxy)-N-(4-morpholin-2-yl-phenyl)-benzamide

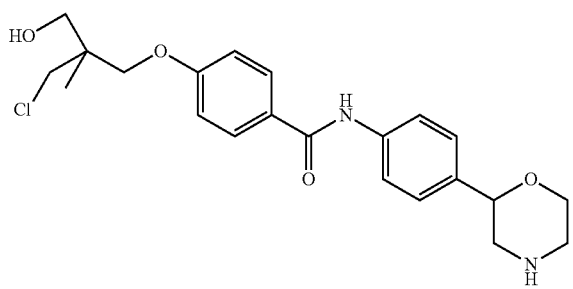 [SMILES: CC(CO)(CCl)COc1ccc(C(=O)Nc2ccc(C3CNCCO3)cc2)cc1]

The title compound was obtained in analogy to Example 214 using 3-bromomethyl-3-methyloxetane (CAS-78385-26-9) instead of (bromomethyl)cyclopropane. White solid. MS (ISP): 419.2 ([M+H]$^+$).

Example 221

(RS)-2,6-Dichloro-N-(4-(morpholin-2-yl)phenyl)isonicotinamide hydrochloride

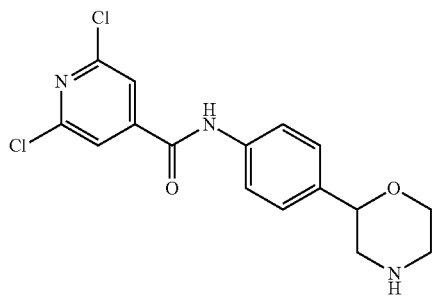 [SMILES: O=C(Nc1ccc(C2CNCCO2)cc1)c1cc(Cl)nc(Cl)c1]

The title compound was obtained in analogy to Example 29 using (RS)-tert-butyl 2-(4-aminophenyl)morpholine-4-carboxylate (CAS-1002726-96-6) instead of (RS)-tert-butyl 3-(4-aminophenyl)pyrrolidine-1-carboxylate, 2,6-dichloroisonicotinic acid (CAS-5398-44-7) instead of (R)-2-phenylpropionic acid and HBTU instead of TBTU. White solid. MS (ISP): 352.3 ([M+H]$^+$).

Example 222

(RS)—N-(4-(Morpholin-2-yl)phenyl)-6-(2,2,2-trifluoroethoxy)nicotinamide hydrochloride

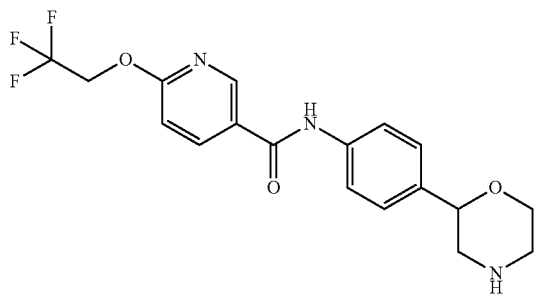 [SMILES: O=C(Nc1ccc(C2CNCCO2)cc1)c1ccc(OCC(F)(F)F)nc1]

The title compound was obtained in analogy to Example 29 using (RS)-tert-butyl 2-(4-aminophenyl)morpholine-4-carboxylate (CAS-1002726-96-6) instead of (RS)-tert-butyl 3-(4-aminophenyl)pyrrolidine-1-carboxylate, 6-(2,2,2-trifluoroethoxy)nicotinic acid (CAS-159783-29-6) instead of (R)-2-phenylpropionic acid and HBTU instead of TBTU (17 h at rt). White solid. MS (ISP): 382.4 ([M+H]$^+$).

Example 223

(R)—N-(4-(Piperidin-3-yl)phenyl)-6-(2,2,2-trifluoroethoxy)nicotinamide hydrochloride

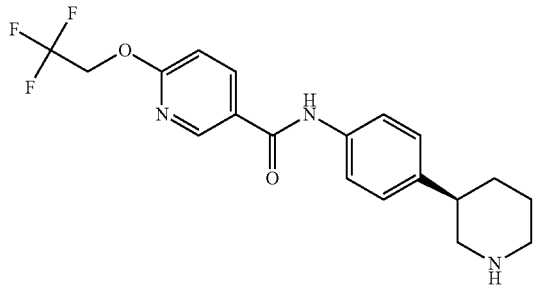 [SMILES: O=C(Nc1ccc([C@H]2CCCNC2)cc1)c1ccc(OCC(F)(F)F)nc1]

The title compound was obtained in analogy to example 29 using (R)-tert-butyl 3-(4-aminophenyl)piperidine-1-carboxylate (example 150a) instead of (RS)-tert-butyl 3-(4-aminophenyl)pyrrolidine-1-carboxylate and 6-(2,2,2-trifluoroethoxy)nicotinic acid (CAS 175204-90-7) instead of (R)-2-phenylpropionic acid. White solid. MS (ISP): 380.3 ([M+H]$^+$).

Example 224

(S)—N-(4-(Piperidin-3-yl)phenyl)-6-(2,2,2-trifluoroethoxy)nicotinamide hydrochloride

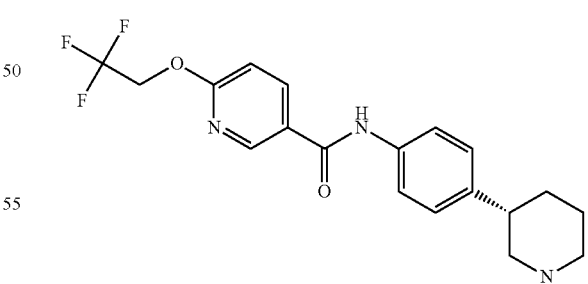

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 6-(2,2,2-trifluoroethoxy)nicotinic acid (CAS 175204-90-7) instead of (R)-2-phenylpropionic acid. White solid. MS (ISP): 380.3 ([M+H]$^+$).

Example 225

(S)-3-Chloro-4-methyl-N-(4-(piperidin-3-yl)phenyl)benzamide hydrochloride

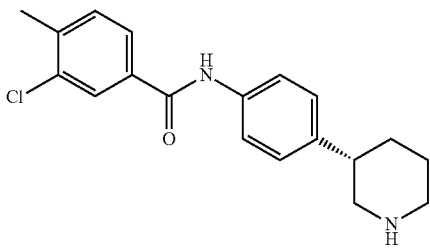 [SMILES: Cc1ccc(C(=O)Nc2ccc([C@@H]3CCCNC3)cc2)cc1Cl]

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 3-chloro-4-methyl-benzoic acid (CAS 5162-82-3) instead of (R)-2-phenylpropionic acid. White solid. MS (ISP): 331.3 ([{$^{37}$Cl}M+H]$^+$), 329.4 ([{$^{35}$Cl}M+H]$^+$).

Example 226

(S)-4-Chloro-3-methyl-N-(4-(piperidin-3-yl)phenyl)benzamide hydrochloride

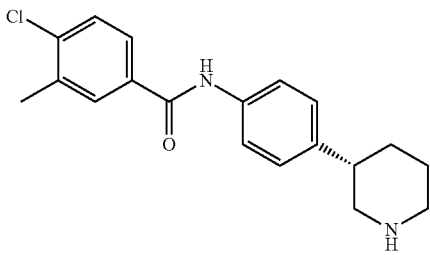 [SMILES: Cc1cc(C(=O)Nc2ccc([C@@H]3CCCNC3)cc2)ccc1Cl]

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 4-chloro-3-methyl-benzoic acid (CAS 7697-29-2) instead of (R)-2-phenylpropionic acid. White solid. MS (ISP): 331.3 ([{$^{37}$Cl}M+H]$^+$), 329.4 ([{$^{35}$Cl}M+H]$^+$).

Example 227

(S)-3,4-Dimethyl-N-(4-(piperidin-3-yl)phenyl)benzamide hydrochloride

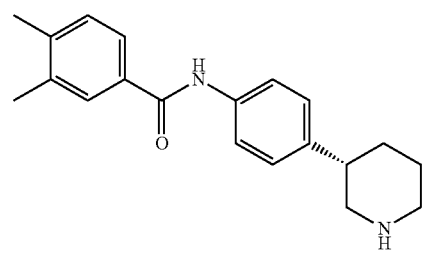 [SMILES: Cc1ccc(C(=O)Nc2ccc([C@@H]3CCCNC3)cc2)cc1C]

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 3,4-dimethyl-benzoic acid (CAS 619-04-5) instead of (R)-2-phenylpropionic acid. White solid. MS (ISP): 309.4 ([M+H]$^+$).

Example 228

(RS)-4-((3-Methyloxetan-3-yl)methoxy)-N-(4-(morpholin-2-yl)phenyl)benzamide

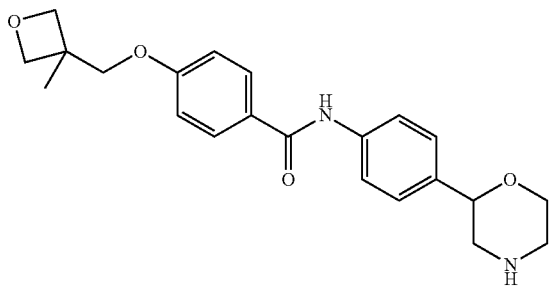 [SMILES: CC1(COc2ccc(C(=O)Nc3ccc(C4CNCCO4)cc3)cc2)COC1]

The title compound was obtained in analogy to Example 214 using 3-bromomethyl-3-methyloxetane (CAS-78385-26-9) instead of (bromomethyl)cyclopropane and using 10 equiv. TFA at −10° C. in dichloromethane (17 h) for the deprotection step. White solid. MS (ISP): 383.2 ([M+H]$^+$).

Example 229

(R)-4-Chloro-2-fluoro-N-(4-(morpholin-2-yl)phenyl)benzamide hydrochloride

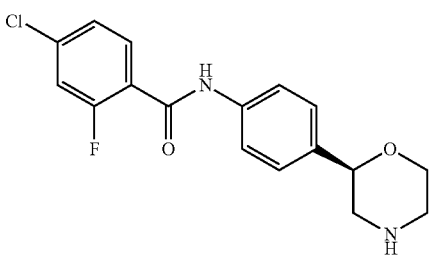 [SMILES: O=C(Nc1ccc([C@@H]2CNCCO2)cc1)c1ccc(Cl)cc1F]

The title compound was obtained in analogy to example 141 using (R)-tert-butyl 2-(4-bromophenyl)morpholine-4-carboxylate (example 207b) instead of (RS)-tert-butyl 2-(4-bromophenyl)morpholine-4-carboxylate and 4-chloro-2-fluoro-benzamide (CAS 104326-93-4) instead of 5-trifluoromethyl-pyridine-2-carboxylic acid amide. White solid. MS (ISP): 337.1 ([{$^{37}$Cl}M+H]$^+$), 335.1 ([{$^{35}$Cl}M+H]$^+$).

Example 230

(S)-4-Chloro-2-fluoro-N-(4-(morpholin-2-yl)phenyl)benzamide hydrochloride

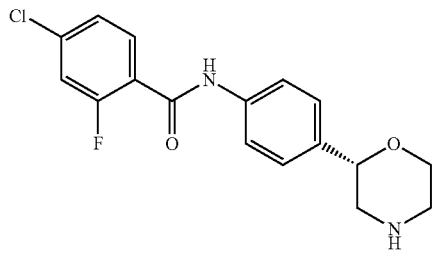

The title compound was obtained in analogy to example 141 using (S)-tert-butyl 2-(4-bromophenyl)morpholine-4-carboxylate (example 208b) instead of (RS)-tert-butyl 2-(4-bromophenyl)morpholine-4-carboxylate and 4-chloro-2-fluoro-benzamide (CAS 104326-93-4) instead of 5-trifluoromethyl-pyridine-2-carboxylic acid amide. White solid. MS (ISP): 320.1 ([{$^{37}$Cl}M+H]$^+$), 318.2 ([{$^{35}$Cl}M+H]$^+$).

Example 231

(RS)—N-(4-(Morpholin-2-yl)phenyl)-2-phenylthiazole-5-carboxamide hydrochloride

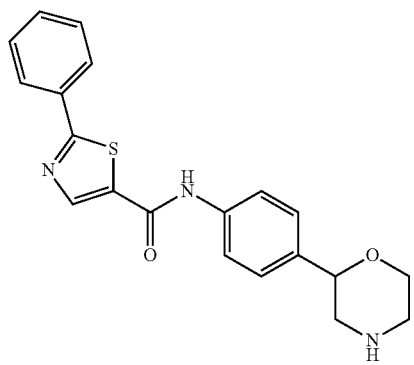 [SMILES: O=C(Nc1ccc(C2CNCCO2)cc1)c1cnc(-c2ccccc2)s1]

The title compound was obtained in analogy to Example 29 using (RS)-tert-butyl 2-(4-aminophenyl)morpholine-4-carboxylate (CAS-1002726-96-6) instead of (RS)-tert-butyl 3-(4-aminophenyl)pyrrolidine-1-carboxylate, 2-Phenyl-thiazole-5-carboxylic acid (CAS-10058-38-5) instead of (R)-2-phenylpropionic acid and HBTU instead of TBTU (17 h at rt). Yellow solid. MS (ISP): 366.1 ([M+H]$^+$).

Example 232

(RS)—N-(4-(Morpholin-2-yl)phenyl)-6-(tetrahydro-2H-pyran-4-yloxy)nicotinamide hydrochloride

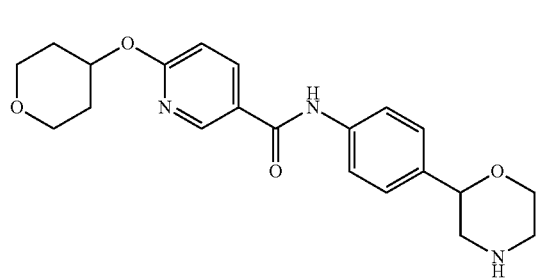 [SMILES: O=C(Nc1ccc(C2CNCCO2)cc1)c1ccc(OC2CCOCC2)nc1]

The title compound was obtained in analogy to Example 29 using (RS)-tert-butyl 2-(4-aminophenyl)morpholine-4-carboxylate (CAS-1002726-96-6) instead of (RS)-tert-butyl 3-(4-aminophenyl)pyrrolidine-1-carboxylate, 6-(tetrahydro-2H-pyran-4-yloxy)nicotinic acid (CAS-886851-55-4) instead of (R)-2-phenylpropionic acid and HBTU instead of TBTU (17 h at rt). White solid. MS (ISP): 384.2 ([M+H]$^+$).

Example 233

(RS)—N-(4-(Morpholin-2-yl)phenyl)-2-phenylthiazole-4-carboxamide hydrochloride

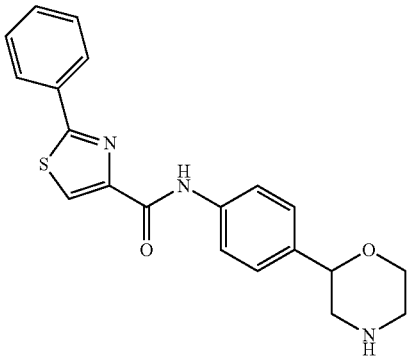

The title compound was obtained in analogy to Example 29 using (RS)-tert-butyl 2-(4-aminophenyl)morpholine-4-carboxylate (CAS-1002726-96-6) instead of (RS)-tert-butyl 3-(4-aminophenyl)pyrrolidine-1-carboxylate, 2-phenylthiazole-4-carboxylic acid (CAS-7113-10-2) instead of (R)-2-phenylpropionic acid and HBTU instead of TBTU (17 h at rt). White solid. MS (ISP): 366.2 ([M+H]$^+$).

Example 234

(S)—N-(4-(Piperidin-3-yl)phenyl)-3-(trifluoromethyl)benzamide hydrochloride

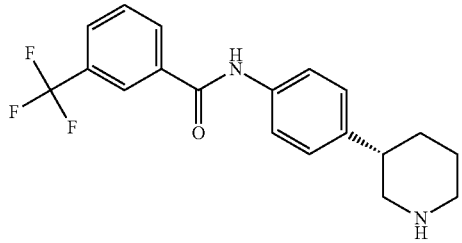 [SMILES: O=C(Nc1ccc([C@@H]2CCCNC2)cc1)c1cccc(C(F)(F)F)c1]

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 3-(trifluoromethyl)benzoic acid (CAS 454-92-2) instead of (R)-2-phenylpropionic acid. White solid. MS (ISP): 349.3 ([M+H]$^+$).

Example 235

(S)-2-(4-Chlorophenoxy)-N-(4-(piperidin-3-yl)phenyl)acetamide hydrochloride

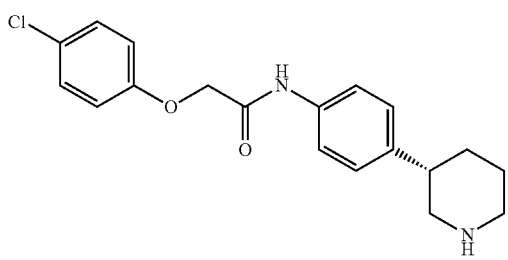 [SMILES: O=C(COc1ccc(Cl)cc1)Nc1ccc([C@@H]2CCCNC2)cc1]

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 2-(4-chlorophenoxy)acetic acid (CAS 122-88-3) instead of (R)-2-phenylpropionic acid. White solid. MS (ISP): 347.2 ([{$^{37}$Cl}M+H]$^+$), 345.2 ([{$^{35}$Cl}M+H]$^+$).

Example 236

(S)-4-(Methylthio)-N-(4-(piperidin-3-yl)phenyl)benzamide hydrochloride

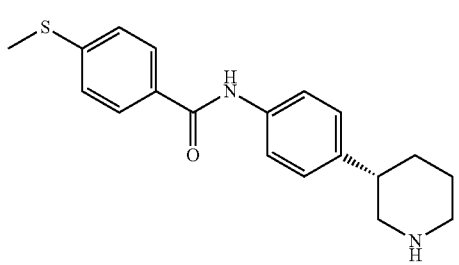 [SMILES: CSc1ccc(C(=O)Nc2ccc([C@@H]3CCCNC3)cc2)cc1]

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 4-(methylthio)benzoic acid (CAS 13205-48-6) instead of (R)-2-phenylpropionic acid. Off-white solid. MS (ISP): 327.3 ([M+H]$^+$).

Example 237

(S)-4-(Ethylthio)-N-(4-(piperidin-3-yl)phenyl)benzamide hydrochloride

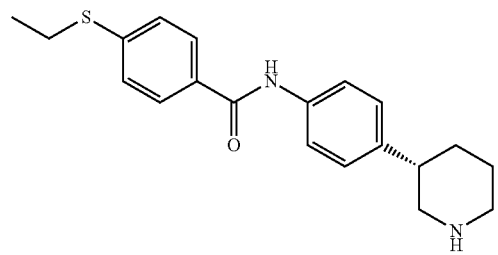 [SMILES: CCSc1ccc(C(=O)Nc2ccc([C@@H]3CCCNC3)cc2)cc1]

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 4-(ethylthio)benzoic acid (CAS 13205-49-7) instead of (R)-2-phenylpropionic acid. White solid. MS (ISP): 341.3 ([M+H]$^+$).

Example 238

5-Chloro-pyrazine-2-carboxylic acid ((S)-4-piperidin-3-yl-phenyl)-amide hydrochloride

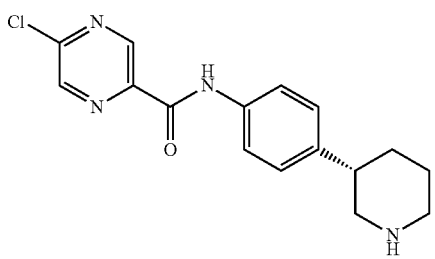 [SMILES: O=C(Nc1ccc([C@@H]2CCCNC2)cc1)c1cnc(Cl)cn1]

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 5-chloro-pyrazine-2-carboxylic acid (CAS 36070-80-1) instead of (R)-2-phenylpropionic acid. White solid. MS (ISP): 319.2 ([{$^{37}$Cl}M+H]$^+$), 317.2 ([{$^{35}$Cl}M+H]$^+$).

Example 239

5-Chloro-pyrazine-2-carboxylic acid ((R)-4-piperidin-3-yl-phenyl)-amide hydrochloride

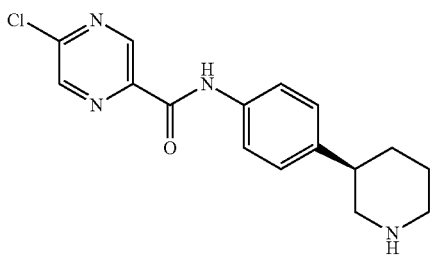 [SMILES: O=C(Nc1ccc([C@H]2CCCNC2)cc1)c1cnc(Cl)cn1]

The title compound was obtained in analogy to example 29 using (R)-tert-butyl 3-(4-aminophenyl)piperidine-1-carboxylate (example 150a) instead of (RS)-tert-butyl 3-(4-aminophenyl)pyrrolidine-1-carboxylate and 5-chloro-pyrazine-2-carboxylic acid (CAS 36070-80-1) instead of (R)-2-phenylpropionic acid. White solid. MS (ISP): 319.2 ([{$^{37}$Cl}M+H]$^+$), 317.2 ([{$^{35}$Cl}M+H]$^+$).

Example 240

(S)-4-chlorobenzyl 4-(piperidin-3-yl)phenylcarbamate hydrochloride

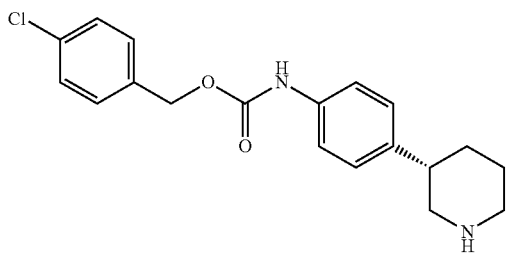 [SMILES: O=C(Nc1ccc([C@@H]2CCCNC2)cc1)OCc1ccc(Cl)cc1]

The title compound was obtained in analogy to example 120 using (S)-tert-butyl 3-(4-aminophenyl)piperidine-1-carboxylate (example 150a) instead of (RS)-tert-butyl 3-(4-aminophenyl)pyrrolidine-1-carboxylate and (4-chlorophenyl)methanol (CAS 873-76-7) instead of 4-chlorophenethyl alcohol. Off-white solid. MS (ISP): 347.1 ([{$^{37}$Cl}M+H]$^+$), 345.2 ([{$^{35}$Cl}M+H]$^+$).

Example 241

(RS)—N-(4-(Morpholin-2-yl)phenyl)-6-morpholinonicotinamide hydrochloride

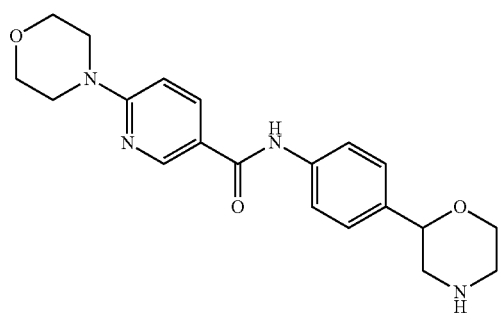 [SMILES: O=C(Nc1ccc(C2CNCCO2)cc1)c1ccc(N2CCOCC2)nc1]

The title compound was obtained in analogy to Example 29 using (RS)-tert-butyl 2-(4-aminophenyl)morpholine-4-carboxylate (CAS-1002726-96-6) instead of (RS)-tert-butyl 3-(4-aminophenyl)pyrrolidine-1-carboxylate, 6-morpholinonicotinic acid (CAS-120800-52-4) instead of (R)-2-phenylpropionic acid and HBTU instead of TBTU (17 h at rt). White solid. MS (ISP): 369.1 ([M+H]$^+$).

Example 242

(S)—N-(4-(Piperidin-3-yl)phenyl)-6-(trifluoromethyl)nicotinamide hydrochloride

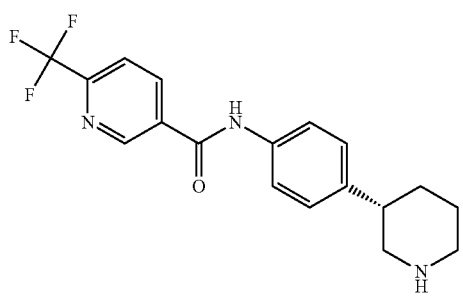 [SMILES: O=C(Nc1ccc([C@@H]2CCCNC2)cc1)c1ccc(C(F)(F)F)nc1]

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 6-(trifluoromethyl)nicotinic acid (CAS 231291-22-8) instead of (R)-2-phenylpropionic acid. White solid. MS (ISP): 350.4 ([M+H]$^+$).

Example 243

(S)-6-Methyl-N-(4-(piperidin-3-yl)phenyl)nicotinamide hydrochloride

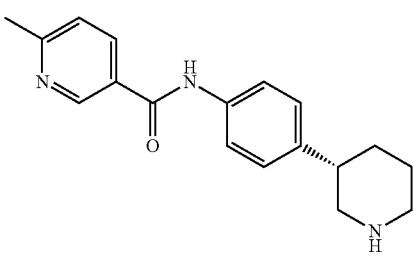 [SMILES: Cc1ccc(C(=O)Nc2ccc([C@@H]3CCCNC3)cc2)cn1]

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 6-methylnicotinic acid (CAS 3222-47-7) instead of (R)-2-phenylpropionic acid. White solid. MS (ISP): 296.4 ([M+H]$^+$).

Example 244

(S)-6-(Methylthio)-N-(4-(piperidin-3-yl)phenyl)nicotinamide hydrochloride

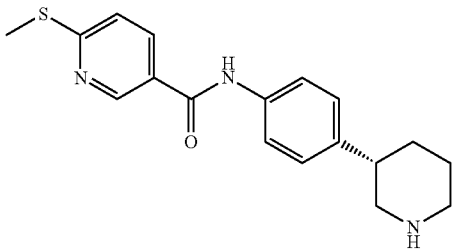 [SMILES: CSc1ccc(C(=O)Nc2ccc([C@@H]3CCCNC3)cc2)cn1]

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 6-(methylthio)nicotinic acid (CAS 74470-25-0) instead of (R)-2-phenylpropionic acid. White solid. MS (ISP): 328.4 ([M+H]$^+$).

Example 245

(RS)-6-Ethoxy-N-(4-(morpholin-2-yl)phenyl)nicotinamide hydrochloride

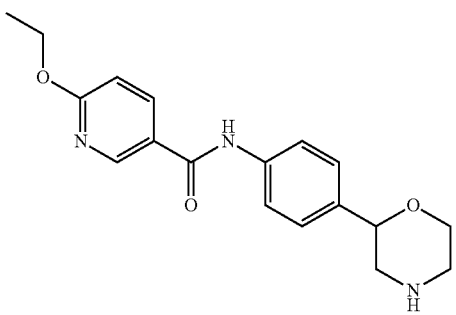 [SMILES: CCOc1ccc(C(=O)Nc2ccc(C3CNCCO3)cc2)cn1]

The title compound was obtained in analogy to Example 29 using (RS)-tert-butyl 2-(4-aminophenyl)morpholine-4-carboxylate (CAS-1002726-96-6) instead of (RS)-tert-butyl 3-(4-aminophenyl)pyrrolidine-1-carboxylate, 6-ethoxynicotinic acid (CAS-97455-65-7) instead of (R)-2-phenylpropionic acid and HBTU instead of TBTU (17 h at rt). White solid. MS (ISP): 328.3 ([M+H]$^+$).

Example 246

(S)-3-(Ethylthio)-N-(4-(piperidin-3-yl)phenyl)benzamide

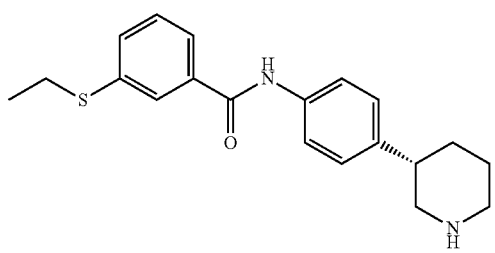 [SMILES: CCSc1cccc(C(=O)Nc2ccc([C@@H]3CCCNC3)cc2)c1]

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 3-(ethylthio)benzoic acid (CAS 5537-74-6) instead of (R)-2-phenylpropionic acid. Colourless gum. MS (ISP): 341.1 ([M+H]$^+$).

Example 247

(S)-5-Methyl-N-(4-(piperidin-3-yl)phenyl)pyrazine-2-carboxamide hydrochloride

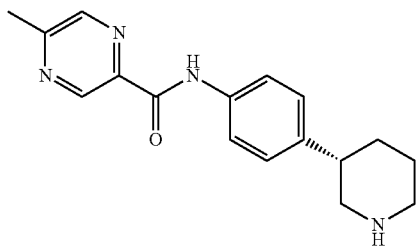 [SMILES: Cc1cnc(C(=O)Nc2ccc([C@@H]3CCCNC3)cc2)cn1]

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 5-methyl-pyrazine-2-carboxylic acid (CAS 5521-55-1) instead of (R)-2-phenylpropionic acid. Yellow solid. MS (ISP): 297.4 ([M+H]$^+$).

Example 248

(S)—N-(4-(Piperidin-3-yl)phenyl)-5-(trifluoromethyl)pyrazine-2-carboxamide hydrochloride

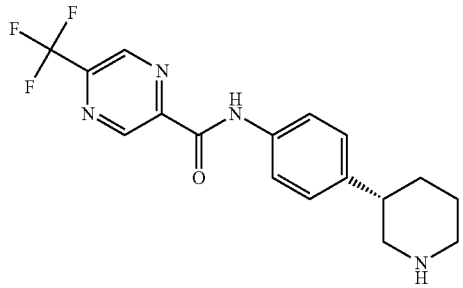 [SMILES: O=C(Nc1ccc([C@@H]2CCCNC2)cc1)c1cnc(C(F)(F)F)cn1]

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 5-(trifluoromethyl)pyrazine-2-carboxylic acid (CAS 1060814-50-7) instead of (R)-2-phenylpropionic acid. White solid. MS (ISP): 351.4 ([M+H]$^+$).

Example 249

(RS)—N-(4-(Morpholin-2-yl)phenyl)-2-phenyloxazole-4-carboxamide hydrochloride

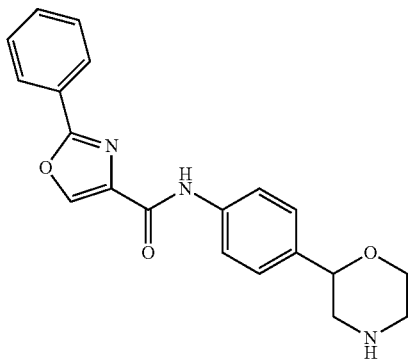 [SMILES: O=C(Nc1ccc(C2CNCCO2)cc1)c1coc(-c2ccccc2)n1]

The title compound was obtained in analogy to Example 29 using (RS)-tert-butyl 2-(4-aminophenyl)morpholine-4-carboxylate (CAS-1002726-96-6) instead of (RS)-tert-butyl 3-(4-aminophenyl)pyrrolidine-1-carboxylate, 2-phenyloxazole-4-carboxylic acid (CAS-23012-16-0) instead of (R)-2-phenylpropionic acid and HBTU instead of TBTU (17 h at rt). White solid. MS (ISP): 350.1 ([M+H]$^+$).

Example 250

(S)—N-(4-(Piperidin-3-yl)phenyl)-5-(2,2,2-trifluoroethoxy)pyrazine-2-carboxamide hydrochloride

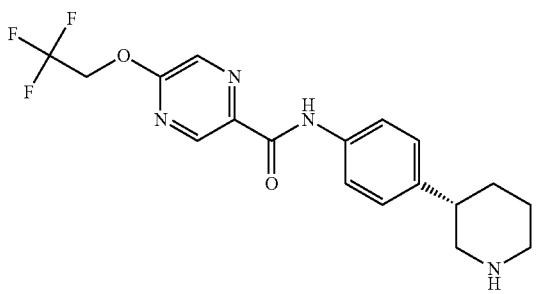 [SMILES: O=C(Nc1ccc([C@@H]2CCCNC2)cc1)c1cnc(OCC(F)(F)F)cn1]

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 5-(2,2,2-trifluoroethoxy)pyrazine-2-carboxylic acid (CAS 1174323-36-4) instead of (R)-2-phenylpropionic acid. White solid. MS (ISP): 381.4 ([M+H]$^+$).

Example 251

(S)-5-Bromo-N-(4-(piperidin-3-yl)phenyl)pyrazine-2-carboxamide 2,2,2-trifluoroacetate

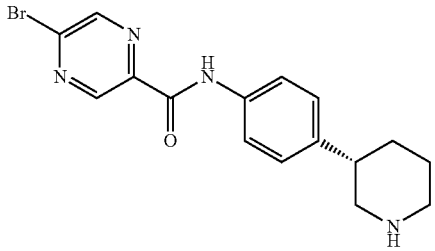

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 5-bromo-pyrazine-2-carboxylic acid (CAS 876161-05-6) instead of (R)-2-phenylpropionic acid. White solid. MS (ISP): 363.2 ([$^{81}$Br}M+H]$^+$), 361.2 ([$^{79}$Br}M+H]$^+$).

Example 252

(S)-6-Bromo-N-(4-(piperidin-3-yl)phenyl)nicotinamide 2,2,2-trifluoroacetate

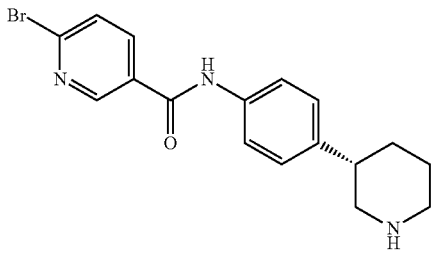

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 6-bromo-nicotinic acid (CAS 6311-35-9) instead of (R)-2-phenylpropionic acid. White solid. MS (ISP): 362.2 ([$^{81}$Br}M+H]$^+$), 360.2 ([$^{79}$Br}M+H]$^+$).

Example 253

(S)-3-Methyl-N-(4-(piperidin-3-yl)phenyl)benzamide

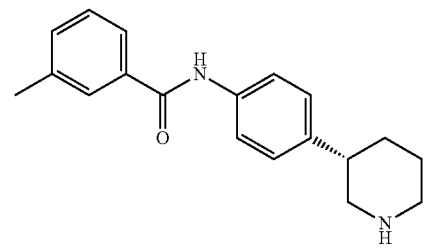 [SMILES: Cc1cccc(C(=O)Nc2ccc([C@@H]3CCCNC3)cc2)c1]

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 3-methylbenzoic acid (CAS 99-04-7) instead of (R)-2-phenylpropionic acid. White solid. MS (ISP): 295.2 ([M+H]$^+$).

Example 254 cis-(RS)-4-Methoxy-N-(4-(morpholin-2-yl)phenyl)cyclohexanecarboxamide hydrochloride

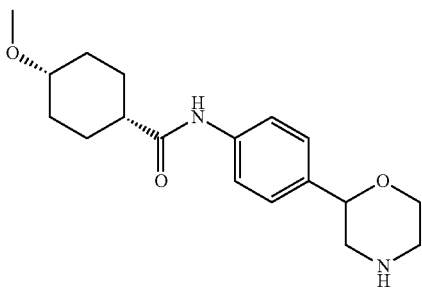 [SMILES: CO[C@H]1CC[C@@H](C(=O)Nc2ccc(C3CNCCO3)cc2)CC1]

The title compound was obtained in analogy to Example 29 using (RS)-tert-butyl 2-(4-aminophenyl)morpholine-4-carboxylate (CAS-1002726-96-6) instead of (RS)-tert-butyl 3-(4-aminophenyl)pyrrolidine-1-carboxylate, 4-methoxycyclohexanecarboxylic acid cis/trans mixture (CAS-95233-12-8) instead of (R)-2-phenylpropionic acid and HBTU instead of TBTU (17 h at rt). Cis/trans isomers were separated by using silicagel chromatography (heptane/ethyl acetate 1:1). Light brown solid. MS (ISP): 319.2 ([M+H]$^+$).

Example 255 trans-(RS)-4-Methoxy-N-(4-(morpholin-2-yl)phenyl)cyclohexanecarboxamide hydrochloride

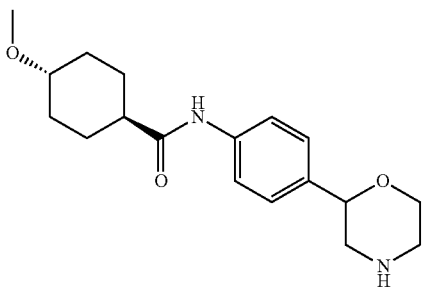 [SMILES: CO[C@H]1CC[C@H](C(=O)Nc2ccc(C3CNCCO3)cc2)CC1]

The title compound was obtained in analogy to Example 29 using (RS)-tert-butyl 2-(4-aminophenyl)morpholine-4-carboxylate (CAS-1002726-96-6) instead of (RS)-tert-butyl 3-(4-aminophenyl)pyrrolidine-1-carboxylate, 4-methoxycyclohexanecarboxylic acid cis/trans mixture (CAS-95233-12-8) instead of (R)-2-phenylpropionic acid and HBTU instead of TBTU (17 h at rt). Cis/trans isomers were separated by using silicagel chromatography (heptane/ethyl acetate 1:1). White solid. MS (ISP): 319.2 ([M+H]$^+$).

Example 256

(S)-6-Ethoxy-N-(4-(piperidin-3-yl)phenyl)nicotinamide

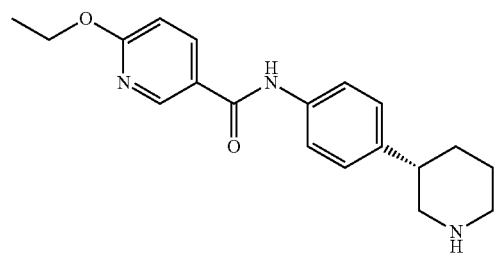 [SMILES: CCOc1ccc(C(=O)Nc2ccc([C@@H]3CCCNC3)cc2)cn1]

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 6-ethoxy-nicotinic acid (CAS 97455-65-7) instead of (R)-2-phenylpropionic acid. White solid. MS (ISP): 326.4 ([M+H]$^+$).

Example 257

(S)-5-(Methylthio)-N-(4-(piperidin-3-yl)phenyl)pyrazine-2-carboxamide

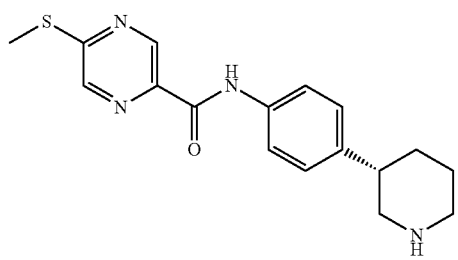 [SMILES: CSc1cnc(C(=O)Nc2ccc([C@@H]3CCCNC3)cc2)cn1]

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 5-(methylthio)-pyrazine-2-carboxylic acid (CAS 1174322-69-0) instead of (R)-2-phenylpropionic acid. White solid. MS (ISP): 329.4 ([M+H]$^+$).

Example 258

(S)-2,3-Dihydro-1H-inden-2-yl 4-(piperidin-3-yl)phenylcarbamate 2,2,2-trifluoroacetate

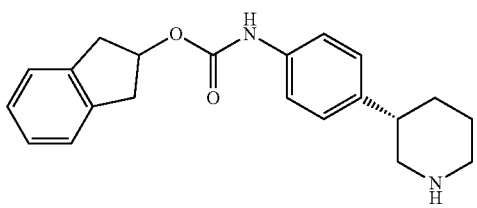 [SMILES: O=C(Nc1ccc([C@@H]2CCCNC2)cc1)OC1Cc2ccccc2C1]

The title compound was obtained in analogy to example 120 using (S)-tert-butyl 3-(4-aminophenyl)piperidine-1-carboxylate (example 150a) instead of (RS)-tert-butyl 3-(4-aminophenyl)pyrrolidine-1-carboxylate and 2-indanol (CAS 4254-29-9) instead of 4-chlorophenethyl alcohol. Off-white solid. MS (ISP): 337.5 ([M+H]+).

Example 259

(S)-3-(Methylthio)-N-(4-(piperidin-3-yl)phenyl)benzamide

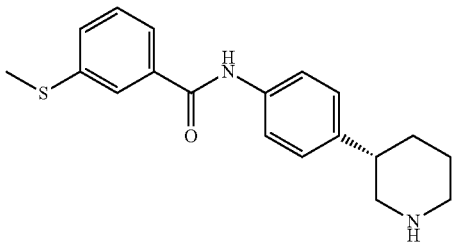 [SMILES: CSc1cccc(C(=O)Nc2ccc([C@@H]3CCCNC3)cc2)c1]

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 3-(methylthio)benzoic acid (CAS 825-99-0) instead of (R)-2-phenylpropionic acid. Off-white solid. MS (ISP): 327.3 ([M+H]+).

Example 260

(R)-3,4-Dimethyl-N-(4-(piperidin-3-yl)phenyl)benzamide hydrochloride

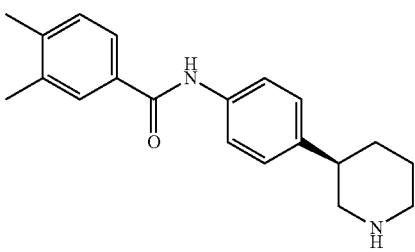 [SMILES: Cc1ccc(C(=O)Nc2ccc([C@H]3CCCNC3)cc2)cc1C]

The title compound was obtained in analogy to example 29 using (R)-tert-butyl 3-(4-aminophenyl)piperidine-1-carboxylate (example 150a) instead of (RS)-tert-butyl 3-(4-aminophenyl)pyrrolidine-1-carboxylate and 3,4-dimethylbenzoic acid (CAS 619-04-5) instead of (R)-2-phenylpropionic acid. Off-white solid. MS (ISP): 309.5 ([M+H]+).

Example 261

(R)—N-(4-(Piperidin-3-yl)phenyl)-3-(trifluoromethyl)benzamide hydrochloride

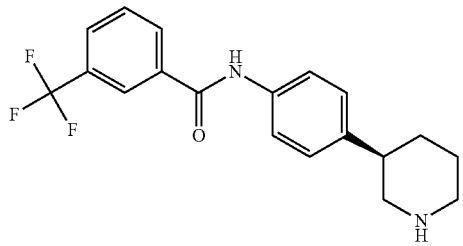 [SMILES: O=C(Nc1ccc([C@H]2CCCNC2)cc1)c1cccc(C(F)(F)F)c1]

The title compound was obtained in analogy to example 29 using (R)-tert-butyl 3-(4-aminophenyl)piperidine-1-carboxylate (example 150a) instead of (RS)-tert-butyl 3-(4-aminophenyl)pyrrolidine-1-carboxylate and 3-(trifluoromethyl)benzoic acid (CAS 454-92-2) instead of (R)-2-phenylpropionic acid. White solid. MS (ISP): 349.3 ([M+H]+).

Example 262

(R)-3-Chloro-N-(4-(morpholin-2-yl)phenyl)benzamide hydrochloride

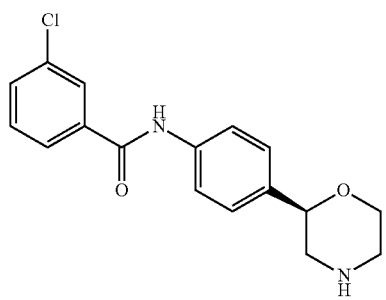 [SMILES: O=C(Nc1ccc([C@@H]2CNCCO2)cc1)c1cccc(Cl)c1]

The title compound was obtained in analogy to Example 29 using (R)-tert-butyl 2-(4-aminophenyl)morpholine-4-carboxylate (Prepared in Example 207-Steps a-d) instead of (RS)-tert-butyl 3-(4-aminophenyl)pyrrolidine-1-carboxylate, 3-chlorobenzoic acid (CAS-535-80-8) instead of (R)-2-phenylpropionic acid, and HBTU instead of TBTU (17 h at rt). White solid. MS (ISP): 317.1 ([M+H]+).

Example 263

(S)-3-Chloro-N-(4-(morpholin-2-yl)phenyl)benzamide hydrochloride

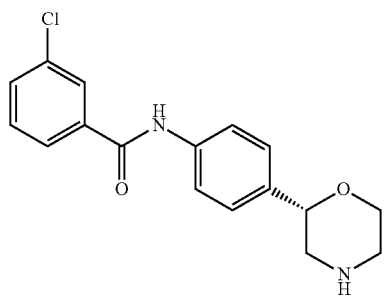 [SMILES: O=C(Nc1ccc([C@H]2CNCCO2)cc1)c1cccc(Cl)c1]

The title compound was obtained in analogy to Example 29 using (S)-tert-butyl 2-(4-aminophenyl)morpholine-4-carboxylate (Prepared in Example 208-Steps a-d) instead of (RS)-tert-butyl 3-(4-aminophenyl)pyrrolidine-1-carboxylate, 3-chlorobenzoic acid (CAS-535-80-8) instead of (R)-2-phenylpropionic acid and HBTU instead of TBTU (17 h at rt). Off-white solid. MS (ISP): 317.1 ([M+H]+).

Example 264

(R)-6-Methyl-N-(4-(piperidin-3-yl)phenyl)nicotinamide hydrochloride

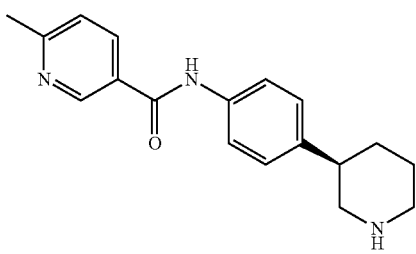 [SMILES: Cc1ccc(C(=O)Nc2ccc([C@H]3CCCNC3)cc2)cn1]

The title compound was obtained in analogy to example 29 using (R)-tert-butyl 3-(4-aminophenyl)piperidine-1-carboxylate (example 150a) instead of (RS)-tert-butyl 3-(4-aminophenyl)pyrrolidine-1-carboxylate and 6-methylnicotinic acid (CAS 3222-47-7) instead of (R)-2-phenylpropionic acid. Off-white solid. MS (ISP): 296.4 ([M+H]+).

Example 265

(R)—N-(4-(Piperidin-3-yl)phenyl)-6-(trifluoromethyl)nicotinamide hydrochloride

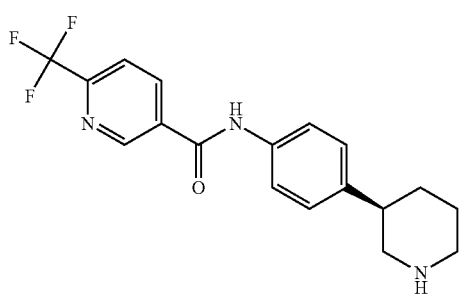 [SMILES: O=C(Nc1ccc([C@H]2CCCNC2)cc1)c1ccc(C(F)(F)F)nc1]

The title compound was obtained in analogy to example 29 using (R)-tert-butyl 3-(4-aminophenyl)piperidine-1-carboxylate (example 150a) instead of (RS)-tert-butyl 3-(4-aminophenyl)pyrrolidine-1-carboxylate and 6-(trifluoromethyl)nicotinic acid (CAS 231291-22-8) instead of (R)-2-phenylpropionic acid. White solid. MS (ISP): 350.4 ([M+H]+).

Example 266

(R)-4-(Methylthio)-N-(4-(morpholin-2-yl)phenyl)benzamide hydrochloride

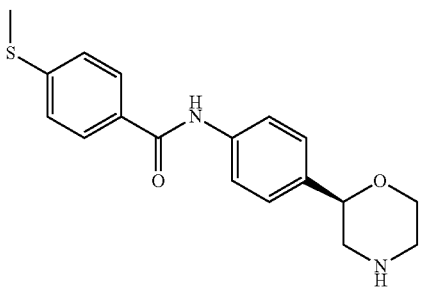 [SMILES: CSc1ccc(C(=O)Nc2ccc([C@@H]3CNCCO3)cc2)cc1]

The title compound was obtained in analogy to Example 29 using (R)-tert-butyl 2-(4-aminophenyl)morpholine-4-carboxylate (Prepared in Example 207-Steps a-d) instead of (RS)-tert-butyl 3-(4-aminophenyl)pyrrolidine-1-carboxylate, 4-(methylthio)benzoic acid (CAS-13205-48-6) instead of (R)-2-phenylpropionic acid and HBTU instead of TBTU. White solid. MS (ISP): 329.1 ([M+H]+).

Example 267

(S)-4-(Methylthio)-N-(4-(morpholin-2-yl)phenyl)benzamide hydrochloride

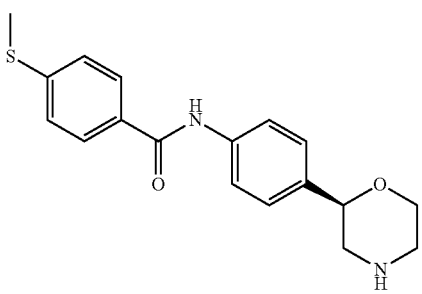 [SMILES: CSc1ccc(C(=O)Nc2ccc([C@@H]3CNCCO3)cc2)cc1]

The title compound was obtained in analogy to Example 29 using (S)-tert-butyl 2-(4-aminophenyl)morpholine-4-carboxylate (Prepared in Example 208-Steps a-d) instead of (RS)-tert-butyl 3-(4-aminophenyl)pyrrolidine-1-carboxylate, 4-(methylthio)benzoic acid (CAS-13205-48-6) instead of (R)-2-phenylpropionic acid and HBTU instead of TBTU (17 h at rt). White solid. MS (ISP): 329.1 ([M+H]+).

Example 268

(R)—N-(4-(Morpholin-2-yl)phenyl)-6-(2,2,2-trifluoroethoxy)nicotinamide hydrochloride

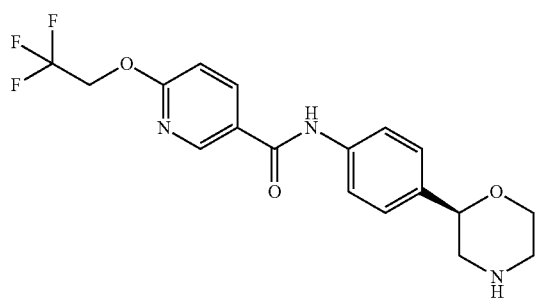 [SMILES: O=C(Nc1ccc([C@@H]2CNCCO2)cc1)c1ccc(OCC(F)(F)F)nc1]

The title compound was obtained in analogy to Example 29 using (R)-tert-butyl 2-(4-aminophenyl)morpholine-4-carboxylate (Prepared in Example 207-Steps a-d) instead of (RS)-tert-butyl 3-(4-aminophenyl)pyrrolidine-1-carboxylate, 6-(2,2,2-trifluoroethoxy)nicotinic acid (CAS-159783-29-6) instead of (R)-2-phenylpropionic acid and HBTU instead of TBTU (17 h at rt). White solid. MS (ISP): 382.1 ([M+H]+).

Example 269

(S)—N-(4-(Morpholin-2-yl)phenyl)-6-(2,2,2-trifluoroethoxy)nicotinamide hydrochloride

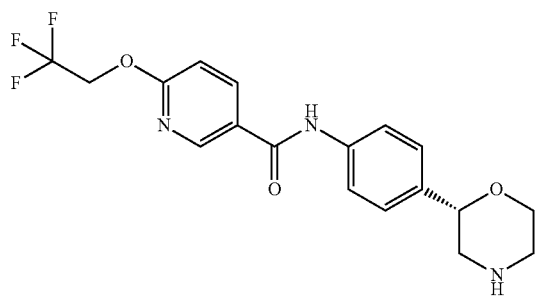 [SMILES: O=C(Nc1ccc([C@H]2CNCCO2)cc1)c1ccc(OCC(F)(F)F)nc1]

The title compound was obtained in analogy to Example 29 using (S)-tert-butyl 2-(4-aminophenyl)morpholine-4-carboxylate (Prepared in Example 208-Steps a-d) instead of (RS)-tert-butyl 3-(4-aminophenyl)pyrrolidine-1-carboxylate, 6-(2,2,2-trifluoroethoxy)nicotinic acid (CAS-159783-29-6) instead of (R)-2-phenylpropionic acid and HBTU instead of TBTU. White solid. MS (ISP): 382.1 ([M+H]+).

Example 270

(R)-2,6-Dichloro-N-(4-(morpholin-2-yl)phenyl)isonicotinamide hydrochloride

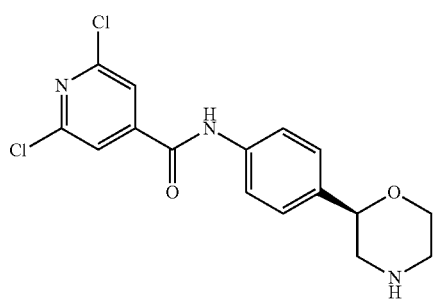 [SMILES: O=C(Nc1ccc([C@@H]2CNCCO2)cc1)c1cc(Cl)nc(Cl)c1]

The title compound was obtained in analogy to Example 29 using (R)-tert-butyl 2-(4-aminophenyl)morpholine-4-carboxylate (Prepared in Example 207-Steps a-d) instead of (RS)-tert-butyl 3-(4-aminophenyl)pyrrolidine-1-carboxylate, 2,6-dichloroisonicotinic acid (CAS-5398-44-7) instead of (R)-2-phenylpropionic acid and HBTU instead of TBTU (17 h at rt). White solid. MS (ISP): 352.1 ([M+H]+).

Example 271

(S)-2,6-Dichloro-N-(4-(morpholin-2-yl)phenyl)isonicotinamide hydrochloride

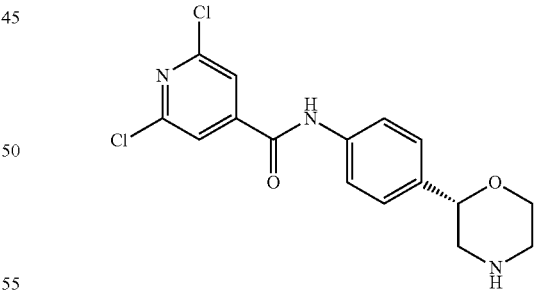

The title compound was obtained in analogy to Example 29 using (S)-tert-butyl 2-(4-aminophenyl)morpholine-4-carboxylate (Prepared in Example 208-Steps a-d) instead of (RS)-tert-butyl 3-(4-aminophenyl)pyrrolidine-1-carboxylate, 2,6-dichloroisonicotinic acid (CAS-5398-44-7) instead of (R)-2-phenylpropionic acid and HBTU instead of TBTU (17 h at rt). White solid. MS (ISP): 352.1 ([M+H]+).

Example 272

(RS)—N-(4-(Morpholin-2-yl)phenyl)-6-(trifluoromethyl)nicotinamide hydrochloride

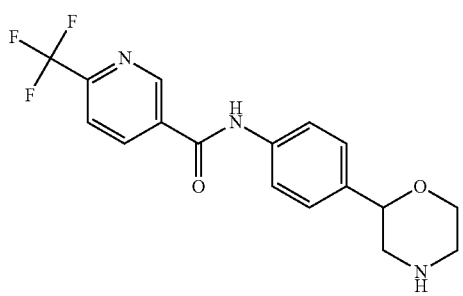 [SMILES: O=C(Nc1ccc(C2CNCCO2)cc1)c1ccc(C(F)(F)F)nc1]

The title compound was obtained in analogy to Example 29 using (RS)-tert-butyl 2-(4-aminophenyl)morpholine-4-carboxylate (CAS-1002726-96-6) instead of (RS)-tert-butyl 3-(4-aminophenyl)pyrrolidine-1-carboxylate, 6-(trifluoromethyl)nicotinic acid (CAS-158063-66-2) instead of (R)-2-phenylpropionic acid and HBTU instead of TBTU (17 h at rt). White solid. MS (ISP): 352.2 ([M+H]$^+$).

Example 273

(RS)-2-Chloro-6-methyl-N-(4-(morpholin-2-yl)phenyl)isonicotinamide hydrochloride

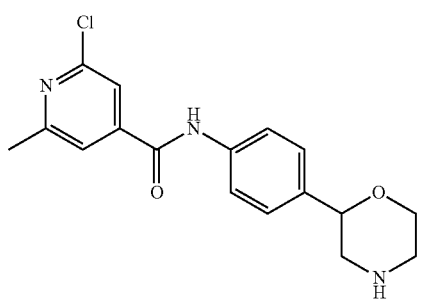 [SMILES: Cc1cc(C(=O)Nc2ccc(C3CNCCO3)cc2)cc(Cl)n1]

The title compound was obtained in analogy to Example 29 using (RS)-tert-butyl 2-(4-aminophenyl)morpholine-4-carboxylate (CAS-1002726-96-6) instead of (RS)-tert-butyl 3-(4-aminophenyl)pyrrolidine-1-carboxylate, 2-chloro-6-methylpyridine-4-carboxylic acid (CAS-25462-85-5) instead of (R)-2-phenylpropionic acid and HBTU instead of TBTU (17 h at rt). White solid. MS (ISP): 332.3 ([M+H]$^+$).

Example 274

(S)-5-Ethyl-N-(4-(piperidin-3-yl)phenyl)pyrazine-2-carboxamide hydrochloride

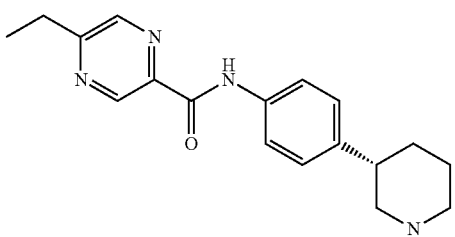

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 5-ethyl-pyrazine-2-carboxylic acid (CAS 13534-75-3) instead of (R)-2-phenylpropionic acid. Yellow solid. MS (ISP): 311.4 ([M+H]$^+$).

Example 275

(R)-4-Ethoxy-N-(4-(morpholin-2-yl)phenyl)benzamide hydrochloride

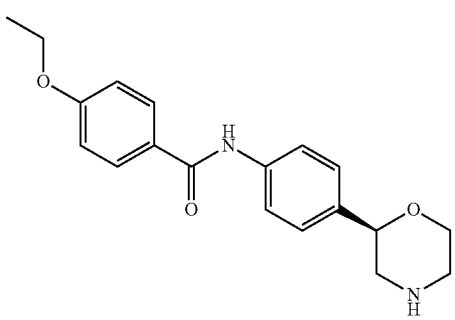 [SMILES: CCOc1ccc(C(=O)Nc2ccc([C@@H]3CNCCO3)cc2)cc1]

The title compound was obtained in analogy to Example 29 using (R)-tert-butyl 2-(4-aminophenyl)morpholine-4-carboxylate (Prepared in Example 207-Steps a-d) instead of (RS)-tert-butyl 3-(4-aminophenyl)pyrrolidine-1-carboxylate, 4-ethoxybenzoic acid (CAS-619-86-3) instead of (R)-2-phenylpropionic acid and HBTU instead of TBTU (17 h at rt). White solid. MS (ISP): 327.2 ([M+H]$^+$).

Example 276

(S)-4-Ethoxy-N-(4-(morpholin-2-yl)phenyl)benzamide hydrochloride

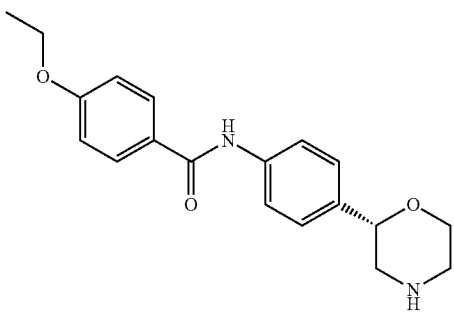 [SMILES: CCOc1ccc(C(=O)Nc2ccc([C@H]3CNCCO3)cc2)cc1]

The title compound was obtained in analogy to Example 29 using (S)-tert-butyl 2-(4-aminophenyl)morpholine-4-carboxylate (Prepared in Example 208-Steps a-d) instead of (RS)-tert-butyl 3-(4-aminophenyl)pyrrolidine-1-carboxylate, 4-ethoxybenzoic acid (CAS-619-86-3) instead of (R)-2-phenylpropionic acid and HBTU instead of TBTU (17 h at rt). White solid. MS (ISP): 327.2 ([M+H]$^+$).

Example 277

(RS)-3-Methyl-N-(4-(morpholin-2-yl)phenyl)benzamide hydrochloride

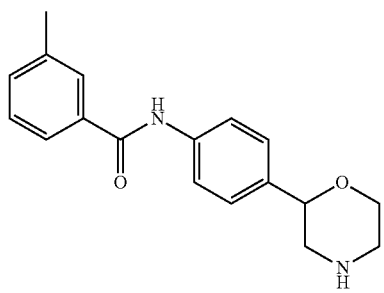 [SMILES: Cc1cccc(C(=O)Nc2ccc(C3CNCCO3)cc2)c1]

The title compound was obtained in analogy to Example 29 using (RS)-tert-butyl 2-(4-aminophenyl)morpholine-4-carboxylate (CAS-1002726-96-6) instead of (RS)-tert-butyl 3-(4-aminophenyl)pyrrolidine-1-carboxylate, 3-methylbenzoic acid (CAS-99-04-7) instead of (R)-2-phenylpropionic acid and HBTU instead of TBTU (17 h at rt). White solid. MS (ISP): 297.2 ([M+H]$^+$).

Example 278

(S)—N-(4-(Piperidin-3-yl)phenyl)-5-propylpyrazine-2-carboxamide hydrochloride

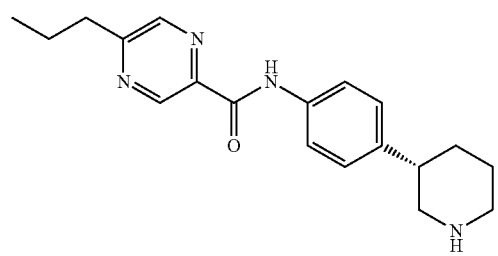 [SMILES: CCCc1cnc(C(=O)Nc2ccc([C@@H]3CCCNC3)cc2)cn1]

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 5-propyl-pyrazine-2-carboxylic acid instead of (R)-2-phenylpropionic acid. Yellow solid. MS (ISP): 325.4 ([M+H]$^+$).

Example 279

(RS)—N-(4-(Morpholin-2-yl)phenyl)-6-(pyrrolidin-1-yl)nicotinamide hydrochloride

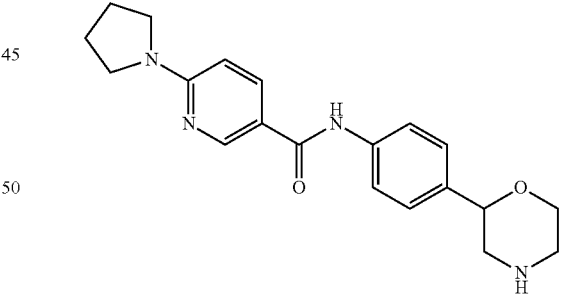

The title compound was obtained in analogy to Example 29 using (RS)-tert-butyl 2-(4-aminophenyl)morpholine-4-carboxylate (CAS-1002726-96-6) instead of (RS)-tert-butyl 3-(4-aminophenyl)pyrrolidine-1-carboxylate, 6-pyrrolidin-1-yl-nicotinic acid (CAS-210963-95-4) instead of (R)-2-phenylpropionic acid and HBTU instead of TBTU (17 h at rt). White solid. MS (ISP): 353.2 ([M+H]$^+$).

Example 280

(RS)—N-(4-(Morpholin-2-yl)phenyl)-2-(trifluoromethyl)isonicotinamide hydrochloride

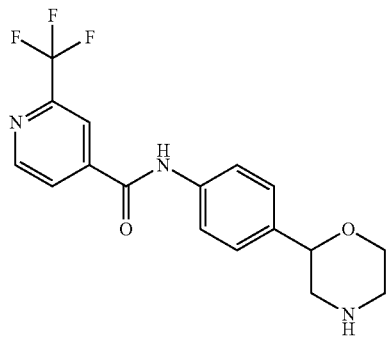 [SMILES: O=C(Nc1ccc(C2CNCCO2)cc1)c1ccnc(C(F)(F)F)c1]

The title compound was obtained in analogy to Example 29 using (RS)-tert-butyl 2-(4-aminophenyl)morpholine-4-carboxylate (CAS-1002726-96-6) instead of (RS)-tert-butyl 3-(4-aminophenyl)pyrrolidine-1-carboxylate, 2-(trifluoromethyl)isonicotinic acid (CAS-131747-41-6) instead of (R)-2-phenylpropionic acid and HBTU instead of TBTU (17 h at rt). White solid. MS (ISP): 353.2 ([M+H]$^+$).

Example 281

(S)-2,6-Dichloro-N-(4-(piperidin-3-yl)phenyl)isonicotinamide hydrochloride

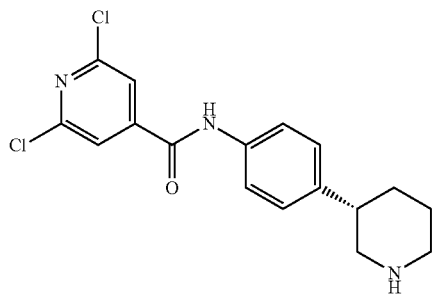 [SMILES: O=C(Nc1ccc([C@@H]2CCCNC2)cc1)c1cc(Cl)nc(Cl)c1]

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 2,6-dichloroisonicotinic acid (CAS 5398-44-7) instead of (R)-2-phenylpropionic acid. White solid. MS (ISP): 354.3 ([$^{37}$Cl]M+H]$^+$), 352.3 ([$^{37}$Cl$^{35}$Cl]M+H]$^+$), 350.3 ([$^{35}$Cl]M+H]$^+$).

Example 282

(S)-2-Chloro-6-methyl-N-(4-(piperidin-3-yl)phenyl)isonicotinamide

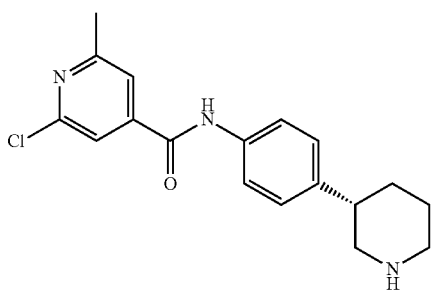 [SMILES: Cc1cc(C(=O)Nc2ccc([C@@H]3CCCNC3)cc2)cc(Cl)n1]

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 2-chloro-6-methylisonicotinic acid (CAS 25462-85-5) instead of (R)-2-phenylpropionic acid. Light yellow solid. MS (ISP): 332.2 ([$^{37}$Cl]M+H]$^+$), 330.3 ([$^{35}$Cl]M+H]$^+$).

Example 283

(R)—N-(4-(Morpholin-2-yl)phenyl)-6-(trifluoromethyl)nicotinamide hydrochloride

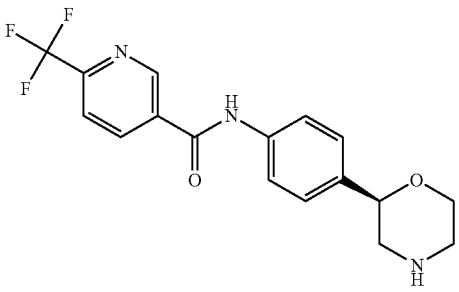 [SMILES: O=C(Nc1ccc([C@@H]2CNCCO2)cc1)c1ccc(C(F)(F)F)nc1]

The title compound was obtained in analogy to Example 29 using (R)-tert-butyl 2-(4-aminophenyl)morpholine-4-carboxylate (Prepared in Example 207-Steps a-d) instead of (RS)-tert-butyl 3-(4-aminophenyl)pyrrolidine-1-carboxylate, 6-(trifluoromethyl)nicotinic acid (CAS-158063-66-2) instead of (R)-2-phenylpropionic acid and HBTU instead of TBTU (17 h at rt). White solid. MS (ISP): 352.2 ([M+H]$^+$).

Example 284

(S)—N-(4-(Morpholin-2-yl)phenyl)-6-(trifluoromethyl)nicotinamide hydrochloride

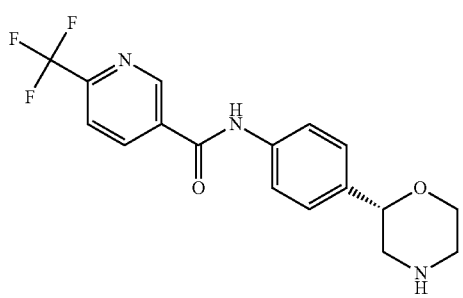 [SMILES: O=C(Nc1ccc([C@H]2CNCCO2)cc1)c1ccc(C(F)(F)F)nc1]

The title compound was obtained in analogy to Example 29 using (S)-tert-butyl 2-(4-aminophenyl)morpholine-4-carboxylate (Prepared in Example 208-Steps a-d) instead of (RS)-tert-butyl 3-(4-aminophenyl)pyrrolidine-1-carboxylate, 6-(trifluoromethyl)nicotinic acid (CAS-158063-66-2) instead of (R)-2-phenylpropionic acid and HBTU instead of TBTU (17 h at rt). White solid. MS (ISP): 352.2 ([M+H]$^+$).

Example 285

(R)-2-Chloro-6-methyl-N-(4-(morpholin-2-yl)phenyl)isonicotinamide hydrochloride

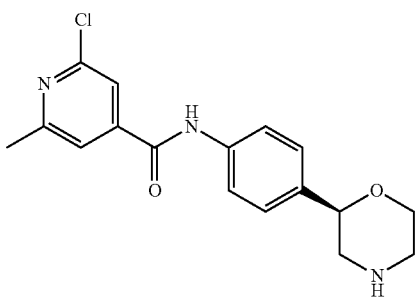 [SMILES: Cc1cc(C(=O)Nc2ccc([C@@H]3CNCCO3)cc2)cc(Cl)n1]

The title compound was obtained in analogy to Example 29 using (R)-tert-butyl 2-(4-aminophenyl)morpholine-4-carboxylate (Prepared in Example 207-Steps a-d) instead of (RS)-tert-butyl 3-(4-aminophenyl)pyrrolidine-1-carboxylate, 2-chloro-6-methylpyridine-4-carboxylic acid (CAS-25462-85-5) instead of (R)-2-phenylpropionic acid and HBTU instead of TBTU (17 h at rt). White solid. MS (ISP): 332.1 ([M+H]$^+$).

Example 286

(S)-2-Chloro-6-methyl-N-(4-(morpholin-2-yl)phenyl)isonicotinamide hydrochloride

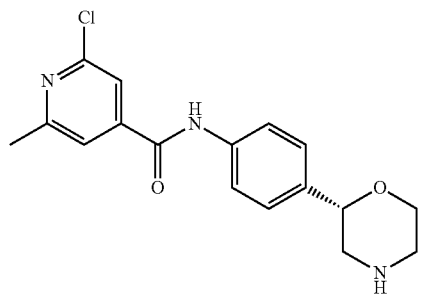 [SMILES: Cc1cc(C(=O)Nc2ccc([C@H]3CNCCO3)cc2)cc(Cl)n1]

The title compound was obtained in analogy to Example 29 using (S)-tert-butyl 2-(4-aminophenyl)morpholine-4-carboxylate (Prepared in Example 208-Steps a-d) instead of (RS)-tert-butyl 3-(4-aminophenyl)pyrrolidine-1-carboxylate, 2-chloro-6-methylpyridine-4-carboxylic acid (CAS-25462-85-5) instead of (R)-2-phenylpropionic acid and HBTU instead of TBTU (17 h at rt). White solid. MS (ISP): 332.1 ([M+H]$^+$).

Example 287

(RS)—N-(4-(Morpholin-2-yl)phenyl)-1-(pyrimidin-4-yl)piperidine-4-carboxamide dihydrochloride

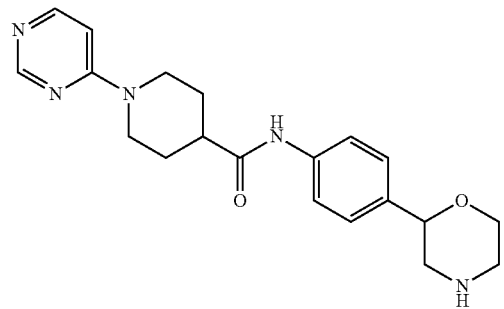 [SMILES: O=C(Nc1ccc(C2CNCCO2)cc1)C1CCN(c2ccncn2)CC1]

The title compound was obtained in analogy to Example 29 using (RS)-tert-butyl 2-(4-aminophenyl)morpholine-4-carboxylate (CAS-1002726-96-6) instead of (RS)-tert-butyl 3-(4-aminophenyl)pyrrolidine-1-carboxylate, 1-(pyrimidin-4-yl)piperidine-4-carboxylic acid hydrochloride (CAS-712261-81-9) instead of (R)-2-phenylpropionic acid and HBTU instead of TBTU (17 h at rt). Off-white solid. MS (ISP): 368.2 ([M+H]$^+$).

Example 288

(RS)—N-(4-(Morpholin-2-yl)phenyl)-2-(pyrazin-2-yl)thiazole-4-carboxamide hydrochloride

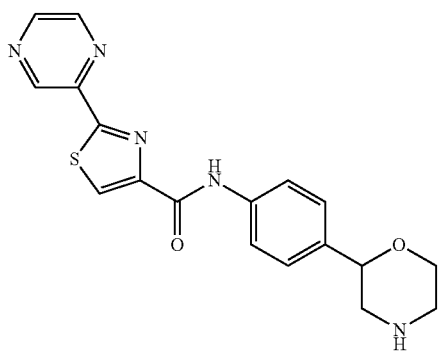 [SMILES: O=C(Nc1ccc(C2CNCCO2)cc1)c1csc(-c2cnccn2)n1]

The title compound was obtained in analogy to Example 29 using (RS)-tert-butyl 2-(4-aminophenyl)morpholine-4-carboxylate (CAS-1002726-96-6) instead of (RS)-tert-butyl 3-(4-aminophenyl)pyrrolidine-1-carboxylate, 2-(pyrazin-2-yl)thiazole-4-carboxylic acid (CAS-115311-44-9) instead of (R)-2-phenylpropionic acid and HBTU instead of TBTU (17 h at rt). Yellow solid. MS (ISP): 368.2 ([M+H]$^+$).

Example 289

(S)—N-(4-(Piperidin-3-yl)phenyl)-6-propylnicotinamide

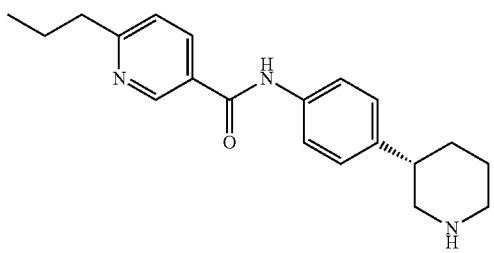

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 6-propylnicotinic acid (CAS 847046-96-2) instead of (R)-2-phenylpropionic acid. White solid. MS (ISP): 324.4 ([M+H]$^+$).

Example 290

(RS)—N-(4-(Morpholin-2-yl)phenyl)-2-(pyrimidin-2-yl)thiazole-4-carboxamide hydrochloride

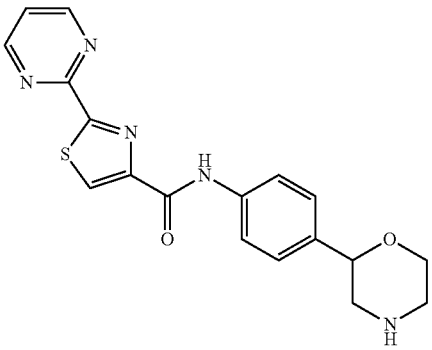 [SMILES: O=C(Nc1ccc(C2CNCCO2)cc1)c1csc(-c2ncccn2)n1]

The title compound was obtained in analogy to Example 29 using (RS)-tert-butyl 2-(4-aminophenyl)morpholine-4-carboxylate (CAS-1002726-96-6) instead of (RS)-tert-butyl 3-(4-aminophenyl)pyrrolidine-1-carboxylate, 2-(pyrimidin-2-yl)thiazole-4-carboxylic acid (CAS-1014631-26-5) instead of (R)-2-phenylpropionic acid and HBTU instead of TBTU (17 h at rt). Light brown solid. MS (ISP): 368.2 ([M+H]$^+$).

Example 291

(RS)-1-(4-(Morpholin-2-yl)phenyl)-3-(4-(trifluoromethyl)phenyl)urea hydrochloride

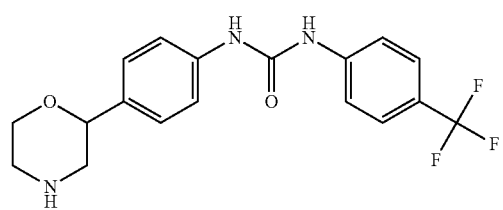 [SMILES: O=C(Nc1ccc(C2CNCCO2)cc1)Nc1ccc(C(F)(F)F)cc1]

a) (RS)-tert-Butyl 2-(4-(3-(4-(trifluoromethyl)phenyl)ureido)phenyl)morpholine-4-carboxylate (RS)-tert-Butyl 2-(4-aminophenyl)morpholine-4-carboxylate (CAS-1002726-96-6) (400 mg; 1.44 mmol), 4-(trifluoromethyl)phenyl isocyanate (CAS-1548-13-6) (336 mg; 1.8 mmol) and triethylamine (182 mg; 1.8 mmol) were dissolved in DMF (13.3 ml) and stirred at 70° C. for 17 h. After cooling down to rt the reaction mixture was poured into water, extracted twice with ethyl acetate, washed with water and brine, dried over magnesium sulfate and concentrated in vacuo. The residue was purified by silicagel chromatography (90 g silicagel; heptane/ethyl acetate 1:1) affording 433 mg of a light yellow solid. MS (ISP): 410.2 mg ([M+H]$^+$-tert-butyl).

b) (RS)-1-(4-(Morpholin-2-yl)phenyl)-3-(4-(trifluoromethyl)phenyl)urea hydrochloride (RS)-tert-Butyl 2-(4-(3-(4-(trifluoromethyl)phenyl)ureido)phenyl)morpholine-4-carboxylate (167 mg; 0.359 mmol) was dissolved in dioxane (1 ml), treated with 4 M HCl in dioxane (1.35 ml; 5.4 mmol) and stirred for 2 h at rt. The resulting suspension was filtered-off and washed with diethyl ether, affording 74 mg white solid. MS (ISP): 366.1 ([M+H]$^+$).

Example 292

(RS)-1-(4-Chlorophenyl)-3-(4-(morpholin-2-yl)phenyl)urea hydrochloride

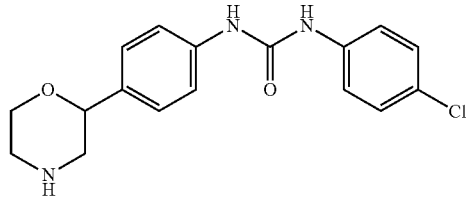 [SMILES: O=C(Nc1ccc(Cl)cc1)Nc1ccc(C2CNCCO2)cc1]

The title compound was obtained in analogy to Example 291 using 4-chlorophenyl isocyanate (CAS-104-12-1) instead of 4-(trifluoromethyl)phenyl isocyanate (CAS-1548-13-6). Light brown solid. MS (ISP): 332.2 ([M+H]$^+$).

Example 293

(RS)-1-(4-(Morpholin-2-yl)phenyl)-3-p-tolylurea hydrochloride

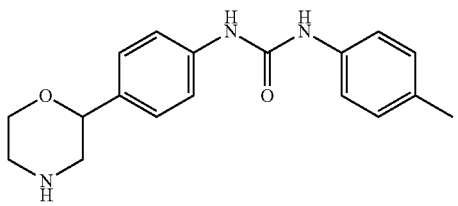 [SMILES: Cc1ccc(NC(=O)Nc2ccc(C3CNCCO3)cc2)cc1]

The title compound was obtained in analogy to Example 291 using p-tolyl isocyanate (CAS-374675-64-6) instead of 4-(trifluoromethyl)phenyl isocyanate (CAS-1548-13-6). White solid. MS (ISP): 312.1 ([M+H]$^+$).

Example 294

(RS)-2-Methyl-N-(4-(morpholin-2-yl)phenyl)isonicotinamide dihydrochloride

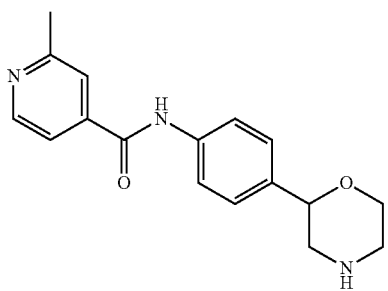

The title compound was obtained in analogy to Example 29 using (RS)-tert-butyl 2-(4-aminophenyl)morpholine-4-carboxylate (CAS-1002726-96-6) instead of (RS)-tert-butyl 3-(4-aminophenyl)pyrrolidine-1-carboxylate, 2-methylisonicotinic acid (CAS-4021-11-8) instead of (R)-2-phenylpropionic acid and HBTU instead of TBTU (17 h at rt). Light yellow solid. MS (ISP): 298.4 ([M+H]$^+$).

Example 295

(RS)-2,6-Dimethyl-N-(4-(morpholin-2-yl)phenyl)isonicotinamide dihydrochloride

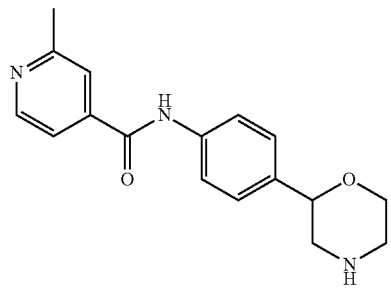 [SMILES: Cc1cc(C(=O)Nc2ccc(C3CNCCO3)cc2)ccn1]

The title compound was obtained in analogy to Example 29 using (RS)-tert-butyl 2-(4-aminophenyl)morpholine-4-carboxylate (CAS-1002726-96-6) instead of (RS)-tert-butyl 3-(4-aminophenyl)pyrrolidine-1-carboxylate, 2,6-dimethylisonicotinic acid (CAS-54221-93-1) instead of (R)-2-phenylpropionic acid and HBTU instead of TBTU (17 h at rt). Yellow solid. MS (ISP): 312.4 ([M+H]$^+$).

Example 296

(RS)-2-(1-Methyl-1H-pyrazol-4-yl)-N-(4-(morpholin-2-yl)phenyl)thiazole-4-carboxamide hydrochloride

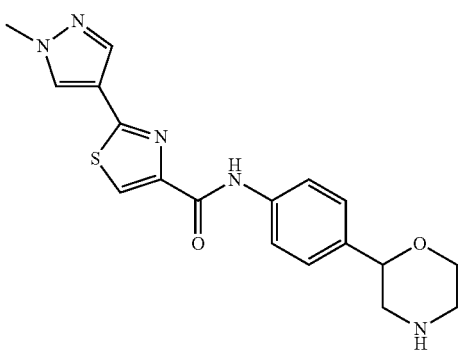 [SMILES: Cn1cc(-c2nc(C(=O)Nc3ccc(C4CNCCO4)cc3)cs2)cn1]

The title compound was obtained in analogy to Example 29 using (RS)-tert-butyl 2-(4-aminophenyl)morpholine-4-carboxylate (CAS-1002726-96-6) instead of (RS)-tert-butyl 3-(4-aminophenyl)pyrrolidine-1-carboxylate, 2-(1-methyl-1H-pyrazol-4-yl)thiazole-4-carboxylic acid (CAS-1152605-07-6) instead of (R)-2-phenylpropionic acid and HBTU instead of TBTU (17 h at rt). White solid. MS (ISP): 370.2 ([M+H]$^+$).

Example 297

(S)-6-Ethyl-N-(4-(piperidin-3-yl)phenyl)nicotinamide

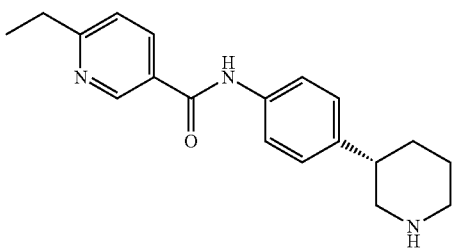 [SMILES: CCc1ccc(C(=O)Nc2ccc([C@@H]3CCCNC3)cc2)cn1]

The title compound was obtained in analogy to example 29 using (S)-tert-butyl 3-(4-aminophenyl)piperidine-1-carboxylate (example 150a) instead of (RS)-tert-butyl 3-(4-aminophenyl)pyrrolidine-1-carboxylate and 6-ethylnicotinic acid (CAS 802828-81-5) instead of (R)-2-phenylpropionic acid. White solid. MS (ISP): 310.4 ([M+H]$^+$).

Example 298

(RS)-4-Methyl-N-(4-(morpholin-2-yl)phenyl)-2-(pyrazin-2-yl)thiazole-5-carboxamide hydrochloride

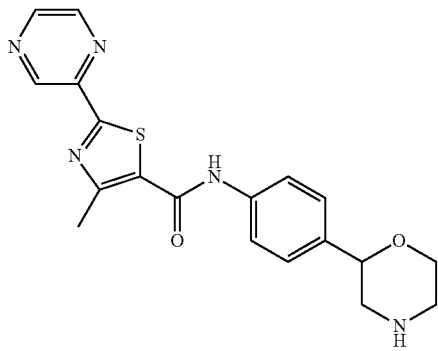 [SMILES: Cc1nc(-c2cnccn2)sc1C(=O)Nc1ccc(C2CNCCO2)cc1]

The title compound was obtained in analogy to Example 29 using (RS)-tert-butyl 2-(4-aminophenyl)morpholine-4-carboxylate (CAS-1002726-96-6) instead of (RS)-tert-butyl 3-(4-aminophenyl)pyrrolidine-1-carboxylate, 4-methyl-2-(pyrazin-2-yl)thiazole-5-carboxylic acid (CAS-216959-92-1) instead of (R)-2-phenylpropionic acid and HBTU instead of TBTU (17 h at rt). Yellow solid. MS (ISP): 382.4 ([M+H]$^+$).

Example 299

(RS)—N-(4-(Morpholin-2-yl)phenyl)-1-phenyl-1H-pyrazole-3-carboxamide hydrochloride

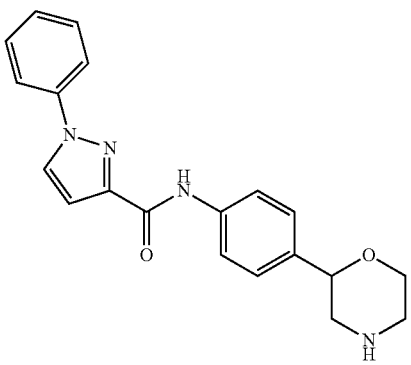 [SMILES: O=C(Nc1ccc(C2CNCCO2)cc1)c1ccn(-c2ccccc2)n1]

The title compound was obtained in analogy to Example 29 using (RS)-tert-butyl 2-(4-aminophenyl)morpholine-4-carboxylate (CAS-1002726-96-6) instead of (RS)-tert-butyl 3-(4-aminophenyl)pyrrolidine-1-carboxylate, 1-phenyl-1H-pyrazole-3-carboxylic acid (CAS-4747-46-0) instead of (R)-2-phenylpropionic acid and HBTU instead of TBTU (17 h at rt). Off-white solid. MS (ISP): 349.2 ([M+H]$^+$).

Example 300

(RS)-2-Ethoxy-N-(4-(morpholin-2-yl)phenyl)isonicotinamide hydrochloride

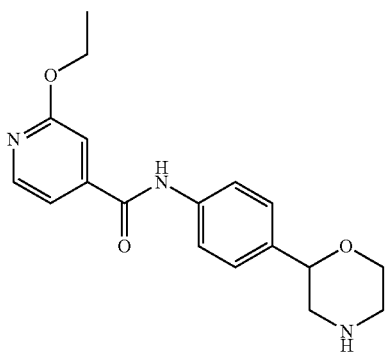 [SMILES: CCOc1cc(C(=O)Nc2ccc(C3CNCCO3)cc2)ccn1]

The title compound was obtained in analogy to Example 29 using (RS)-tert-butyl 2-(4-aminophenyl)morpholine-4-carboxylate (CAS-1002726-96-6) instead of (RS)-tert-butyl 3-(4-aminophenyl)pyrrolidine-1-carboxylate, 2-ethoxyisonicotinic acid (CAS-91940-86-2) instead of (R)-2-phenylpropionic acid and HBTU instead of TBTU (17 h at rt). Light yellow solid. MS (ISP): 328.2 ([M+H]$^+$).

Example 301

(S)-4-Chloro-2-iodo-N-(4-(morpholin-2-yl)phenyl) benzamide

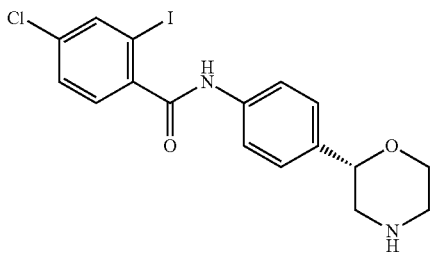 [SMILES: O=C(Nc1ccc([C@H]2CNCCO2)cc1)c1ccc(Cl)cc1I]

The title compound was obtained in analogy to example 141 using (S)-tert-butyl 2-(4-bromophenyl)morpholine-4-carboxylate (example 208b) instead of (RS)-tert-butyl 2-(4-bromophenyl)morpholine-4-carboxylate and 4-chloro-2-iodo-benzamide (CAS 942319-20-2) instead of 5-trifluoromethyl-pyridine-2-carboxylic acid amide. White solid. MS (ISP): 445.0 ([{$^{37}$Cl}M+H]$^+$), 443.0 ([{$^{35}$Cl}M+H]$^+$).

Example 302

(RS)-1-(6-Chloropyridin-3-yl)-3-(4-(morpholin-2-yl)phenyl)urea hydrochloride

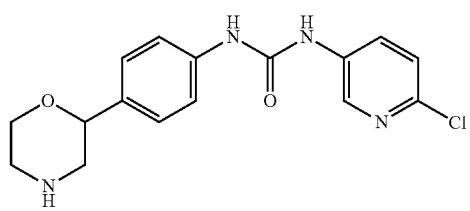 [SMILES: O=C(Nc1ccc(C2CNCCO2)cc1)Nc1ccc(Cl)nc1]

The title compound was obtained in analogy to Example 291 using 2-chloro-5-isocyanatopyridine (CAS-125117-96-6) instead of 4-(trifluoromethyl)phenyl isocyanate (CAS-1548-13-6). Orange solid. MS (ISP): 333.3 ([M+H]$^+$).

Example 303

(RS)-1-(3-Chlorophenyl)-3-(4-(morpholin-2-yl)phenyl)urea hydrochloride

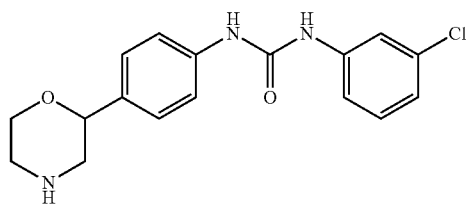 [SMILES: O=C(Nc1ccc(C2CNCCO2)cc1)Nc1cccc(Cl)c1]

The title compound was obtained in analogy to Example 291 using 3-chlorophenyl isocyanate (CAS-2909-38-8) instead of 4-(trifluoromethyl)phenyl isocyanate (CAS-1548-13-6). Light grey solid. MS (ISP): 332.1 ([M+H]$^+$).

Example 304

(RS)-1-(4-(Morpholin-2-yl)phenyl)-3-m-tolylurea hydrochloride

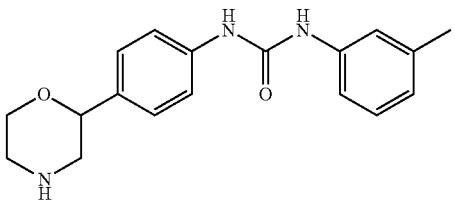 [SMILES: Cc1cccc(NC(=O)Nc2ccc(C3CNCCO3)cc2)c1]

The title compound was obtained in analogy to Example 291 using m-tolyl isocyanate (CAS-621-29-4) instead of 4-(trifluoromethyl)phenyl isocyanate (CAS-1548-13-6). Light grey solid. MS (ISP): 312.4 ([M+H]$^+$).

Example 305

(RS)-1-(2-Chlorophenyl)-3-(4-(morpholin-2-yl)phenyl)urea hydrochloride

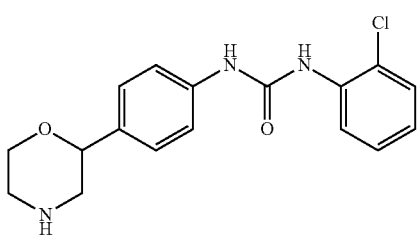 [SMILES: O=C(Nc1ccc(C2CNCCO2)cc1)Nc1ccccc1Cl]

The title compound was obtained in analogy to Example 291 using 2-chlorophenyl isocyanate (CAS-3320-83-0) instead of 4-(trifluoromethyl)phenyl isocyanate (CAS-1548-13-6). Light grey solid. MS (ISP): 332.2 ([M+H]$^+$).

Example 306

(RS)-1-(4-Methylbenzyl)-3-(4-(morpholin-2-yl)phenyl)urea hydrochloride

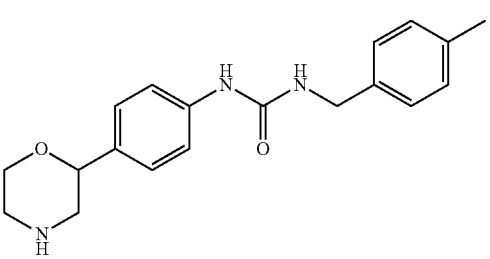 [SMILES: Cc1ccc(CNC(=O)Nc2ccc(C3CNCCO3)cc2)cc1]

The title compound was obtained in analogy to Example 291 using 4-methylbenzyl isocyanate (CAS-56651-57-1) instead of 4-(trifluoromethyl)phenyl isocyanate (CAS-1548-13-6). Light brown solid. MS (ISP): 326.3 ([M+H]$^+$).

Example 307

(RS)-1-cyclohexyl-3-(4-(morpholin-2-yl)phenyl)urea hydrochloride

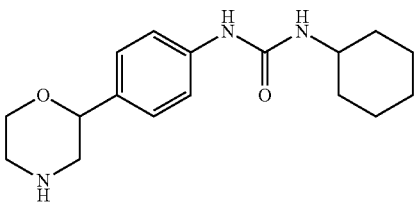 [SMILES: O=C(Nc1ccc(C2CNCCO2)cc1)NC1CCCCC1]

The title compound was obtained in analogy to Example 291 using cyclohexyl isocyanate (CAS-3173-53-3) instead of 4-(trifluoromethyl)phenyl isocyanate (CAS-1548-13-6). Off-white solid. MS (ISP): 304.3 ([M+H]$^+$).

Example 308

(S)—N-(4-(1,4-Oxazepan-2-yl)phenyl)-3-chlorobenzamide hydrochloride

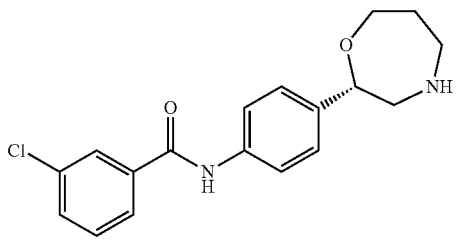 [SMILES: O=C(Nc1ccc([C@H]2CNCCCO2)cc1)c1cccc(Cl)c1]

a) (S)-3-(2-Hydroxy-2-(4-nitrophenyl)ethylamino)propan-1-ol (S)-2-(4-nitrophenyl)oxirane (5 g, 30.3 mmol, CAS 78038-42-3) was mixed with isopropanol (2.33 ml), and 3-aminopropan-1-ol (2.27 g, 2.3 ml, 30.3 mmol) was added. The yellow suspension was stirred for 17 hours at room temperature. The reaction mixture was quenched by addition of 150 ml of brine. A mixture of dichloromethane and methanol (9:1, 200 ml) was added, the organic layer was separated and the aqueous phase was extracted twice with dichloromethane/methanol (9:1). The organic layer was dried over MgSO$_4$ and evaporated to give a brown solid which was re-crystallised from ethyl acetate/heptane/TBME to yield (S)-3-(2-hydroxy-2-(4-nitrophenyl)ethylamino)propan-1-ol (2.74 g, 38%) as light yellow solid MS (ISP): 241.2 ([M+H]$^+$).

b) (S)-tert-Butyl 2-hydroxy-2-(4-nitrophenyl)ethyl(3-hydroxypropyl)carbamate (S)-3-(2-Hydroxy-2-(4-nitrophenyl)ethylamino)propan-1-ol (2.4 g, 10 mmol) was suspended in 8 ml of dichloromethane. A solution of di-tert-butyl dicarbonate (2.18 g, 10 mmol) in 5 ml dichloromethane was added dropwise and the reaction mixture was stirred at room temperature for 2 hours. The mixture was washed with water, the organic layer was washed with brine, dried over MgSO$_4$ and evaporated. The solid was stirred in a mixture of heptane and ethyl acetate and filtered off to yield (S)-tert-butyl 2-hydroxy-2-(4-nitrophenyl)ethyl(3-hydroxypropyl)carbamate (2.1 g, 62%) as light yellow solid MS (ISP): 241.3 (100%, [M-BOC+H]$^+$), 341.1 (20%, [M+H]$^+$).

c) (S)-tert-Butyl 2-(4-nitrophenyl)-1,4-oxazepane-4-carboxylate (S)-tert-Butyl 2-hydroxy-2-(4-nitrophenyl)ethyl(3-hydroxypropyl)carbamate (2 g, 5.88 mmol) was dissolved in TBME (8.2 ml) and triphenylphosphine (1.85 g, 7.05 mmol) was added. A thick white suspension was obtained. Diisopropyl diazodicarboxylate (DIAD, 1.52 g, 1.46 ml, 7.05 mmol) was slowly added (the solids dissolved) and the mixture was stirred at room temperature for 17 hours. The white solid formed during the reaction was filtered and the filtrate was evaporated. The crude material was purified by flash chromatography (silica gel, heptane/ethyl acetate, gradient from 90:10 to 80:20) to give (S)-tert-butyl 2-(4-nitrophenyl)-1,4-oxazepane-4-carboxylate (369 mg, 20%) as light yellow oil, which was used directly for the next step.

d) (S)-tert-Butyl 2-(4-aminophenyl)-1,4-oxazepane-4-carboxylate (S)-tert-Butyl 2-(4-nitrophenyl)-1,4-oxazepane-4-carboxylate (0.36 g, 1.12 mmol) was dissolved in methanol (4 ml) and palladium on carbon (10%, 35.7 mg, 33.5 µmol) was added. After evacuation, the reaction mixture was stirred at room temperature under an atmosphere of hydrogen for 45 min. The catalyst was filtered off and the filtrate was evaporated to give (S)-tert-butyl 2-(4-aminophenyl)-1,4-oxazepane-4-carboxylate (288 mg, 88%) as light yellow oil. MS (ISP): 193.3 (100%, [M-BOC+H]$^+$), 293.3 (3%, [M+H]$^+$).

e) (S)-tert-Butyl 2-(4-(3-chlorobenzamido)phenyl)-1,4-oxazepane-4-carboxylate In a 250 ml round-bottomed flask, (S)-tert-butyl 2-(4-aminophenyl)-1,4-oxazepane-4-carboxylate (106 mg, 0.36 mmol), 3-chlorobenzoic acid (74 mg, 0.47 mmol), N-methylmorpholine (110 mg, 120 µl, 1.09 mmol) and HBTU (206 mg, 0.544 mmol) were combined with tetrahydrofuran (5 ml) to give a light yellow suspension. The reaction mixture was stirred at room temperature for 17 h. The reaction suspension was poured into water (100 ml) and extracted twice with ethyl acetate. The organic layers were dried (MgSO$_4$), filtered and concentrated in vacuo. The residue was purified by column chromatography (SiO$_2$; gradient: heptane/EtOAc) to give (S)-tert-butyl 2-(4-(3-chlorobenzamido)phenyl)-1,4-oxazepane-4-carboxylate (143 mg, 92%) as a light brown gum. MS (ISP): 431.3 ([{$^{35}$Cl}M+H]$^+$), 433.3 ([{$^{37}$Cl}M+H]$^+$).

f) (S)—N-(4-(1,4-Oxazepan-2-yl)phenyl)-3-chlorobenzamide hydrochloride (S)-tert-butyl 2-(4-(3-chlorobenzamido)phenyl)-1,4-oxazepane-4-carboxylate (0.14 g, 0.325 mmol) was dissolved in dioxane (5 ml) and a solution of HCl in dioxane (4 M, 1.22 ml, 4.87 mmol) was added. The reaction mixture was stirred at 60° C. overnight. The solvent was evaporated and the residue was dissolved in ethanol. After sonication and heating a light yellow suspension was obtained. The solid was filtered and dried in vacuo at 60° C. to afford (S)—N-(4-(1,4-oxazepan-2-yl)phenyl)-3-chlorobenzamide hydrochloride (119 mg) as a light-yellow solid. MS (ISP): 331.2 ([{$^{35}$Cl}M+H]$^+$), 333.3 ([{$^{37}$Cl}M+H]$^+$).

Example 309

3-Chloro-N-(4-((2S,6S)-6-methylmorpholin-2-yl)phenyl)benzamide hydrochloride

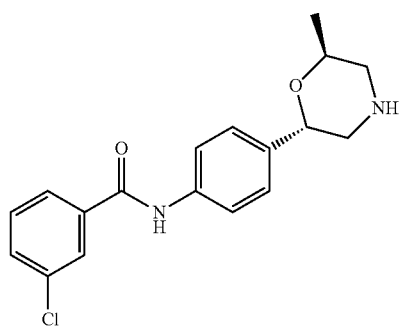 [SMILES: C[C@H]1CNC[C@H](c2ccc(NC(=O)c3cccc(Cl)c3)cc2)O1]

The title compound was obtained in analogy to example 308 using (R)-1-aminopropan-2-ol instead of 3-aminopropanol in step a). Off-white solid. MS (ISP): 331.2 ([{$^{35}$Cl}M+H]$^+$), 333.3 ([{$^{37}$Cl}M+H]$^+$).

Example 310

6-Chloro-N-(4-((2S,6R)-6-methylmorpholin-2-yl)phenyl)nicotinamide hydrochloride

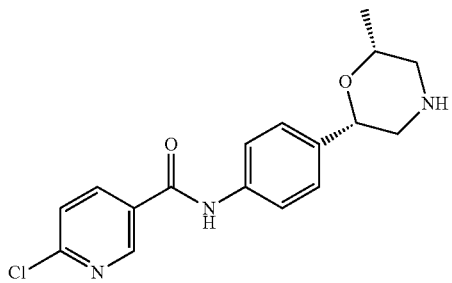 [SMILES: C[C@@H]1CNC[C@H](c2ccc(NC(=O)c3ccc(Cl)nc3)cc2)O1]

The title compound was obtained in analogy to example 308 using (S)-1-aminopropan-2-ol instead of 3-aminopropanol in step a). Off-white solid. MS (ISP): 332.2 ([{$^{35}$Cl}M+H]$^+$), 334.3 ([{$^{37}$Cl}M+H]$^+$).

Example 311

(R)-1-(4-(Morpholin-2-yl)phenyl)-3-(4-(trifluoromethyl)phenyl)urea hydrochloride

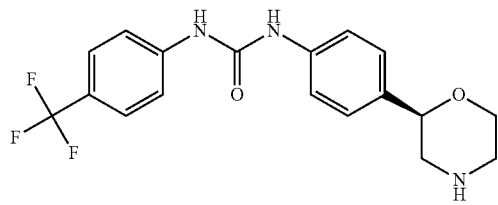 [SMILES: O=C(Nc1ccc([C@@H]2CNCCO2)cc1)Nc1ccc(C(F)(F)F)cc1]

The title compound was obtained in analogy to Example 291 using (R)-tert-butyl 2-(4-aminophenyl)morpholine-4-carboxylate (Prepared in Example 207-Steps a-d) instead of (RS)-tert-butyl 2-(4-aminophenyl)morpholine-4-carboxylate (CAS-1002726-96-6). Off-white solid. MS (ISP): 366.1 ([M+H]$^+$).

Example 312

(S)-1-(4-(Morpholin-2-yl)phenyl)-3-(4-(trifluoromethyl)phenyl)urea hydrochloride

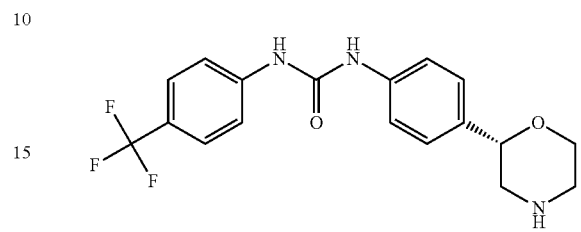

The title compound was obtained in analogy to Example 291 using (S)-tert-butyl 2-(4-aminophenyl)morpholine-4-carboxylate (Prepared in Example 208-Steps a-d) instead of (RS)-tert-butyl 2-(4-aminophenyl)morpholine-4-carboxylate (CAS-1002726-96-6). Off-white solid. MS (ISP): 366.1 ([M+H]$^+$).

Example 313

(R)-3-Chloro-N-(4-(morpholin-2-yl)benzyl)benzamide hydrochloride

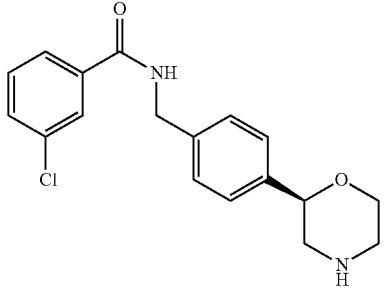 [SMILES: O=C(NCc1ccc([C@@H]2CNCCO2)cc1)c1cccc(Cl)c1]

a) (R)-tert-Butyl 2-(4-formylphenyl)morpholine-4-carboxylate (R)-tert-butyl 2-(4-bromophenyl)morpholine-4-carboxylate (342 mg, 1 mmol, Example 207 step b) in THF (3 ml) was cooled to −74° C. and treated dropwise with n-BuLi (0.938 ml, 1.5 mmol, 1.6 M solution in hexane) and stirred 30 min at −74° C. DMF (0.5 ml, 1 mmol) was added dropwise and the mixture was stirred for 2 h at −74° C. and then allowed to warm-up to −10° C. The mixture was then quenched with sat. aqueous ammonium chloride (2 ml) and water (2 ml) and the resulting mixture was partitioned between water and ethyl acetate. The organic layer was washed with water and brine, dried over magnesium sulfate and concentrated in vacuo. The residue was purified by flash chromatography (20 g SILICYCLE-Silica gel, heptane/Ethal acetate 4:1) leading to 160 mg off-white solid. MS (ISP): 292.3 ([M+H]$^+$).

b) (R,E)-tert-Butyl 2-(4-((hydroxyimino)methyl)phenyl)morpholine-4-carboxylate (R)-tert-butyl 2-(4-formylphenyl)morpholine-4-carboxylate (155 mg, 0.532 mmol) was dissolved in ethanol (0.9 ml).

183

Molecular sieves 0.3 nm were added followed by hydroxylamine hydrochloride (74 mg, 1.06 mmol). The reaction mixture was refluxed for 2 h, cooled down to rt and partitioned between water and dichloromethane. The organic layer was washed with water and brine, dried over magnesium sulfate and concentrated in vacuo leading to 159 mg off-white solid which was used in the next step without further purification.

c) (R)-tert-Butyl 2-(4-(aminomethyl)phenyl)morpholine-4-carboxylate (R,E)-tert-butyl 2-(4-((hydroxyimino)methyl)phenyl) morpholine-4-carboxylate (138 mg, 0.45 mmol) was dissolved in methanol (8.2 ml) and hydrogenated over 5% Pd/C (41 mg) for 1 h. The reaction mixture was filtered off and concentrated in vacuo, dissolved in ethyl acetate and extracted with 0.5 M aq. HCl (2×1.2 ml). The combined aqueous layers were basified with 1 M aq. NaOH to pH 10 and extracted twice with dichloromethane. The combined organic phases were washed with water, dried over magnesium sulfate and concentrated in vacuo to yield 63 mg of a colorless oil. MS (ISP): 293.2 ([M+H]$^+$).

d) (R)-3-Chloro-N-(4-(morpholin-2-yl)benzyl)benzamide hydrochloride

The title compound was obtained in analogy to Example 29 using (R)-tert-butyl 2-(4-(aminomethyl)phenyl)morpholine-4-carboxylate instead of (RS)-tert-butyl 3-(4-aminophenyl)pyrrolidine-1-carboxylate, 3-chlorobenzoic acid (CAS-535-80-8) instead of (R)-2-phenylpropionic acid and HBTU instead of TBTU at 60° C. (17 h) in DMF instead of THF. Colorless amorphous solid. MS (ISP): 331.1 ([M+H]$^+$).

Example 314

(R)-4-Chloro-N-(4-(morpholin-2-yl)benzyl)benzamide hydrochloride

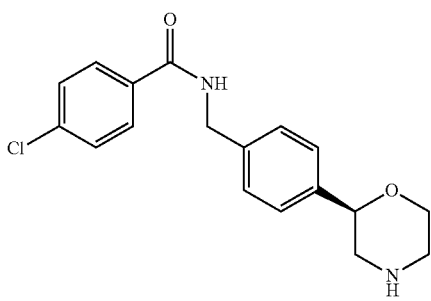 [SMILES: O=C(NCc1ccc([C@@H]2CNCCO2)cc1)c1ccc(Cl)cc1]

The title compound was obtained in analogy to Example 313 using 4-chlorobenzoic acid (CAS-74-11-3) instead of 3-chlorobenzoic acid. Colorless amorphous solid. MS (ISP): 331.1 ([M+H]$^+$).

Example 315

(R)-6-Chloro-N-(4-(morpholin-2-yl)benzyl)nicotinamide hydrochloride

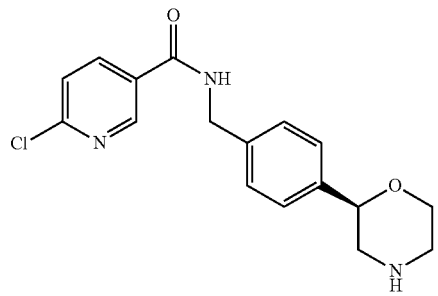 [SMILES: O=C(NCc1ccc([C@@H]2CNCCO2)cc1)c1ccc(Cl)nc1]

The title compound was obtained in analogy to Example 313 using 6-chloronicotinic acid (CAS-5326-23-8) instead of 3-chlorobenzoic acid. Colorless amorphous solid. MS (ISP): 332.2 ([M+H]$^+$).

Example 316

(R)—N-(4-(Morpholin-2-yl)benzyl)-6-(2,2,2-trifluoroethoxy)nicotinamide hydrochloride

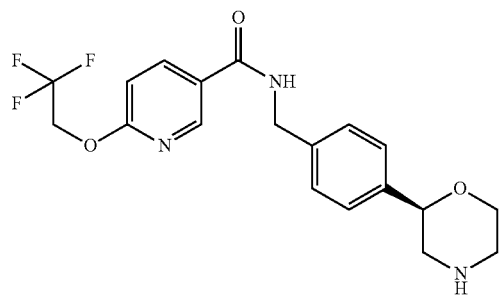 [SMILES: O=C(NCc1ccc([C@@H]2CNCCO2)cc1)c1ccc(OCC(F)(F)F)nc1]

The title compound was obtained in analogy to Example 313 using 6-(2,2,2-trifluoroethoxy)nicotinic acid (CAS-159783-29-6) instead of 3-chlorobenzoic acid. Colorless amorphous solid. MS (ISP): 396.3 ([M+H]$^+$).

Example 317

(S)-4-Chloro-N-(4-(morpholin-2-yl)benzyl)benzamide hydrochloride

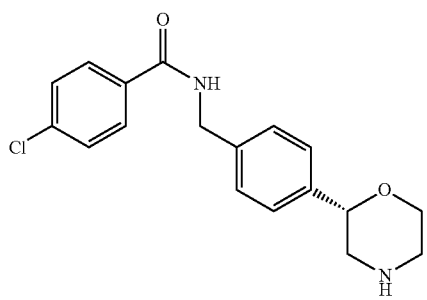 [SMILES: O=C(NCc1ccc([C@H]2CNCCO2)cc1)c1ccc(Cl)cc1]

Step a) (S)-tert-Butyl 2-(4-formylphenyl)morpholine-4-carboxylate (S)-tert-Butyl 2-(4-bromophenyl)morpholine-4-carboxylate (5 g, 14.6 mmol, Example 208b) in THF (40 ml) was cooled to −74° C. and treated dropwise with n-BuLi (13.7 ml, 21.9 mmol, 1.6 M solution in hexane) and stirred 30 min at −74° C. DMF (7.3 ml, 14.6 mmol) was added dropwise (15 min) and the mixture was stirred for 2 h at −74° C. and then allowed to warm-up to −10° C. The mixture was then quenched with sat. aqueous ammonium chloride (30 ml) and water (30 ml) and the resulting mixture was partitioned between water and ethyl acetate. The organic layer was washed with water and brine, dried over magnesium sulfate and concentrated in vacuo leading to 4.7 g crude product. MS (ISP): 292.3 ([M+H]$^+$).

b) (S,E)-tert-Butyl 2-(4-((hydroxyimino)methyl)phenyl)morpholine-4-carboxylate (S)-tert-Butyl 2-(4-formylphenyl)morpholine-4-carboxylate (2.2 g, 7.55 mmol) was dissolved in ethanol (13 ml). Molecular sieves (0.3 nm) were added followed by hydroxylamine hydrochloride (1.05, 15.1 mmol). The reaction mixture was refluxed for 2 h, cooled down to rt and partitioned between water and dichloromethane. The organic layer was washed with water and brine, dried over magnesium sulfate and concentrated in vacuo leading to 1.72 g off-white solid which was used in the next step without further purification. MS (ISP): 207.2 ([M+H]$^+$-BOC).

c) (S)-tert-Butyl 2-(4-(aminomethyl)phenyl)morpholine-4-carboxylate (S,E)-tert-Butyl 2-(4-((hydroxyimino)methyl)phenyl)morpholine-4-carboxylate (1.63 g, 5.32 mmol) was dissolved in methanol (25 ml) and hydrogenated over 5% Pd/C (543 mg, 0.255 mmol) for 1 h. The reaction mixture was filtered off and concentrated in vacuo, dissolved in ethyl acetate and extracted with 0.5 M aq. HCl (2×10 ml). The combined aqueous layers were basified with 1 M aq. NaOH to pH 10 and extracted twice with dichloromethane. The combined organic phases were washed with water, dried over magnesium sulfate and concentrated in vacuo to yield 991 mg of light yellow viscous oil. MS (ISP): 293.2 ([M+H]$^+$).

d) (S)-4-Chloro-N-(4-(morpholin-2-yl)benzyl)benzamide hydrochloride

The title compound was obtained in analogy to Example 29 using (S)-tert-butyl 2-(4-(aminomethyl)phenyl)morpholine-4-carboxylate instead of (RS)-tert-butyl 3-(4-aminophenyl)pyrrolidine-1-carboxylate, 4-chlorobenzoic acid (CAS-74-11-3) instead of (R)-2-phenylpropionic acid and HBTU instead of TBTU at 60° C. (4 h) in DMF instead of THF. White solid. MS (ISP): 331.2 ([M+H]$^+$).

Example 318

(S)-3-Chloro-N-(4-(morpholin-2-yl)benzyl)benzamide hydrochloride

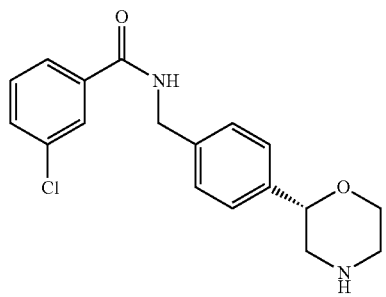 [SMILES: O=C(NCc1ccc([C@H]2CNCCO2)cc1)c1cccc(Cl)c1]

The title compound was obtained in analogy to Example 317 using 3-chlorobenzoic acid (CAS-535-80-8) instead of 4-chlorobenzoic acid. Colorless amorphous solid. MS (ISP): 331.2 ([M+H]$^+$).

Example 319

(S)-6-Chloro-N-(4-(morpholin-2-yl)benzyl)nicotinamide hydrochloride

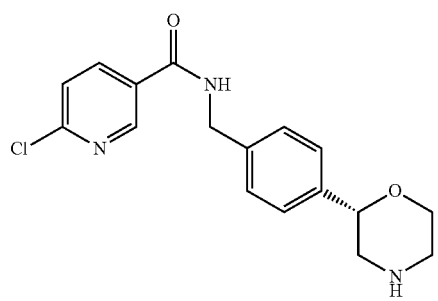 [SMILES: O=C(NCc1ccc([C@H]2CNCCO2)cc1)c1ccc(Cl)nc1]

The title compound was obtained in analogy to Example 317 using 6-chloronicotinic acid (CAS-5326-23-8) instead of 4-chlorobenzoic acid. Colorless amorphous solid. MS (ISP): 332.1 ([M+H]$^+$).

Example 320

(S)—N-(4-(Morpholin-2-yl)benzyl)-6-(trifluoromethyl)nicotinamide hydrochloride

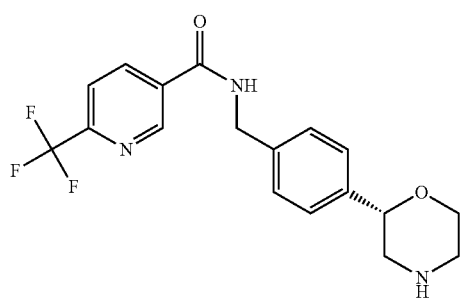 [SMILES: O=C(NCc1ccc([C@H]2CNCCO2)cc1)c1ccc(C(F)(F)F)nc1]

The title compound was obtained in analogy to Example 317 using 6-(trifluoromethyl)nicotinic acid (CAS-158063-66-2) instead of 4-chlorobenzoic acid. Colorless amorphous solid. MS (ISP): 366.2 ([M+H]$^+$).

Example 321

(R)—N-(4-(Morpholin-2-yl)benzyl)-6-(trifluoromethyl)nicotinamide hydrochloride

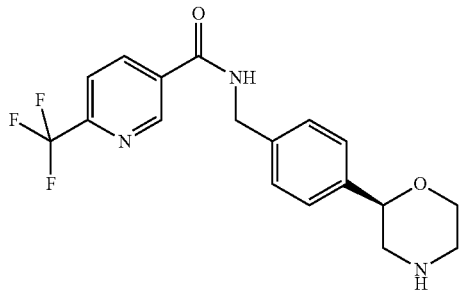 [SMILES: O=C(NCc1ccc([C@@H]2CNCCO2)cc1)c1ccc(C(F)(F)F)nc1]

The title compound was obtained in analogy to Example 313 using 6-(trifluoromethyl)nicotinic acid (CAS-158063-66-2) instead of 3-chlorobenzoic acid. Colorless amorphous solid. MS (ISP): 366.1 ([M+H]$^+$).

Example 322

3-Chloro-N-[4-((2S,5S)-5-methyl-morpholin-2-yl)-phenyl]-benzamide hydrochloride

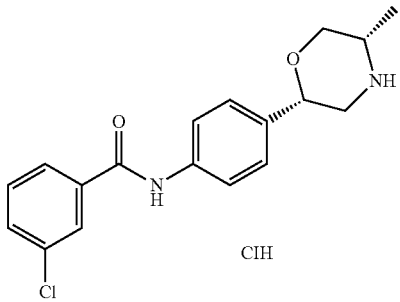 [SMILES: C[C@H]1CO[C@@H](c2ccc(NC(=O)c3cccc(Cl)c3)cc2)CN1 ; "CIH"]

The title compound was obtained in analogy to example 308 using (S)-2-aminopropanol instead of 3-aminopropanol in step a). Off-white solid. MS (ISP): 331.2 ([{$^{35}$Cl}M+H]$^+$), 333.3 ([{$^{37}$Cl}M+H]$^+$).

Example 323

3-Chloro-N-[4-((2S,5R)-5-methyl-morpholin-2-yl)-phenyl]-benzamide hydrochloride

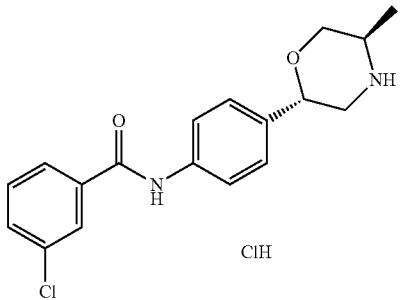 [SMILES: C[C@@H]1CO[C@@H](c2ccc(NC(=O)c3cccc(Cl)c3)cc2)CN1 ; Cl]

The title compound was obtained in analogy to example 308 using (R)-2-aminopropanol instead of 3-aminopropanol in step a). Off-white solid. MS (ISP): 331.2 ([{$^{35}$Cl}M+H]$^+$), 333.4 ([{$^{37}$Cl}M+H]$^+$).

The compounds of formula I and their pharmaceutically usable addition salts possess valuable pharmacological properties. Specifically, compounds of the present invention have a good affinity to the trace amine associated receptors (TAARs), especially TAAR1.

The compounds were investigated in accordance with the test given hereinafter.

Materials and Methods

Construction of TAAR Expression Plasmids and Stably Transfected Cell Lines

For the construction of expression plasmids the coding sequences of human, rat and mouse TAAR1 were amplified from genomic DNA essentially as described by Lindemann et al. [14]. The Expand High Fidelity PCR System (Roche Diagnostics) was used with 1.5 mM Mg$^{2+}$ and purified PCR products were cloned into pCR2.1-TOPO cloning vector (Invitrogen) following the instructions of the manufacturer. PCR products were subcloned into the pIRESneo2 vector (BD Clontech, Palo Alto, Calif.), and expression vectors were sequence verified before introduction in cell lines.

HEK293 cells (ATCC #CRL-1573) were cultured essentially as described by Lindemann et al. (2005). For the generation of stably transfected cell lines HEK293 cells were transfected with the pIRESneo2 expression plasmids containing the TAAR coding sequences (described above) with Lipofectamine 2000 (Invitrogen) according to the instructions of the manufacturer, and 24 hrs post transfection the culture medium was supplemented with 1 mg/ml G418 (Sigma, Buchs, Switzerland). After a culture period of about 10 d clones were isolated, expanded and tested for responsiveness to trace amines (all compounds purchased from Sigma) with the cAMP Biotrak Enzyme immunoassay (EIA) System (Amersham) following the non-acetylation EIA procedure provided by the manufacturer. Monoclonal cell lines which displayed a stable EC$_{50}$ for a culture period of 15 passages were used for all subsequent studies.

Radioligand Binding Assay on Rat TAAR1

Membrane Preparation and Radioligand Binding.

HEK-293 cells stably expressing rat TAAR1 were maintained at 37° C. and 5% CO$_2$ in DMEM high glucose medium, containing fetal calf serum (10%, heat inactivated for 30 min at 56° C.), penicillin/streptomycin (1%), and 375 µg/ml geneticin (Gibco). Cells were released from culture flasks using trypsin/EDTA, harvested, washed twice with ice-cold PBS (without Ca$^{2+}$ and Mg$^{2+}$), pelleted at 1,000 rpm for 5 min at 4° C., frozen and stored at −80° C. Frozen pellets were suspended in 20 ml HEPES-NaOH (20 mM, pH 7.4) containing 10 mM EDTA and homogenized with a Polytron (PT 6000, Kinematica) at 14,000 rpm for 20 s. The homogenate was centrifuged at 48,000×g for 30 min at 4° C. Subsequently, the supernatant was removed and discarded, and the pellet resuspended in 20 ml HEPES-NaOH (20 mM, pH 7.4) containing 0.1 mM EDTA using the Polytron (20 s at 14,000 rpm). This procedure was repeated and the final pellet resuspended in HEPES-NaOH containing 0.1 mM EDTA and homogenized using the Polytron. Typically, aliquots of 2 ml membrane portions were stored at −80° C. With each new membrane batch the dissociation constant (Kd) was determined via a saturation curve. The TAAR1 radioligand $^3$[H]—(S)-4-[(ethyl-phenyl-amino)-methyl]-4,5-dihydro-oxazol-2-ylamine (described in WO 2008/098857) was used at a concentration equal to the calculated Kd value, that was usually around 2.3 nM, resulting in the binding of approximately 0.2% of the radioligand and a specific binding representing approximately 85% of the total binding. Nonspecific binding was defined as the amount of $^3$[H]—(S)-4-[(ethyl-phenyl-amino)-methyl]-4,5-dihydro-oxazol-2-ylamine bound in the presence of 10 µM unlabeled ligand. All compounds were tested at a broad range of concentrations (10 pM to 10 µM) in duplicates. The test compounds (20 µl/well) were transferred into a 96 deep well plate (TreffLab), and 180 µl of HEPES-NaOH (20 mM, pH 7.4) containing MgCl$_2$ (10 mM) and CaCl$_2$ (2 mM) (binding buffer), 300 µl of the radioligand $^3$[H]—(S)-4-[(ethyl-phenyl-amino)-methyl]-4,5-dihydro-oxazol-2-ylamine at a concentration of 3.3×Kd in nM and 500 µl of the membranes (resuspended at 50 µg protein per ml) added. The 96 deep well plates were incubated for 1 hr at 4° C. Incubations were terminated by rapid filtration through Unifilter-96 plates (Packard Instrument Company) and glass filters GF/C (Perkin Elmer) presoaked for 1 hr in polyethylenimine (0.3%) and washed 3 times with 1 ml of cold binding buffer. After addition of 45 µl of Microscint 40 (PerkinElmer) the Unifilter-96 plate was sealed and after 1 hr the ratioactivity counted using a TopCount Microplate Scintillation Counter (Packard Instrument Company).

Radioligand Binding Assay on Mouse TAAR1
Membrane Preparation and Radioligand Binding.

HEK-293 cells stably expressing mouse TAAR1 were maintained at 37° C. and 5% CO$_2$ in DMEM high glucose medium, containing fetal calf serum (10%, heat inactivated for 30 min at 56° C.), penicillin/streptomycin (1%), and 375 µg/ml geneticin (Gibco). Cells were released from culture flasks using trypsin/EDTA, harvested, washed twice with ice-cold PBS (without Ca$^{2+}$ and Mg$^{2+}$), pelleted at 1,000 rpm for 5 min at 4° C., frozen and stored at −80° C. Frozen pellets were suspended in 20 ml HEPES-NaOH (20 mM, pH 7.4) containing 10 mM EDTA and homogenized with a Polytron (PT 6000, Kinematica) at 14,000 rpm for 20 s. The homogenate was centrifuged at 48,000×g for 30 min at 4° C. Subsequently, the supernatant was removed and discarded, and the pellet resuspended in 20 ml HEPES-NaOH (20 mM, pH 7.4) containing 0.1 mM EDTA using the Polytron (20 s at 14,000 rpm). This procedure was repeated and the final pellet resuspended in HEPES-NaOH containing 0.1 mM EDTA and homogenized using the Polytron. Typically, aliquots of 2 ml membrane portions were stored at −80° C. With each new membrane batch the dissociation constant (Kd) was determined via a saturation curve. The TAAR1 radioligand $^3$[H]—(S)-4-[(ethyl-phenyl-amino)-methyl]-4,5-dihydro-oxazol-2-ylamine (described in WO 2008/098857) was used at a concentration equal to the calculated Kd value, that was usually around 0.7 nM, resulting in the binding of approximately 0.5% of the radioligand and a specific binding representing approximately 70% of the total binding. Nonspecific binding was defined as the amount of $^3$[H]—(S)-4-[(ethyl-phenyl-amino)-methyl]-4,5-dihydro-oxazol-2-ylamine bound in the presence of 10 µM unlabeled ligand. All compounds were tested at a broad range of concentrations (10 pM to 10 µM) in duplicates. The test compounds (20 µl/well) were transferred into a 96 deep well plate (TreffLab), and 180 µl of HEPES-NaOH (20 mM, pH 7.4) containing MgCl$_2$ (10 mM) and CaCl$_2$ (2 mM) (binding buffer), 300 µl of the radioligand $^3$[H]—(S)-4-[(ethyl-phenyl-amino)-methyl]-4,5-dihydro-oxazol-2-ylamine at a concentration of 3.3×Kd in nM and 500 µl of the membranes (resuspended at 60 µg protein per ml) added. The 96 deep well plates were incubated for 1 hr at 4° C. Incubations were terminated by rapid filtration through Unifilter-96 plates (Packard Instrument Company) and glass filters GF/C (Perkin Elmer) presoaked for 1 hr in polyethylenimine (0.3%) and washed 3 times with 1 ml of cold binding buffer. After addition of 45 µl of Microscint 40 (PerkinElmer) the Unifilter-96 plate was sealed and after 1 hr the ratioactivity counted using a TopCount Microplate Scintillation Counter (Packard Instrument Company).

The preferred compounds show a Ki value (µM) in mouse or rat on TAAR1 in the range of <0.01 µM. Representative compounds are shown in the table below.

| Example | Ki (µM) mouse/rat |
|---|---|
| 1 | 0.0056/0.0072 |
| 2 | 0.0006/0.001 |
| 3 | 0.0013/0.0016 |
| 4 | 0.0189/0.0837 |
| 5 | 0.0015/0.0027 |
| 6 | 0.0032/0.0295 |
| 7 | 0.0028/0.0036 |
| 8 | 0.0015/0.0044 |
| 9 | —/1.1128 |
| 10 | —/0.3092 |
| 11 | 0.0065/0.0315 |
| 12 | —/0.2899 |
| 13 | 0.008/0.0995 |
| 14 | —/0.6449 |
| 15 | 0.0021/0.0081 |
| 16 | 0.0007/0.0043 |
| 17 | 0.0083/0.0363 |
| 18 | 0.0011/0.0036 |
| 19 | 0.0035/0.0189 |
| 20 | 0.0005/0.0077 |
| 21 | —/0.3591 |
| 22 | 0.5263/2.3697 |
| 23 | 0.0022/0.0025 |
| 24 | 0.0164/0.0497 |
| 25 | 0.3195/0.0758 |
| 26 | 0.0112/0.0279 |
| 27 | 0.0013/0.0015 |
| 28 | 0.4336/0.4733 |
| 29 | 0.1024/0.0501 |
| 30 | 0.053/0.0722 |
| 31 | 0.0017/0.0613 |
| 32 | 0.0005/0.0858 |
| 33 | 0.0006/0.0545 |
| 34 | 0.0269/0.2136 |
| 35 | 0.0103/0.078 |
| 36 | —/0.3239 |
| 37 | 0.0556/0.0114 |
| 38 | 0.0407/0.0606 |
| 39 | 0.0007/0.0139 |
| 40 | —/0.5218 |
| 41 | —/2.9809 |
| 42 | 0.0033/0.0354 |
| 43 | 0.0041/0.0242 |
| 44 | 0.0013/0.0022 |
| 45 | 0.0131/0.0077 |
| 46 | 0.0011/0.0011 |
| 47 | 0.0019/0.0048 |
| 48 | —/0.6132 |
| 49 | —/1.6848 |
| 50 | —/0.1217 |
| 51 | —/0.0985 |
| 52 | 0.0017/0.0109 |
| 53 | 0.0016/0.0053 |
| 54 | 0.0021/0.0152 |
| 55 | 0.0048/0.0745 |
| 56 | 0.0008/0.0018 |
| 57 | 0.0055/0.0005 |
| 58 | 0.0007/0.0022 |
| 59 | 0.0256/0.0014 |
| 60 | 2.826/0.0457 |
| 61 | 0.0172/0.0033 |
| 62 | 0.0278/0.0046 |
| 63 | 0.0837/0.1743 |
| 64 | 0.1241/0.0215 |
| 65 | 0.1249/0.3523 |
| 66 | 0.137/0.6447 |
| 67 | 0.4987/0.0555 |
| 68 | 0.1466/0.102 |
| 69 | 0.0048/0.023 |
| 70 | 0.0097/0.0935 |
| 71 | —/0.0121 |

-continued

| Example | Ki (μM) mouse/rat |
|---|---|
| 72 | 0.5073/0.1072 |
| 73 | 0.0056/0.0257 |
| 74 | 0.0049/0.0672 |
| 75 | 0.0255/1.4768 |
| 76 | 0.1363/0.2958 |
| 77 | 0.0017/0.0238 |
| 78 | 0.0067/0.0466 |
| 79 | 0.0075/0.0924 |
| 80 | 0.0035/0.7418 |
| 81 | 0.0227/0.0124 |
| 82 | 0.7131/1.7688 |
| 83 | 0.002/0.012 |
| 84 | 0.008/0.0381 |
| 85 | 0.0041/0.0205 |
| 86 | 0.0051/0.1156 |
| 87 | 0.0051/0.017 |
| 88 | 0.0052/0.1016 |
| 89 | 0.0059/0.006 |
| 90 | 0.0192/0.0101 |
| 91 | 0.0039/0.0223 |
| 92 | 0.0238/0.0238 |
| 93 | 0.04/0.1729 |
| 94 | 0.0601/0.3787 |
| 95 | 0.0385/0.3216 |
| 96 | 0.0016/0.0067 |
| 97 | 0.0038/0.0193 |
| 98 | 0.0041/0.0114 |
| 99 | 0.013/0.0501 |
| 100 | 0.0036/0.0308 |
| 101 | 0.002/0.0263 |
| 102 | 0.0108/0.0894 |
| 103 | 0.7047/0.0646 |
| 104 | 0.0454/0.0276 |
| 105 | 0.0296/0.0135 |
| 106 | 0.0248/1.4273 |
| 107 | 0.0027/0.0445 |
| 108 | 0.0046/0.0081 |
| 109 | 0.0017/0.0176 |
| 110 | 0.0021/0.0375 |
| 111 | 0.0349/0.0382 |
| 112 | 0.2107/0.0018 |
| 113 | 0.0095/0.004 |
| 114 | 0.0836/0.0074 |
| 115 | 0.3199/0.0118 |
| 116 | 0.0608/0.0014 |
| 117 | 0.0531/0.0029 |
| 118 | 0.1305/0.0081 |
| 119 | 0.0365/0.0018 |
| 120 | 0.0004/0.0013 |
| 121 | 0.0005/0.0004 |
| 122 | 0.0003/0.0011 |
| 123 | 0.0014/0.0022 |
| 124 | 0.0013/0.0036 |
| 125 | 0.0003/0.0007 |
| 126 | 0.0019/0.0022 |
| 127 | 0.0006/0.002 |
| 128 | 0.0003/0.0003 |
| 129 | 0.004/0.0062 |
| 130 | 0.0017/0.0169 |
| 131 | 0.0208/0.0219 |
| 132 | 9.9919/0.1406 |
| 133 | 1.5228/0.0174 |
| 134 | 2.0573/0.1057 |
| 134 | 2.0573/0.1057 |
| 135 | 1.2658/0.0134 |
| 136 | 0.1529/0.0008 |
| 137 | 0.0062/0.0015 |
| 138 | 0.035/0.0059 |
| 139 | 0.0158/0.0051 |
| 140 | 0.2452/0.0358 |
| 141 | 0.0201/0.0024 |
| 142 | 0.0126/0.0004 |
| 143 | 0.0054/0.0006 |
| 144 | 0.0188/0.0011 |
| 145 | 0.0227/0.0013 |
| 146 | 0.0268/0.001 |

-continued

| Example | Ki (μM) mouse/rat |
|---|---|
| 147 | 0.001/— |
| 148 | 0.0393/0.0049 |
| 149 | 0.0011/0.001 |
| 150 | 0.002/0.0004 |
| 151 | 0.011/0.0008 |
| 152 | 0.0086/0.0003 |
| 153 | 0.0715/0.0005 |
| 154 | 0.0082/0.0002 |
| 155 | 0.0107/0.0009 |
| 156 | 0.1528/0.0007 |
| 157 | 0.1418/0.0007 |
| 158 | 0.0326/0.0014 |
| 159 | 6.3782/0.6298 |
| 160 | 0.0851/0.0046 |
| 161 | 0.0403/0.0101 |
| 162 | 0.2312/0.0092 |
| 163 | 0.0573/0.0121 |
| 164 | 0.0871/0.0121 |
| 165 | 0.1256/0.0411 |
| 166 | 0.3936/0.0212 |
| 167 | 0.0271/0.0048 |
| 168 | 0.6078/0.0026 |
| 169 | 0.0607/0.0027 |
| 170 | 0.234/0.0158 |
| 171 | 0.1978/0.0101 |
| 172 | 0.1126/0.0077 |
| 173 | 0.8235/0.0218 |
| 174 | 0.437/0.0159 |
| 175 | 0.0473/0.0027 |
| 176 | 0.0253/0.001 |
| 177 | 0.1143/0.0067 |
| 178 | 0.0032/0.002 |
| 179 | 0.0008/0.0022 |
| 180 | 0.0507/0.0131 |
| 181 | 0.0663/— |
| 182 | 0.0253/0.0025 |
| 183 | 0.0526/— |
| 184 | 0.1529/— |
| 185 | 0.0333/0.0026 |
| 186 | 0.0486/0.0027 |
| 187 | —/0.0123 |
| 188 | 0.1384/0.0055 |
| 189 | 0.0343/0.0016 |
| 190 | 0.0501/0.0021 |
| 191 | 0.011/0.0074 |
| 192 | 0.0052/0.0113 |
| 193 | 0.0406/0.0034 |
| 194 | 0.0982/0.005 |
| 195 | 0.0135/0.0022 |
| 196 | 0.0524/0.001 |
| 197 | 0.0177/0.0016 |
| 198 | 0.0147/0.0028 |
| 199 | 1.1582/0.2381 |
| 200 | 0.0039/0.0022 |
| 201 | 0.1133/0.0022 |
| 202 | 0.0087/0.0015 |
| 203 | 0.0603/0.0014 |
| 204 | 0.005/0.0043 |
| 205 | 0.0034/0.0035 |
| 206 | 0.0026/0.0011 |
| 207 | 0.0525/0.0042 |
| 208 | 0.0762/0.0044 |
| 209 | 0.0078/0.0016 |
| 210 | 0.0436/0.0062 |
| 211 | 0.004/0.0009 |
| 212 | 2.4986/0.2958 |
| 213 | 0.0012/0.001 |
| 214 | 0.0057/0.0016 |
| 215 | 2.8201/2.3101 |
| 216 | 0.0176/0.0012 |
| 217 | 0.3346/0.0941 |
| 218 | 0.0872/0.0087 |
| 219 | 0.0059/0.0031 |
| 220 | 0.0435/0.0024 |
| 221 | 0.005/0.0037 |
| 222 | 0.0037/0.0033 |

-continued

| Example | Ki (μM) mouse/rat |
|---|---|
| 223 | 0.0016/0.0018 |
| 224 | 0.051/0.0029 |
| 225 | 0.0189/0.0006 |
| 226 | 0.0555/0.001 |
| 227 | 0.1773/0.0012 |
| 228 | 0.1992/0.0608 |
| 229 | 0.0218/0.0019 |
| 230 | 0.0997/0.0016 |
| 231 | 0.0043/0.0014 |
| 232 | 0.1499/0.0317 |
| 233 | 0.0008/0.0014 |
| 234 | 0.0217/0.001 |
| 235 | 0.0334/0.0006 |
| 236 | 0.2143/0.0014 |
| 237 | 0.0677/0.0008 |
| 238 | 1.1185/0.0056 |
| 239 | 0.0396/0.0085 |
| 240 | 0.0146/0.0009 |
| 241 | 1.5546/0.116 |
| 242 | 0.037/0.0089 |
| 243 | 2.1198/0.0062 |
| 244 | 0.2679/0.0049 |
| 245 | 0.0649/0.0063 |
| 246 | 0.0151/0.0012 |
| 247 | —/0.0677 |
| 248 | 0.1884/0.0143 |
| 249 | 0.0025/0.0024 |
| 250 | 0.2879/0.0056 |
| 251 | 0.4798/0.0054 |
| 252 | 0.0783/0.0044 |
| 253 | 0.3599/0.0035 |
| 254 | 2.8174/0.7255 |
| 255 | 5.1005/0.4278 |
| 256 | 1.166/0.012 |
| 257 | 0.7857/0.004 |
| 258 | 0.0225/0.0062 |
| 259 | 0.044/0.0009 |
| 260 | 0.016/0.0012 |
| 261 | 0.0027/0.0015 |
| 262 | 0.0052/0.0013 |
| 263 | 0.0152/0.0011 |
| 264 | 0.2974/0.0143 |
| 265 | 0.0209/0.0059 |
| 266 | 0.0163/0.0012 |
| 267 | 0.0476/0.0011 |
| 268 | 0.002/0.0024 |
| 269 | 0.0099/0.003 |
| 270 | 0.0049/0.0045 |
| 271 | 0.0067/0.004 |
| 272 | 0.0214/0.0169 |
| 273 | 0.0343/0.008 |
| 274 | 2.5115/0.0174 |
| 275 | 0.0082/0.0036 |
| 276 | 0.0558/0.0008 |
| 277 | 0.0472/0.0036 |
| 278 | 0.8286/0.0118 |
| 279 | 0.1463/0.0044 |
| 280 | 0.0172/0.0069 |
| 281 | 0.0128/0.0014 |
| 282 | 0.2429/0.0048 |
| 283 | 0.006/0.0059 |
| 284 | 0.0128/0.005 |
| 285 | 0.0082/0.005 |
| 286 | 0.0222/0.0044 |
| 287 | —/0.3789 |
| 288 | 0.0278/0.0075 |
| 289 | 0.1433/0.0027 |
| 290 | 0.0608/0.3236 |
| 291 | 0.0012/0.0017 |
| 292 | 0.001/0.001 |
| 293 | 0.0074/0.0014 |
| 294 | 1.1756/0.0226 |
| 295 | 0.2349/1.1968 |
| 296 | 0.0645/0.0847 |
| 297 | 0.018/0.0044 |
| 298 | 0.0506/0.0143 |

-continued

| Example | Ki (μM) mouse/rat |
|---|---|
| 299 | 0.0022/0.0014 |
| 300 | 0.0726/0.002 |
| 301 | 0.0509/0.007 |
| 302 | 0.0574/0.0056 |
| 303 | 0.002/0.0005 |
| 304 | 0.0071/0.0012 |
| 305 | 0.0266/0.0038 |
| 306 | 0.0266/0.0038 |
| 307 | 0.0778/0.0305 |
| 308 | 0.2868/0.0018 |
| 309 | 0.1159/0.0023 |
| 310 | 0.0476/0.0108 |
| 311 | 0.0005/0.0014 |
| 312 | 0.0007/0.0011 |
| 313 | 0.547/0.0154 |
| 314 | 1.8855/0.0062 |
| 315 | 1.3506/0.009 |
| 316 | 0.2726/0.0121 |
| 317 | —/0.0226 |
| 318 | 12909/0.0312 |
| 319 | —/0.0206 |
| 320 | —/0.0249 |
| 321 | 1.3138/0.026 |
| 322 | 0.0188/0.0017 |
| 323 | 0.0592/0.0013 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a process for the manufacture of pharmaceutical compositions. Such process comprises bringing the compound of formula I and/or pharmaceutically acceptable acid addition salt thereof and, fir desired, one or more other therapeutically valuable substances into a galenical administration form together with one or more therapeutically inert carriers.

The most preferred indications in accordance with the present invention are those which include disorders of the central nervous system, for example the treatment or prevention of depression, psychosis, Parkinson's disease, anxiety and attention deficit hyperactivity disorder (ADHD).

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

| Tablet Formulation (Wet Granulation) | | | | |
|---|---|---|---|---|
| | | mg/tablet | | |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Capsule Formulation | | | | |
|---|---|---|---|---|
| | | mg/capsule | | |
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The invention claimed is:

1. A compound selected from the group consisting of (RS)-6-Pyrazol-1-yl-N-(4-pyrrolidin-3-yl-phenyl)-nicotinamide;
or a pharmaceutically suitable acid addition salt thereof.

2. A compound selected from the group consisting of (RS)—N-(4-Pyrrolidin-3-yl-phenyl)-6-(2,2,2-trifluoro-ethoxy)-nicotinamide
or a pharmaceutically suitable acid addition salt thereof.

3. A compound selected from the group consisting of (RS)-5-Trifluoromethyl-pyridine-2-carboxylic acid (4-piperidin-3-yl-phenyl)-amide;
(RS)-5-Trifluoromethyl-pyridine-2-carboxylic acid (4-pyrrolidin-3-yl-phenyl)-amide; and
(RS)-5-Trifluoromethyl-pyridine-2-carboxylic acid (4-morpholin-2-yl-phenyl)-amide; or a pharmaceutically suitable acid addition salt thereof.

4. A compound wherein said compound is (RS)—N-(4-(Piperidin-3-yl)phenyl)-6-(2,2,2-trifluoroethoxy)nicotinamide
or a pharmaceutically suitable acid addition salt thereof.

5. A compound selected from the group consisting of (RS)—N-(4-(Piperidin-3-yl)phenyl)-5-(2,2,2-trifluoroethoxy)picolinamide; and
(RS)-2-(4-(6-cyanonicotinamido)phenyl)morpholin-4-ium chloride;
or a pharmaceutically suitable acid addition salt thereof.

6. A compound selected from the group consisting of (R)—N-(4-(Pyrrolidin-3-yl)phenyl)-6-(2,2,2-trifluoroethoxy)nicotinamide; and
(S)—N-(4-(Pyrrolidin-3-yl)phenyl)-6-(2,2,2-trifluoroethoxy)nicotinamide;
or a pharmaceutically suitable acid addition salt thereof.

7. A compound selected from the group consisting of (RS)—N-(4-(Morpholin-2-yl)phenyl)-6-(2,2,2-trifluoroethoxy)nicotinamide; and
(R)—N-(4-(Piperidin-3-yl)phenyl)-6-(2,2,2-trifluoroethoxy)nicotinamide;
or a pharmaceutically suitable acid addition salt thereof.

8. A compound selected from the group consisting of (S)—N-(4-(Piperidin-3-yl)phenyl)-6-(2,2,2-trifluoroethoxy)nicotinamide;
(RS)—N-(4-(Morpholin-2-yl)phenyl)-2-phenylthiazole-5-carboxamide; and
(RS)—N-(4-(Morpholin-2-yl)phenyl)-2-phenylthiazole-4-carboxamide;
or a pharmaceutically suitable acid addition salt thereof.

9. A compound selected from the group consisting of (S)-5-(Methylthio)-N-(4-(piperidin-3-yl)phenyl)pyrazine-2-carboxamide; and
(R)—N-(4-(Piperidin-3-yl)phenyl)-6-(trifluoromethyl)nicotinamide;
or a pharmaceutically suitable acid addition salt thereof.

10. A compound selected from the group consisting of (R)—N-(4-(Morpholin-2-yl)phenyl)-6-(2,2,2-trifluoroethoxy)nicotinamide;
(S)—N-(4-(Morpholin-2-yl)phenyl)-6-(2,2,2-trifluoroethoxy)nicotinamide; and
(RS)—N-(4-(Morpholin-2-yl)phenyl)-6-(pyrrolidin-1-yl)nicotinamide;
or a pharmaceutically suitable acid addition salt thereof.

11. A compound selected from the group consisting of N-(4-(Morpholin-2-yl)phenyl)-2-(trifluoromethyl)isonicotinamide;
(R)—N-(4-(Morpholin-2-yl)phenyl)-6-(trifluoromethyl)nicotinamide;
(S)—N-(4-(Morpholin-2-yl)phenyl)-6-(trifluoromethyl)nicotinamide;
(RS)—N-(4-(Morpholin-2-yl)phenyl)-2-(pyrazin-2-yl)thiazole-4-carboxamide;
(S)—N-(4-(Piperidin-3-yl)phenyl)-6-propylnicotinamide; and
(S)-6-Ethyl-N-(4-(piperidin-3-yl)phenyl)nicotinamide;
or a pharmaceutically suitable acid addition salt thereof.

12. A compound wherein said compound is (RS)—N-(4-(Morpholin-2-yl)phenyl)-1-phenyl-1H-pyrazole-3-carboxamide
or a pharmaceutically suitable acid addition salt thereof.

13. The compound of claim 11 wherein said compound is N-(4-(Morpholin-2-yl)phenyl)-2-(trifluoromethyl)isonicotinamide or a pharmaceutically suitable acid addition salt thereof.

14. The compound of claim 13 wherein said compound is (RS)—N-(4-(Morpholin-2-yl)phenyl)-2-(trifluoromethyl)isonicotinamide or a pharmaceutically suitable acid addition salt thereof.

* * * * *